United States Patent
Mukasa et al.

(10) Patent No.: US 12,071,478 B2
(45) Date of Patent: *Aug. 27, 2024

(54) METHODS FOR TREATING AUTOIMMUNE DISEASES INCORPORATING AN ANTI-LAG3 ANTIBODY

(71) Applicant: Daiichi Sankyo Company, Limited, Tokyo (JP)

(72) Inventors: Ryuta Mukasa, Taito-ku (JP); Kensuke Nakamura, Bunkyo-ku (JP); Sumie Muramatsu, Sumida-ku (JP); Naoyuki Makita, Nishinomiya (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 13 days.

This patent is subject to a terminal disclaimer.

(21) Appl. No.: 16/331,171

(22) PCT Filed: Sep. 7, 2017

(86) PCT No.: PCT/JP2017/032212
§ 371 (c)(1),
(2) Date: Mar. 7, 2019

(87) PCT Pub. No.: WO2018/047894
PCT Pub. Date: Mar. 15, 2018

(65) Prior Publication Data
US 2019/0202911 A1  Jul. 4, 2019

(30) Foreign Application Priority Data

Sep. 8, 2016  (JP) .................................. 2016-175491

(51) Int. Cl.
| | | |
|---|---|---|
| A61P 21/00 | (2006.01) | |
| A61K 31/56 | (2006.01) | |
| A61K 39/00 | (2006.01) | |
| A61K 39/395 | (2006.01) | |
| A61K 45/00 | (2006.01) | |
| A61P 1/04 | (2006.01) | |
| A61P 3/10 | (2006.01) | |
| A61P 5/16 | (2006.01) | |
| A61P 7/04 | (2006.01) | |
| A61P 7/06 | (2006.01) | |
| A61P 17/00 | (2006.01) | |
| A61P 17/06 | (2006.01) | |
| A61P 19/02 | (2006.01) | |
| A61P 21/04 | (2006.01) | |

(Continued)

(52) U.S. Cl.
CPC .......... *C07K 16/2803* (2013.01); *A61K 31/56* (2013.01); *A61K 39/0008* (2013.01); *A61K 39/395* (2013.01); *A61K 45/00* (2013.01); *A61P 1/04* (2018.01); *A61P 3/10* (2018.01); *A61P 5/16* (2018.01); *A61P 7/04* (2018.01); *A61P 7/06* (2018.01); *A61P 17/00* (2018.01); *A61P 17/06* (2018.01); *A61P 19/02* (2018.01); *A61P 21/00* (2018.01); *A61P 21/04* (2018.01); *A61P 25/00* (2018.01); *A61P 27/02* (2018.01); *A61P 29/00* (2018.01); *A61P 31/00* (2018.01); *A61P 35/00* (2018.01); *A61P 37/02* (2018.01); *A61P 37/06* (2018.01); *A61P 37/08* (2018.01); *A61P 43/00* (2018.01); *C07K 16/28* (2013.01); *C07K 16/46* (2013.01); *C12N 5/10* (2013.01); *C12N 15/09* (2013.01); *A61K 2035/122* (2013.01); *A61K 2039/505* (2013.01); *A61K 2039/577* (2013.01); *C07K 2317/24* (2013.01); *C07K 2317/41* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,787,513 B2 * | 9/2020 | Pardoll | ............. A01K 67/0271 |
| 2010/0233183 A1 | 9/2010 | Triebel et al. | |
| 2015/0259420 A1 | 9/2015 | Triebel et al. | |

FOREIGN PATENT DOCUMENTS

| | | | |
|---|---|---|---|
| JP | 2010-526052 A | 7/2010 | |
| JP | 2016-516681 A | 6/2016 | |

(Continued)

OTHER PUBLICATIONS

Edwards, B.M., etal. J. Mol. Biol. 2003;334:103-118 Torres, M., and Casadevall, A. Trends Immunol. 2008;91 -97 (Year: 2003).*
Khan, T., and Salunke, D.M. J. Immunol. 2014; 192:5398-5405 (Year: 2014).*
Poosarla, V.G., etal. Biotechnol. Bioengin. 2017; 114(6): 1331-1342 (Year: 2017).*

(Continued)

*Primary Examiner* — G. R. Ewoldt
(74) *Attorney, Agent, or Firm* — Christensen O'Connor Johnson Kindness PLLC

(57) ABSTRACT

Provided are methods for treatment or prevention of an autoimmune disease that comprise administering a monoclonal antibody or a binding fragment thereof that binds to domain 3 of human LAG-3 and has one or more of the properties described in (ii) to (v), and the properties described in (i) and (vi) below: (i) having in vitro ADCC activity; (ii) reducing the number of LAG-3 positive cells in vivo in low fucose form; (iii) suppressing experimental autoimmune encephalomyelitis in vivo in low fucose form; (iv) binding to human activated T cells; (v) human LAG-3 binds to human major histocompatibility complex class II molecules in the presence of the antibody or the binding fragment thereof; and (vi) the presence of the antibody or the binding fragment thereof allowing human LAG-3 to exert a human T cell suppression function.

11 Claims, 33 Drawing Sheets

Specification includes a Sequence Listing.

(51) Int. Cl.
| | |
|---|---|
| A61P 25/00 | (2006.01) |
| A61P 27/02 | (2006.01) |
| A61P 29/00 | (2006.01) |
| A61P 31/00 | (2006.01) |
| A61P 35/00 | (2006.01) |
| A61P 37/02 | (2006.01) |
| A61P 37/06 | (2006.01) |
| A61P 37/08 | (2006.01) |
| A61P 43/00 | (2006.01) |
| C07K 16/28 | (2006.01) |
| C07K 16/46 | (2006.01) |
| C12N 5/10 | (2006.01) |
| C12N 15/09 | (2006.01) |
| A61K 35/12 | (2015.01) |

(56) References Cited

FOREIGN PATENT DOCUMENTS

| | | |
|---|---|---|
| RU | 2448729 C2 | 8/2007 |
| WO | 2008025848 A2 | 3/2008 |
| WO | 2008/132601 A1 | 11/2008 |
| WO | 2014/140180 A1 | 9/2014 |
| WO | 2016/126858 A2 | 8/2016 |

OTHER PUBLICATIONS

Ruffo., E., et al. Sem. Immunol. 2019;42:1-11 (Year: 2019).*
Haudebourg, T., et al., "Depletion of LAG-3 Positive Cells in Cardiac Allograft Reveals Their Role in Rejection and Tolerance," Transplantation 84(11):1500-1506, Dec. 2007.
Huard, B., et al., "Characterization of the Major Histocompatibility Complex Class II Binding Site on LAG-3 Protein," Proceedings of the National Academy of Sciences of the USA (PNAS) 94:5744-5749, May 1997.
Huard, B., et al., "T Cell Major Histocompatibility Complex Class II Molecules Down-Regulate CD4+ T Cell Clone Responses Following LAG-3 Binding," European Journal of Immunology 26(5):1180-1186, May 1996.
Li, M., et al., "Reconstitution of Human FcγRIII Cell Type Specificity in Transgenic Mice," Journal of Experimental Medicine 183:1259-1263, Mar. 1996.
Maçon-Lemaître, L., and F. Triebel, "The Negative Regulatory Function of the Lymphocyte-Activation Gene-3 Co-Receptor (CD223) on Human T Cells," Immunology 115(2):170-178, Jun. 2005.
Miller, S.D., et al., "Experimental Autoimmune Encephalomyelitis in the Mouse," Current Protocols in Immunology 88:15.1.1-15.1.20, Feb. 2010.
Nguyen, L.T., and P.S. Ohashi, "Clinical Blockade of PD1 and LAG3—Potential Mechanisms of Action," Nature Reviews. Immunology 15(1):45-56, Jan. 2015.
Okazaki, T., et al., "PD-1 and LAG-3 Inhibitory Co-Receptors Act Synergistically to Prevent Autoimmunity in Mice," Journal of Experimental Medicine 208(2):395-407, Feb. 2011.
Poirier, N., et al., "Antibody-Mediated Depletion of Lymphocyte-Activation Gene-3 (LAG-3+)-Activated T Lymphocytes Prevents Delayed-Type Hypersensitivity in Non-Human Primates," Clinical and Experimental Immunology 164(2):265-274, May 2011.
Triebel, F., "LAG-3: A Regulator of T-Cell and DC Responses and Its Use in Therapeutic Vaccination," Trends in Immunology 24(12):619-622, Dec. 2003.
Turnis, M.E., et al., "Inhibitory Receptors as Targets for Cancer Immunotherapy," European Journal of Immunology 45(7):1892-1905, Jul. 2015.
Matsuzaki, J., "Basic Biology and Clinical Application of LAG-3," The Medical Frontline 70(3):360-365, 2015.
Avice, M.-N., et al., "Lymphocyte Activation of Gene-3, a MHC Class II Ligand Expressed on Activated T Cells, Stimulates TNF-a and IL-12 Production by Monocytes and Dendritic Cells," The Journal of Immunology 162(5):2748-2753, Mach 1999.
Mariuzza, et al., "The structural basis of antigen-antibody recognition", Ann. Rev. Biophys. Biophys. Chem., 1987, vol. 16, pp. 139-159.
Rudikoff, et al. "Single amino acid substation altering antigen-binding specificity", Immunology, 1982, vol. 78, pp. 1979-1983.
Japanese Notice of Reasons for Refusal dated Mar. 25, 2022, issued in corresponding Japanese Application No. 2021-064662, filed Apr. 6, 2021, 6 pages.
Canadian Office Action mailed Jan. 20, 2021, issued in corresponding Canadian Application No. 3036350, filed Mar. 8, 2019, 5 pages.
Russian Office Action mailed Dec. 18, 2020, issued in corresponding Russian Application No. 2019110133/10 (019504), filed Sep. 7, 2017, 18 pages.
Russian Search Report, mailed Dec. 18, 2020, issued in corresponding Russian Application No. 2019110133/10 (019504), filed Sep. 7, 2017, 4 pages.
Colman, P. M., "Effects of amino acid sequence changes on antibody-antigen interactions," Research in Immunology, 1994, vol. 145, Issue 1; pp. 33-36.
Roitt, et al., "Immunologia," Mir Publishers, Moscow, 2000, pp. 110-111, 6 pages.
Singer, et al. "Geny i genomy," Mir Publishers, Moscow, 1998, vol. 1, pp. 63-64, 8 pages.
Extended European Search Report mailed Oct. 21, 2020, issued in corresponding European Application No. 17848832.6, filed Sep. 7, 2017, 6 pages.
Malaysian Search Report mailed Nov. 2, 2021, issued in corresponding Malaysian Application No. PI2019000598, filed Sep. 7, 2017, 1 page [in English].
Malaysian Modified Substantive Examination Report mailed Jan. 30, 2022, issued in corresponding Malaysian Application No. PI2019000598, filed Sep. 7, 2017, 1 page [in English].
International Search Report mailed Nov. 28, 2017, issued in corresponding International Application No. PCT/JP2017/032212, filed Sep. 7, 2017, 9 pages.
Japanese Notice of Reasons for Refusal dated Aug. 5, 2020, issued in related Japanese Application No. 2018-538460, filed Sep. 7, 2017, 9 pages.
Mexican First Office Action mailed Feb. 10, 2023, issued in corresponding Mexican Application No. MX/a/2019/002742, filed Sep. 7, 2017, 8 pages.
Colombian Office Action mailed Jun. 26, 2020, issued in corresponding Colombian Application No. CO2019/0002477, filed Mar. 15, 2019, 19 pages.

* cited by examiner

Figure 5
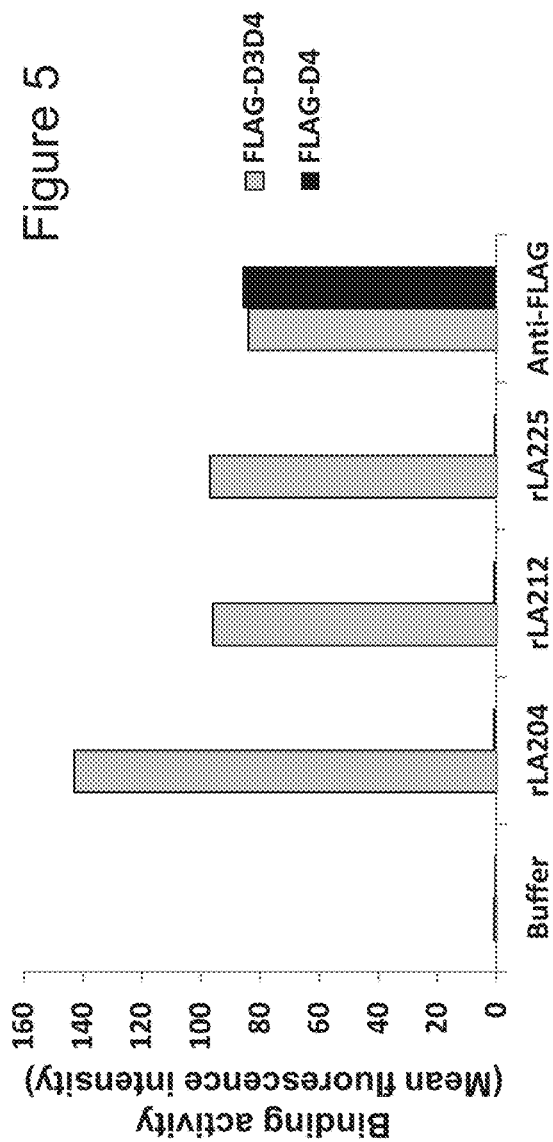
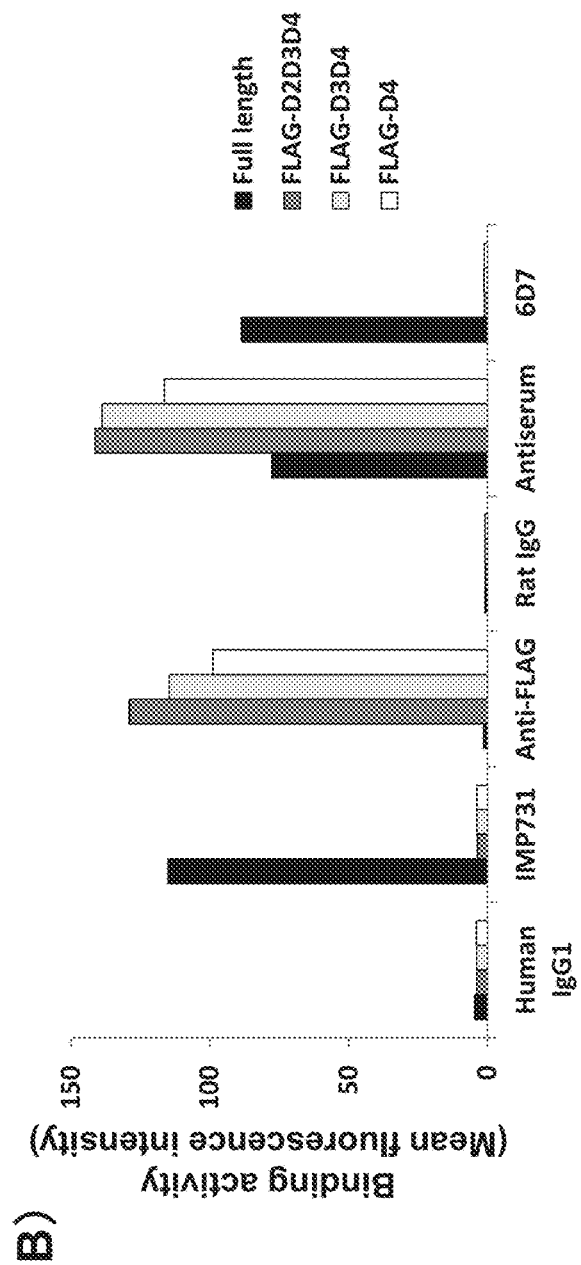

| | Antibodies | KD (nM) |
|---|---|---|
| 1 | hLA212_H2/L1 | 0.11 |
| 2 | hLA212_H2/L2 | 0.12 |
| 3 | hLA212_H2/L3 | 0.15 |
| 4 | hLA212_H2/L4 | 0.096 |
| 5 | hLA212_H2/L5 | 0.12 |
| 6 | hLA212_H3/L1 | 0.092 |
| 7 | hLA212_H3/L2 | 0.062 |
| 8 | hLA212_H3/L3 | 0.10 |
| 9 | hLA212_H3/L4 | 0.076 |
| 10 | hLA212_H3/L5 | 0.10 |

Figure 7

Figure 16
GAGGTAGAGCTGGTGGAGTCTGGGGGCGGCTTAGTGCAGCCTGGAAGGTCCATGAAACTCTC
CTGTGCAGCCTCAGGATTCACTTTCAGAACCTATGGCATGGCCTGGGTCCGCCAGGCTCCAAC
GAAGGGTCTGGAGTGGGTCGCATCCATTAGTACTGGTGGTGGTAGCACTTACTATCGCGACTC
CGTGAAGGGCCGATTCACTATCTCCAGAGATAATGCAAAAGCACCCTATACCTGCAAATGGA
CAGTCTGAGGTCTGAGGACACGGCCACTTATTACTGTACAACAGATCTAATTAACTACCCGGG
TATAGGGGGGTTTGCTTTCTGGGGCCAAGGCACTCTGGTCACTGTCTCTTCA
variable region(1-366)
(SEQ ID No:1)

Figure 17
EVELVESGGGLVQPGRSMKLSCAASGFTFRTYGMAWVRQAPTKGLEWVASISTGGGSTYYRDSV
KGRFTISRDNAKSTLYLQMDSLRSEDTATYYCTTDLINYPGIGGFAFWGQGTLVTVSS
variable region(1-122)
(SEQ ID No:2)

Figure 18
AACATTGTGATGACCCAGTCTCCCAAATCCATGTCCATATCAGTAGGAGACAGGGTCACCATG
AACTGCAAGGCCAGTCAGAATGTGTATAATAATATAGCCTGGTATCAACAGAAGCCAGGGAA
ATCTCCTAAACTGTTGATCTACTATGCATCTAACCGGTACACTGGGGTCCCTGATCGCTTCACA
GGCAGTGGCTCTGGGACAGATTTCACTCTCACCATCCATAGTGTGCAAGCTGAAGATGCAGCC
TTTTATTACTGTCAGCGTCTTTACAATTCTCCTCCGACGTTCGGTGGAGGCACCAAGCTGGAAT
TGAAACGGGCT
variable region(1-327)
(SEQ ID No:3)

Figure 19
NIVMTQSPKSMSISVGDRVTMNCKASQNVYNNIAWYQQKPGKSPKLLIYYASNRYTGVPDRFTG
SGSGTDFTLTIHSVQAEDAAFYYCQRLYNSPPTFGGGTKLELKRA
variable region(1-109)
(SEQ ID No:4)

Figure 20
GAGGTGCAGCTGGTGGAGTCTGGGGGAGGCTTAGTGCAGCCTGGAAGGTCCCTGAAACTCTC
CTGTGCAGCCTCAGGATTCACTTACCGTAGCTATGTCATGGCCTGGGTCCGCCAGGCTCCAAC
GAGGGGTCTGGAGTGGGTCGCATCCATTAGTACTGGTGGTGGTAACACTTACTATCGAGACTC
CGTGAAGGGCCGATTCACTATCTCCAGAGATAATGCAAAGAACACCCTATACCTACAAATGGA
CAGTCTGAGGTCTGAGGACACGGCCACTTATTACTGTGCAAGAGACATGAGTAATTCGGGAT
ACGGGCTCTTTGATTACTGGGGCCAAGGAGTCATGGTCACAGTCTCCTCA
variable region(1-363)
(SEQ ID No:5)

Figure 21
EVQLVESGGGLVQPGRSLKLSCAASGFTYRSYVMAWVRQAPTRGLEWVASISTGGGNTYYRDSV
KGRFTISRDNAKNTLYLQMDSLRSEDTATYYCAEDMSNSGYGLFDYWGQGVMVTVSS
variable region(1-121)
(SEQ ID No:6)

Figure 22
AACATTGTGATGACCCAGTCTCCCAAATCCATGTCCATATCAGTAGGAGACAGGGTCACCATG
AACTGCAAGGCCGGTCAGAATGTGGATAATAATATAGCCTGGTATCAAAAGAAACCAGGGCA
GTCTCCTAAACTGTTGATCTACTATGCATCTAACCGGAACACTGGGGTCCCTGATCGCTTCACA
GGCGGTGGATATGGGACAGATTTCACTCTCACCATCAATAGTGTGCAAGCTGAAGATGCAGC
CTTTTATTACTGTCAGCGTATTTCCAATTCTCCGTACACGTTTGGCGCTGGGACCGAGCTGGAA
CTGAAACGGGCT
variable region(1-327)
(SEQ ID No:7)

Figure 23
NIVMTQSPKSMSISVGDRVTMNCKAGQNVDNNIAWYQKKPGQSPKLLIYYASNRNTGVPDRFT
GGGYGTDFTLTINSVQAEDAAFYYCQRISNSPYTFGAGTELELKRA
variable region(1-109)
(SEQ ID No:8)

Figure 24
GAGGTGCAGCTGGTGGAGTCTGGGGGAGGCTTAGTGCAGCCTGGAAGGTCCATGAAACTCTC
CTGTGTAGCCTCAGGATTCACTTTCAGTAACTATTACATGGCCTGGGTCCGCCAGGCTCCAACG
AAGGGTCTGGAGTGGGTCGCATCCATTAGTACTGGTGGTGGTAACACTTACTATCGAGACTCC
GTGAAGGGCCGATTCACTATCTCCAGAGATAATGCAAAAGCACCCTATACCTGCAAATGGAC
AGTCTGAGGTCTGAGGACACGGCCACTTATTACTGTGCAAGACCCCCATATGGCTATAACTAC
GGTTGGTTTACTTACTGGGGCCAAGGCACTCTGGTCACTGTCTCTTCA
variable region(1-363)
(SEQ ID No:9)

Figure 25
EVQLVESGGGLVQPGRSMKLSCVASGFTFSNYYMAWVRQAPTKGLEWVASISTGGGNTYYRDS
VKGRFTISRDNAKSTLYLQMDSLRSEDTATYYCARPPYGYNYGWFTYWGQGTLVTVSS
variable region(1-121)
(SEQ ID No:10)

Figure 26
GACATCCAGATGACACAGTCTCCAGCTTCCCTGTCTGCATCTCTGGGAGAAACTGTCACCATCG
AATGTCGAGCAAGTGAGGACATTCACAATGGTTTAGTATGGTATCAGCAGAAGCCAGGGAAA
TCTCCTCAGCTCCTGATCTATAATGCAAATAGTATGCATACTGGGGTCCCATCACGGTTCAGTG
GCAGTGGATCTGGTACACAGTATTCTCTCAAGATAAACAGCCTGCAGTCTGAAGATGTCGCAA
GTTATTTCTGTCAACAGTATTACAATTATCCTCGGACGTTCGGTGGAGGCACCAAGCTGGAATT
GAAACGGGCT
variable region(1-327)
(SEQ ID No:11)

Figure 27
DIQMTQSPASLSASLGETVTIECRASEDIHNGLVWYQQKPGKSPQLLIYNANSMHTGVPSRFSGSG
SGTQYSLKINSLQSEDVASYFCQQYYNYPRTFGGGTKLELKRA
variable region(1-109)
(SEQ ID No:12)

Figure 28
GAGGTGCAGCTGGTGGAGTCTGGGGGAGGCTTAGTGCAGCCTGGAAGGTCCCTGAAACTCTC
CTGTGCAGCCTCAGGATTCACTTATCGTACCTATGTCATGGCCTGGGTCCGCCAGGGTCCAAC
GCAGGGTCTGGAGTGGGTCGCATCCATTAGTACTGGTGGTGTTAGCACTTATTATCGAGACTC
CGTGAAGGGCCGATTCACTATCTCCAGAGATAATGCAAAAAACACCCTATACTTGCAAATGGA
CAGTCTGAGGTCTGAGGACACGGCCACTTATTACTGTGCAAAAGACATGTTGAATGGTTATAA
CTCTCAGGGGCTTTTTGATTACTGGGGCCAAGGAGTCATGGTCACAGTCTCCTCA
variable region(1-369)
(SEQ ID No:13)

Figure 29
EVQLVESGGGLVQPGRSLKLSCAASGFTYRTYVMAWVRQGPTQGLEWVASISTGGVSTYYRDSV
KGRFTISRDNAKNTLYLQMDSLRSEDTATYYCAKDMLNGYNSQGLFDYWGQGVMVTVSS
variable region(1-123)
(SEQ ID No:14)

Figure 30
AACATTGTGATGACCCAGTCTCCCAAATCCATGTCCATATCAGTGGGAGACAGGGTCACCATG
AACTGCAGGGCCAGTCAGAATGTGGATAATACTATAGCCTGGTATCAACAGAAACCAGGGCA
GTCTCCTAAACTGTTGATCTACTTTGCATCTGACCGGTACACTGGGGTCCCTGATCGCTTCACA
GGCGGTGGATATGGGACAGATTTCACTCTCACCATCAATAGTGTGCAAGCTGAAGATGCAGC
CTTTTATTACTGTCAGCGTATTTACAATTCTCCACTCACGTTCGGTTCTGGGACCAAGCTGGAG
ATCAGACGGGCT
variable region(1-327)
(SEQ ID No:15)

Figure 31
NIVMTQSPKSMSISVGDRVTMNCRASQNVDNTIAWYQQKPGQSPKLLIYFASDRYTGVPDRFTG
GGYGTDFTLTINSVQAEDAAFYYCQRIYNSPLTFGSGTKLEIRRA
variable region(1-109)
(SEQ ID No:16)

Figure 32
GAGGTGCAGCTGGTGGAATCTGGGGGAGGCTTAGTGCAGCCTGGAAGGTCCCTGAAACTCTC
CTGTGCAGCCTCAGGATTCACTTTCAGTTCCTATTACATGGCCTGGGTCCGCCAGGCTCCAACG
AAGGGTCTGGAGTGGGTCGCATACATCAGTAATGGTGGTTATAGCACTTACTATCGAGACTCC
GTGAAGGGCCGATTCACTATCTCCAGAGAAAATGCAAAAGCACCCTTTACCTGCAAATGGAC
AGTCTGAGGTCTGAGGACACGGCCACTTATTACTGTACAATCACAGATCATTCGGGGTACAGG
TTTACTTACTGGGGCCAAGGCACTCTGGTCACTGTCTCTTCA
variable region (1-357)
(SEQ ID No:17)

Figure 33
EVQLVESGGGLVQPGRSLKLSCAASGFTFSSYYMAWVRQAPTKGLEWVAYISNGGYSTYYRDSVK
GRFTISRENAKSTLYLQMDSLRSEDTATYYCTITDHSGYRFTYWGQGTLVTVSS
variable region (1-119)
(SEQ ID No:18)

Figure 34
GACATCCAGATGACCCAGTCTCCTTCACTCCTGTCAGCATCTGTGGGAGACAGAGTCACTCTCA
GCTGCAAAGCAAGTCAGAGTATTTACAACAGCTTAGCCTGGTATCAGCAAAAACTTGGAGAA
GCTCCCAAACTCCTCATATATGATGCAAACAGTTTGCAAACGGGCATCCCATCAAGGTTCAGT
GGCAGTGGATCTGGTACAGATTTCACACTCACCATCAGCAGCCTGCAGCCTGAAGATGTTGCC
ACATATTTCTGCCAGAAGTATTATAGCGGGAACACGTTTGGAGCTGGGACCAAGCTGGAACT
GAAACGGGCT
variable region (1-324)
(SEQ ID No:19)

Figure 35
DIQMTQSPSLLSASVGDRVTLSCKASQSIYNSLAWYQQKLGEAPKLLIYDANSLQTGIPSRFSGSGS
GTDFTLTISSLQPEDVATYFCQKYYSGNTFGAGTKLELKRA
variable region (1-108)
(SEQ ID No:20)

Figure 36
gcctccggactctagagccaccATGGTGCTGCAGACCCAGGTGTTCATCTCCCTGCTGCTGTGGATCT
CCGGCGCGTACGGCGATATCGTGATGATTAAACGTACGGTGGCCGCCCCTCCGTGTTCATCT
TCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCC
CAGGAGAGCGTGACCGAGCAGGACAGCAAGGACAGCACCTACAGCCTGAGCAGCACCCTGA
CCCTGAGCAAAGCCGACTACGAGAAGCACAAGGTGTACGCCTGCGAGGTGACCCACCAGGGC
CTGAGCTCCCCCGTCACCAAGAGCTTCAACAGGGGGGAGTGTtaggggcccgtttaaacggggaggc
ta
(SEQ ID No:21)

Figure 37
gcctccggactctagagccaccATGAAACACCTGTGGTTCTTCCTCCTGCTGGTGGCAGCTCCCAGAT
GGGTGCTGAGCCAGGTGCAATTGTGCAGGCGGTTAGCTCAGCCTCCACCAAGGGCCCAAGCG
TCTTCCCCCTGGCACCCTCCTCCAAGAGCACCTCTGGCGGCACAGCCGCCCTGGGCTGCCTGG
TCAAGGACTACTTCCCCGAACCCGTGACCGTGAGCTGGAACTCAGGCGCCCTGACCAGCGGC
GTGCACACCTTCCCCGCTGTCCTGCAGTCCTCAGGACTCTACTCCCTCAGCAGCGTGGTGACCG
TGCCCTCCAGCAGCTTGGGCACCCAGACCTACATCTGCAACGTGAATCACAAGCCCAGCAACA
CCAAGGTGGACAAGAGAGTTGAGCCCAAATCTTGTGACAAAACTCACACATGCCCACCCTGCC
CAGCACCTGAACTCCTGGGGGGACCCTCAGTCTTCCTCTTCCCCCCAAAACCCAAGGACACCCT
CATGATCTCCCGGACCCCTGAGGTCACATGCGTGGTGGTGGACGTGAGCCACGAAGACCCTG
AGGTCAAGTTCAACTGGTACGTGGACGGCGTGGAGGTGCATAATGCCAAGACAAAGCCCCGG
GAGGAGCAGTACAACAGCACGTACCGGGTGGTCAGCGTCCTCACCGTCCTGCACCAGGACTG
GCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCC
GGGAGGAGATGACCAAGAACCAGGTCAGCCTGACCTGCCTGGTCAAAGGCTTCTATCCCAGC
GACATCGCCGTGGAGTGGGAGAGCAATGGCCAGCCCGAGAACAACTACAAGACCACCCCTCC
CGTGCTGGACTCCGACGGCTCCTTCTTCCTCTACAGCAAGCTCACCGTGGACAAGAGCAGGTG
GCAGCAGGGCAACGTCTTCTCATGCTCCGTGATGCATGAGGCTCTGCACAACCACTACACCCA
GAAGAGCCTCTCCCTGTCTCCGGCAAAtgagatatcgggcccgtttaaacggggaggcta
(SEQ ID No:22)

Figure 38
ATGAAACACCTGTGGTTCTTCCTCCTGCTGGTGGCAGCTCCCAGATGGGTGCTGAGCGAGGTG
CAGCTGGTGGAGTCTGGGGGAGGCTTAGTGCAGCCTGGAAGGTCCCTGAAACTCTCCTGTGC
AGCCTCAGGATTCACTTACCGTAGCTATGTCATGGCCTGGGTCCGCCAGGCTCCAACGAGGGG
TCTGGAGTGGGTCGCATCCATTAGTACTGGTGGTGGTAACACTTACTATCGAGACTCCGTGAA
GGGCCGATTCACTATCTCCAGAGATAATGCAAAGAACACCCTATACCTACAAATGGACAGTCT
GAGGTCTGAGGACACGGCCACTTATTACTGTGCAGAAGACATGAGTAATTCGGGATACGGGC
TCTTTGATTACTGGGGCCAAGGAGTCATGGTCACAGTCAGCTCAGCCTCCACCAAGGGCCCAA
GCGTCTTCCCCCTGGCACCCTCCTCCAAGAGCACCTCTGGCGGCACAGCCGCCCTGGGCTGCC
TGGTCAAGGACTACTTCCCCGAACCCGTGACCGTGAGCTGGAACTCAGGCGCCCTGACCAGC
GGCGTGCACACCTTCCCCGCTGTCCTGCAGTCCTCAGGACTCTACTCCCTCAGCAGCGTGGTG
ACCGTGCCCTCCAGCAGCTTGGGCACCCAGACCTACATCTGCAACGTGAATCACAAGCCCAGC
AACACCAAGGTGGACAAGAGAGTTGAGCCCAAATCTTGTGACAAAACTCACACATGCCCACCC
TGCCCAGCACCTGAACTCCTGGGGGGACCCTCAGTCTTCCTCTTCCCCCCAAAACCCAAGGACA
CCCTCATGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACAAAGCC
CCGGGAGGAGCAGTACAACAGCACGTACCGGGTGGTCAGCGTCCTCACCGTCCTGCACCAGG
ACTGGCTGAATGGCAAGGAGTACAAGTGCAAGGTCTCCAACAAAGCCCTCCCAGCCCCCATC
GAGAAAACCATCTCCAAAGCCAAAGGCCAGCCCCGGGAACCACAGGTGTACACCCTGCCCCC
ATCCCGGGAGGAGATGACCAAGAACCAGGTCAGCCTGACCTGCCTGGTCAAAGGCTTCTATC
CCAGCGACATCGCCGTGGAGTGGGAGAGCAATGGCCAGCCCGAGAACAACTACAAGACCAC
CCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTAC
ACCCAGAAGAGCCTCTCCCTGTCTCCCGGCAAA
signal sequence(1-57), heavy chain variable region(58-420), heavy chain constant region(421-1410)
(SEQ ID No:23)

Figure 39
MKHLWFFLLLVAAPRWVLSEVQLVESGGGLVQPGRSLKLSCAASGFTYRSYVMAWVRQAPTRGL
EWVASISTGGGNTYYRDSVKGRFTISRDNAKNTLYLQMDSLRSEDTATYYCAEDMSNSGYGLFDY
WGQGVMVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALH
NHYTQKSLSLSPGK
signal sequence(1-19), heavy chain variable region(20-140), heavy chain constant region(141-470)
(SEQ ID No:24)

Figure 40
ATGGTGCTGCAGACCCAGGTGTTCATCTCCCTGCTGCTGTGGATCTCCGGCGCGTACGGCAAC
ATTGTGATGACCCAGTCTCCCAAATCCATGTCCATATCAGTAGGAGACAGGGTCACCATGAAC
TGCAAGGCCGGTCAGAATGTGGATAATAATATAGCCTGGTATCAAAAGAAACCAGGGCAGTC
TCCTAAACTGTTGATCTACTATGCATCTAACCGGAACACTGGGGTCCTGATCGCTTCACAGGC
GGTGGATATGGGACAGATTTCACTCTCACCATCAATAGTGTGCAAGCTGAAGATGCAGCCTTT
TATTACTGTCAGCGTATTTCCAATTCTCCGTACACGTTTGGCGCTGGGACCGAGCTGGAACTGA
AACGGGCTGTGGCCGCCCCCTCCGTGTTCATCTTCCCCCCCTCCGACGAGCAGCTGAAGTCCG
GCACCGCCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGACAGCA
AGGACAGCACCTACAGCCTGAGCAGCACCCTGACCCTGAGCAAAGCCGACTACGAGAAGCAC
AAGGTGTACGCCTGCGAGGTGACCCACCAGGGCCTGAGCTCCCCCGTCACCAAGAGCTTCAA
CAGGGGGGAGTGT signal sequence(1-60), light chain variable region(61-387), light chain constant region(388-702)

(SEQ ID No:25)

Figure 41
MVLQTQVFISLLLWISGAYGNIVMTQSPKSMSISVGDRVTMNCKAGQNVDNNIAWYQKKPGQS
PKLLIYYASNRNTGVPDRFTGGGYGTDFTLTINSVQAEDAAFYYCQRISNSPYTFGAGTELELKRAV
AAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC signal sequence(1-20), light chain variable region(21-129), light chain constant region(130-234)

(SEQ ID No:26)

Figure 42
ATGAAACACCTGTGGTTCTTCCTCCTGCTGGTGGCAGCTCCCAGATGGGTGCTGAGCGAAGTG
CAGCTGGTGGAATCTGGCGGCGGACTGGTGCAGCCTGGCGGATCTCTGAGACTGAGCTGTGC
CGCCAGCGGCTTCACCTACCGGTCTTACGTGATGGCCTGGGTGCGCCAGGCCCCTGGAAAAG
GACTGGAATGGGTGGGATCCATCAGCACCGGCGGAGGCAACACCTACTACCGGGATAGCGT
GAAGGGCCGGTTCACCATCAGCCGGGACAACGCCAAGAACACCCTGTACCTGCAGATGAACA
GCCTGCGGGCCGAGGACACCGCCGTGTACTATTGCGCCGAGGATATGAGCAACAGCGGCTAC
GGCCTGTTCGACTACTGGGGCCAGGGAACCCTCGTGACCGTCAGCTCAGCCTCCACCAAGGG
CCCAAGCGTCTTCCCCCTGGCACCCTCCTCCAAGAGCACCTCTGGCGGCACAGCCGCCCTGGG
CTGCCTGGTCAAGGACTACTTCCCCGAACCCGTGACCGTGAGCTGGAACTCAGGCGCCCTGAC
CAGCGGCGTGCACACCTTCCCCGCTGTCCTGCAGTCCTCAGGACTCTACTCCCTCAGCAGCGTG
GTGACCGTGCCCTCCAGCAGCTTGGGCACCCAGACCTACATCTGCAACGTGAATCACAAGCCC
AGCAACACCAAGGTGGACAAGAGAGTTGAGCCCAAATCTTGTGACAAAACTCACACATGCCC
ACCCTGCCCAGCACCTGAACTCCTGGGGGGACCCTCAGTCTTCCTCTTCCCCCCAAAACCCAAG
GACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAA
AGCCCCGGGAGGAGCAGTACAACAGCACGTACCGGGTGGTCAGCGTCCTCACCGTCCTGCAC
CAGGACTGGCTGAATGGCAAGGAGTACAAGTGCAAGGTCTCCAACAAAGCCCTCCCAGCCCC
CATCGAGAAAACCATCTCCAAAGCCAAAGGCCAGCCCCGGGAACCACAGGTGTACACCCTGC
CCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGCCAGCCCGAGAACAACTACAAGAC
CACCCCTCCCGTGCTGGACTCCGACGGCTCCTTCTTCCTCTACAGCAAGCTCACCGTGGACAAG
AGCAGGTGGCAGCAGGGCAACGTCTTCTCATGCTCCGTGATGCATGAGGCTCTGCACAACCAC
TACACCCAGAAGAGCCTCTCCCTGTCTCCGGCAAA
signal sequence(1-57), heavy chain variable region(58-420), heavy chain constant region(421-1410)
(SEQ ID No:27)

Figure 43
MKHLWFFLLLVAAPRWVLSEVQLVESGGGLVQPGGSLRLSCAASGFTYRSYVMAWVRQAPGKG
LEWVGSISTGGGNTYYRDSVKGRFTISRDNAKNTLYLQMNSLRAEDTAVYYCAEDMSNSGYGLFD
YWGQGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALH
NHYTQKSLSLSPGK
signal sequence(1-19), heavy chain variable region(20-140), heavy chain constant region(141-470)
(SEQ ID No:28)

Figure 44
ATGAAACACCTGTGGTTCTTCCTCCTGCTGGTGGCAGCTCCCAGATGGGTGCTGAGCGAAGTG
CAGCTGGTGGAATCTGGCGGCGGACTGGTGCAGCCTGGCGGATCTCTGAGACTGAGCTGTGC
CGCCAGCGGCTTCACCTACCGGTCTTACGTGATGGCCTGGGTGCGCCAGGCCCCTGGAAAAG
GACTGGAATGGGTGGCCAGCATCAGCACCGGCGGAGGCAACACCTACTACCGGGATAGCGT
GAAGGGCCGGTTCACCATCAGCCGGGACAACGCCAAGAACACCCTGTACCTGCAGATGGACA
GCCTGCGGGCCGAGGATACCGCCGTGTACTACTGTGCCGAGGACATGAGCAACAGCGGCTAC
GGCCTGTTCGACTACTGGGGCCAGGGAACCCTCGTGACCGTCAGCTCAGCCTCCACCAAGGG
CCCAAGCGTCTTCCCCCTGGCACCCTCCTCCAAGAGCACCTCTGGCGGCACAGCCGCCCTGGG
CTGCCTGGTCAAGGACTACTTCCCCGAACCCGTGACCGTGAGCTGGAACTCAGGCGCCCTGAC
CAGCGGCGTGCACACCTTCCCCGCTGTCCTGCAGTCCTCAGGACTCTACTCCCTCAGCAGCGTG
GTGACCGTGCCCTCCAGCAGCTTGGGCACCCAGACCTACATCTGCAACGTGAATCACAAGCCC
AGCAACACCAAGGTGGACAAGAGAGTTGAGCCCAAATCTTGTGACAAAACTCACACATGCCC
ACCCTGCCCAGCACCTGAACTCCTGGGGGGACCCTCAGTCTTCCTCTTCCCCCCAAAACCCAAG
GACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAA
AGCCCCGGGAGGAGCAGTACAACAGCACGTACCGGGTGGTCAGCGTCCTCACCGTCCTGCAC
CAGGACTGGCTGAATGGCAAGGAGTACAAGTGCAAGGTCTCCAACAAAGCCCTCCCAGCCCC
CATCGAGAAAACCATCTCCAAAGCCAAAGGCCAGCCCCGGGAACCACAGGTGTACACCCTGC
CCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGCCAGCCCGAGAACAACTACAAGAC
CACCCCTCCCGTGCTGGACTCCGACGGCTCCTTCTTCCTCTACAGCAAGCTCACCGTGGACAAG
AGCAGGTGGCAGCAGGGCAACGTCTTCTCATGCTCCGTGATGCATGAGGCTCTGCACAACCAC
TACACCCAGAAGAGCCTCTCCCTGTCTCCGGCAAA
signal sequence(1-57), heavy chain variable region(58-420), heavy
chain constant region(421-1410)
(SEQ ID No:29)

Figure 45
MKHLWFFLLLVAAPRWVLSEVQLVESGGGLVQPGGSLRLSCAASGFTYRSYVMAWVRQAPGKG
LEWVASISTGGGNTYYRDSVKGRFTISRDNAKNTLYLQMDSLRAEDTAVYYCAEDMSNSGYGLFD
YWGQGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALH
NHYTQKSLSLSPGK
signal sequence(1-19), heavy chain variable region(20-140), heavy
chain constant region(141-470)
(SEQ ID No:30)

Figure 46
ATGGTGCTGCAGACCCAGGTGTTCATCTCCCTGCTGCTGTGGATCTCCGGCGCGTACGGCGAC
ATCCAGATGACCCAGAGCCCTAGCAGCCTGAGCGCCAGCGTGGGCGACAGAGTGACCATCAC
CTGTAAAGCCGGCCAGAACGTGGACAACAATATCGCCTGGTATCAGCAGAAGCCCGGCCAGG
CCCCTAAGCTGCTGATCTACTACGCCAGCAACCGGAACACCGGCGTGCCCAGCAGATTTTCTG
GCAGCGGCTCCGGCACCGACTTCACCCTGACAATCAGCAGCCTGCAGCCCGAGGACTTCGCCA
CCTACTACTGCCAGAGAATCAGCAACAGCCCTACACCTTCGGCCAGGGCACCAAGGTGGAA
ATCAAGCGTACGGTGGCCGCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACA
GCAAGGACAGCACCTACAGCCTGAGCAGCACCCTGACCCTGAGCAAAGCCGACTACGAGAAG
CACAAGGTGTACGCCTGCGAGGTGACCCACCAGGGCCTGAGCTCCCCCGTCACCAAGAGCTTC
AACAGGGGGGAGTGT
signal sequence(1-60), light chain variable region(61-387), light chain constant region(388-702)
(SEQ ID No:31)

Figure 47
MVLQTQVFISLLLWISGAYGDIQMTQSPSSLSASVGDRVTITCKAGQNVDNNIAWYQQKPGQAP
KLLIYYASNRNTGVPSRFSGSGSGTDFTLTISSLQPEDFATYYCQRISNSPYTFGQGTKVEIKRTVAAP
SVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC
signal sequence(1-20), light chain variable region(21-129), light chain constant region(130-234)
(SEQ ID No:32)

Figure 48
ATGGTGCTGCAGACCCAGGTGTTCATCTCCCTGCTGCTGTGGATCTCCGGCGCGTACGGCGAC
ATCCAGATGACCCAGAGCCCTAGCAGCCTGAGCGCCAGCGTGGGCGACAGAGTGACCATCAC
CTGTAAAGCCGGCCAGAACGTGGACAACAATATCGCCTGGTATCAGCAGAAGCCCGGCCAGA
GCCCCAAGCTGCTGATCTACTACGCCAGCAACCGGAACACCGGCGTGCCCAGCAGATTTTCCG
GCAGCGGCTACGGCACCGACTTCACCCTGACAATCAGCAGCCTGCAGCCCGAGGACTTCGCCA
CCTACTACTGCCAGAGAATCAGCAACAGCCCTACACCTTCGGCCAGGGCACCAAGGTGGAA
ATCAAGCGTACGGTGGCCGCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACA
GCAAGGACAGCACCTACAGCCTGAGCAGCACCCTGACCCTGAGCAAAGCCGACTACGAGAAG
CACAAGGTGTACGCCTGCGAGGTGACCCACCAGGGCCTGAGCTCCCCCGTCACCAAGAGCTTC
AACAGGGGGGAGTGT
signal sequence(1-60), light chain variable region(61-387), light chain constant region(388-702)
(SEQ ID No:33)

Figure 49
MVLQTQVFISLLLWISGAYGDIQMTQSPSSLSASVGDRVTITCKAGQNVDNNIAWYQQKPGQSP
KLLIYYASNRNTGVPSRFSGSGYGTDFTLTISSLQPEDFATYYCQRISNSPYTFGQGTKVEIKRTVAAP
SVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC
signal sequence(1-20), light chain variable region(21-129), light
chain constant region(130-234)
(SEQ ID No:34)

Figure 50
ATGGTGCTGCAGACCCAGGTGTTCATCTCCCTGCTGCTGTGGATCTCCGGCGCGTACGGCAAC
ATCCAGATGACCCAGAGCCCCAGCAGCCTGTCTGCCAGCGTGGGCGACAGAGTGACCATCAC
ATGCAAGGCCGGCCAGAACGTGGACAACAATATCGCCTGGTATCAGAAGAAGCCCGGCCAGT
CCCCCAAGCTGCTGATCTACTACGCCAGCAACCGGAACACCGGCGTGCCCGACAGATTTTCCG
GCGGAGGCTACGGCACCGACTTCACCCTGACCATCAGCTCCCTGCAGCCCGAGGACTTCGCCT
TCTACTACTGTCAGCGGATCAGCAACAGCCCCTACACCTTCGGCCAGGGCACCAAGGTGGAAA
TCAAGCGTACGGTGGCCGCCCCCTCCGTGTTCATCTTCCCCCCTCCGACGAGCAGCTGAAGTC
CGGCACCGCCTCCGTGGTGTGCCTGCTGAATAACTTCTACCCCAGAGAGGCCAAGGTGCAGTG
GAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCA
CAAGGTGTACGCCTGCGAGGTGACCCACCAGGGCCTGAGCTCCCCCGTCACCAAGAGCTTCA
ACAGGGGGGAGTGT
signal sequence(1-60), light chain variable region(61-387), light
chain constant region(388-702)
(SEQ ID No:35)

Figure 51
MVLQTQVFISLLLWISGAYGNIQMTQSPSSLSASVGDRVTITCKAGQNVDNNIAWYQKKPGQSPK
LLIYYASNRNTGVPDRFSGGGYGTDFTLTISSLQPEDFAFYYCQRISNSPYTFGQGTKVEIKRTVAAP
SVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC
signal sequence(1-20), light chain variable region(21-129), light
chain constant region(130-234)
(SEQ ID No:36)

Figure 52
ATGGTGCTGCAGACCCAGGTGTTCATCTCCCTGCTGCTGTGGATCTCCGGCGCGTACGGCGAC
ATCCAGATGACCCAGAGCCCCAGCAGCATGAGCATCAGCGTGGGCGACAGAGTGACCATGAC
CTGCAAGGCCGGCCAGAACGTGGACAACAATATCGCCTGGTATCAGAAGAAGCCCGGCCAGT
CCCCCAAGCTGCTGATCTACTACGCCAGCAACCGGAACACCGGCGTGCCCAGCAGATTTTCTG
GCAGCGGCTCCGGCACCGACTTCACCCTGACAATCAGCAGCGTGCAGCCCGAGGACTTCGCC
ACCTACTACTGCCAGAGAATCAGCAACAGCCCCTACACCTTCGGCCAGGGCACCAAGCTGGAA
CTGAAGCGTACGGTGGCCGCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACA
GCAAGGACAGCACCTACAGCCTGAGCAGCACCCTGACCCTGAGCAAAGCCGACTACGAGAAG
CACAAGGTGTACGCCTGCGAGGTGACCCACCAGGGCCTGAGCTCCCCCGTCACCAAGAGCTTC
AACAGGGGGGAGTGT
signal sequence(1-60), light chain variable region(61-387), light
chain constant region(388-702)
(SEQ ID No:37)

Figure 53
MVLQTQVFISLLLWISGAYGDIQMTQSPSSMSISVGDRVTMTCKAGQNVDNNIAWYQKKPGQS
PKLLIYYASNRNTGVPSRFSGSGSGTDFTLTISSVQPEDFATYYCQRISNSPYTFGQGTKLELKRTVA
APSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC
signal sequence(1-20), light chain variable region(21-129), light
chain constant region(130-234)
(SEQ ID No:38)

Figure 54
ATGGTGCTGCAGACCCAGGTGTTCATCTCCCTGCTGCTGTGGATCTCCGGCGCGTACGGCAAC
ATCCAGATGACCCAGAGCCCCAGCAGCATGAGCATCAGCGTGGGCGACAGAGTGACCATGAC
CTGCAAGGCCGGCCAGAACGTGGACAACAATATCGCCTGGTATCAGAAGAAGCCCGGCCAGT
CCCCCAAGCTGCTGATCTACTACGCCAGCAACCGGAACACCGGCGTGCCCGACAGATTTTCCG
GCGGAGGCTACGGCACCGACTTCACCCTGACAATCAGCAGCGTGCAGCCCGAGGACGCCGCC
TTCTACTACTGTCAGCGGATCAGCAACAGCCCCTACACCTTCGGCCAGGGCACCAAGCTGGAA
CTGAAGCGTACGGTGGCCGCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACA
GCAAGGACAGCACCTACAGCCTGAGCAGCACCCTGACCCTGAGCAAAGCCGACTACGAGAAG
CACAAGGTGTACGCCTGCGAGGTGACCCACCAGGGCCTGAGCTCCCCCGTCACCAAGAGCTTC
AACAGGGGGGAGTGT
signal sequence(1-60), light chain variable region(61-387), light
chain constant region(388-702)
(SEQ ID No:39)

Figure 55
MVLQTQVFISLLLWISGAYGNIQMTQSPSSMSISVGDRVTMTCKAGQNVDNNIAWYQKKPGQS
PKLLIYYASNRNTGVPDRFSGGGYGTDFTLTISSVQPEDAAFYYCQRISNSPYTFGQGTKLELKRTVA
APSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC
signal sequence(1-20), light chain variable region(21-129), light
chain constant region(130-234)
(SEQ ID No:40)

Figure 56
GFTFRTYGMA
(SEQ ID No:41)

Figure 57
SISTGGGSTYYRDSVKG
(SEQ ID No:42)

Figure 58
DLINYPGIGGFAF
(SEQ ID No:43)

Figure 59
KASQNVYNNIA
(SEQ ID No:44)

Figure 60
YASNRYT
(SEQ ID No:45)

Figure 61
QRLYNSPPT
(SEQ ID No:46)

Figure 62
GFTYRSYVMA
(SEQ ID No:47)

Figure 63
SISTGGGNTYYRDSVKG
(SEQ ID No:48)

Figure 64
DMSNSGYGLFDY
(SEQ ID No:49)

Figure 65
KAGQNVDNNIA
(SEQ ID No:50)

Figure 66
YASNRNT
(SEQ ID No:51)

Figure 67
QRISNSPYT
(SEQ ID No:52)

Figure 68
GFTFSNYYMA
(SEQ ID No:53)

Figure 69
SISTGGGNTYYRDSVKG
(SEQ ID No:54)

Figure 70
PPYGYNYGWFTY
(SEQ ID No:55)

Figure 71
RASEDIHNGLV
(SEQ ID No:56)

Figure 72
NANSMHT
(SEQ ID No:57)

Figure 73
QQYYNYPRT
(SEQ ID No:58)

Figure 74
GFTYRTYVMA
(SEQ ID No:59)

Figure 75
SISTGGVSTYYRDSVKG
(SEQ ID No:60)

Figure 76
DMLNGYNSQGLFDY
(SEQ ID No:61)

Figure 77
RASQNVDNTIA
(SEQ ID No:62)

Figure 78
FASDRYT
(SEQ ID No:63)

Figure 79
QRIYNSPLT
(SEQ ID No:64)

Figure 80
GFTFSSYYMA
(SEQ ID No:65)

Figure 81
YISNGGYSTYYRDSVKG
(SEQ ID No:66)

Figure 82
TDHSGYRFTY
(SEQ ID No:67)

Figure 83
KASQSIYNSLA
(SEQ ID No:68)

Figure 84
DANSLQT
(SEQ ID No:69)

Figure 85
QKYYSGNT
(SEQ ID No:70)

Figure 86
CTCCAGAGTTCCAGGTCACGGTGACTGGC
(SEQ ID No:71)

Figure 87
TCAGTAACACTGTCCAGGACACCATCTC
(SEQ ID No:72)

Figure 88
TATACCGTCGACCTCTAGCTAGAGCTTGGC
(SEQ ID No:73)

Figure 89
GCTATGGCAGGGCCTGCCGCCCCGACGTTG
(SEQ ID No:74)

Figure 90
CCAGATGGGTGCTGAGCGAGGTGCAGCTGGTGGAGTCTGGGGGAGG
(SEQ ID No:75)

Figure 91
CTTGGTGGAGGCTGAGCTGACTGTGACCATGACTCCTTGGCCCCAG
(SEQ ID No:76)

Figure 92
ATCTCCGGCGCGTACGGCAACATTGTGATGACCCAGTCTCCCAAATCC
(SEQ ID No:77)

Figure 93
GGAGGGGGCGGCCACAGCCCGTTTCAGTTCCAGCTCGGTCCCAGC
(SEQ ID No:78)

Figure 94
ATGTGGGAGGCTCAGTTCCTGGGCTTGCTGTTTC
(SEQ ID No:79)

Figure 95
GCCCGAGCCCGAGCCCGAGCCGGAGCAGCTCTGA
(SEQ ID No:80)

Figure 96
GAGTATGTGTTGACTGGTTGATAACTATCG
(SEQ ID No:81)

Figure 97
GCCATGACAGATTAGCCATGTCTGCAGCAC
(SEQ ID No:82)

Figure 98
CAGGACCTTTTTCTAACCTCCCTTGGAGGGCTGGGGAGGCCCGGGCCATAGAGGAG
(SEQ ID No:83)

Figure 99
CCTGGAGCCGAGGCAGCCAGCAGGTCTCAGCAGCTCCGCCCGCCCGCCCGCCCGCC
(SEQ ID No:84)

Figure 100
ATGTGGGAGGCTCAGTTCCTGGGCTTGCTGTTTCTGCAGCCGCTTTGGGTGGCTCCAGTGAAG
CCTCTCCAGCCAGGGGCTGAGGTCCCGGTGGTGTGGGCCCAGGAGGGGGCTCCTGCCCAGCT
CCCCTGCAGCCCCACAATCCCCCTCCAGGATCTCAGCCTTCTGCGAAGAGCAGGGGTCACTTG
GCAGCATCAGCCAGACAGTGGCCCGCCCGCTGCCGCCCCGGCCATCCCTGGCCCCGGCCC
TCACCCGGCGGCGCCCTCCTCCTGGGGCCCAGGCCCCGCCGCTACACGGTGCTGAGCGTGG
GTCCCGGAGGCCTGCGCAGCGGGAGGCTGCCCCTGCAGCCCCGCGTCCAGCTGGATGAGCGC
GGCCGGCAGCGCGGGGACTTCTCGCTATGGCTGCGCCCAGCCCGGCGCGCGGACGCCGGCG
AGTACCGCGCCGCGGTGCACCTCAGGGACCGCGCCCTCCTGCCGCCTCCGTCTGCGCCTGG
GCCAGGCCTCGATGACTGCCAGCCCCCAGGATCTCTCAGAGCCTCCGACTGGGTCATTTTGA
ACTGCTCCTTCAGCCGCCCTGACCGCCCAGCCTCTGTGCATTGGTTCCGGAACCGGGGCCAGG
GCCGAGTCCTGTCCGGGAGTCCCCCATCACCACTTAGCGGAAAGCTTCCTCTTCCTGCCCCA
AGTCAGCCCCATGGACTCTGGGCCCTGGGGCTGCATCCTCACCTACAGAGATGGCTTCAACGT
CTCCATCATGTATAACCTCACTGTTCTGGGTCTGGAGCCCCCAACTCCCTTGACAGTGTACGCT
GGAGCAGGTTCCAGGGTGGGGCTGCCCTGCCGCCTGCCTGCTGGTGTGGGGACCCGGTCTTT
CCTCACTGCCAAGTGGACTCCTCCTGGGGGAGGCCCTGACCTCCTGGTGACTGGAGACAATG
GCGACTTTACCCTTCGACTAGAGGATGTGAGCCAGGCCCAGGCTGGGACCTACACCTGCCATA
TCCATCTGCAGGAACAGCAGCTCAATGCCACTGTCACATTGGCAATCATCACAGTGACTCCCA
AATCCTTTGGGTCACCTGGATCCCTGGGGAAGCTGCTTTGTGAGGTGACTCCAGTATCTGGAC
AAGAACGCTTTGTGTGGAGCTCTCTGGACACCCCATCCCAGAGGAGTTTCTCAGGACCTTGGC
TGGAGGCACAGGAGGCCCAGCTCCTTTCCCAGCCTTGGCAATGCCAGCTGTACCAGGGGGAG
AGGCTTCTTGGAGCAGCAGTGTACTTCACAGAGCTGTCTAGCCCAGGTGCCCAACGCTCTGGG
AGAGCCCCAGGTGCCCTCCCAGCAGGCCACCTCCTGCTGTTTCTCATCCTTGGTGTCCTTTCTCT
GCTCCTTTTGGTGACTGGAGCCTTTGGCTTTCACCTTTGGAGAAGACAGTGGCGACCAAGACG
ATTTTCTGCCTTAGAGCAAGGGATTCACCCTCCGCAGGCTCAGAGCAAGATAGAGGAGCTGG
AGCAAGAACCGGAGCCGGAGCCGGAGCCGGAACCGGAGCCCGAGCCCGAGCCCGAGCCGG
AGCAGCTC
(SEQ ID No:85)

Figure 101
MWEAQFLGLLFLQPLWVAPVKPLQPGAEVPVVWAQEGAPAQLPCSPTIPLQDLSLLRRAGVTW
QHQPDSGPPAAAPGHPLAPGPHPAAPSSWGPRPRRYTVLSVGPGGLRSGRLPLQPRVQLDERGR
QRGDFSLWLRPARRADAGEYRAAVHLRDRALSCRLRLRLGQASMTASPPGSLRASDWVILNCSFS
RPDRPASVHWFRNGQGRVPVRESPHHHLAESFLFLPQVSPMDSGPWGCILTYRDGFNVSIMYN
LTVLGLEPPTPLTVYAGAGSRVGLPCRLPAGVGTRSFLTAKWTPPGGGPDLLVTGDNGDFTLRLED
VSQAQAGTYTCHIHLQEQQLNATVTLAIITVTPKSFGSPGSLGKLLCEVTPVSGQERFVWSSLDTPS
QRSFSGPWLEAQEAQLLSQPWQCQLYQGERLLGAAVYFTELSSPGAQRSGRAPGALPAGHLLLFL
ILGVLSLLLLVTGAFGFHLWRRQWRPRRFSALEQGIHPPQAQSKIEELEQEPEPEPEPEPEPEPEPEP
EQL
(SEQ ID No:86)

METHODS FOR TREATING AUTOIMMUNE DISEASES INCORPORATING AN ANTI-LAG3 ANTIBODY

TECHNICAL FIELD

The present invention relates to an antibody, a binding fragment thereof, a molecule comprising an antibody or a binding fragment thereof, a polynucleotide, a vector, a cell, a method for producing an antibody or a binding fragment thereof, an antibody or a binding fragment obtained by the production method, a composition comprising an antibody or a binding fragment thereof, a pharmaceutical composition comprising an antibody or a binding fragment thereof, the pharmaceutical composition for treatment or prevention of diseases associated with LAG-3 positive cells such as autoimmune diseases, use of an antibody or a binding fragment thereof for treatment or prevention of such diseases, and a method for treating such diseases, the method comprising the step of administering an antibody or a binding fragment thereof.

BACKGROUND ART

T lymphocytes (T cells) are cells that play a central role in the immune response, and therefore T cells having various antigen specificities, which are said to number from 10 million to 10 billion clones, are present in vivo, in order to deal with diverse antigens. When an antigen invades the body, only a very limited number of clones specific to the antigen out of such enormous T cell repertoires are proliferated and activated to work for the defense of the body through cytokine production and cytotoxic activity, etc. In autoimmune diseases, various pathological conditions are considered to be triggered by abnormal immune responses to some self antigens. Even under such situations, most other clones that do not have such antigen specificity are not proliferated and activated and instead remain in a resting state. Therefore, selective removal of only activated T cells can suppress immunity specifically, without affecting most T cells having other antigen specificities and thus can be a useful treatment or prevention method against autoimmune diseases, rejection of transplants, allergic diseases, etc. Meanwhile, in a situation where T cells that negatively regulate the immune system, such as regulatory T cells, are mainly activated, removal of such cells can be a useful treatment or prevention method against malignant tumors, chronic infections, etc.

LAG-3 (CD223) is a single-pass transmembrane molecule that belongs to the immunoglobulin superfamily and is known to be expressed selectively in activated T cells (Non Patent Literature 1). It is reported that, when rabbit antiserum having complement dependent cytotoxic (CDC) activity against the rat LAG-3 molecule is administered to a rat allogeneic heart transplant model, LAG-3 positive cells in a graft decrease, so that the period to the rejection of the graft is slightly extended (Non Patent Literature 2). It is also reported that anti-human LAG-3 chimeric antibody A9H12 having cross-reactivity with baboons and exhibiting antibody-dependent cell-mediated cytotoxic (ADCC) activity suppresses the delayed-type hypersensitivity reaction of baboons, though its dose response is unclear (Non Patent Literature 3), and humanized antibodies thereof were fabricated (Patent Literature 2).

LAG-3 is known to bind to major histocompatibility complex (or, major histocompatibility gene complex) (MHC) class II molecules, thereby transmitting some inhibitory signals to T cells to regulate the T cell function negatively (Non Patent Literature 1). For binding of LAG-3 to MHC class II molecules, N-terminal domains 1 and 2 of the four extracellular immunoglobulin-like domains of LAG-3 are considered to be important (Non Patent Literature 4), and it is also reported that such suppression of T cell function via LAG-3 is cooperatively demonstrated with other signals that suppress the T cell function via the PD-1 molecule, etc. (Non Patent Literature 5). Actually, novel cancer treatment methods for activating the immune cell function by inhibiting the T cell suppression function of LAG-3 to attack cancer cells have been actively developed in recent years (Non Patent Literatures 6 and 7). Therefore, in the case of applying LAG-3 antibody that depletes LAG-3 positive cells by ADCC activity, etc., to autoimmune diseases, an antibody having no activity of inhibiting the T cell suppression function inherent to LAG-3 is considered more desirable, since there is thus no risk that autoimmune diseases rather get worse due to abnormal activation of the immune system. In both the anti-rat LAG-3 rabbit antiserum having CDC activity and the anti-human LAG-3 chimeric antibody A9H12 exhibiting ADCC activity (IMP731: Patent Literatures 1 and 2) described above, LAG-3 positive cells are not completely depleted (Non Patent Literatures 2 and 3), and thus the possibilities of side reactions due to abnormal reaction of remaining T cells that have not been depleted and negative influences on suppression of autoimmune diseases are assumed.

CITATION LIST

Patent Literature

Patent Literature 1: US 2011/0070238 A1
Patent Literature 2: WO 2014/140180

Non Patent Literature

Non Patent Literature 1: Triebel, F., LAG-3: a regulator of T-cell and DC responses and its use in therapeutic vaccination., Trends Immunol., December 2003; Vol. 24 (No. 12): p. 619-22

Non Patent Literature 2: Haudebourg, T. et al., Depletion of LAG-3 positive cells in cardiac allograft reveals their role in rejection and tolerance., Transplantation, December 2007; Vol. 84 (No. 11): p. 1500-06

Non Patent Literature 3: Poirier, N. et al., Antibody-mediated depletion of lymphocyte-activation gene-3 (LAG-3 (+))-activated T lymphocytes prevents delayed-type hypersensitivity in non-human primates, Clin. Exp. Immunol., May 2011; Vol. 164 (No. 2): p. 265-74

Non Patent Literature 4: Huard, B. et al., Characterization of the major histocompatibility complex class II binding site on LAG-3 protein, Proc. Natl. Acad. Sci. U.S.A., May 27, 1997; Vol. 94 (No. 11): p. 5744-49

Non Patent Literature 5: Okazaki, T. et al., PD-1 and LAG-3 inhibitory co-receptors act synergistically to prevent autoimmunity in mice, J. Exp. Med., Feb. 7, 2011; Vol. 208 (No. 2): p. 395-407

Non Patent Literature 6: Nguyen, L. T. and Ohashi, P. S., Clinical blockade of PD1 and LAG3—potential mechanisms of action, Nat. Rev. Immunol., January 2015; Vol. 15 (No. 1): p. 45-56

Non Patent Literature 7: Turnis, M. E. et al., Inhibitory receptors as targets for cancer immunotherapy, Eur. J. Immunol. July 2015; Vol. 45 (No. 7): p. 1892-905

Non Patent Literature 8: Huard, B. et al., T cell major histocompatibility complex class II molecules downregulate CD4+ T cell clone responses following LAG-3 binding, Eur. J. Immunol., May 1996; Vol. 26 (No. 5): p. 1180-06

Non Patent Literature 9: Macon-Lemaitre, L and Triebel, F, The negative regulatory function of the lymphocyte-activation gene-3 co-receptor (CD223) on human T cells, Immunology, June 2005; Vol. 115 (No. 2): p. 170-08

Non Patent Literature 10: Li, M. et al., Reconstitution of human Fc gamma RIII cell type specificity in transgenic mice, J. Exp. Med., May 1, 1996; Vol. 183 (No. 3): p. 1259-63

Non Patent Literature 11: Miller, Stephen D. et al., Experimental Autoimmune Encephalomyelitis in the Mouse, Current Protocols in Immunology, UNIT 15.1, Wiley, 2010: p. 15.1.1-15.1.20

SUMMARY OF INVENTION

Technical Problem

It is intended to provide a novel anti-LAG-3 antibody, etc., where various properties are improved or the risks are eliminated or reduced compared with known anti-LAG-3 antibodies.

Solution to Problem

The present invention relates to:
(1) a monoclonal antibody or a binding fragment thereof that binds to domain 3 of human LAG-3 and has one or more of the properties described in (ii) to (v), and the properties described in (i) and (vi) below:
  (i) having in vitro ADCC activity;
  (ii) reducing the number of LAG-3 positive cells in vivo in low fucose form;
  (iii) suppressing experimental autoimmune encephalomyelitis in vivo in low fucose form;
  (iv) binding to human activated T cells;
  (v) human LAG-3 binds to human major histocompatibility complex class II molecules in the presence of the antibody or the binding fragment thereof; and
  (vi) the presence of the antibody or the binding fragment thereof allowing human LAG-3 to exert a human T cell suppression function;
(2) the antibody or the binding fragment thereof according to (1), having the properties described in (ii) and/or (iii),
(3) the antibody or the binding fragment thereof according to (1) or (2), having all the properties described in (ii) to (v);
(4) the antibody or the binding fragment thereof according to any one of (1) to (3), being a chimeric antibody, a humanized antibody, or a human antibody;
(5) the antibody or the binding fragment thereof according to any one of (1) to (4), comprising a light chain comprising CDRL1 having the amino acid sequence represented by SEQ ID No: 50 or FIG. 65, CDRL2 having the amino acid sequence represented by SEQ ID No: 51 or FIG. 66, and CDRL3 having the amino acid sequence represented by SEQ ID No: 52 or FIG. 67, and a heavy chain comprising CDRH1 having the amino acid sequence represented by SEQ ID No: 47 or FIG. 62, CDRH2 having the amino acid sequence represented by SEQ ID No: 48 or FIG. 63, and CDRH3 having the amino acid sequence represented by SEQ ID No: 49 or FIG. 64;
(6) the antibody or the binding fragment thereof according to (4) or (5), being a humanized antibody;
(7) the antibody or the binding fragment thereof according to (6), comprising a heavy chain comprising an amino acid sequence derived from the amino acid sequence represented by SEQ ID No: 28 or FIG. 43 with the amino acid corresponding to position 68 being Gly or substituted with Ala, and the amino acid corresponding to position 103 being Asn or substituted with Asp, and a light chain comprising an amino acid sequence derived from the amino acid sequence represented by SEQ ID No: 32 or FIG. 47 with the amino acid corresponding to position 21 being Asp or substituted with Asn, the amino acid corresponding to position 31 being Leu or substituted with Met, the amino acid corresponding to position 33 being Ala or substituted with Ile, the amino acid corresponding to position 41 being Ile or substituted with Met, the amino acid corresponding to position 58 being Gln or substituted with Lys, the amino acid corresponding to position 63 being Ala or substituted with Ser, the amino acid corresponding to position 80 being Ser or substituted with Asp, the amino acid corresponding to position 85 being Ser or substituted with Gly, the amino acid corresponding to position 87 being Ser or substituted with Tyr, the amino acid corresponding to position 98 being Leu or substituted with Val, the amino acid corresponding to position 103 being Phe or substituted with Ala, the amino acid corresponding to position 105 being Thr or substituted with Phe, the amino acid corresponding to position 124 being Val or substituted with Leu, and the amino acid corresponding to position 126 being Ile or substituted with Leu;
(8) the antibody or the binding fragment thereof according to (6) or (7), comprising a light chain variable region amino acid sequence comprising amino acid 21 to amino acid 129 of the amino acid sequence selected from the group consisting of SEQ ID Nos: 32, 34, 36, 38, and 40, and a heavy chain variable region amino acid sequence comprising amino acid 20 to amino acid 140 of the amino acid sequence selected from the group consisting of SEQ ID Nos: 28 and 30;
(9) the antibody or the binding fragment thereof according to any one of (6) to (8), comprising a light chain amino acid sequence comprising amino acid 21 to amino acid 234 of the amino acid sequence selected from the group consisting of SEQ ID Nos: 32, 34, 36, 38, and 40, and a heavy chain amino acid sequence comprising amino acid 20 to amino acid 470 of the amino acid sequence selected from the group consisting of SEQ ID Nos: 28 and 30;
(10) the antibody or the binding fragment thereof according to any one of (6) to (9), being selected from the group consisting of [i] to [x] below:
[i] an antibody or a binding fragment thereof comprising a heavy chain having an amino acid sequence consisting of amino acid positions 20 to 470 of SEQ ID No: 30 (FIG. 45) and a light chain having an amino acid sequence consisting of amino acid positions 21 to 234 of SEQ ID No: 34 (FIG. 49);
[ii] an antibody or a binding fragment thereof comprising a heavy chain having an amino acid sequence consisting of amino acid positions 20 to 470 of SEQ ID No: 28 (FIG. 43) and a light chain having an amino acid sequence consisting of amino acid positions 21 to 234 of SEQ ID No: 32 (FIG. 47);

[iii] an antibody or a binding fragment thereof comprising a heavy chain having an amino acid sequence consisting of amino acid positions 20 to 470 of SEQ ID No: 30 (FIG. 45) and a light chain having an amino acid sequence consisting of amino acid positions 21 to 234 of SEQ ID No: 36 (FIG. 51);

[iv] an antibody or a binding fragment thereof comprising a heavy chain having an amino acid sequence consisting of amino acid positions 20 to 470 of SEQ ID No: 28 (FIG. 43) and a light chain having an amino acid sequence consisting of amino acid positions 21 to 234 of SEQ ID No: 34 (FIG. 49);

[v] an antibody or a binding fragment thereof comprising a heavy chain having an amino acid sequence consisting of amino acid positions 20 to 470 of SEQ ID No: 28 (FIG. 43) and a light chain having an amino acid sequence consisting of amino acid positions 21 to 234 of SEQ ID No: 36 (FIG. 51);

[vi] an antibody or a binding fragment thereof comprising a heavy chain having an amino acid sequence consisting of amino acid positions 20 to 470 of SEQ ID No: 28 (FIG. 43) and a light chain having an amino acid sequence consisting of amino acid positions 21 to 234 of SEQ ID No: 38 (FIG. 53);

[vii] an antibody or a binding fragment thereof comprising a heavy chain having an amino acid sequence consisting of amino acid positions 20 to 470 of SEQ ID No: 28 (FIG. 43) and a light chain having an amino acid sequence consisting of amino acid positions 21 to 234 of SEQ ID No: 40 (FIG. 55);

[viii] an antibody or a binding fragment thereof comprising a heavy chain having an amino acid sequence consisting of amino acid positions 20 to 470 of SEQ ID No: 30 (FIG. 45) and a light chain having an amino acid sequence consisting of amino acid positions 21 to 234 of SEQ ID No: 32 (FIG. 47);

[ix] an antibody or a binding fragment thereof comprising a heavy chain having an amino acid sequence consisting of amino acid positions 20 to 470 of SEQ ID No: 30 (FIG. 45) and a light chain having an amino acid sequence consisting of amino acid positions 21 to 234 of SEQ ID No: 38 (FIG. 53); and

[x] an antibody or a binding fragment thereof comprising a heavy chain having an amino acid sequence consisting of amino acid positions 20 to 470 of SEQ ID No: 30 (FIG. 45) and a light chain having an amino acid sequence consisting of amino acid positions 21 to 234 of SEQ ID No: 40 (FIG. 55);

(11) the antibody or the binding fragment thereof according to (1), comprising a light chain variable region and a heavy chain variable region comprising amino acid sequences having 95% or higher identity respectively to the amino acid sequences of the light chain variable region and the heavy chain variable region of the antibody or the binding fragment thereof according to (10);

(12) the antibody or the binding fragment thereof according to (1), comprising a light chain variable region amino acid sequence encoded by a nucleotide sequence of a second nucleic acid molecule that hybridizes under stringent conditions to a first nucleic acid molecule having a nucleotide sequence encoding the amino acid sequence of the light chain variable region of the antibody or the binding fragment thereof according to (10) or a nucleotide sequence complementary thereto, and a heavy chain variable region amino acid sequence encoded by a nucleotide sequence of a fourth nucleic acid molecule that hybridizes under stringent conditions to a third nucleic acid molecule having a nucleotide sequence encoding the amino acid sequence of the heavy chain variable region of the antibody or the binding fragment thereof according to (10) or a nucleotide sequence complementary thereto;

(13) the antibody or the binding fragment thereof according to (1), having the property described in (i) or (ii) below:

(i) binding to a site on domain 3 of human LAG-3 recognized by the antibody or the binding fragment thereof according to (10); or (ii) competing with the antibody or the binding fragment thereof according to (10) for binding to domain 3 of human LAG-3;

(14) the antibody or the binding fragment thereof according to any one of (1) to (13), being in low fucose form;

(15) a molecule comprising the antibody or the binding fragment thereof according to any one of (1) to (14);

(16) a nucleic acid molecule comprising a nucleotide sequence encoding the amino acid sequence of the antibody or the binding fragment thereof according to any one of (1) to (14);

(17) a vector comprising the nucleic acid molecule according to (16),

(18) a cell comprising the nucleic acid molecule according to (16), or the vector according to (17);

(19) a cell that produces the antibody or the binding fragment thereof according to any one of (1) to (14);

(20) a method for producing the antibody or the binding fragment thereof according to any one of (1) to (14), comprising the step of culturing the cell according to (18) or (19);

(21) an antibody or a binding fragment thereof prepared by the method according to (20);

(22) a composition comprising the antibody or the binding fragment thereof according to any one of (1) to (14) and (21), or the molecule according to (15);

(23) a pharmaceutical composition comprising the antibody or the binding fragment thereof according to any one of (1) to (14) and (21), or the molecule according to (15);

(24) the pharmaceutical composition according to (23), for treatment or prevention of autoimmune diseases;

(25) the pharmaceutical composition according to (24), wherein the autoimmune disease is one or two or more selected from the group consisting of autoimmune diseases of connective tissue and musculoskeletal system, autoimmune diseases of the blood system, autoimmune diseases of the digestive system, autoimmune diseases of the nervous system, autoimmune diseases of the visual system, autoimmune diseases of the vascular system, autoimmune diseases of the epidermal system, autoimmune diseases of the respiratory system, autoimmune diseases of the endocrine system, autoimmune hepatitis, and nephritis due to an immune disorder;

(26) the pharmaceutical composition according to (25), wherein the autoimmune disease of the connective tissue and musculoskeletal system is one or two or more selected from the group consisting of rheumatoid arthritis, ankylosing spondylitis, systemic lupus erythematosus, scleroderma, polymyositis, dermatomyositis, inclusion body myositis, and idiopathic inflammatory myopathies such as immune-mediated necrotizing myopathy; the autoimmune disease of the blood system is one or two or more selected from the group consisting of aplastic anemia and idiopathic thrombocytopenic purpura; the autoimmune disease of the digestive system is one or two or more selected from the group consisting of Crohn's disease and ulcerative colitis; the autoimmune disease of the nervous system is one or two or more selected from the group consisting of multiple sclerosis and myasthenia gravis; the autoimmune disease of the visual system is one or two or more selected from the group consisting of uveitis, keratitis, and Sjogren's syndrome; the autoimmune disease of the vascular system is one or two or more selected from the group consisting of Behcet's disease and Wegener's granulomatosis; the autoimmune disease of the epidermal system is one or two or more selected from the group consisting of psoriasis, pemphigus, Stevens-Johnson syndrome, and vitiligo; the autoimmune disease of the respiratory system is one or two or more selected from the group consisting of chronic obstructive pulmonary disease and interstitial pneumonia; and the autoimmune disease of the endocrine system is one or two or more selected from the group consisting of type 1 diabetes, autoimmune thyroiditis, Graves' disease, and Hashimoto's thyroiditis;

(27) the pharmaceutical composition according to (23), for treatment or prevention of rejection of transplants;

(28) the pharmaceutical composition according to (27), wherein the rejection of transplants is rejection and host-versus-graft reaction in transplantation of an organ selected from the group consisting of the heart, the kidney, the liver, the bone marrow, and the skin or tissues thereof, and/or graft-versus-host disease caused by transplantation of hematopoietic cells selected from the group consisting of: transplantation of bone marrow; transplantation of peripheral blood; and transplantation of umbilical cord blood;

(29) the pharmaceutical composition according to any one of (24) to (28), combined with one or two or more selected from the group consisting of antifolates, calcineurin inhibitors, corticosteroids, antithymocyte globulins, nucleic acid antimetabolites, nucleic acid synthesis inhibitors, biologics targeting cell surface antigens, biologics targeting cytokines or cytokine receptors, intravenous immunoglobulin, and plasma exchange;

(30) the pharmaceutical composition according to (23), for treatment or prevention of allergic diseases, malignant tumors, and/or chronic infections; and the like.

Advantageous Effects of Invention

The antibody, the binding fragment thereof, the molecule comprising them, the pharmaceutical composition comprising them, etc., which are provided by the present invention have features such as allowing human LAG-3 to bind to human major histocompatibility complex class II molecules and allowing human LAG-3 to exert human T cell suppression function even in the presence thereof, while having ADCC activity, LAG-3 positive cell number-reducing activity, experimental autoimmune encephalomyelitis inhibitory activity, human activated T cell binding activity, etc., and thus can be used for treatment and/or prevention of diseases associated with LAG-3 positive cells such as autoimmune diseases, preferably wherein the antibody is in low fucose form.

BRIEF DESCRIPTION OF DRAWINGS

FIG. 5A is a diagram showing the results of testing the human LAG-3 binding epitope of rat anti-LAG-3 antibodies (rLA204, rLA212 and rLA225) by flow cytometry. The vertical axis represents the mean fluorescence intensity measured by flow cytometry. The binding of anti-FLAG antibody, used as a positive control, is also shown. Each antibody was evaluated at 10 µg/mL.

FIG. 5B is a diagram showing the results of testing the human LAG-3 binding epitope of human chimeric anti-LAG-3 antibody IMP731, which is a conventional antibody in the Citation List, by flow cytometry. The vertical axis represents the mean fluorescence intensity measured by flow cytometry. The antiserum obtained from the rat immunized in Example 1)-1 was used at 500-fold dilution as antiserum. Each of the other antibodies was evaluated at 10 µg/mL. 6D7 is the rat anti-LAG-3 antibody that was developed in Example 2)-6 and recognizes domain 1 of LAG-3.

FIG. 7 is a table showing the binding ability of humanized anti-LAG-3 antibodies as dissociation constants.

FIG. 16 is a nucleotide sequence encoding the amino acid sequence of the heavy chain variable region of rLA204 antibody (SEQ ID No: 1).

FIG. 17 is the amino acid sequence of the heavy chain variable region of rLA204 antibody (SEQ ID No: 2).

FIG. 18 is a nucleotide sequence encoding the amino acid sequence of the light chain variable region of rLA204 antibody (SEQ ID No: 3).

FIG. 19 is the amino acid sequence of the light chain variable region of rLA204 antibody (SEQ ID No: 4).

FIG. 20 is a nucleotide sequence encoding the amino acid sequence of the heavy chain variable region of rLA212 antibody (SEQ ID No: 5).

FIG. 21 is the amino acid sequence of the heavy chain variable region of rLA212 antibody (SEQ ID No: 6).

FIG. 22 is a nucleotide sequence encoding the amino acid sequence of the light chain variable region of rLA212 antibody (SEQ ID No: 7).

FIG. 23 is the amino acid sequence of the light chain variable region of rLA212 antibody (SEQ ID No: 8).

FIG. 24 is a nucleotide sequence encoding the amino acid sequence of the heavy chain variable region of rLA225 antibody (SEQ ID No: 9).

FIG. 25 is the amino acid sequence of the heavy chain variable region of rLA225 antibody (SEQ ID No: 10).

FIG. 26 is a nucleotide sequence encoding the amino acid sequence of the light chain variable region of rLA225 antibody (SEQ ID No: 11).

FIG. 27 is the amino acid sequence of the light chain variable region of rLA225 antibody (SEQ ID No: 12).

FIG. 28 is a nucleotide sequence encoding the amino acid sequence of the heavy chain variable region of rLA869 antibody (SEQ ID No: 13).

FIG. 29 is the amino acid sequence of the heavy chain variable region of rLA869 antibody (SEQ ID No: 14).

FIG. 30 is a nucleotide sequence encoding the amino acid sequence of the light chain variable region of rLA869 antibody (SEQ ID No: 15).

FIG. 31 is the amino acid sequence of the light chain variable region of rLA869 antibody (SEQ ID No: 16).

FIG. 32 is a nucleotide sequence encoding the amino acid sequence of the heavy chain variable region of rLA1264 antibody (SEQ ID No: 17).

FIG. 33 is the amino acid sequence of the heavy chain variable region of rLA1264 antibody (SEQ ID No: 18).

FIG. 34 is a nucleotide sequence encoding the amino acid sequence of the light chain variable region of rLA1264 antibody (SEQ ID No: 19).

FIG. 35 is the amino acid sequence of the light chain variable region of rLA1264 antibody (SEQ ID No: 20).

FIG. 36 is a nucleotide sequence encoding the amino acid sequences of the human light chain secretion signal and the human κ chain constant region (SEQ ID No: 21).

FIG. 37 is a nucleotide sequence encoding the amino acid sequences of the human heavy chain secretion signal and the human IgG1 constant region (SEQ ID No: 22).

FIG. 38 is a nucleotide sequence encoding the amino acid sequence of the heavy chain of cLA212 antibody (SEQ ID No: 23).

FIG. 39 is the amino acid sequence of the heavy chain of cLA212 antibody (SEQ ID No: 24).

FIG. 40 is a nucleotide sequence encoding the amino acid sequence of the light chain of cLA212 antibody (SEQ ID No: 25).

FIG. 41 is the amino acid sequence of the light chain of cLA212 antibody (SEQ ID No: 26).

FIG. 42 is a nucleotide sequence encoding the amino acid sequence of the heavy chain H2 of hLA212 antibody (SEQ ID No: 27).

FIG. 43 is the amino acid sequence of the heavy chain H2 of hLA212 antibody (SEQ ID No: 28).

FIG. 44 is a nucleotide sequence encoding the amino acid sequence of the heavy chain H3 of hLA212 antibody (SEQ ID No: 29).

FIG. 45 is the amino acid sequence of the heavy chain H3 of hLA212 antibody (SEQ ID No: 30).

FIG. 46 is a nucleotide sequence encoding the amino acid sequence of the light chain L1 of hLA212 antibody (SEQ ID No: 31).

FIG. 47 is the amino acid sequence of the light chain L1 of hLA212 antibody (SEQ ID No: 32).

FIG. 48 is a nucleotide sequence encoding the amino acid sequence of the light chain L2 of hLA212 antibody (SEQ ID No: 33).

FIG. 49 is the amino acid sequence of the light chain L2 of hLA212 antibody (SEQ ID No: 34).

FIG. 50 is a nucleotide sequence encoding the amino acid sequence of the light chain L3 of hLA212 antibody (SEQ ID No: 35).

FIG. 51 is the amino acid sequence of the light chain L3 of hLA212 antibody (SEQ ID No: 36).

FIG. 52 is a nucleotide sequence encoding the amino acid sequence of the light chain L4 of hLA212 antibody (SEQ ID No: 37).

FIG. 53 is the amino acid sequence of the light chain L4 of hLA212 antibody (SEQ ID No: 38).

FIG. 54 is a nucleotide sequence encoding the amino acid sequence of the light chain L5 of hLA212 antibody (SEQ ID No: 39).

FIG. 55 is the amino acid sequence of the light chain L5 of hLA212 antibody (SEQ ID No: 40).

FIG. 56 is the amino acid sequence of the heavy chain CDRH1 of rLA204 antibody (SEQ ID No: 41).

FIG. 57 is the amino acid sequence of the heavy chain CDRH2 of rLA204 antibody (SEQ ID No: 42).

FIG. 58 is the amino acid sequence of the heavy chain CDRH3 of rLA204 antibody (SEQ ID No: 43).

FIG. 59 is the amino acid sequence of the light chain CDRL1 of rLA204 antibody (SEQ ID No: 44).

FIG. 60 is the amino acid sequence of the light chain CDRL2 of rLA204 antibody (SEQ ID No: 45).

FIG. 61 is the amino acid sequence of the light chain CDRL3 of rLA204 antibody (SEQ ID No: 46).

FIG. 62 is the amino acid sequence of the heavy chain CDRH1 of rLA212 antibody (SEQ ID No: 47).

FIG. 63 is the amino acid sequence of the heavy chain CDRH2 of rLA212 antibody (SEQ ID No: 48).

FIG. 64 is the amino acid sequence of the heavy chain CDRH3 of rLA212 antibody (SEQ ID No: 49).

FIG. 65 is the amino acid sequence of the light chain CDRL1 of rLA212 antibody (SEQ ID No: 50).

FIG. 66 is the amino acid sequence of the light chain CDRL2 of rLA212 antibody (SEQ ID No: 51).

FIG. 67 is the amino acid sequence of the light chain CDRL3 of rLA212 antibody (SEQ ID No: 52).

FIG. 68 is the amino acid sequence of the heavy chain CDRH1 of rLA225 antibody (SEQ ID No: 53).

FIG. 69 is the amino acid sequence of the heavy chain CDRH2 of rLA225 antibody (SEQ ID No: 54).

FIG. 70 is the amino acid sequence of the heavy chain CDRH3 of rLA225 antibody (SEQ ID No: 55).

FIG. 71 is the amino acid sequence of the light chain CDRL1 of rLA225 antibody (SEQ ID No: 56).

FIG. 72 is the amino acid sequence of the light chain CDRL2 of rLA225 antibody (SEQ ID No: 57).

FIG. 73 is the amino acid sequence of the light chain CDRL3 of rLA225 antibody (SEQ ID No: 58).

FIG. 74 is the amino acid sequence of the heavy chain CDRH1 of rLA869 antibody (SEQ ID No: 59).

FIG. 75 is the amino acid sequence of the heavy chain CDRH2 of rLA869 antibody (SEQ ID No: 60).

FIG. 76 is the amino acid sequence of the heavy chain CDRH3 of rLA869 antibody (SEQ ID No: 61).

FIG. 77 is the amino acid sequence of the light chain CDRL1 of rLA869 antibody (SEQ ID No: 62).

FIG. 78 is the amino acid sequence of the light chain CDRL2 of rLA869 antibody (SEQ ID No: 63).

FIG. 79 is the amino acid sequence of the light chain CDRL3 of rLA869 antibody (SEQ ID No: 64).

FIG. 80 is the amino acid sequence of the heavy chain CDRH1 of rLA1264 antibody (SEQ ID No: 65).

FIG. 81 is the amino acid sequence of the heavy chain CDRH2 of rLA1264 antibody (SEQ ID No: 66).

FIG. 82 is the amino acid sequence of the heavy chain CDRH3 of rLA1264 antibody (SEQ ID No: 67).

FIG. 83 is the amino acid sequence of the light chain CDRL1 of rLA1264 antibody (SEQ ID No: 68).

FIG. 84 is the amino acid sequence of the light chain CDRL2 of rLA1264 antibody (SEQ ID No: 69).

FIG. 85 is the amino acid sequence of the light chain CDRL3 of rLA1264 antibody (SEQ ID No: 70).

FIG. 86 is primer RG2AR3 (SEQ ID No: 71).
FIG. 87 is primer RKR5 (SEQ ID No: 72).
FIG. 88 is primer 3.3-F1 (SEQ ID No: 73).
FIG. 89 is primer 3.3-R1 (SEQ ID No: 74).
FIG. 90 is primer 212H-F (SEQ ID No: 75).
FIG. 91 is primer 212H-R (SEQ ID No: 76).
FIG. 92 is primer 212L-F (SEQ ID No: 77).
FIG. 93 is primer 212L-R (SEQ ID No: 78).
FIG. 94 is oligonucleotide LAG-3-H1 (SEQ ID No: 79).
FIG. 95 is oligonucleotide LAG-3-H2 (SEQ ID No: 80).
FIG. 96 is oligonucleotide LAG-3-H3 (SEQ ID No: 81).
FIG. 97 is oligonucleotide LAG-3-H4 (SEQ ID No: 82).
FIG. 98 is oligonucleotide LAG-3-H5 (SEQ ID No: 83).
FIG. 99 is oligonucleotide LAG-3-H6 (SEQ ID No: 84).

FIG. 100 is a nucleotide sequence encoding the amino acid sequence of human LAG-3 (SEQ ID No: 85).

FIG. 101 is the amino acid sequence of human LAG-3 (SEQ ID No: 86).

DESCRIPTION OF EMBODIMENTS

1. Definition

Figure 1:
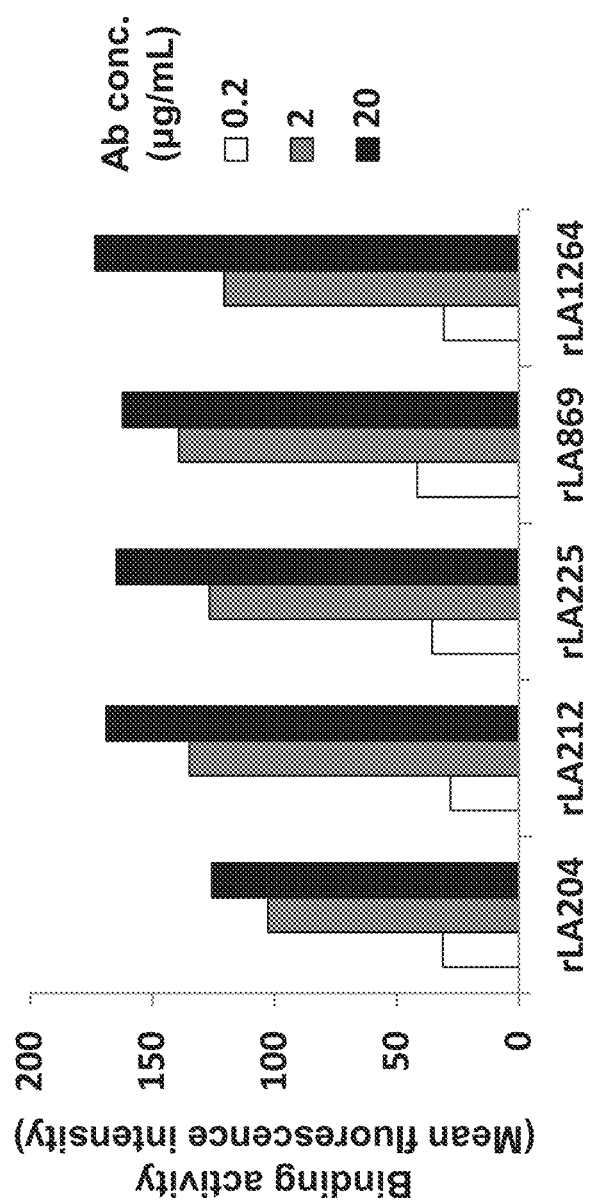
FIG. 1 is a diagram showing the results of testing, by flow cytometry, the binding activity of rat anti-LAG-3 antibodies (rLA204, rLA212, rLA225, rLA869, and rLA1264) to human PHA blasts expressing LAG-3. The vertical axis represents the mean fluorescence intensity measured by flow cytometry.

In the present invention, the term "gene" means a nucleic acid molecule comprising a nucleotide sequence encoding the amino acids of a protein, or its complementary strand. The "gene" is meant to include, for example, a polynucleotide, an oligonucleotide, DNA, mRNA, cDNA, and cRNA comprising a nucleotide sequence encoding the amino acids of a protein or a nucleotide sequence complementary thereto. Such a gene is a single-stranded, double-stranded, or triple or more stranded nucleotide. The "gene" is also meant to include an association of DNA and RNA strands, a mixture of ribonucleotides (RNAs) and deoxyribonucleotides (DNAs) on one nucleotide strand, and a double-stranded or triple or more stranded nucleotide comprising such a nucleotide strand. Examples of the "LAG-3 gene" of the present invention can include DNA, mRNA, cDNA, and cRNA comprising a nucleotide sequence encoding the amino acid sequence of the LAG-3 protein.

In the present invention, the term "nucleotide" has the same meaning as "nucleic acid" and "nucleic acid molecule", and is also meant to include, for example, DNA, RNA, probe, oligonucleotide, polynucleotide, and primer. Such a nucleotide is a single-stranded, double-stranded, or triple or more stranded nucleotide. The "nucleotide" is also meant to include an association of DNA and RNA strands, a mixture of ribonucleotides (RNAs) and deoxyribonucleotides (DNAs) on one nucleotide strand, and an association of two strands or three or more strands comprising such a nucleotide strand.

In the present invention, the terms "polypeptide", "peptide", and "protein" have the same meaning.

In the present invention, the term "antigen" has the same meaning as "immunogen".

In the present invention, the term "cell" also includes, for example, various cells derived from individual animals, subcultured cells, primary cultured cells, cell lines, recombinant cells, and microbial cells.

In the present invention, each of an antibody that binds to LAG-3 and an antibody that recognizes LAG-3 may be referred to as an "anti-LAG-3 antibody" or abbreviated as an "LAG-3 antibody". The anti-LAG-3 antibody includes monoclonal antibodies, chimerized antibodies, humanized antibodies, human antibodies, chimeric antibodies, and the like.

The term "binding fragment of an antibody" in the present invention means an antibody fragment that exerts at least a part of the functions exerted by the original antibody. Examples of the "binding fragment of the antibody" can include, but are not limited to, Fab, F(ab')2, scFv, Fab', and single chain immunoglobulin. Such a binding fragment of the antibody may be obtained by treating a full-length molecule of the antibody protein with an enzyme such as papain or pepsin or may be a recombinant protein produced in an appropriate host cell using a recombinant gene.

In the present invention, the "site" to which an antibody binds, i.e., the "site" recognized by an antibody, means a partial peptide or partial conformation on an antigen bound or recognized by the antibody. In the present invention, such a site is also referred to as an epitope or an antibody binding site. Examples of the site on the LAG-3 protein bound or recognized by the anti-LAG-3 antibody of the present invention can include a partial peptide or partial conformation on the LAG-3 protein.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are usually separated at three positions on the respective primary structures of heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the three-dimensional structure and determine specificity for the antigen to be bound. The portions other than CDRH1 to CDRH3 in the heavy chain variable region amino acid sequence are called frameworks (Framework Regions: Hereinafter, FR), and the portions from the amino terminus up to but not including CDRH1, from just after CDRH1 up to but not including CDRH2, from just after CDRH2 up to but not including CDRH3, and from just after CDRH3 to the carboxyl terminus are respectively called FRH1 to FRH4. Likewise, the portions other than CDRL1 to CDRL3 in the light chain variable region amino acid sequence are also FRs, and the portions from the amino terminus up to but not including CDRL1, from just after CDRL1 up to but not including CDRL2, from just after CDRL2 up to but not including CDRL3, and from just after CDRL3 to the carboxyl terminus are respectively called FRL1 to FRL4. That is, in (the amino acid sequence(s) of) the heavy chain and light chain variable regions, FRH1-CDRH1-FRH2-CDRH2-FRH3-CDRH3-FRH4 and FRL1-CDRL1-FRL2-CDRL2-FRL3-CDRL3-FRL4 are continuously aligned from the amino terminus side toward the carboxyl terminus in this order.

In the present invention, the term "antibody mutant" means a polypeptide that has an amino acid sequence derived from the amino acid sequence of the original antibody by the substitution, deletion, addition, and/or insertion (hereinafter, collectively referred to as a "mutation") of amino acid(s) and binds to the LAG-3 protein of the present invention. The number of mutated amino acids in the antibody mutant is 1, 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50. The antibody mutant is also encompassed by the "antibody" of the present invention.

In the present invention, the term "several" in "1 to several" refers to 3 to 10.

Examples of activities or properties exerted by the antibody of the present invention can include biological activities or physicochemical properties and can specifically include various biological activities, binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under conditions equivalent thereto. SSC means an aqueous solution of 150 mM NaCl-15 mM sodium citrate, and n×SSC means SSC with an n-fold concentration.

In the present invention, the term "cytotoxicity" refers to some pathological change brought about to cells and means not only direct trauma but every type of structural or functional damage to cells, including DNA cleavage, formation of base dimers, chromosomal break, damage on mitotic apparatus, and reduction in the activities of various enzymes.

In the present invention, the term "cytotoxic activity" means activity that causes the cytotoxicity mentioned above.

In the present invention, the term "antibody dependent cell-mediated cytotoxic activity", also called "antibody dependent cellular cytotoxic activity" or "ADCC activity", means the effect or activity of damaging target cells by NK cells or the like via antibodies.

In the present invention, the term "host-versus-graft reaction" means the hyperimmune state of a recipient observed after organ transplantation, and the damage to the transplanted organ by such a state.

In the present invention, the term "graft-versus-host disease" means symptoms, caused by immunological attack by the transplanted cells to a recipient after transplantation of hematopoietic cells.

2. Antigen Protein (2-1) Properties

LAG-3 protein (which may be hereinafter referred to simply as "LAG-3") is a transmembrane receptor protein and is composed of an extracellular region composed of immunoglobulin-like domains (IgD1 to 4), which contains a ligand binding site, a type-I single-pass transmembrane region, and an intracellular region. LAG-3 has the same meaning as CD223.

In the present invention, LAG-3 is derived from vertebrates, preferably derived from mammals, more preferably derived from humans.

The LAG-3 protein has the following properties:
(i) binding to major histocompatibility complex (MHC) class II molecules on antigen presenting cells;
(ii) binding to MHC class II molecules and transmitting inhibitory signals to T cells expressing such molecules, to regulate T cell function negatively;
(iii) the LAG-3 protein in the present invention comprising an amino acid sequence (which will be hereinafter referred to as "LAG-3 amino acid sequence") according to any one of (a) to (d) below, consisting of an amino acid sequence comprising the LAG-3 amino acid sequence, or consisting of the LAG-3 amino acid sequence:
(a) the amino acid sequence represented by SEQ ID No: 86 (FIG. 101);
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher sequence identity to the amino acid sequence represented by SEQ ID No: 86 (FIG. 101) and is comprised in a polypeptide having MHC class II molecule binding activity;
(c) an amino acid sequence that is derived from the amino acid sequence represented by SEQ ID No: 86 (FIG. 101) by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid and is comprised in a polypeptide having MHC class II molecule binding activity; and
(d) an amino acid sequence that is encoded by the nucleotide sequence of a polynucleotide (nucleic acid molecule) hybridizing under stringent conditions to a polynucleotide (nucleic acid molecule) having a nucleotide sequence complementary to a nucleotide sequence encoding the amino acid sequence represented by SEQ ID No: 86 (FIG. 101) and is comprised in a polypeptide having MHC class II molecule binding activity.

The polypeptide according to any one of (b) to (d) may have other activities of LAG-3 in addition to the MHC class II molecule binding activity.
(iv) The LAG-3 protein of the present invention can be obtained from LAG-3-expressing cells, tissues, or cancer tissues, cells derived from the tissues, cultures of the cells, and the like, of a vertebrate, preferably of a mammal, more preferably of a rodent such as a mouse or a rat and a human, even more preferably of a human, a rat, or a mouse.

The expression of LAG-3 is observed in activated T cells, inflammation sites and the like in vivo, and almost no expression or a very low level of expression is seen in cells of normal tissues.

The LAG-3 protein of the present invention may be a native (non-recombinant) or recombinant protein. The LAG-3 protein is also intended to include fusion products with another peptide or protein such as a carrier or a tag. The LAG-3 protein is further intended to include forms provided with chemical modification including the addition of a polymer such as PEG and/or with biological modification including sugar chain modification. Moreover, the LAG-3 protein of the present invention is intended to include an LAG-3 protein fragment. Of the LAG-3 protein fragments, those having the properties described in (i) and/or (ii) above are called LAG-3 protein binding fragments.

(2-2) Antigen Gene

The LAG-3 gene in the present invention comprises a nucleotide sequence (which will be hereinafter referred to as the "LAG-3 gene sequence") according to any one of (a) to (c) below, consists of a nucleotide sequence comprising the LAG-3 gene sequence, or consists of the LAG-3 gene sequence:
(a) a nucleotide sequence encoding the amino acid sequence represented by SEQ ID No: 86 (FIG. 101);
(b) the nucleotide sequence of a polynucleotide (nucleic acid molecule) that hybridizes under stringent conditions to a polynucleotide (nucleic acid molecule) consisting of a nucleotide sequence complementary to the nucleotide sequence encoding the amino acid sequence represented by SEQ ID No: 86 (FIG. 101) and encodes an amino acid sequence of a polypeptide having MHC class II molecule binding activity; and
(c) a nucleotide sequence that encodes an amino acid sequence derived from the amino acid sequence represented by SEQ ID No: 86 (FIG. 101) by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 base and encodes an amino acid sequence of a polypeptide having MHC class II molecule binding activity.

The polypeptide having the amino acid sequence encoded by the nucleotide sequence according to (b) or (c) may have other activities of LAG-3 in addition to the MHC class II molecule binding activity.

The expression and the expression level of the LAG-3 gene may be assayed with either a LAG-3 gene transcript or the LAG-3 protein as an index. The former index can be determined by RT-PCR, Northern blot hybridization, or the like, while the latter index can be determined by immunoassay such as flow cytometry, Western blotting, immunohistochemical staining, or the like, respectively.

(2-3) Preparation of Antigenic Protein

The LAG-3 protein of the present invention can be prepared by purification or isolation from animal tissues (including body fluids), cells derived from the tissues, or cultures of the cells, gene recombination, in vitro translation, chemical synthesis, etc.

(2-3-1) Purification or Isolation of Non-Recombinant LAG-3

The non-recombinant LAG-3 protein can be purified or isolated from LAG-3-expressing cells. Examples of the LAG-3-expressing cells can include those described in (iv) of (2-1), but the origin of the non-recombinant LAG-3 protein is not limited thereto.

The purification or isolation from such tissues, cells, cell cultures, or the like, can be performed by the combination of approaches well known by those skilled in the art, such as fractionation and chromatography.

(2-3-2) Preparation of Recombinant LAG-3 Protein

The LAG-3 protein of the present invention can also be prepared in a recombinant form. Specifically, host cells are transfected with a gene encoding the amino acid sequence of the LAG-3 protein or an LAG-3 protein fragment, and the LAG-3 protein can be recovered from cultures of the cells. Also, the LAG-3 protein can be expressed not only as a molecule having the same amino terminus (N terminus) and/or carboxy terminus (C terminus) as native ones, but also as a fusion protein with a secretory signal, an intracellular localization signal, a tag for affinity purification, or a partner peptide. The LAG-3 protein can be purified or isolated from such recombinant cell cultures by an appropriate combination of methods such as fractionation and chromatography described in (2-3-1) Purification or isolation of non-recombinant LAG-3 protein. Further, the LAG-3 protein-containing solution can be subjected to buffer exchange and/or concentration using gel filtration or a concentrator such as Centriprep.

(2-3-3) In Vitro Translation

The LAG-3 protein of the present invention can also be prepared by in vitro translation. Such a translation method is not particularly limited as long as the method employs a cell-free translation system involving enzymes necessary for transcription and translation, substrates, and energy substances. Examples thereof can include a method using the Rapid Translation System (RTS) manufactured by Roche Diagnostics K.K.

(2-3-4) Chemical Synthesis

The LAG-3 protein of the present invention can also be prepared by chemical synthesis. Examples of the chemical synthesis method can include solid-phase peptide synthesis methods such as Fmoc and Boc synthesis methods.

3. Antibody (3-1) Classification of Antibody

The antibodies of the present invention may be either monoclonal or polyclonal antibodies. Examples of the monoclonal antibody of the present invention can include non-human animal-derived antibodies (non-human animal antibodies), human-derived antibodies (human antibodies), chimerized antibodies (chimeric antibodies), and humanized antibodies.

Examples of the non-human animal antibody can include antibodies derived from vertebrates such as mammals and birds. Examples of the mammal-derived antibody can include rodent-derived antibodies such as mouse antibodies and rat antibodies. Examples of the bird-derived antibody can include chicken antibodies. Examples of the anti-human LAG-3 rat monoclonal antibody can include rLA204, rLA212, rLA225, rLA869, and rLA1264.

Examples of the chimerized antibody can include, but are not limited to, an antibody comprising non-human animal antibody-derived variable regions bound to human antibody (human immunoglobulin) constant regions. Examples of the chimerized antibody comprising non-human animal antibody-derived variable regions bound to human antibody constant regions can include those having heavy and light chain variable regions derived from the rat monoclonal antibody rLA204, rLA212, rLA225, rLA869, or rLA1264, and having human heavy and light chain constant regions (which are referred to as "cLA204", "cLA212", "cLA225", "cLA869", or "cLA1264", respectively).

Examples of the humanized antibody can include, but are not limited to, a human antibody (human immunoglobulin variable regions) grafted with CDRs in the variable regions of a non-human animal antibody, a human antibody grafted with the CDRs as well as with partial sequences of FRs of a non-human animal antibody, and an antibody having human antibody amino acids or other amino acids substituted for one or two or more non-human animal antibody-derived amino acids in any of these human (humanized) antibodies. Examples of the CDRs in the variable regions of a non-human animal antibody can include CDRH1 to CDRH3 in the heavy chain variable region and CDRL1 to CDRL3 in the light chain variable region derived from rLA204, rLA212, rLA225, rLA869, or rLA1264 mentioned above. Examples of the humanized antibody comprising CDRH1 to CDRH3 in the heavy chain variable region and CDRL1 to CDRL3 in the light chain variable region derived from rLA212 can include hLA212_H2/L1 to H2/L5, hLA212_H3/L1 to H3/L5, and hLA212_H4/L2.

The human antibody is not specifically limited, as long as the antibody recognizes the antigen of the present invention, but examples thereof can include a human antibody binding to the same site as an antibody having the CDRs of the antibody of the present invention, and a human antibody binding to the same site on LAG-3 as any one of the non-human animal antibodies, the chimeric antibodies, the humanized antibodies, and the like, and an antibody competing with any one of such antibodies for binding to LAG-3.

The antibody according to the present invention may be comprised of portions derived from a plurality of different antibodies as long as the antibody has LAG-3 binding activity. Examples of such an antibody can include an antibody comprising heavy and/or light chains exchanged among a plurality of different antibodies, an antibody comprising full-length heavy and/or light chains exchanged thereamong, an antibody comprising variable or constant regions exchanged thereamong, and an antibody comprising all or some CDRs exchanged thereamong. The heavy and light chain variable regions of the chimeric antibody may be derived from different antibodies of the present invention. CDRH1 to CDRH3 and CDRL1 to CDRL3 in the heavy and light chain variable regions of the humanized antibody may be derived from two or more different antibodies of the present invention. CDRH1 to CDRH3 and CDRL1 to CDRL3 in the heavy and light chain variable regions of the human antibody may be a combination of CDRs carried by two or more different antibodies of the present invention. The antibody or the binding fragment thereof composed of such portions derived from a plurality of different antibodies each has the following properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

Examples of the isotype of the monoclonal antibody of the present invention can include, but are not particularly limited to, IgG such as IgG1, IgG2, IgG3, and IgG4, IgM, IgA such as IgA1 and IgA2, IgD, and IgE and can preferably include IgG and IgM. The isotype and subclass of the monoclonal antibody can be determined by, for example, an Ouchterlony test, Enzyme-linked immuno-sorbent assay (hereinafter, referred to as "ELISA"), or radio immunoassay (hereinafter, referred to as "RIA"). A commercially available kit for identification (e.g., Mouse Typer Kit; Bio-Rad Laboratories, Inc., and RAT MONOCLONAL ANTIBODY ISO-TYPING TEST KIT: AbD Serotec) also may be used.

(3-2) Binding Specificity of Antibody

The antibody of the present invention recognizes LAG-3 protein. In other words, the antibody of the present invention binds to LAG-3 protein. Such an antibody is also expressed as an "anti-LAG-3 antibody". Preferably, the antibody of the present invention specifically recognizes LAG-3 protein. In other words, the antibody of the present invention preferably specifically binds to LAG-3 protein (the above properties will be collectively referred to as "LAG-3 binding activity" of the antibody). More preferably, the antibody of the present invention specifically binds to the extracellular region(s) of LAG-3 protein, further more preferably, the antibody specifically binds to the immunoglobulin-like domains (which will be hereinafter referred to as "Ig-like domains") of LAG-3 protein, still further more preferably, the antibody specifically binds to Ig-like domain 3.

In the present invention, the "specific recognition", i.e., "specific binding", means binding which is not non-specific adsorption. Examples of criteria for determination of whether binding is specific or not can include a dissociation constant (hereinafter, referred to as "KD"). Preferably, the antibody of the present invention has a KD value of $1\times10^{-5}$ or lower, $5\times10^{-6}$ or lower, $2\times10^{-6}$ or lower, or $1\times10^{-6}$ or lower, more preferably $5\times10^{-7}$ or lower, $2\times10^{-7}$ or lower, or $1\times10^{-7}$ or lower, even more preferably $5\times10^{-8}$ or lower, $2\times10^{-8}$ or lower, or $1\times10^{-8}$ or lower, further more preferably $5\times10^{-9}$ or lower, $2\times10^{-9}$ or lower, or $1\times10^{-9}$ or lower, most preferably $5\times10^{-10}$ or lower, $2\times10^{-10}$ or lower, or $1\times10^{-10}$ or lower for the LAG-3 protein.

In the present invention, the binding of the antibody to the antigen can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Corp.), ProteOn™ (manufactured by Bio-Rad Laboratories, Inc.), SPR-Navi™ (manufactured by BioNavis Oy Ltd.), Spreeta™ (manufactured by Texas Instruments Inc.), SPRi-Plex II™ (manufactured by Horiba, Ltd.), and Autolab SPR™ (manufactured by Metrohm Japan Ltd.). The binding of the antibody to the antigen expressed on cell surface can be assayed by flow cytometry, Cell-ELISA, or the like.

(3-3) Cytotoxic Activity of Antibody

According to an aspect, the anti-LAG-3 antibody of the present invention has antibody dependent cellular cytotoxic (ADCC) activity, preferably has ADCC activity in vitro, more preferably has ADCC activity against LAG-3-expressing T cells. The anti-LAG-3 antibody of the present invention may have complement dependent cytotoxic (CDC) activity and/or antibody dependent cellular phagocytosis (ADCP) activity in addition to the ADCC activity.

The ADCC activity can be assayed by a known method. Cells expressing the antigen of interest (target cells) and effector cells capable of killing the target cells are used in the ADCC activity assay. The effector cells recognize the Fc regions of antibodies binding to the target cells via Fcγ receptors. The effector cells kill the target cells by signals transduced from the Fcγ receptors. In the case of assaying the ADCC activity of an antibody having a human-derived Fc region, human NK cells are used as the effector cells. The human NK cells can be prepared from human peripheral blood mononuclear cells (PBMCs) by a method known in the art. Alternatively, PBMCs may be used directly as the effector cells.

(3-4) In Vivo LAG-3 Positive Cell Number Reducing Activity of Antibody

According to an aspect, the antibody of the present invention reduces the number of LAG-3 positive cells, preferably reduces the number of LAG-3 positive cells in vivo, and more preferably reduces the number of LAG-3 positive cells in vivo in low fucose form.

The LAG-3 positive cells include cells forced to express LAG-3 and cells having LAG-3 expression induced by stimulation, but are not limited thereto, as long as they are cells expressing LAG-3.

The number of LAG-3 positive cells can be counted by a conventional method such as flow cytometry.

In the present invention, the "low fucose form" means the state where (i) the amount of fucose (fucose residue) binding to an antibody or a binding fragment thereof in N-glycoside-linked complex-type sugar chains is smaller than the amount of fucose (fucose residue) binding to the original (parent) antibody or a binding fragment thereof in N-glycoside-linked complex-type sugar chains, (ii) the amount of fucose (fucose residue) binding to an antibody or a binding fragment thereof in N-glycoside-linked complex-type sugar chains is smaller than the amount of fucose (fucose residue) naturally binding to an antibody or a binding fragment thereof in N-glycoside-linked complex-type sugar chains, or (iii) the amount of fucose (fucose residues) or sugar chains comprising fucose (fucose residues) binding to an antibody or a binding fragment thereof in N-glycoside-linked complex-type sugar chains is at or below the detection limit in a physical or chemical analysis (preferably mass spectrometry). In the case where the amount of fucose (fucose residue) binding to a modified antibody or a binding fragment thereof in N-glycoside-linked complex-type sugar chains is smaller than that before the modification, the modified antibody or the binding fragment thereof is understood to be in "low fucose form". The modified form hLA212_H4/L2 described below, which is a humanized antibody of the present invention, is an aspect of the antibody in low fucose form. An antibody or a binding fragment in low fucose form has higher affinity for Fcγ receptors IIIA and stronger ADCC activity than when not in low fucose form.

(3-5) In Vivo Experimental Autoimmune Encephalomyelitis Inhibitory Activity of Antibody According to an aspect, the antibody of the present invention has encephalomyelitis inhibitory activity, preferably has experimental autoimmune encephalomyelitis inhibitory activity in vivo, more preferably has experimental autoimmune encephalomyelitis inhibitory activity in vivo in low fucose form.

In the present invention, experimental autoimmune encephalomyelitis means encephalomyelitis induced by injection of a peptide derived from MOG (Myelin Oligodendrocyte Glycoprotein) which is one of the central nervous myelin component proteins, to mice together with Freund's Adjuvant.

Experimental autoimmune encephalomyelitis inhibitory activity can be assayed by daily observation of clinical scores that reflect the degrees of paralysis. The clinical score can be set, for example, as follows:

Score 0: Asymptomatic;
Score 1: Limp tail;
Score 2: Abnormal gait or loss of righting reflex;
Score 3: Hind leg paralysis;
Score 4: Partial paralysis of forelimbs; and
Score 5: Death or euthanasia.

(3-6) Human Activated T Cell Binding Activity of Antibody

According to an aspect, the antibody of the present invention binds to human activated T cells, preferably binds to LAG-3 positive human activated T cells. The binding of the antibody to the human activated T cells can be assayed or detected, for example, by flow cytometry.

(3-7) Presence of Antibody Allowing Human LAG-3 to Bind to Human MHC Class II Molecules According to an aspect of the present invention, human LAG-3 can bind to human MHC class II molecules in the presence of the antibody, or the antibody of the present invention does not inhibit binding of human LAG-3 to human MHC class II molecules.

The binding of fusion proteins of the extracellular region of LAG-3 molecule and the Fc part of IgG to Raji cells that endogenously highly express MHC class II molecules can be evaluated, for example, by assay or detection by flow cytometry.

(3-8) Presence of Antibody Allowing Human LAG-3 to Exert Human T Cell Suppression Function According to another aspect, human LAG-3 exerts human T cell suppression function in the presence of the antibody of the present invention.

The term "T cell suppression function" in the present invention means to reduce or suppress the amount of cytokine produced upon stimulation of T cells.

The T cell suppression function by human LAG-3 can be assayed, for example, by quantitating cytokines produced when human T cells are stimulated to induce LAG-3 expression.

In the present invention, the stimulation of human T cells is not specifically limited, but examples thereof can include stimulation with specific antigens, anti-CD3 antibodies, combinations of anti-CD3 antibodies and anti-CD28 antibodies, super antigens, cells derived from other donors, preferably stimulation with Staphylococcal Enterotoxin B, cells derived from other donors having different MHC, and the like.

Examples of the cytokines can include cytokines produced from activated T cells, preferably various interleukins and interferons, more preferably interleukin 2 (IL-2) and interferon γ.

(3-9) Monoclonal Antibody

The present invention provides an anti-LAG-3 monoclonal antibody and a binding fragment thereof. The monoclonal antibody includes monoclonal antibodies derived from non-human animals such as rat antibodies, mouse antibodies, rabbit antibodies, chicken antibodies, and fish antibodies, chimeric antibodies, humanized antibodies, human antibodies, binding fragments thereof, and modified forms thereof. Of them, examples of the rat monoclonal antibody can include rLA204, rLA212, rLA225, rLA869, and rLA1264.

rLA204 is an anti-human LAG-3 rat monoclonal antibody obtained by the method described in Example 1. The nucleotide sequence of the heavy chain variable region of rLA204 is described in SEQ ID No: 1 (FIG. 16), and its amino acid sequence is described in SEQ ID No: 2 (FIG. 17). The nucleotide sequence of the light chain variable region of rLA204 is described in SEQ ID No: 3 (FIG. 18), and its amino acid sequence is described in SEQ ID No: 4 (FIG. 19). The amino acid sequence of CDRH1 of rLA204 is described in SEQ ID No: 41 (FIG. 56), the amino acid sequence of CDRH2 thereof is described in SEQ ID No: 42 (FIG. 57), the amino acid sequence of CDRH3 thereof is described in SEQ ID No: 43 (FIG. 58), the amino acid sequence of CDRL1 thereof is described in SEQ ID No: 44 (FIG. 59), the amino acid sequence of CDRL2 thereof is described in SEQ ID No: 45 (FIG. 60), and the amino acid sequence of CDRL3 thereof is described in SEQ ID No: 46 (FIG. 61), respectively.

The rLA212 is an anti-human LAG-3 rat monoclonal antibody obtained according to the method described in Example 1. The nucleotide sequence of the heavy chain variable region of rLA212 is described in SEQ ID No: 5 (FIG. 20), and its amino acid sequence is described in SEQ ID No: 6 (FIG. 21). The nucleotide sequence of the light chain variable region of rLA212 is described in SEQ ID No: 7 (FIG. 22), and its amino acid sequence is described in SEQ ID No: 8 (FIG. 23). The amino acid sequence of CDRH1 of rLA212 is described in SEQ ID No: 47 (FIG. 62), the amino acid sequence of CDRH2 thereof is described in SEQ ID No: 48 (FIG. 63), the amino acid sequence of CDRH3 thereof is described in SEQ ID No: 49 (FIG. 64), the amino acid sequence of CDRL1 thereof is described in SEQ ID No: 50 (FIG. 65), the amino acid sequence of CDRL2 thereof is described in SEQ ID No: 51 (FIG. 66), and the amino acid sequence of CDRL3 thereof is described in SEQ ID No: 52 (FIG. 67), respectively.

The rLA225 is an anti-human LAG-3 rat monoclonal antibody obtained according to the method described in Example 1. The nucleotide sequence of the heavy chain variable region of rLA225 is described in SEQ ID No: 9 (FIG. 24), and its amino acid sequence is described in SEQ ID No: 10 (FIG. 25). The nucleotide sequence of the light chain variable region of rLA225 is described in SEQ ID No: 11 (FIG. 26), and its amino acid sequence is described in SEQ ID No: 12 (FIG. 27). The amino acid sequence of CDRH1 of rLA225 is described in SEQ ID No: 53 (FIG. 68), the amino acid sequence of CDRH2 thereof is described in SEQ ID No: 54 (FIG. 69), the amino acid sequence of CDRH3 thereof is described in SEQ ID No: 55 (FIG. 70), the amino acid sequence of CDRL1 thereof is described in SEQ ID No: 56 (FIG. 71), the amino acid sequence of CDRL2 thereof is described in SEQ ID No: 57 (FIG. 72), and the amino acid sequence of CDRL3 thereof is described in SEQ ID No: 58 (FIG. 73).

The rLA869 is an anti-human LAG-3 rat monoclonal antibody obtained according to the method described in Example 1. The nucleotide sequence of the heavy chain variable region of rLA869 is described in SEQ ID No: 13 (FIG. 28), and its amino acid sequence is described in SEQ ID No: 14 (FIG. 29). The nucleotide sequence of the light chain variable region of rLA869 is described in SEQ ID No: 15 (FIG. 30), and its amino acid sequence is described in SEQ ID No: 16 (FIG. 31). The amino acid sequence of CDRH1 of rLA869 is described in SEQ ID No: 59 (FIG. 74), the amino acid sequence of CDRH2 thereof is described in SEQ ID No: 60 (FIG. 75), the amino acid sequence of CDRH3 thereof is described in SEQ ID No: 61 (FIG. 76), the amino acid sequence of CDRL1 thereof is described in SEQ ID No: 62 (FIG. 77), the amino acid sequence of CDRL2 thereof is described in SEQ ID No: 63 (FIG. 78), and the amino acid sequence of CDRL3 thereof is described in SEQ ID No: 64 (FIG. 79).

The rLA1264 is an anti-human LAG-3 rat monoclonal antibody obtained according to the method described in Example 1. The nucleotide sequence of the heavy chain variable region of rLA1264 is described in SEQ ID No: 17 (FIG. 32), and its amino acid sequence is described in SEQ ID No: 18 (FIG. 33). The nucleotide sequence of the light chain variable region of rLA1264 is described in SEQ ID No: 19 (FIG. 34), and its amino acid sequence is described in SEQ ID No: 20 (FIG. 35). The amino acid sequence of CDRH1 of rLA1264 is described in SEQ ID No: 65 (FIG. 80), the amino acid sequence of CDRH2 thereof is described in SEQ ID No: 66 (FIG. 81), the amino acid sequence of CDRH3 thereof is described in SEQ ID No: 67 (FIG. 82), the amino acid sequence of CDRL1 thereof is described in SEQ ID No: 68 (FIG. 83), the amino acid sequence of CDRL2 thereof is described in SEQ ID No: 69 (FIG. 84), and the amino acid sequence of CDRL3 thereof is described in SEQ ID No: 70 (FIG. 85).

The antibody mutant of the present invention preferably exhibits, for example, reduced sensitivity to protein degradation or oxidation, an improved biological activity, an improved ability to bind to the antigen, or physicochemical or functional properties imparted thereto. Examples of such an antibody mutant can include an antibody having an amino acid sequence derived from the amino acid sequence of the original antibody by conservative amino acid substitution of 1 or 2 or more, preferably 1 to several amino acids. The conservative amino acid substitution is a substitution that occurs in an amino acid group having related amino acid side chains.

Preferred amino acid groups are as follows: an acidic group including aspartic acid and glutamic acid; a basic group including lysine, arginine, and histidine; a nonpolar group including alanine, valine, leucine, isoleucine, proline, phenylalanine, methionine, and tryptophan; and an uncharged polar family including glycine, asparagine, glutamine, cysteine, serine, threonine, and tyrosine. Other preferred amino acid groups are as follows: an aliphatic hydroxy group including serine and threonine; an amide-containing group including asparagine and glutamine; an aliphatic group including alanine, valine, leucine, and isoleucine; and an aromatic group including phenylalanine, tryptophan, and tyrosine. Such amino acid substitution in the antibody mutant is preferably performed without reducing the antigen binding activity of the original (parent) antibody.

Aspartic acid contained in a protein is easily converted to isoaspartic acid by isomerization when an amino acid linked thereto on the C terminal side has a small side chain. On the other hand, asparagine is easily converted to aspartic acid by deamidation and may be further converted to isoaspartic acid by isomerization. The progression of such isomerization or deamidation may influence the stability of the protein. Accordingly, aspartic acid or asparagine in the protein or, for example, an amino acid adjacent thereto, can be substituted by a different amino acid in order to circumvent such isomerization or deamidation. Preferably, an antibody mutant having such amino acid substitution maintains the antigen binding activity of the original antibody.

The present invention also encompasses, for example: an antibody mutant having an amino acid sequence derived from the amino acid sequence of rLA204, rLA212, rLA225, rLA869, or rLA1264 of the present invention by conservative amino acid substitution; and a mouse antibody, a rat antibody, a chimerized antibody, a humanized antibody, or a human antibody comprising a CDR having an amino acid sequence in which a conservative amino acid mutation is introduced in the amino acid sequence of any of CDRH1 to CDRH3 and CDRL1 to CDRL3 derived from rLA204, rLA212, rLA225, rLA869, or rLA1264.

The mutant of the antibody of the present invention encompasses a human LAG-3-binding antibody mutant comprising CDRH1 to CDRH3 and CDRL1 to CDRL3 having amino acid sequences where 1 to several, preferably 1 to 3, more preferably 1 or 2, most preferably 1 amino acid(s) is substituted by different amino acid(s) in the amino acid sequences of any one or two or more of CDRH1 to CDRH3 and CDRL1 to CDRL3 derived from rLA204, rLA212, rLA225, rLA869, or rLA1264 of the present invention.

The antibody mutant also includes an antibody having CDRH1 to CDRH3 and CDRL1 to CDRL3 derived from a plurality of antibodies. Examples of such a mutant can include an antibody mutant comprising CDRH3 derived from a certain antibody and CDRH1, CDRH2, and CDRL1 to CDRL3 derived from another antibody.

The "antibody" according to the present invention also encompasses these antibody mutants.

The constant regions of the antibody of the present invention are not particularly limited. Preferably, constant regions derived from a human antibody are used in the antibody of the present invention for the treatment or prevention of a disease in a human.

Examples of the heavy chain constant region of the human antibody can include Cγ1, Cγ2, Cγ3, Cγ4, Cμ, Cδ, Cα1, Cα2, and Cε. Examples of the light chain constant region of the human antibody can include Cκ and Cλ.

(3-10) Chimeric Antibody

The anti-LAG-3 chimerized antibody or the binding fragment thereof of the present invention has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

The nucleotide sequence and amino acid sequence of the heavy chain of cLA212 exemplified as the rat-human chimeric antibody of the present invention and the nucleotide sequence and amino acid sequence of the light chain thereof are respectively shown in SEQ ID No: 23, 24, 25, and 26 (FIGS. 38, 39, 40, and 41). Nucleotide positions 1 to 57 in the nucleotide sequence of the heavy chain and amino acid positions 1 to 19 in the amino acid sequence of the heavy chain each represent a signal sequence, which is normally not contained in the nucleotide sequences and amino acid sequences of most mature heavy chains. Likewise, nucleotide positions 1 to 60 in the nucleotide sequence of the light chain and amino acid positions 1 to 20 in the amino acid sequence of the light chain each represent a signal sequence, which is normally not contained in the nucleotide sequences and amino acid sequences of most mature light chains.

Rat-human chimeric antibodies cLA204, cLA225, cLA869, and cLA1264 are described elsewhere.

(3-11) Binding Fragment of Antibody

According to one aspect, the present invention provides a binding fragment of the anti-LAG-3 antibody of the present invention. The binding fragment of the antibody means a fragment that maintains at least a part of the functions of the antibody. Examples of such functions of the antibody can generally include antigen binding activity, antigen activity-regulating activity, and antibody dependent cellular cytotoxic (ADCC) activity. Preferably, the binding fragment of the anti-LAG-3 antibody of the present invention has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

The binding fragment of the antibody is not particularly limited as long as the fragment of the antibody maintains at least a portion of the activities of the antibody. Examples thereof can include, but are not limited to, Fab, F(ab')2, Fv, single chain Fv (scFv) comprising heavy and light chain Fvs linked via an appropriate linker, diabodies, linear antibodies, multispecific antibodies formed from antibody fragments, and Fab', which is a monovalent fragment of antibody variable regions obtained by the treatment of F(ab')2 under reducing conditions. The binding fragment of the antibody of the present invention is also meant to include a molecule comprising the fragment of the antibody of the present invention as well as other portions, such as scFv retaining a linker portion.

A molecule that is derived from the antibody protein by the deletion of 1 to several or more amino acid(s) at its amino terminus and/or carboxy terminus and maintains at least a portion of the functions of the antibody is also encompassed in the meaning of the binding fragment of the antibody. For example, the heavy chain of an antibody produced by cultured mammalian cells is known to lack a lysine residue at the carboxy terminus (Journal of Chromatography A, 705: 129-134 (1995)). Also, the heavy chain of such an antibody is known to lack two amino acid residues (glycine and lysine) at the carboxy terminus and instead have an amidated proline residue at the carboxy terminus (Analytical Biochemistry, 360: 75-83 (2007)). The deletion and the modification in these heavy chain sequences, however, do not influence the ability of the antibody to bind to the antigen or its effector functions (complement activation, antibody dependent cellular cytotoxic effects, etc.). Such a modified form of the binding fragment of the antibody is also encompassed by the antibody or the binding fragment thereof of the present invention, or a modified form (described later) thereof.

The antibody of the present invention or the binding fragment thereof may be a multispecific antibody having specificity for at least 2 types of different antigens. The multispecific antibody is not limited to a bispecific antibody, which binds to 2 types of different antigens, and an antibody having specificity for 3 or more types of different antigens is also encompassed in the meaning of the "multispecific antibody" of the present invention.

The multispecific antibody of the present invention may be a full-length antibody or a binding fragment thereof (e.g., bispecific F(ab')2 antibody). The bispecific antibody can also be prepared by linking the heavy and light chains (HL pairs) of two types of antibodies. Alternatively, the bispecific antibody may be obtained by fusing two or more types of monoclonal antibody-producing hybridomas to prepare bispecific antibody-producing fusion cells (Millstein et al., Nature (1983) 305, p. 537-539). The multispecific antibody can also be prepared in the same way as above.

According to one aspect, the antibody of the present invention is a single chain antibody (single chain Fv; hereinafter, referred to as "scFv"). The scFv is obtained by linking the heavy and light chain V regions of the antibody via a polypeptide linker (Pluckthun, The Pharmacology of Monoclonal Antibodies, 113, Rosenburg and Moore, ed., Springer Verlag, New York, p. 269-315 (1994); and Nature Biotechnology (2005), 23, p. 1126-1136). Also, bi-scFv comprising two scFvs linked via a polypeptide linker can be used as a bispecific antibody. Alternatively, multi-scFv comprising three or more scFvs may be used as a multispecific antibody.

The present invention includes a single chain immunoglobulin comprising full-length heavy and light chain sequences of the antibody linked via an appropriate linker (Lee, H-S, et al., Molecular Immunology (1999), 36, p. 61-71; and Shirrmann, T. et al., mAbs (2010), 2 (1) p. 1-4). Such a single chain immunoglobulin can be dimerized to thereby maintain a structure and activities similar to those of the antibody, which was originally a tetramer. Also, the antibody of the present invention may be an antibody that has a single heavy chain variable region and has no light chain sequence. Such an antibody, called a single domain antibody (sdAb) or a nanobody, has been reported to maintain the ability to bind to an antigen (Muyldemans S. et al., Protein Eng. (1994), 7 (9), 1129-35; and Hamers-Casterman C. et al., Nature (1993), 363 (6428), 446-8). These antibodies are also encompassed in the meaning of the functional fragment of the antibody according to the present invention.

(3-12) Humanized Antibody and Human Antibody

According to one aspect, the present invention provides a humanized antibody or a binding fragment thereof.

Preferably, the humanized anti-LAG-3 antibody or the binding fragment thereof of the present invention has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

Preferred examples of the humanized antibody of the present invention can include humanized antibodies having the heavy chain CDRH1 to CDRH3 and the light chain CDRL1 to CDRL3 of rLA204, rLA212, rLA225, rLA869, or rLA1264, as described below in A to E.

(A. Humanized Antibody Having Heavy Chain CDRH1 to CDRH3 and Light Chain CDRL1 to CDRL3 of rLA204 Antibody)

Examples of the humanized anti-LAG-3 antibody or the binding fragment thereof of the present invention can include a humanized antibody that consists of a heavy chain having a variable region comprising CDRH1 consisting of the amino acid sequence represented by SEQ ID No: 41 (FIG. 56), CDRH2 consisting of the amino acid sequence represented by SEQ ID No: 42 (FIG. 57), and CDRH3 consisting of the amino acid sequence represented by SEQ ID No: 43 (FIG. 58), and a light chain having a variable region comprising CDRL1 consisting of the amino acid sequence represented by SEQ ID No: 44 (FIG. 59), CDRL2 consisting of the amino acid sequence represented by SEQ ID No: 45 (FIG. 60), and CDRL3 consisting of the amino acid sequence represented by SEQ ID No: 46 (FIG. 61), and recognizes the LAG-3 protein of the present invention, a binding fragment thereof, or a mutant thereof.

(B. Humanized Antibody Having Heavy Chain CDRH1 to CDRH3 and Light Chain CDRL1 to CDRL3 of rLA212 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 47 (FIG. 62), CDRH2 consisting of the amino acid sequence represented by SEQ ID No: 48 (FIG. 63), and CDRH3 consisting of the amino acid sequence represented by SEQ ID No: 49 (FIG. 64), and a light chain having a variable region comprising CDRL1 consisting of the amino acid sequence represented by SEQ ID No: 50 (FIG. 65), CDRL2 consisting of the amino acid sequence represented by SEQ ID No: 51 (FIG. 66), and CDRL3 consisting of the amino acid sequence represented by SEQ ID No: 52 (FIG. 67), and recognizes the LAG-3 protein of the present invention, a binding fragment thereof, or a mutant thereof.

(C. Humanized Antibody Having Heavy Chain CDRH1 to CDRH3 and Light Chain CDRL1 to CDRL3 of rLA225 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 53 (FIG. 68), CDRH2 consisting of the amino acid sequence represented by SEQ ID No: 54 (FIG. 69), and CDRH3 consisting of the amino acid sequence represented by SEQ ID No: 55 (FIG. 70), and a light chain having a variable region comprising CDRL1 consisting of the amino acid sequence represented by SEQ ID No: 56 (FIG. 71), CDRL2 consisting of the amino acid sequence represented by SEQ ID No: 57 (FIG. 72), and CDRL3 consisting of the amino acid sequence represented by SEQ ID No: 58 (FIG. 73), and recognizes the LAG-3 protein of the present invention, a binding fragment thereof, or a mutant thereof.

(D. Humanized Antibody Having Heavy Chain CDRH1 to CDRH3 and Light Chain CDRL1 to CDRL3 of rLA869 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 59 (FIG. 74), CDRH2 consisting of the amino acid sequence represented by SEQ ID No: 60 (FIG. 75), and CDRH3 consisting of the amino acid sequence represented by SEQ ID No: 61 (FIG. 76), and a light chain having a variable region comprising CDRL1 consisting of the amino acid sequence represented by SEQ ID No: 62 (FIG. 77), CDRL2 consisting of the amino acid sequence represented by SEQ ID No: 63 (FIG. 78), and CDRL3 consisting of the amino acid sequence represented by SEQ ID No: 64 (FIG. 79), and recognizes the LAG-3 protein of the present invention, a binding fragment thereof, or a mutant thereof.

(E. Humanized Antibody Having Heavy Chain CDRH1 to CDRH3 and Light Chain CDRL1 to CDRL3 of rLA1264 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 65 (FIG. 80), CDRH2 consisting of the amino acid sequence represented by SEQ ID No: 66 (FIG. 81), and CDRH3 consisting of the amino acid sequence represented by SEQ ID No: 67 (FIG. 82), and a light chain having a variable region comprising CDRL1 consisting of the amino acid sequence represented by SEQ ID No: 68 (FIG. 83), CDRL2 consisting of the amino acid sequence represented by SEQ ID No: 69 (FIG. 84), and CDRL3 consisting of the amino acid sequence represented by SEQ ID No: 70 (FIG. 85), and recognizes the LAG-3 protein of the present invention, a binding fragment thereof, or a mutant thereof.

Preferred examples of the humanized antibody of the present invention include those described in A to E above. More preferred examples of the humanized antibody can include, but are not limited to, hLA212_H2/L1 to hLA212_H2/L5, hLA212_H3/L1 to hLA212_H3/L5, and hLA212_H4/L2 (see [i] to [x] below). For example, the more preferred examples of the humanized antibody of the present invention also include an antibody comprising a heavy chain comprising the heavy chain variable region of any one of the humanized antibodies hLA212_H2/L1 to hLA212_H2/L5, hLA212_H3/L1 to hLA212_H3/L5, and hLA212_H4/L2, and a light chain comprising the light chain variable region of any one of the humanized antibodies hLA212_H2/L1 to hLA212_H2/L5, hLA212_H3/L1 to hLA212_H3/L5, and hLA212_H4/L2.

[i]

[i-1] The hLA212_H3/L2 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3), the property described in (3-8), that is, the presence of the antibody allowing the human LAG-3 to exert human T cell suppression function (see the Examples), and has the activities, the properties, etc., described in (3-4) to (3-7).

[i-2] The hLA212_H4/L2 is a humanized antibody which was obtained in Example 8 and whose sugar chain modification is adjusted, and is a low fucose form for hLA212_H3/L2. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity, the in vitro ADCC activity, the in vivo LAG-3 positive cell number reducing activity, and the in vivo experimental autoimmune encephalomyelitis inhibitory activity described in (3-2) to (3-5) (see the Examples), has the human activated T cell binding activity described in (3-6), and has the properties described in (3-7) and (3-8), that is, the presence of the antibody allowing the human LAG-3 to exhibit its given activities.

[ii] The hLA212_H2/L1 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 31 (FIG. 46) (where the variable region is 61 to 387), and its amino acid sequence comprises amino acid positions 21 to 234 of SEQ ID No: 32 (FIG. 47) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[iii] The hLA212_H3/L3 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 35 (FIG. 50) (where the variable region is 61 to 387), and its amino acid sequence comprises amino acid positions 21 to 234 of SEQ ID No: 36 (FIG. 51) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[iv] The hLA212_H2/L2 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[v] The hLA212_H2/L3 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 35 (FIG. 50) (where the variable region is 61 to 387), and its amino acid sequence comprises amino acid positions 21 to 234 of SEQ ID No: 36 (FIG. 51) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[vi] The hLA212_H2/L4 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 37 (FIG. 52) (where the variable region is 61 to 387), and its amino acid sequence comprises amino acid positions 21 to 234 of SEQ ID No: 38 (FIG. 53) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see Examples), and has the activities, the properties, etc., described in (3-4) to (3-8).

[vii] The hLA212_H2/L5 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 39 (FIG. 54) (where the variable region is 61 to 387), and its amino acid sequence comprises amino acid positions 21 to 234 of SEQ ID No: 40 (FIG. 55) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[viii] The hLA212_H3/L1 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 31 (FIG. 46) (where the variable region is 61 to 387), and its amino acid sequence comprises amino acid positions 21 to 234 of SEQ ID No: 32 (FIG. 47) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[ix] The hLA212_H3/L4 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 37 (FIG. 52) (where the variable region is 61 to 387), and its amino acid sequence comprises amino acid positions 21 to 234 of SEQ ID No: 38 (FIG. 53) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[x] The hLA212_H3/L5 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 39 (FIG. 54) (where the variable region is 61 to 387), and its amino acid sequence comprises amino acid positions 21 to 234 of SEQ ID No: 40 (FIG. 55) (where the variable region is 21 to 129). It can be evaluated by the methods described in the Examples that the antibody has physical properties that are suitable for the pharmaceutical composition, the method for treatment or prevention, the use for treatment or prevention, etc., of the present invention (data not shown), has the LAG3-binding activity and the in vitro ADCC activity described in (3-2) and (3-3) (see the Examples), and has the activities, the properties, etc., described in (3-4) to (3-8).

In [i] to [x] above, the activities described in (3-4) and (3-5) can be preferably evaluated in low fucose form. The term "physical properties" in the present invention means the stability of the antibody and the binding fragment thereof of the present invention as a physical body, which can be evaluated using a known index. Examples of the stability as a physical body can include thermostability and storage stability, and examples of their indices can include Tm values obtained from thermograms and changes in antigen binding activity under storage conditions or accelerated deterioration conditions or changes over time.

Further, hLA212 antibody H4/L2 was administered to the human LAG-3/human FcγRIIIA double transgenic mice of Example 10 in a single dose, as a result of which, weight loss and other remarkable toxic events were not observed. Thus, the humanized antibody of the present invention possesses safety suitable for methods for treatment or prevention of diseases associated with LAG-3 positive cells (defined elsewhere), use for such treatment or prevention, pharmaceutical compositions for treatment or prevention, etc. Of the more preferred examples of the humanized anti-LAG-3 antibody and the binding fragment thereof of the present invention described above, hLA212_H3/L2, hLA212_H2/L1, hLA212_H3/L3, hLA212_H3/L6, and hLA212_H4/L2 are further more preferable.

The hLA212_H2/L1 to H2/L5, hLA212_H3/L1 to H3/L5, hLA212_H4/L2, etc., included in the more preferred range of the humanized anti-LAG-3 antibody of the present invention can comprise the heavy chain consisting of an amino acid sequence in which 1 to several, preferably 1 or 2 amino acids are substituted with other amino acids in FRH1 to FRH4 of the amino acid sequence of the heavy chain and the light chain consisting of an amino acid sequence in which 1 or more, preferably any number of amino acids selected from 1 to 14 are substituted with other amino acids in FRL1 to FRL4 of the amino acid sequence of the light chain.

More preferably, in the light chain of the humanized antibody, amino acid 1 of FRL1, that is, amino acid 1 in the mature variable region (the amino acid corresponding to position 21 of SEQ ID No: 32 or FIG. 47) is Asp or Asn, amino acid 11 of FRL1, that is, amino acid 11 of the mature variable region (the amino acid corresponding to position 31 of SEQ ID No: 32 or FIG. 47) is Leu or Met, amino acid 13 of FRL1, that is, amino acid 13 of the mature variable region (the amino acid corresponding to position 33 of SEQ ID No: 32 or FIG. 47) is Ala or Ile, amino acid 21 of FRL1, that is, amino acid 21 of the mature variable region (the amino acid corresponding to position 41 of SEQ ID No: 32 or FIG. 47) is Ile or Met, amino acid 4 of FRL2, that is, amino acid 38 of the mature variable region (the amino acid corresponding to position 58 of SEQ ID No: 32 or FIG. 47) is Gln or Lys, amino acid 9 of FRL2, that is, amino acid 43 of the mature variable region (the amino acid corresponding to position 63 of SEQ ID No: 32 or FIG. 47) is Ala or Ser, amino acid 4 of FRL3, that is, amino acid 60 of the mature variable region (the amino acid corresponding to position 80 of SEQ ID No: 32 or FIG. 47) is Ser or Asp, amino acid 9 of FRL3, that is, amino acid 65 of the mature variable region (the amino acid corresponding to position 85 of SEQ ID No: 32 or FIG. 47) is Ser or Gly, amino acid 11 of FRL3, that is, amino acid 67 of the mature variable region (the amino acid corresponding to position 87 of SEQ ID No: 32 or FIG. 47) is Ser or Tyr, amino acid 22 of FRL3, that is, amino acid 78 of the mature variable region (the amino acid corresponding to position 98 of SEQ ID No: 32 or FIG. 47) is Leu or Val, amino acid 27 of FRL3, that is, amino acid 83 of the mature variable region (the amino acid corresponding to position 103 of SEQ ID No: 32 or FIG. 47) is Phe or Ala, amino acid 29 of FRL3, that is, amino acid 85 of the mature variable region (the amino acid corresponding to position 105 of SEQ ID No: 32 or FIG. 47) is Thr or Phe, amino acid 7 of FRL4, that is, amino acid 104 of the mature variable region (the amino acid corresponding to position 124 of SEQ ID No: 32 or FIG. 47) is Val or Leu, and amino acid 9 of FRL4, that is, amino acid 106 of the mature variable region (the amino acid corresponding to position 126 of SEQ ID No: 32 or FIG. 47) is Ile or Leu.

More preferably, in the heavy chain of the humanized antibody, amino acid 14 of FRH2, that is, amino acid 49 of the mature variable region (the amino acid corresponding to position 68 of SEQ ID No: 28 or FIG. 43) is Gly or Ala, and amino acid 25 of FRH3, that is, amino acid 84 of the mature variable region (the amino acid corresponding to position 103 of SEQ ID No: 28 or FIG. 43) is Asn or Asp.

The present invention also encompasses an antibody that comprises a heavy chain and/or a light chain comprising an amino acid sequence having 80% or higher, 82% or higher, 84% or higher, 86% or higher, 88% or higher, 90% or higher, 92% or higher, 94% or higher, 96% or higher, 98% or higher, or 99% or higher identity to the amino acid sequence of the full length or the variable regions of the heavy chain and/or the light chain of any one of the rLA204, rLA212, rLA225, rLA869, rLA1264, cLA204, cLA212, cLA225, cLA869, and cLA1264 antibodies, and the humanized hLA212_H2/L1 to hLA212_H2/L5, hLA212_H3/L1 to hLA212_H3/L5, and hLA212_H4/L2 antibodies of the present invention, and binds to LAG-3, or a binding fragment thereof. Such sequence identity is preferably 94% or higher, more preferably 96% or higher, further more preferably 98% or higher, optimally 99% or higher. Further, the antibody or the binding fragment thereof has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

The identity or homology between two types of amino acid sequences can be determined using the default parameters of the Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res.

25: 3389-3402). The Blast algorithm is also available, for example, by Internet access at http://blast.ncbi.nlm.nih.gov/.

The present invention also encompasses an antibody that comprises a heavy chain and/or a light chain comprising an amino acid sequence that is derived from the full-length or variable-region amino acid sequence of the heavy chain and/or the light chain of any one of the rLA204, rLA212, rLA225, rLA869, rLA1264, cLA204, cLA212, cLA225, cLA869, and cLA1264 antibodies, and the hLA212_H2/L1 to hLA212_H2/L5, hLA212_H3/L1 to hLA212_H3/L5 and hLA212_H4/L2 antibodies of the present invention by the substitution, deletion, addition, and/or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid, and binds to LAG-3, or a binding fragment thereof. Such an amino acid mutation is preferably a substitution. The number of amino acids mutated is preferably 1 to 5, more preferably 1 to 4, even more preferably 1 to 3, further more preferably 1 or 2, most preferably 1. Further, the antibody or the binding fragment thereof has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

The present invention also encompasses an antibody that comprises a heavy chain and/or light chain comprising an amino acid sequence encoded by a nucleotide sequence of a nucleotide that hybridizes under stringent conditions to a nucleotide having a nucleotide sequence complementary to a nucleotide sequence encoding the full-length or variable-region amino acid sequence of the heavy chain and/or the light chain of any one of the rLA204, rLA212, rLA225, rLA869, rLA1264, cLA204, cLA212, cLA225, cLA869 and cLA1264 antibodies, and the hLA212_H2/L1 to hLA212_H2/L5, hLA212_H3/L1 to hLA212_H3/L5, and hLA212_H4/L2 antibodies of the present invention, and binds to LAG-3, or a binding fragment thereof. The antibody or the binding fragment thereof has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

According to another aspect, the present invention provides a human antibody or a binding fragment thereof. The human antibody or the binding fragment thereof of the present invention is not specifically limited, as long as it is a human-derived antibody that binds to LAG-3 or a binding fragment thereof, but has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4), (3-5), (3-6) and/or (3-7) in addition to the above, optimally all of (3-2) to (3-8).

(3-13) Antibody Binding to Epitope

An "antibody binding to the same site" as in the case of the antibody provided by the present invention is also included in the antibody of the present invention. An "antibody binding to the same site" as a certain antibody means a different antibody that binds to a site on an antigen molecule recognized by the antibody. If a second antibody binds to a partial peptide or a partial three-dimensional structure on an antigen molecule bound by a first antibody, the first and second antibodies are determined as binding to the same site. Alternatively, the first and second antibodies are determined as binding to the same site by confirming that the second antibody competes with the first antibody for binding to the antigen, i.e., the second antibody interferes with the binding of the first antibody to the antigen, even if the peptide sequence or three-dimensional structure of the specific binding site is not determined. When the first and second antibodies bind to the same site, and the first antibody has an effect characteristic of one aspect of the antibody of the present invention, such as its presence allowing LAG-3 to exert T cell suppression function, the second antibody also has an exceedingly high probability of having the same activity thereas. Thus, if a second anti-LAG-3 antibody binds to a site bound by a first anti-LAG-3 antibody, the first and second antibodies are determined as binding to the same site on the LAG-3 protein. Alternatively, the first and second anti-LAG-3 antibodies are determined as binding to the same site on the LAG-3 protein by confirming that the second anti-LAG-3 antibody competes with the first anti-LAG-3 antibody for binding to the LAG-3 protein.

The present invention also encompasses an antibody binding to a site on the LAG-3 protein recognized by the monoclonal antibody of the present invention. The antibody and the binding fragment thereof has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8).

The antibody binding site can be determined by a method well known by those skilled in the art, such as an immunoassay. For example, a series of peptides are prepared by appropriately sequentially cleaving the amino acid sequence of the antigen from its C terminus or N terminus, and the reactivity of the antibody thereto is studied to determine a recognition site roughly. Then, shorter peptides are synthesized, and the reactivity of the antibody to these peptides can be studied thereby to determine the binding site. The antigen fragment peptides can be prepared using a technique such as gene recombination or peptide synthesis.

When the antibody binds to or recognizes the partial conformation of the antigen, the binding site for the antibody can be determined by identifying amino acid residues on the antigen adjacent to the antibody using X-ray structural analysis. For example, the antibody or its fragment and the antigen or its fragment can be bound to each other and crystallized, followed by structural analysis to identify each amino acid residue on the antigen having an interaction distance with the antibody. The interaction distance is 8 angstroms or shorter, preferably 6 angstroms or shorter, more preferably 4 angstroms or shorter. One or more such amino acid residues having an interaction distance with the antibody can constitute a site (epitope) on the antigen to which the antibody binds. Two or more such amino acid residues may not be adjacent to each other on the primary sequence.

The epitope of the antibody of the present invention is present in human LAG-3 or its amino acid sequence. The antibody or the binding fragment thereof of the present invention, or the modified form thereof also encompasses an antibody binding to this epitope, competing with the antibody of the present invention for binding to the epitope, or having an interaction distance with these amino acid residues, a binding fragment thereof, or a modified form thereof.

(3-14) Modified Form of Antibody

The present invention provides a modified form of the antibody or the binding fragment thereof. The modified form of the antibody or the binding fragment thereof of the present invention means the antibody or the binding fragment thereof of the present invention provided with chemical or biological modification. The chemically modified form includes, for example, a form having an amino acid skeleton conjugated with a chemical moiety, and a form having a chemically modified N-linked or O-linked carbohydrate chain. The biologically modified form includes, for example, a form that has undergone post-translational modification (e.g., N-linked or O-linked glycosylation, N-terminal or C-terminal processing, deamidation, isomerization of aspartic acid, or oxidation of methionine), and a form containing a methionine residue added to the N-terminus by expression using prokaryotic host cells. Such a modified form is also meant to include a form labeled to permit detection or isolation of the antibody or the antigen of the present invention, for example, an enzyme-labeled form, a fluorescently labeled form, or an affinity-labeled form.

Such a modified form of the antibody or the binding fragment thereof of the present invention is useful for improvement of the stability or blood retention of the original antibody of the present invention or the original binding fragment thereof, reduction in antigenicity, detection or isolation of the antibody or the antigen, etc.

Examples of the chemical moiety contained in the chemically modified form can include water-soluble polymers such as polyethylene glycol, ethylene glycol/propylene glycol copolymers, carboxymethylcellulose, dextran, and polyvinyl alcohol.

Examples of the biologically modified form can include a form modified by enzymatic treatment, cell treatment, or the like, a form fused with another peptide, such as a tag, added by gene recombination, and a form prepared from host cells expressing an endogenous or exogenous sugar chain-modifying enzyme.

The antibody dependent cellular cytotoxic activity of the antibody or the binding fragment thereof of the present invention may be enhanced by regulating the modification (glycosylation, defucosylation, etc.) of the sugar chain bound with the antibody or the binding fragment. For example, methods described in WO99/54342, WO00/61739, and WO02/31140 are known as such a technique of regulating the sugar chain modification of the antibody, though this technique is not limited thereto. The modified form of the antibody of the present invention also includes an antibody that has undergone the sugar chain modification thus regulated.

Such a modification may be made at an arbitrary position or a desired position in the antibody or binding fragment thereof. The same or two or more different modifications may be made at one or two or more positions therein.

In the present invention, the "modified form of the antibody fragment" is also meant to include even a "fragment of the modified form of the antibody".

In the present invention, the modified form of the antibody or the modified form of the binding fragment thereof is also simply referred to as an "antibody" or a "binding fragment of the antibody".

As described above, the hLA212_H4/L2 is the humanized antibody which was obtained in Example 8 and whose sugar chain modification is adjusted. The humanized antibody is also encompassed by the antibody of the present invention.

The antibody or the binding fragment thereof of the present invention, and the modified forms thereof as described above preferably have physical properties, pharmacokinetics, blood retention, safety, etc., that are suitable for the pharmaceutical composition, the method for treatment or prevention, the use for treatment or prevention, etc., of the present invention.

4. Method for Producing Antibody (4-1) Method Using Hybridoma

The anti-LAG-3 antibody of the present invention can be prepared according to the method of Kohler and Milstein (Kohler and Milstein, Nature (1975), 256, p. 495-497; and Kennet, R. ed., Monoclonal Antibodies, p. 365-367, Plenum Press, N.Y. (1980)). Thus, anti-LAG-3 antibody-producing cells are isolated from the spleens of animals immunized with the LAG-3 protein or its soluble form and the cells are fused with myeloma cells thereby to establish hybridomas. Monoclonal antibodies can be obtained from cultures of these hybridomas.

(4-1-1) Preparation of Antigen

The antigen for the preparation of the anti-LAG-3 antibody can be obtained according to, for example, the method for preparing a native or recombinant LAG-3 protein described in other paragraphs of the present invention. Examples of the antigen that may be thus prepared can include the LAG-3 protein, a LAG-3 protein fragment comprising a partial sequence with at least 6 consecutive amino acids of the LAG-3 protein, and their derivatives further comprising an arbitrary amino acid sequence or carrier added thereto (hereinafter, collectively referred to as an "LAG-3 antigen").

The recombinant LAG-3 antigen can be prepared by transfecting host cells with a gene comprising a nucleotide sequence encoding the amino acid sequence of the LAG-3 antigen, and recovering the antigen from cultures of the cells. Such a recombinant antigen may be a fusion protein with another protein such as an immunoglobulin Fc region. An LAG-3 antigen obtained in a cell-free in vitro translation system from a gene comprising a nucleotide sequence encoding the amino acid sequence of the LAG-3 antigen is also included in the recombinant LAG-3 antigen. The non-recombinant LAG-3 antigen can be purified and isolated from LAG-3-expressing cells or the like.

In order to obtain an anti-LAG-3 monoclonal antibody the presence of which allows LAG-3 to exert T cell function suppression function or does not suppress or inhibit the T cell function suppression function of LAG-3, a LAG-3 mutant in which immunoglobulin-like domains 1 and 2 are deleted, for example, can be used as a preferable immunogen.

(4-1-2) Production of Anti-LAG-3 Monoclonal Antibody

The monoclonal antibody is typically produced through the following steps of:
 (a) preparing an antigen,
 (b) preparing antibody-producing cells,
 (c) preparing myeloma cells (hereinafter, referred to as "myelomas"),
 (d) fusing the antibody-producing cells with the myelomas,
 (e) screening for a hybridoma group producing the antibody of interest, and
 (f) obtaining single cell clones (cloning).

This production method further involves the steps of (g) culturing the hybridomas, raising hybridoma-transplanted animals, etc., and (h) assaying or determining the biological activity of the monoclonal antibody, etc., if necessary.

Hereinafter, the method for preparing the monoclonal antibody will be described in detail with reference to these steps. However, the method for preparing the antibody is not limited to those steps, and antibody-producing cells other than spleen cells, for example, may be used.

(a) Purification of Antigen

This step is performed according to the method for preparing the LAG-3 protein described above in (2-3).

(b) Step of Preparing Antibody-Producing Cell

The antigen obtained in step (a) is mixed with an adjuvant such as a complete or incomplete Freund's adjuvant or potassium aluminum sulfate, and laboratory animals are immunized with the resulting immunogen. Any laboratory animal used in a hybridoma preparation method known in the art can be used without limitations. Specifically, for example, mice, rats, goats, sheep, cattle, or horses can be used. From the viewpoint of readily available myeloma cells to be fused with isolated antibody-producing cells, etc., the animals to be immunized are preferably mice or rats.

The strain of mice or rats actually used is not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, or 129 can be used. In the case of rats, for example, Wistar, Low, Lewis, Sprague-Dawley, ACI, BN, or Fischer can be used.

These mice and rats are available from laboratory animal breeders or distributors, for example, CLEA Japan, Inc. or Charles River Laboratories Japan Inc.

Of those mice and rats, a BALB/c mouse strain or Wistar and Low rat strains are particularly preferred as animals to be immunized in consideration of fusion compatibility with the myeloma cells described later.

Also, in consideration of the homology between human and mouse antigens, mice whose biological mechanism to remove autoantibodies has been reduced, i.e., autoimmune disease mice, are also preferably used.

In this context, these mice or rats are preferably 5 to 12 weeks old, more preferably 6 to 8 weeks old, at the time of immunization.

The animals can be immunized with the LAG-3 protein using, for example, the method of Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Illinois (1964).

Examples of methods for determining antibody titers can include, but are not limited to, immunoassays such as RIA and ELISA.

Antibody-producing cells derived from spleen cells or lymphocytes isolated from the immunized animals, can be prepared according to a method known in the art, for example, Kohler et al., Nature (1975) 256, p. 495; Kohler et al., Eur. J. Immnol. (1977) 6, p. 511; Milstein et al., Nature (1977), 266, p. 550; Walsh, Nature, (1977) 266, p. 495.

In the case of spleen cells, a general method can be adopted, which involves chopping the spleens, filtering cells through a stainless mesh, and then suspending the resulting cells in an Eagle's minimum essential medium (MEM) or the like, to isolate antibody-producing cells.

(c) Step of Preparing Myeloma

The myeloma cells used in cell fusion are not particularly limited and can be selected appropriately for use from cell lines known in the art. For example, a hypoxanthine-guanine phosphoribosyl transferase (HGPRT)-deficient line, i.e., mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, S149/5XXO, or BU.1, rat-derived 210.RSY3.Ag.1.2.3 (Y3), or human-derived U266AR (SKO-007), GM1500-GTG-A12 (GM1500), UC729-6, LICR-LOW-HMy2 (HMy2), or 8226AR/NIP4-1 (NP41), and the like, whose screening procedures have already been established, is preferably used in consideration of convenience in the selection of hybridomas from fused cells. These HGPRT-deficient lines are available from, for example, American Type Culture Collection (ATCC).

These cell lines are subcultured in an appropriate medium, for example, an 8-azaguanine medium [RPMI-1640 medium supplemented with glutamine, 2-mercaptoethanol, gentamicin, and fetal bovine serum (hereinafter, referred to as "FBS") and further supplemented with 8-azaguanine], an Iscove's modified Dulbecco's medium (hereinafter, referred to as "IMDM"), or a Dulbecco's modified Eagle medium (hereinafter, referred to as "DMEM") and subcultured in a normal medium [e.g., ASF104 medium (manufactured by Ajinomoto Co., Inc.) containing 10% FBS] 3 to 4 days before cell fusion to secure that the number of cells is equal to or greater than $2 \times 10^7$ cells on the day of cell fusion.

(d) Step of Fusing Antibody-Producing Cell with Myeloma Cell

The antibody-producing cells can be fused with the myeloma cells under conditions that prevent cell viability from being exceedingly reduced, according to any method known in the art (e.g., Weir, D. M., Handbook of Experimental Immunology Vol. I. II. III., Blackwell Scientific Publications, Oxford (1987), and Kabat, E. A. and Mayer, M. M., Experimental Immunochemistry, Charles C Thomas Publisher Springfield, Illinois (1964)). For example, a chemical method which involves mixing antibody-producing cells with myeloma cells in a high-concentration solution of a polymer such as polyethylene glycol, or a physical method using electric stimulation can be used.

(e) Step of Screening for Hybridoma Group Producing Antibody of Interest

A method for selection of the hybridomas obtained by cell fusion is not particularly limited, and a hypoxanthine-aminopterin-thymidine (HAT) selection method (Kohler et al., Nature (1975) 256, p. 495; Milstein et al., Nature (1977) 266, p. 550) is typically used. This method is effective for obtaining hybridomas using an HGPRT-deficient myeloma cell line, which cannot survive in the presence of aminopterin. Specifically, unfused cells and hybridomas can be cultured in a HAT medium to thereby allow only hybridomas resistant to aminopterin to selectively live and grow.

(f) Step of Obtaining Single Cell Clone (Cloning)

The hybridomas can be cloned using any method known in the art, for example, a methylcellulose, soft agarose, or limiting dilution method (see e.g., Barbara, B. M. and Stanley, M. S.: Selected Methods in Cellular Immunology, W.H. Freeman and Company, San Francisco (1980)). The limiting dilution method is preferred.

(g) Step of Culturing Hybridoma and Step of Raising Hybridoma-Transplanted Animal The selected hybridomas can be cultured to thereby produce monoclonal antibodies. Preferably, the desired hybridomas are cloned and then subjected to antibody production.

The monoclonal antibody produced by such a hybridoma can be recovered from cultures of the hybridoma. Also, a recombinant antibody can be recovered from cultures of cells introduced with the monoclonal antibody gene. Alternatively, the hybridoma may be injected intraperitoneally to mice of the same strain (e.g., BALB/cAnNCrj described above) or Nu/Nu mice and allowed to grow. Then, the monoclonal antibody can be recovered from their ascites.

(h) Step of Assaying or Determining Biological Activity of Monoclonal Antibody

Various biological tests can be selected and applied thereto according to purpose.

(4-2) Cell Immunization Method

Cells expressing the native LAG-3 protein, cells expressing the recombinant LAG-3 protein or its fragment, or the like, can be used as immunogens thereby to prepare an anti-LAG-3 antibody by the hybridoma method described above.

These LAG-3-expressing cells are used in an amount of $1 \times 10^5$ to $1 \times 10^9$ cells, preferably $1 \times 10^6$ to $1 \times 10^8$ cells, more preferably 0.5 to $2 \times 10^7$ cells, even more preferably $1 \times 10^7$ cells, per immunization shot. The number of cells used for immunization can be changed according to the expression level of the LAG-3 protein. The immunogens are generally administered intraperitoneally and may be administered through an intradermal route or the like. The hybridomas can be prepared by the application of the method described in paragraph (4-1-2).

(4-3) Gene Recombination

In order to prepare the antibody of the present invention, a nucleotide (heavy chain nucleotide) comprising a nucleotide sequence encoding the amino acid sequence of its heavy chain and a nucleotide (light chain nucleotide) comprising a nucleotide sequence encoding the amino acid sequence of its light chain, or a vector having an insert of the heavy chain nucleotide and a vector having an insert of the light chain nucleotide are introduced into host cells, and then the cells are cultured, and the antibody can be recovered from the cultures. The heavy chain nucleotide and the light chain nucleotide may be inserted in one vector.

Prokaryotic or eukaryotic cells can be used as the host cells. In the case of using host eukaryotic cells, animal cells, plant cells, or eukaryotic microbes can be used.

Examples of the animal cells can include mammal-derived cells, i.e., monkey-derived COS cells (Gluzman, Y. Cell (1981), 23, p. 175-182, ATCC CRL-1650), mouse fibroblast NIH3T3 (ATCC No. CRL-1658), a mouse NS0 cell line (ECACC), Chinese hamster ovary cells (CHO cells, ATCC CCL-61), dihydrofolate reductase-deficient lines thereof ($CHO^{dhfr-}$; Urlaub, G. and Chasin, L. A. Proc. Natl. Acad. Sci. U.S.A. (1980), 77, p. 4126-4220), CHOK1SV (Lonza Biologics), cells derived from birds such as chickens, and cells derived from insects.

Also, cells modified to adjust the sugar chain modification of proteins such as antibodies can be used as the hosts. For example, CHO cells modified such that fucose bound to N-acetylglucosamine at the reducing ends of sugar chains is reduced on or removed from complex-type N-glycoside-linked sugar chains binding to the Fc region of the antibody may be used in antibody expression thereby to prepare a low-fucose or defucosylated antibody (also referred to as a modified form of the antibody) (WO00/61739, WO02/31140, etc.).

Examples of the eukaryotic microbes can include yeasts.

Examples of the prokaryotic cells can include *E. coli* and *Bacillus subtilis*.

A signal peptide for the secretion of the antibody of the present invention (monoclonal antibody derived from any animal, rat antibody, mouse antibody, chimeric antibody, humanized antibody, human antibody, etc.) is not limited to the secretory signal of an antibody of the same species, the same type, and the same subtype as the antibody of the present invention or to the antibody of the present invention's own secretory signal. Any secretory signal of an antibody of different type or subtype therefrom or any secretory signal of a protein derived from a different eukaryotic species therefrom or a prokaryotic species can be selected and used.

(4-4) Methods for Designing and Preparing Humanized Antibody

Examples of the humanized antibody can include, but are not limited to, a human-derived antibody having CDRs replaced with the CDRs of a non-human animal antibody (see Nature (1986), 321, p. 522-525), a human antibody grafted with the CDR sequences and with some amino acid residues of framework regions by CDR grafting (see WO90/07861 and U.S. Pat. No. 6,972,323), and any of said humanized antibodies wherein one or two or more non-human animal antibody-derived amino acid(s) have been replaced with human antibody-derived amino acid(s).

(4-5) Method for Preparing Human Antibody

Further examples of the antibody of the present invention can include a human antibody. The anti-LAG-3 human antibody means an anti-LAG-3 antibody consisting of the amino acid sequence of a human-derived antibody. The anti-LAG-3 human antibody can be obtained by a method using human antibody-producing mice carrying human genomic DNA fragments comprising human antibody heavy and light chain genes (see e.g., Tomizuka, K. et al., Nature Genetics (1997) 16, p. 133-143; Kuroiwa, Y. et. al., Nuc. Acids Res. (1998) 26, p. 3447-3448; Yoshida, H. et. al., Animal Cell Technology: Basic and Applied Aspects vol. 10, p. 69-73 (Kitagawa, Y., Matuda, T. and Iijima, S. eds.), Kluwer Academic Publishers, 1999.; and Tomizuka, K. et.al., Proc. Natl. Acad. Sci. USA (2000) 97, p. 722-727).

Specifically, such human antibody-producing animals may be any of recombinant animals that are obtained by disrupting the endogenous immunoglobulin heavy and light chain gene loci of non-human mammals and instead introducing thereto human immunoglobulin heavy and light chain gene loci via yeast artificial chromosome (YAC) vectors or the like, and recombinant animals that are created by crossing these animals.

Alternatively, eukaryotic cells may be transfected (transformed) with cDNAs encoding the heavy and light chains, respectively, of such a human antibody, preferably with vectors comprising the cDNAs, by a gene recombination technique. The transfected (transformed) cells producing a recombinant human monoclonal antibody can be cultured. This antibody can be obtained from the culture supernatant.

In this context, for example, eukaryotic cells, preferably mammalian cells such as CHO cells, lymphocytes, or myelomas, can be used as the hosts.

Also, a method for obtaining a phage display-derived human antibody selected from a human antibody library (see e.g., Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; and Siriwardena, D. et.al., Opthalmology (2002) 109 (3), p. 427-431) is known.

For example, a phage display method (Nature Biotechnology (2005), 23, (9), p. 1105-1116) can be used, which involves allowing the variable regions of a human antibody to be expressed as a single chain antibody (scFv) on phage surface and selecting a phage binding to the antigen.

The phage selected on the basis of its ability to bind to the antigen can be subjected to gene analysis thereby to determine DNA sequences encoding the variable regions of the human antibody binding to the antigen.

If the DNA sequence of an scFv binding to the antigen is determined, an expression vector having this sequence can be prepared and introduced into appropriate hosts to allow them to express the human antibody (WO92/01047, WO92/20791, WO93/06213, WO93/11236, WO93/19172, WO95/01438, WO95/15388, Annu. Rev. Immunol (1994) 12, p. 433-455, and Nature Biotechnology (2005) 23 (9), p. 1105-1116).

(4-6) Method for Preparing Binding Fragment of Antibody

The method for preparing a single chain antibody is well known in the art (see e.g., U.S. Pat. Nos. 4,946,778, 5,260,203, 5,091,513, and 5,455,030). In this scFv, a heavy chain variable region and a light chain variable region are linked via a linker that prevents them from forming a conjugate, preferably a polypeptide linker (Huston, J. S. et al., Proc. Natl. Acad. Sci. U.S.A. (1988), 85, p. 5879-5883). The heavy chain variable region and the light chain variable region in an scFv may be derived from the same antibody or may be derived from different antibodies.

For example, an arbitrary single chain peptide consisting of 12 to 19 residues is used as the polypeptide linker that links these variable regions.

In order to obtain scFv-encoding DNA, of the sequences of DNA encoding the heavy chain or heavy chain variable region of the antibody and DNA encoding the light chain or light chain variable region thereof, each DNA portion encoding the whole or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the obtained fragment can be linked at its ends to the heavy and light chain DNAs, respectively.

The scFv-encoding DNA can be used thereby to prepare, according to a routine method, an expression vector containing the DNA and host cells transformed with the expression vector. In addition, the host cells can be cultured, and the scFv can be recovered from the cultures according to a routine method.

Also in order to obtain any other binding fragment of the antibody, a gene encoding the binding fragment is obtained according to the method described above and introduced into cells. The binding fragment of interest can be recovered from cultures of the cells.

The antibody of the present invention may be multimerized thereby to increase its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding thereof to streptavidin, and the introduction of a helix-turn-helix motif.

The antibody of the present invention may be a mixture of plural types of anti-LAG-3 antibodies differing in amino acid sequence, i.e., a polyclonal antibody. Examples of the polyclonal antibody can include a mixture of plural types of antibodies differing in a portion or the whole of their CDRs. Such a polyclonal antibody can be recovered from cultures of different antibody-producing cells mixed-cultured (WO2004/061104). Alternatively, separately prepared antibodies may be mixed. Antiserum, which is one embodiment of the polyclonal antibody, can be prepared by immunizing animals with the desired antigen and recovering serum from the animals according to a standard method.

Antibodies conjugated with various molecules such as polyethylene glycol (PEG) can also be used as modified forms of the antibody.

The antibody of the present invention may further be any of the conjugates formed by these antibodies with other drugs (immunoconjugates). Examples of such an antibody can include an antibody conjugated with a radioactive material or a compound having a pharmacological action (Nature Biotechnology (2005), 23, p. 1137-1146).

The antibody or the binding fragment thereof of the present invention, and the modified forms thereof as exemplified or described in (3-11), (3-14), (4-6), etc., are also called "the antibody of the present invention or molecules comprising the binding fragment thereof".

(4-7) Purification of Antibody

The obtained antibody can be purified to be homogeneous. Usual protein separation and purification methods can be used for the separation and purification of the antibody.

The antibody can be separated and purified by appropriately selected or combined approach(es), for example, chromatography columns, filters, ultrafiltration, salting out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)) though the separation and purification method is not limited thereto.

Examples of chromatography include affinity chromatography, ion-exchange chromatography, hydrophobic chromatography, gel filtration, reverse-phase chromatography, and adsorption chromatography.

These chromatography approaches can be performed using liquid-phase chromatography such as HPLC or FPLC.

Examples of columns used in affinity chromatography can include protein A, protein G, and antigen columns.

Examples of the protein A columns include Hyper D (manufactured by Pall Corp.), POROS (manufactured by Applied Biosystems, Inc.), and Sepharose F.F. (manufactured by GE Healthcare Bio-Sciences Corp.).

Also, the antibody may be purified using its binding activity against the antigen using an antigen-immobilized carrier.

(4-8) Nucleotides Encoding Antibody, Recombinant Vector, and Recombinant Cell

The present invention also provides a nucleotide encoding the antibody or the binding fragment thereof of the present invention, or the modified form thereof (hereinafter, this nucleotide is referred to as an "antibody gene"), a recombinant vector having an insert of the gene, a cell comprising the gene or the vector (hereinafter, this cell is referred to as an "antibody gene-transfected cell"), and a cell producing the antibody or the binding fragment thereof of the present invention, or the modified form thereof (hereinafter, this cell is referred to as an "antibody-producing cell").

Preferably, the antibody gene of the present invention comprises a nucleotide sequence described in any one of (a) to (e) below (hereinafter, referred to as an "antibody gene sequence"), consists of a nucleotide sequence comprising the antibody gene sequence, or consists of the antibody gene sequence:

(a) a combination of a nucleotide sequence encoding the amino acid sequence of the heavy chain of any one of the rat antibodies rLA204, rLA212, rLA225, rLA869, and rLA1264, their chimeric antibodies cLA204, cLA212, cLA225, cLA869, and cLA1264 in which the heavy chain and light chain constant regions are substituted with those of human antibodies, and their humanized antibodies hLA212_H2/L1 to hLA212_H2/L5 and LA212_H3/L1 to hLA212_H3/L5 and a nucleotide sequence encoding the amino acid sequence of the light chain thereof;

(b) a combination of a nucleotide sequence encoding the amino acid sequence of the heavy chain comprising CDRH1 to CDRH3 of any one of the rat antibodies rLA204, rLA212, rLA225, rLA869, and rLA1264, their chimeric antibodies cLA204, cLA212, cLA225, cLA869, and cLA1264 in which the heavy chain and light chain constant regions are substituted with those of human antibodies, and their humanized antibodies hLA212_H2/L1 to hLA212_H2/L5 and LA212_H3/L1 to hLA212_H3/L5 and a nucleotide sequence encoding the amino acid sequence of the light chain comprising CDRL1 to CDRL3 thereof;

(c) a combination of a nucleotide sequence encoding the amino acid sequence of the heavy chain comprising the amino acid sequence of the heavy chain variable region of any one of the rat antibodies rLA204, rLA212, rLA225, rLA869, and rLA1264, their chimeric antibodies cLA204, cLA212, cLA225, cLA869, and cLA1264 in which the heavy chain and light chain constant regions are substituted with those of human antibodies, and their humanized antibodies hLA212_H2/L1 to hLA212_H2/L5 and LA212_H3/L1 to hLA212_H3/L5 and a nucleotide sequence encoding the amino acid sequence of the light chain comprising the amino acid sequence of the light chain variable region;

(d) a nucleotide sequence that hybridizes under stringent conditions to a nucleotide consisting of a nucleotide sequence complementary to the nucleotide sequence according to any one of (a) to (c), and encodes the amino acid sequence of an antibody binding to LAG-3; and (e) a nucleotide sequence that encodes an amino acid sequence derived from the amino acid sequence according to any one of (a) to (c) by the substitution, deletion, addition, and/or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 base, and encodes an amino acid sequence of an antibody binding to LAG-3, where the antibody having an amino acid sequence encoded by the nucleotide sequence according to (d) or (e) has the properties, functions, activities, etc., described in (3-2), (3-3), and (3-8), preferably one or more of (3-4) to (3-7) in addition to the above, more preferably (3-4) and/or (3-5) in addition to the above, further more preferably (3-4) and (3-5) in addition to the above, further more preferably (3-4) and (3-5), and (3-6) and/or (3-7) in addition to the above, optimally all of (3-2) to (3-8), but the antibody gene of the present invention is not limited to the aforementioned (a) to (e).

The present invention also provides a method for producing an antibody or a binding fragment thereof, or a modified form thereof, comprising the steps of culturing antibody gene-transfected cells of the present invention and recovering an antibody or a binding fragment thereof, or a modified form thereof from the culture, as described in (4-3). The antibody or the binding fragment thereof, or the modified form thereof obtained by this production method is also included in the present invention.

5. Pharmaceutical Composition

The present invention provides a pharmaceutical composition comprising an anti-LAG-3 antibody or a binding fragment thereof, or a modified form thereof.

The pharmaceutical composition of the present invention is useful for treatment and/or prevention of various diseases (which will be hereinafter referred to as "diseases associated with LAG-3 positive cells") initiated or exacerbated by LAG-3 positive activated T cells, that is, effector T cells, memory T cells, or regulatory T cells, especially such as autoimmune diseases, rejection of transplants, allergic diseases, malignant tumors, and chronic infections.

Examples of the causes for the initiation or exacerbation of such diseases to be treated or prevented can include various genetic factors and environmental factors (including pharmaceutical agents, diets, light rays, etc.), or combined effects of these factors.

Examples of such autoimmune diseases can include rheumatoid arthritis, ankylosing spondylitis, systemic lupus erythematosus, scleroderma, polymyositis, dermatomyositis, inclusion body myositis, and idiopathic inflammatory myopathy including immune-mediated necrotizing myopathy as autoimmune diseases of connective tissue/musculoskeletal system, aplastic anemia and idiopathic thrombocytopenic purpura as autoimmune diseases of the blood system, Crohn's disease and ulcerative colitis as autoimmune diseases of the digestive system, multiple sclerosis and myasthenia gravis as autoimmune diseases of the nervous system, uveitis, keratitis, and Sjogren's syndrome as autoimmune diseases of the visual system, Behcet's disease and Wegener's granulomatosis as autoimmune diseases of the vascular system, psoriasis, pemphigus, Stevens-Johnson syndrome, and vitiligo as autoimmune diseases of the epidermal system, chronic obstructive pulmonary disease and interstitial pneumonia as autoimmune diseases of the respiratory system, type 1 diabetes, autoimmune thyroiditis, Graves' disease, and Hashimoto's thyroiditis as autoimmune diseases of the endocrine system, and other autoimmune diseases such as autoimmune hepatitis and nephritis due to an immune disorder, preferably such diseases with the presence of LAG-3 positive cells in disease sites and/or lymphoid tissues.

Examples of the rejection of transplants can include rejection and host-versus-graft reaction in transplantation of organs such as the heart, the kidney, the liver, the bone marrow, and the skin or tissues thereof, and graft-versus-host disease caused by transplantation of hematopoietic cells in the bone marrow, the peripheral blood, and the umbilical cord blood, etc., preferably, such reactions, symptoms, and diseases with the presence of LAG-3 positive cells in the site and/or the lymphoid tissues relating to the rejection.

Examples of the allergic diseases can include atopic dermatitis, asthma, anaphylaxis, anaphylactoid reaction, food allergy, rhinitis, otitis media, drug reaction, insect sting reactions, plant reaction, latex allergy, conjunctivitis, urticaria, and contact dermatitis, preferably, such diseases with the presence of LAG-3 positive cells in disease sites and/or lymphoid tissues.

Examples of the malignant tumors can include breast cancer, lung cancer, skin cancer (including melanoma), leukemia, lymphoma, multiple myeloma, myelodysplastic syndrome, glioma, liver cancer, colorectal cancer, stomach cancer, pancreatic cancer, kidney cancer, prostate cancer, head and neck cancer, cervical cancer, endometrial cancer, ovarian cancer, osteosarcoma, soft tissue sarcoma, and gastrointestinal stromal tumor, preferably, such cancers and such malignant tumors with the presence of LAG-3 positive cells.

Examples of the chronic infections can include infections by bacteria, viruses, fungi, and other microorganisms, preferably, such diseases with the presence of LAG-3 positive cells.

In the present invention, the treatment or prevention of a disease includes, but is not limited to, the prevention of the onset of the disease, preferably the disease in an individual expressing the LAG-3 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, etc.

The pharmaceutical composition of the present invention can comprise a therapeutically or prophylactically effective amount of the anti-LAG-3 antibody or the binding fragment of the antibody, and pharmaceutically acceptable diluents, vehicles (carriers), solubilizers, emulsifiers, preservatives, and/or additives.

The "therapeutically or prophylactically effective amount" means an amount that exerts therapeutic or prophylactic effects on a particular disease by means of a particular dosage form and administration route and has the same meaning as a "pharmacologically effective amount".

The pharmaceutical composition of the present invention may comprise materials for changing, maintaining, or retaining pH, osmotic pressure, viscosity, transparency, color, isotonicity, sterility, or the stability, solubility, sustained release, absorbability, permeability, dosage form, strength, properties, shape, etc., of the composition or the antibody comprised therein (hereinafter, referred to as "pharmaceutical materials"). The pharmaceutical materials are not particularly limited as long as the materials are pharmacologically acceptable. For example, no or low toxicity is a property preferably possessed by these pharmaceutical materials.

Examples of pharmaceutical materials can include, but are not limited to, amino acids such as glycine, alanine, glutamine, asparagine, histidine, arginine, or lysine, antibacterial agents, anti-oxidizing agents such as ascorbic acid, sodium sulfate, or sodium bisulfite, buffers such as phosphophate, citrate, borate buffers, sodium bicarbonate, and tris-hydrochloric acid (Tris-HCl) solution, fillers such as mannitol and glycine, chelating agents such as ethylenediaminetetraacetic acid (EDTA), complexing agents such as caffeine, polyvinyl pyrrolidine, β-cyclodextrin, and hydroxypropyl-β-cyclodextrin, extenders such as glucose, mannose, or dextrin, monosaccharides, disaccharides, other carbohydrates such as glucose, mannose, and dextrin, coloring agents, flavoring agents, diluents, emulsifiers, preservatives such as hydrophilic polymer, e.g., polyvinyl pyrrolidine, low molecular weight polypeptide, salt-forming counterion, benzalkonium chloride, benzoic acid, salicylic acid, thimerosal, phenethyl alcohol, methylparaben, propylparaben, chlorhexidine, sorbic acid, or hydrogen peroxide, solvents such as glycerin, propylene glycol, or polyethylene glycol, sugar alcohols such as mannitol or sorbitol, suspending agents, surfactants such as PEG, sorbitan ester, polysorbates, e.g., polysorbate 20 and polysorbate 80, triton, tromethamine, lecithin, or cholesterol, stability enhancers such as sucrose and sorbitol, elasticity enhancers such as sodium chloride, potassium chloride, mannitol, and sorbitol, transport agents, diluents, excipients, and/or pharmaceutical additives.

The amount of these pharmaceutical materials added is 0.001 to 1000 times, preferably 0.01 to 100 times, more preferably 0.1 to 10 times the weight of the anti-LAG-3 antibody or the binding fragment thereof, or the modified form thereof.

An immunoliposome comprising the anti-LAG-3 antibody or binding fragment thereof, or the modified form of the antibody or binding fragment encapsulated in a liposome, or a modified antibody form comprising the antibody conjugated with a liposome (U.S. Pat. No. 6,214,388, etc.) is also included in the pharmaceutical composition of the present invention.

The excipients or vehicles (carriers) are usually liquid or solid and are not particularly limited as long as they are materials used for oral or parenteral administration such as injectable water, saline, artificial cerebrospinal fluids, etc. Examples of saline can include neutral saline and serum albumin-containing saline.

Examples of buffers can include a Tris buffer adjusted to bring the final pH of the pharmaceutical composition to 7.0 to 8.5, an acetate buffer adjusted to bring the final pH thereof to 4.0 to 5.5, a citrate buffer adjusted to bring the final pH thereof to 5.0 to 8.0, and a histidine buffer adjusted to bring the final pH thereof to 5.0 to 8.0.

The pharmaceutical composition of the present invention is a solid, a liquid, a suspension, or the like. Another example of the pharmaceutical composition of the present invention can include freeze-dried preparations. The freeze-dried preparations can be formed using an excipient such as sucrose.

The administration route of the pharmaceutical composition of the present invention may be any of enteral administration, local administration, and parenteral administration. Examples thereof can include intravenous administration, intraarterial administration, intramuscular administration, intradermal administration, hypodermic administration, intraperitoneal administration, transdermal administration, intraosseous administration, intraarticular administration, and the like.

The composition of the pharmaceutical composition can be determined according to the administration method, the binding affinity of the antibody for the LAG-3 protein, etc. The anti-LAG-3 antibody or the binding fragment thereof of the present invention, or the modified form thereof having higher affinity (lower KD value) for the LAG-3 protein can exert its efficacy at a lower dose.

The dose of the anti-LAG-3 antibody of the present invention is not limited as long as the dose is a pharmacologically effective amount. The dose can be appropriately determined according to the species of an individual, the type of disease, symptoms, sex, age, pre-existing conditions, the binding affinity of the antibody for the LAG-3 protein or its biological activity, and other factors. A dose of usually 0.01 to 1000 mg/kg, preferably 0.1 to 100 mg/kg, can be administered once every day to every 180 days or twice or three or more times a day.

Examples of the form of the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The pharmaceutical composition comprising the anti-LAG-3 antibody or the binding fragment thereof, or the modified form thereof as an active ingredient can be administered concurrently with or separately from an additional drug. For example, the pharmaceutical composition comprising the anti-LAG-3 antibody or the binding fragment thereof as an active ingredient may be administered after administration of the additional drug, or the additional drug may be administered after administration of the pharmaceutical composition. Alternatively, the pharmaceutical composition and the additional drug may be administered concurrently.

Examples of the additional drug that is used in combination with the pharmaceutical composition of the present invention can include antifolates, calcineurin inhibitors, corticosteroids, antithymocyte globulins, nucleic acid antimetabolites, nucleic acid synthesis inhibitors, biologics targeting cell surface antigens, and biologics targeting cytokines or cytokine receptors, and these are preferable for treatment or prevention of autoimmune diseases and/or rejection of transplants. Examples of the additional drug can include Methotrexate that is an antifolate, Cyclosporin and Tacrolimus that are calcineurin inhibitors, Methylprednisolone and Prednisolone that are corticosteroids, Cyclophosphamide and Azathioprine that are nucleic acid synthesis inhibitors, Zetbulin, Lymphoglobuline, and Thymoglobulin that are antithymocyte globulins, Mycophenolate mofetil that is a nucleic acid antimetabolite, Alemtuzumab, Rituximab, Abatacept, and Denosumab that are biologics targeting cell surface antigens, and Adalimumab, Infliximab, Etanercept, and Tocilizumab that are biologics targeting cytokines or cytokine receptors. Further, the pharmaceutical composition of the present invention can be used also for treatment or prevention of autoimmune diseases and/or rejection of transplants in combination with intravenous immunoglobulin (IVIg), plasma exchange, etc. Such additional drugs and therapies can be combined with the pharmaceutical composition of the present invention also in treating or preventing diseases other than the autoimmune diseases and the rejection of transplants.

Examples of the drugs and therapies that can be combined with the pharmaceutical composition of the present invention in treating or preventing malignant tumors can include anticancer agents such as various molecular targeted drugs, chemotherapeutic agents, radiation therapies, and various cancer immunotherapeutic agents typified by anti-PD-1 antibody, anti-PD-L1 antibody, and anti-CTLA-4 antibody.

One of these additional drugs and therapies, or two, three, or more of them can be administered or received. These are collectively referred to as "combined use of the additional drug" or "combination with the additional drug". The present invention also encompasses the pharmaceutical composition of the present invention comprising such an additional drug or used in combination with another therapy, in addition to the antibody or the binding fragment thereof of the present invention, or the modified form thereof, as an aspect of the "combined use of the additional drug" or "combination with the additional drug".

The present invention also provides a method for treating or preventing diseases associated with LAG-3 positive cells such as autoimmune diseases, use of the antibody of the present invention for preparing a pharmaceutical composition for treatment or prevention of the diseases, and use of the antibody of the present invention for treating or preventing the diseases. The present invention also encompasses a kit for treatment or prevention comprising the antibody of the present invention.

6. Reagent

The antibody or the binding fragment thereof of the present invention, or the modified form thereof is also useful as a reagent. Such a reagent is used for testing or diagnosis as mentioned above, for research, and for any other use.

EXAMPLES

Hereinafter, the present invention will be described further specifically with reference to the Examples. However, the present invention is not intended to be limited to them.

Procedures related to gene manipulation in the Examples below were performed according to the methods described in "Molecular Cloning" (Sambrook, J., Fritsch, E. F. and Maniatis, T., Cold Spring Harbor Laboratory Press, 1989) or the methods described in other experimental manuals used by those skilled in the art, or using commercially available reagents or kits according to the instruction manuals, unless otherwise specified.

Example 1. Preparation of Rat Anti-Human LAG-3 Antibody

1)-1 Immunization

A mutant deficient in the 1st and 2nd domains (region of positions 23 to 262) from the N terminus out of four extracellular immunoglobulin-like domains of human LAG-3 (SEQ ID No: 86: FIG. 101) was cloned into pcDNA3.1 (Life Technologies Corp.) to prepare a large amount of expression plasmid pcDNA3.1-hLAG-3_D3D4 using EndoFree Plasmid Giga Kit (Qiagen N.V). After pretreatment of both lower legs of a female WKY/Izm rat (Japan SLC, Inc.) with Hyaluronidase (Sigma-Aldrich), the pcDNA3.1-hLAG-3_D3D4 was injected intramuscularly to the same sites. Subsequently, using ECM830 (BTX Global Logistics), the same sites were subjected to in vivo electroporation using a two-needle electrode. Once in two weeks, the same in vivo electroporation was repeated 3 or 5 times in total, and thereafter lymph nodes of the rat were collected to be used for development of hybridomas.

1)-2 Hybridoma Preparation

The lymph node cells or the spleen cells were electrically fused with mouse myeloma SP2/0-ag14 cells using the Hybrimune Hybridoma Production System (manufactured by Cyto Pulse Sciences, Inc.). The fused cells were diluted with ClonaCell-HY Selection Medium D (manufactured by StemCell Technologies Inc.) and cultured. Hybridoma colonies that appeared were recovered to prepare monoclonal hybridomas. Each hybridoma colony thus recovered was cultured, and the obtained hybridoma culture supernatant was used to screen for an anti-LAG-3 antibody-producing hybridoma.

1)-3 Antibody Screening by Cell-ELISA

Expression plasmids (pcDNA3.1/hLAG-3 and pcDNA3.1/cynoLAG-3) constructed by cloning human or cynomolgus monkey LAG-3 into pcDNA3.1 or a control plasmid was introduced into HEK293 cells using Lipofectamine 2000 (manufactured by Life Technologies Corp.), and the cells were cultured in a 96-well microplate (manufactured by Corning Inc.) overnight under conditions of 37° C. and 5% $CO_2$ in a DMEM medium containing 10% FBS. After removal of the culture supernatant, each hybridoma culture supernatant was added, and the plate was left standing at 4° C. for 1 hour. The cells in the wells were washed once with PBS containing 5% FBS. Then, Anti-Rat IgG-Peroxidase antibody produced in rabbit (manufactured by Sigma-Aldrich Corp.) diluted 500-fold with PBS containing 5% FBS was added thereto, and the plate was left standing at 4° C. for 1 hour. The cells in the wells were washed 5 times with PBS containing 5% FBS. Then, an OPD chromogenic solution (prepared by dissolving o-phenylenediamine dihydrochloride (manufactured by Wako Pure Chemicals Industries, Ltd.) and $H_2O_2$ at concentrations of 0.4 mg/mL and 0.6% (v/v), respectively, in the OPD solvent (0.05 M trisodium citrate and 0.1 M disodium hydrogen phosphate dodecahydrate, pH 4.5)) was added thereto at 25 µL/well. Color reaction was performed with occasional stirring and stopped by adding 25 µL/well of 1 M HCl. Then, the absorbance was measured at 490 nm using a plate reader (ENVISION; PerkinElmer, Inc.). In order to select hybridomas producing an antibody that specifically binds to LAG-3 expressed on the cell membrane surface, hybridomas that yielded a culture supernatant exhibiting higher absorbance for the LAG-3 expression vector-transfected HEK293 cells than for the control plasmid-transfected HEK293 cells free from the LAG-3 gene were selected as anti-LAG-3 antibody production-positive hybridomas.

1)-4 Antibody Screening by Flow Cytometry

It was further confirmed by flow cytometry that the antibody produced by the hybridomas determined to be positive by the Cell-ELISA in Example 1)-3 binds to PHA (phytohemagglutinin) activated human T cells (PHA blasts), more physiological cells expressing LAG-3. To human PBMCs stimulated with 2 µg/mL of PHA (manufactured by Sigma-Aldrich) for three days, was added a hybridoma culture supernatant for suspension, followed by reaction at 4° C. for 30 minutes. After washing with a FACS buffer (PBS, 0.1% BSA, and 0.1% sodium azide), a secondary antibody such as an Anti-Rat IgG PE conjugate (manufactured by Jackson ImmunoResearch Laboratories, Inc.) diluted 200-fold with a FACS buffer comprising LIVE/DEAD Fixable Dead Cell Stain Kit-near-IR fluorescent reactive dye (manufactured by Invitrogen Corp.) was added thereto for suspension, followed by standing at 4° C. for 30 minutes. After washing with a FACS buffer, the cells were resuspended in PBS containing 1 to 2% paraformaldehyde, followed by detection using a flow cytometer (Cantoll: manufactured by Becton, Dickinson and Company or FC500: manufactured by Beckman Coulter Inc.). The data was analyzed using FlowJo (manufactured by Tree Star Inc). After removal of LIVE/DEAD Fixable Dead Cell Stain Kit-near-IR fluorescent reactive dye-positive dead cells by gating, a histogram of the fluorescence intensity of living cells was plotted.

1)-5 Screening by ADCC Assay

1)-5-1 Preparation of Target Cells

293FT cells (Invitrogen Corp.) were transfected with pLenti6/V5-GW/lacZ, and ViraPower™ Packaging Mix (Invitrogen Corp.) according to the attached protocols to prepare a recombinant lentivirus to express the β-galactosidase gene. 293T cells were infected by the obtained recombinant lentivirus according to the protocol of ViraPower Lentiviral Expression Systems (Invitrogen Corp). Virus-infected cells were selected using 10 µg/mL Blasticidin (Invitrogen Corp.) to obtain a line stably expressing β-galactosidase. An expression plasmid of the full-length human LAG-3 was introduced into the 293T cells stably expressing the β-galactosidase (hereinafter, referred to as 293T-lacZ) using Lipofectamine 2000 (manufactured by Invitrogen Corp.), and the cells were cultured for 1 day and then dissociated and recovered using TrypLExpress (manufactured by Invitrogen Corp). The cells were washed twice with phenol red-free RPMI1640 containing 5% FBS (hereinafter, referred to as a "medium for ADCC"). The number of live cells was counted by the trypan blue dye exclusion test. The cells were resuspended to $1\times10^5$ cells/ml in a medium for ADCC and used as target cells.

1)-5-2 Preparation of Effector Cells

PBMCs were separated from human peripheral blood by Ficoll centrifugation, and a suspension adjusted to a live cell density of $1.2\times10^6$ cells/mL in a medium for ADCC was used as effector cells.

1)-5-3 ADCC Assay

To a 96-well U-bottom microplate containing 50 µL/well of the hybridoma culture supernatant, was added 50 µL/well of the target cells of 1)-5-1, followed by standing at 4° C. for 30 minutes. After adding 150 µL/well of a medium for ADCC thereto, followed by stirring, the plate was centrifuged at room temperature at 1200 rpm for 5 minutes to remove 200 µL/well of the supernatant. Then, 125 µL/well of the effector cells of 1)-5-2 was added thereto, followed by centrifugation at room temperature at 1200 rpm for 5 minutes. Thereafter, the cells were cultured overnight under conditions of 37° C. and 5% $CO_2$. On the next day, 50 µL of the supernatant was recovered into a black plate (manufactured by Corning Inc). 50 µL of a β-Glo assay system (manufactured by Promega Corp.) solution was added thereto. The luminescence intensity was measured using a plate reader (ENVISION; manufactured by PerkinElmer, Inc). The percentage of cells lysed by ADCC activity was calculated according to the following formula.

Percentage of cells lysed (%)=$(A-B)/(C-B)\times100$

A: Count of each sample well

B: Average of spontaneous release (antibody non-added wells) counts (n=3)

When adding the antibody, 50 µL of a medium for ADCC was added thereto. Except for that, the same operation as in the sample well was performed.

C: Average of maximum release (wells containing target cells lysed with a surfactant) counts (n=3)

When adding the antibody and adding the effector cells, 50 µL and 75 µL of a medium for ADCC were added thereto respectively. For the assay, 175 µl of the β-Glo assay system solution was added to each well containing the target cells and mixed therewith. A 100 µl aliquot thereof was added to a black plate to carry out the assay.

1)-6 Screening by LAG-3/MHC Class II Binding Test

It was conducted according to the previous report (Non Patent Literature 8). That is, 20 µL/well of LAG-3-Fc (manufactured by R&D Systems, Inc.) diluted with RPMI1640 containing 10% FBS to 25 nM was added to a 96-well U-bottom microplate, and 20 µL/well of the hybridoma culture supernatant was added thereto, followed by stirring and standing at 4° C. for 20 minutes. Then, 10 µL/well ($2.5\times10^5$ cells/well) of Raji cells, which endogenously highly express MHC class II molecules, was added thereto, followed by stirring and standing at 4° C. for a further 30 minutes. The cells were washed twice with PBS or a FACS buffer, then an Anti-Human IgG PE conjugate (manufactured by Jackson ImmunoResearch Laboratories, Inc.) diluted 200-fold with a FACS buffer was added thereto for suspension, followed by standing at 4° C. for 20 minutes. After washing with PBS or a FACS buffer, the cells were resuspended in PBS containing 1 to 2% paraformaldehyde, followed by detection using a flow cytometer (Cantoll: manufactured by Becton, Dickinson and Company or FC500: manufactured by Beckman Coulter Inc). The data was analyzed using FlowJo (manufactured by Tree Star Inc.), and the percentage of inhibition was calculated by the following formula.

Percentage of inhibition (%)=100−(A−B)/(C−B)×100

A: Mean fluorescence intensity of each sample well
B: Mean fluorescence intensity of background
When adding LAG-3-Fc and the antibody, 20 μL of a medium was added each time. Except for that, the same operation as in the sample well was performed.
C: Mean fluorescence intensity of maximum binding
When adding the antibody, 20 μL of a medium was added thereto.

1)-7 Purification of Monoclonal Antibody

A rat anti-human LAG-3 monoclonal antibody was purified from the hybridoma culture supernatant. That is, the hybridoma culture supernatant was first applied to a ProteinG column (manufactured by GE Healthcare) equilibrated with PBS. After washing the column with PBS, antibody-containing fractions were collected by elution with a 0.1 M glycine/hydrochloric acid aqueous solution (pH 2.7). To the collected fractions, was added 1M Tris-HCl (pH 9.0) for adjustment to pH 7.0 to 7.5, and thereafter Centrifugal UF Filter Device VIVASPIN20 (fraction molecular weight UF30K, manufactured by Sartorius AG) was used to replace the buffer with PBS and concentrate the antibody to adjust to 2 mg/mL or more. Finally, filtration with a Minisart-Plus filter (manufactured by Sartorius AG) was performed to give a purified sample.

Example 2. In Vitro Evaluation of Rat Anti-Human LAG-3 Antibodies (rLA204, rLA212, rLA225, rLA869, and rLA1264)

2)-1 Binding Activity of the Obtained Rat Anti-LAG-3 Antibodies (rLA204, rLA212, rLA225, rLA869, and rLA1264) to Human Activated T Cells The binding activity of the rat anti-human LAG-3 antibodies rLA204, rLA212, rLA225, rLA869, and rLA1264 purified by the method described in Example 1)-7 to human activated T cells was investigated. As shown in FIG. 1, all the rat anti-human LAG-3 antibodies bound to PHA blasts prepared as in vitro activated human T cells in a concentration-dependent manner.

2)-2 ADCC Activity of Obtained Rat Anti-LAG-3 Antibodies (rLA204, rLA212, rLA225, rLA869, and rLA1264)

The ADCC activity of the purified rat anti-human LAG-3 antibodies rLA204, rLA212, rLA225, rLA869, and rLA1264 was investigated by the following method. To a 96-well U-bottom microplate containing 50 μL/well of the antibody solution, was added 50 μL/well of the target cells (which will be hereinafter referred to as 293T-lacZ/hLAG-3 cells) of Example 1)-5-1, followed by standing at 4° C. for 30 minutes. Then, 75 μL/well of effector cells prepared as in Example 1)-5-2 (which was however suspended to 2×10⁶ cells/mL) was added thereto, followed by centrifugation at room temperature at 1200 rpm for 5 minutes, and thereafter the cells were cultured overnight under conditions of 37° C. and 5% CO$_2$. On the next day, 50 μl of the supernatant was recovered into a black plate (manufactured by Corning Inc). A solution of β-Glo assay system (manufactured by Promega Corp.) was added thereto at 50 μl/well. The luminescence intensity was measured using a plate reader (ENVISION; manufactured by PerkinElmer, Inc). The percentage of cells lysed by ADCC activity was calculated according to the following formula.

Percentage of cells lysed (%)=(A−B)/(C−B)×100

A: Count of each sample well
B: Average of spontaneous release (antibody non-added wells) counts (n=3)
When adding the antibody, 50 μL of a medium for ADCC was added thereto. Except for that, the same operation as in the sample well was performed.
C: Average of maximum release (wells containing target cells lysed with a surfactant) counts (n=3)
When adding the antibody and adding the effector cells, 50 μL and 75 μL of a medium for ADCC were added thereto respectively. For the assay, 175 μl of the β-Glo assay system solution was added to each well containing the target cells and mixed therewith. A 100 μl aliquot thereof was added to a black plate to carry out the assay.

Figure 2:
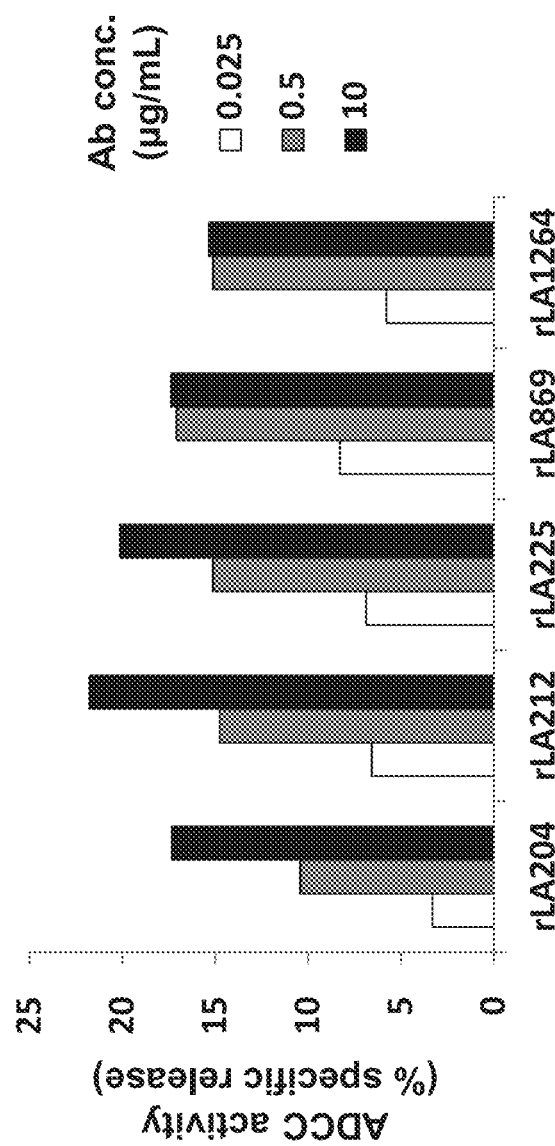
FIG. 2 is a diagram showing ADCC activity of rat anti-LAG-3 antibodies (rLA204, rLA212, rLA225, rLA869, and rLA1264). 293T-lacZ cells expressing human LAG-3 were used as target cells, and human PBMCs were used as effector cells.

As shown in FIG. 2, all the rat anti-human LAG-3 antibodies showed a concentration-dependent in vitro ADCC activity on the cells expressing human LAG-3. In contrast, these antibodies showed no ADCC activity on the 293T-lacZ cells into which the human LAG-3 gene was not transfected, so the action was specific.

Figure 3:
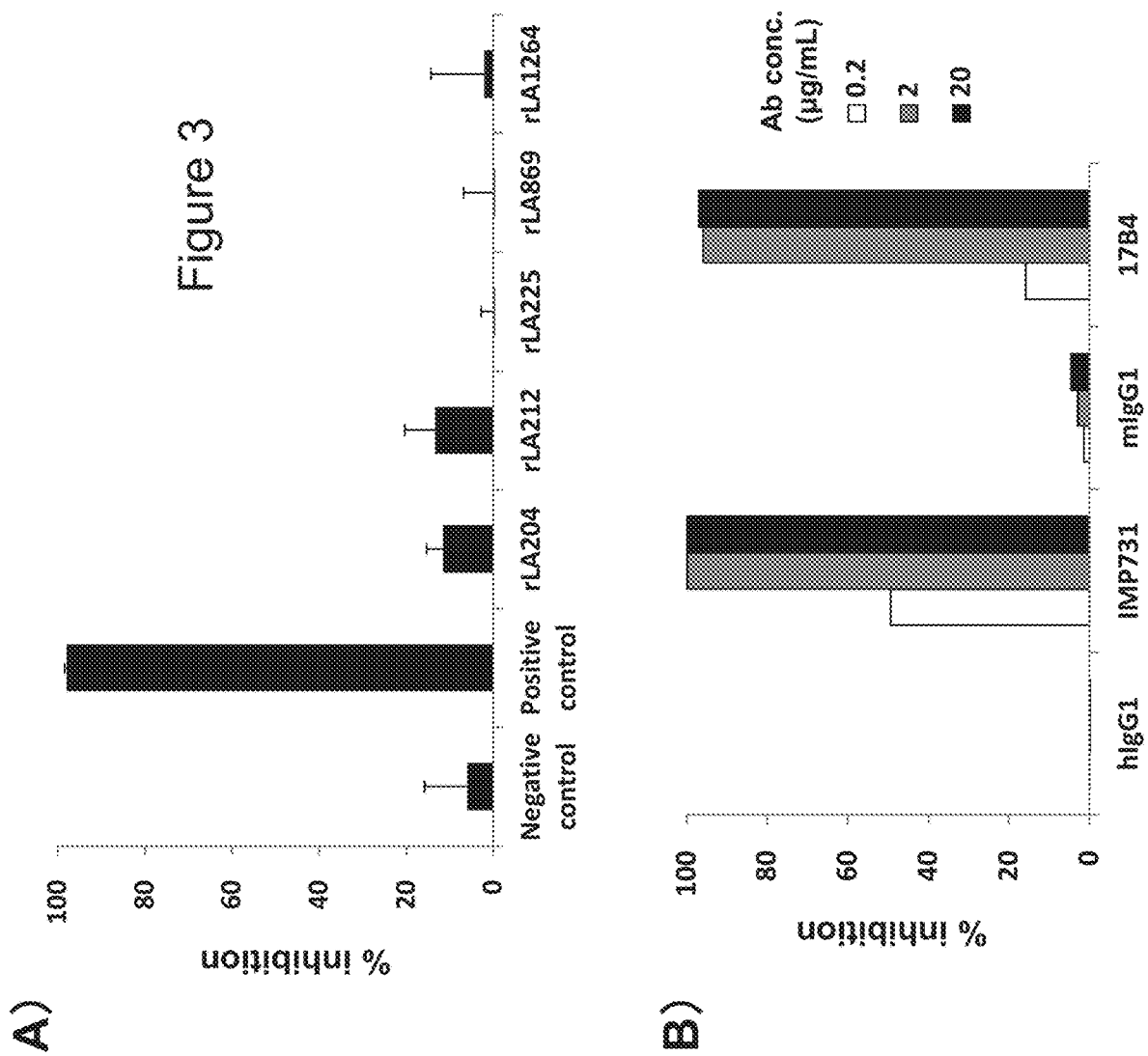
FIG. 3A is a diagram showing the inhibitory activity of the rat anti-LAG-3 antibodies (rLA204, rLA212, rLA225, rLA869, and rLA1264) in a LAG-3/MHC class II binding test. Rat IgG2b was used as a negative control, and a rat anti-LAG-3 antibody that has been separately developed and recognizes domain 1 of LAG-3 was used as a positive control, respectively. Each antibody was evaluated at 10 µg/mL.
FIG. 3B is a diagram showing that human chimeric anti-LAG-3 antibody IMP731, which is a known antibody, exhibits inhibitory activity in the LAG-3/MHC class II binding test. 17B4, which is a commercially available mouse anti-human LAG-3 antibody, also exhibited inhibitory activity.

2)-3 Investigation on Inhibitory Activity of Obtained Rat Anti-LAG-3 Antibodies (rLA204, rLA212, rLA225, rLA869, and rLA1264) in LAG-3/MHC Class II Binding Test It was investigated by the LAG-3/MHC class II binding test according to Example 1)-6 whether the purified anti-LAG-3 antibodies (rLA204, rLA212, rLA225, rLA869, and rLA1264) had an inhibitory activity against the binding of LAG-3 to MHC class II molecules, which were reported to be its ligands. As shown in FIG. 3A, the results revealed that all the 5 clones of antibodies showed almost no inhibitory activity in the LAG-3/MHC class II binding test and had no influence on the binding to MHC class II molecules, which is considered to be necessary for LAG-3 to exert T cell suppression function. In contrast, as shown in FIG. 3B, the human chimeric anti-LAG-3 antibody IMP731 (Patent Literature 1) that is a conventional antibody in the Citation List showed a powerful inhibitory activity in a concentration-dependent manner in the LAG-3/MHC class II binding test.

2)-4 Investigation on Inhibitory Activity of Obtained Rat Anti-LAG-3 Antibodies (rLA204, rLA212, rLA225, rLA869, and rLA1264) in 293T-hLAG-3/Raji Cell Adhesion Test In the LAG-3/MHC class II binding test according to Example 2)-3, binding of secondary antibody Anti-Human IgG PE conjugate for detecting binding of LAG-3-Fc to Raji cells could be inhibited by steric hindrance caused by binding of the anti-LAG-3 antibody to LAG-3-Fc, and thus the possibility of apparently showing a low fluorescence intensity cannot be completely excluded, despite that the antibody does not directly inhibit the binding of LAG-3/MHC class II actually. Therefore, as an evaluation system without using a secondary antibody for detection, the following 293T-hLAG-3/Raji cell adhesion test system was constructed to evaluate the antibody.

Human LAG-3 expression plasmid pcDNA3.1/hLAG-3 was introduced into 293T cells using Lipofectamine 2000 (manufactured by Life Technologies Corp.), and the cells were inoculated onto a BioCoat Poly-D-Lysine-coated 96-well microplate (manufactured by Becton, Dickinson and Company) and cultured overnight. Meanwhile, Raji cells were labeled in a medium (RPMI1640 containing 10% FBS) with fluorescent dye BCECF-AM (manufactured by DOJINDO LABORATORIES, used at 10 μM) at 37° C. for 1 hour, followed by washing and then suspending in a medium to 1.6×10⁶ cells/mL. After the transfection, the medium of the cells (293T-hLAG-3 cells) cultured overnight was removed, and 50 µL/well of a medium and 25 µL/well of an antibody solution were added thereto, followed by pre-incubation at 37° C. for 30 minutes. Thereafter, 25 µL/well of the BCECF-AM labeled Raji cells was added thereto, followed by centrifugation at 900 rpm for 30 seconds and incubation at 37° C. for 1 hour. After the reaction, the well was washed with medium two to three times to remove nonadherent cells, and the cells were lysed in 100 µL/well of a Tris buffer (25 mM, pH 8.0) containing 0.1% NP-40, to measure the fluorescence intensity of the well with a plate reader (ENVISION: manufactured by PerkinElmer Inc). The percentage of inhibition was calculated by the following formula.

Percentage of inhibition (%)=100−(A−B)/(C−B)×100

Figure 4:
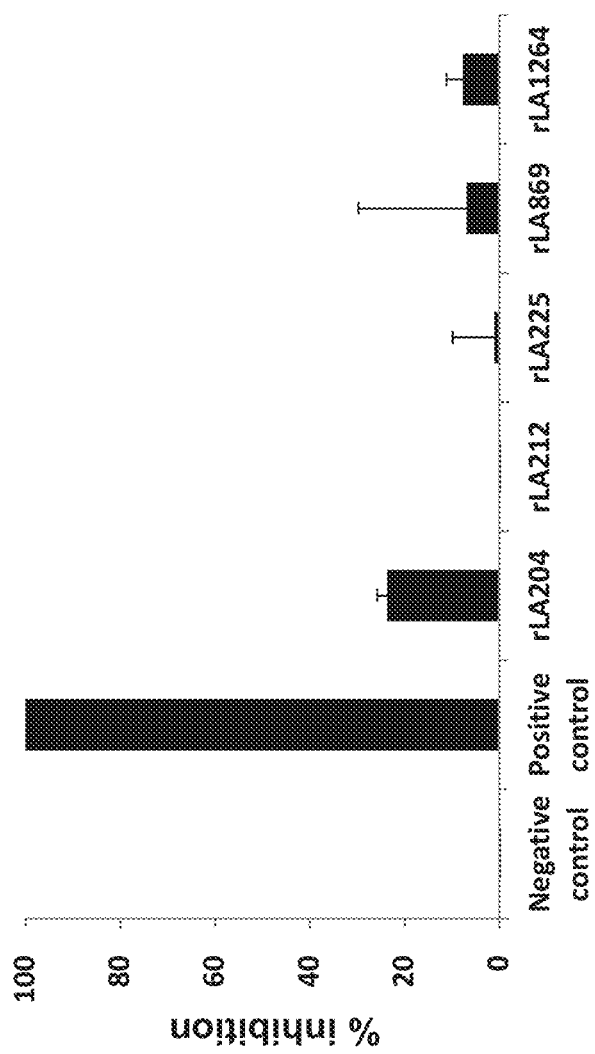
FIG. 4 is a diagram showing the inhibitory activity of the rat anti-LAG-3 antibodies (rLA204, rLA212, rLA225, rLA869, and rLA1264) in a 293T-hLAG-3/Raji cell adhesion test. Rat IgG2b was used as a negative control, and the rat anti-LAG-3 antibody (clone 6D7) that was developed in Example 2)-6 and recognized domain 1 of LAG-3 was used as a positive control, respectively. Each antibody was evaluated at 10 µg/mL.

A: Fluorescence intensity of each sample well
B: Fluorescence intensity of background
When adding the Raji cells and the antibody, a medium was added thereto. Except for that, the same operation as in the sample well was performed.
C: Fluorescence intensity of maximum binding
When adding the antibody, a medium was added thereto.
As shown in FIG. 4, the results revealed that all the purified rat anti-LAG-3 antibodies rLA204, rLA212, rLA225, rLA869, and rLA1264 showed almost no inhibitory activity in the 293T-hLAG-3/Raji cell adhesion test, further supporting the notion that the antibodies had no influence on binding to MHC class II molecules, which is considered to be necessary for LAG-3 to exert T cell suppression function. In contrast, the human chimeric anti-LAG-3 antibody IMP731 (Patent Literature 1) that is a conventional antibody in the Citation List showed a powerful inhibitory activity with an inhibition percentage of 90% at a concentration of 10 µg/mL in this test.

2)-5 Identification of Epitope of Obtained Rat Anti-LAG-3 Antibodies (rLA204, rLA212, rLA225, rLA869, and rLA1264)

Based on the fact that the rat anti-LAG-3 antibodies rLA204, rLA212, rLA225, rLA869, and rLA1264 are antibodies developed using a mutant deficient in the 1st and 2nd domains (which will be hereinafter referred to respectively as domains 1 and 2) from the N terminus out of four immunoglobulin-like domains present in the extracellular region of LAG-3 as an immunogen, in order to reveal which of the remaining 3rd and 4th domains (which will be hereinafter referred to respectively as domains 3 and 4) from the N terminus these antibodies bind to, binding of the obtained rat anti-LAG-3 antibodies to cells expressing the domains 3 and 4, or only the domain 4, was investigated by flow cytometry.

Each expression plasmid (cloned into pcDNA3.1) of either domain 3 and onwards (263-525) or domain 4 and onwards (353-525) of human LAG-3 with a FLAG tag sequence (DYKDDDDK) added to the N terminus was introduced into HEK293T cells using Lipofectamine 2000 (manufactured by Life Technologies Corp.), and the cells were cultured for 1 day and then recovered, to investigate the binding activity of the antibodies by flow cytometry according to the method described in Example 1)-4. As a result, all the purified rat anti-LAG-3 antibodies rLA204, rLA212, and rLA225 bound to the cells expressing the construct containing domains 3 and 4, whereas none of them bound to the cells expressing the construct containing only domain 4, as shown in FIG. 5A. These results revealed that all the obtained rat anti-LAG-3 antibodies rLA204, rLA212, and rLA225 bound to domain 3 out of the four immunoglobulin-like domains present in the extracellular region of LAG-3.

The same type of experiment using a hybridoma culture supernatant revealed that the obtained rat anti-LAG-3 antibodies rLA869 and rLA1264 also bound to domain 3.

FIG. 5B shows the results of investigating the binding domain of the human-chimeric anti-human LAG-3 antibody IMP731 that is a conventional antibody in the Citation List by the same method. In addition to the two types of constructs in FIG. 5A, expression plasmids were used of domain 2 and onwards (amino acid positions 173-525 of human LAG-3 amino acid sequence in SEQ ID No: 86, FIG. 101) of human LAG-3 with a FLAG tag sequence (DYKDDDDK) added to the N terminus and the full length of human LAG-3 (both were constructed using pcDNA3.1; the nucleotide sequence encoding the amino acid sequence of human LAG-3 is described in SEQ ID No: 85, FIG. 100). Both the IMP731 and the rat anti-human LAG-3 antibody clone 6D7 developed in Example 2)-6 bound to the cells expressing the full length of human LAG-3 but did not bind to the mutants (FLAG-D2D3D4, FLAG-D3D4, and FLAG-D4) deficient in domain 1, thereby revealing that they bind to domain 1. That is, it revealed that the obtained rat anti-LAG-3 antibodies rLA204, rLA212, rLA225, rLA869, and rLA1264 binding to domain 3 out of the four immunoglobulin-like domains present in the extracellular region of LAG-3 recognize an epitope different from IMP731 which binds to domain 1.

2)-6 Obtaining Rat Anti-Human LAG-3 Antibody Using Purified LAG-3 Protein as Immunogen As an alternative immunization method to Example 1)-1, rat anti-human LAG-3 antibodies were obtained using a purified LAG-3 protein as an immunogen. An emulsion formed by mixing a protein with a His tag added to the C terminus of the extracellular region (1-450) of human LAG-3 with Freund's Complete Adjuvant (manufactured by Wako Pure Chemical Industries, Ltd.) (at a volume ratio of 1:2) was administered to the tail bases of 8 week-old female WKY/Izm rats (Japan SLC, Inc.) in an amount of 200 µg per mouse. Three weeks later, only an antigen protein was administered to the tail bases in an amount of 200 µg per mouse, and two further weeks later, lymph nodes were collected to develop hybridomas by the method of Example 1)-2. Screening by the methods of Example 1)-3 and 1)-4, etc., and analysis of the obtained monoclonal antibody epitope by the method of Example 2)-5 revealed that, out of the four immunoglobulin-like domains present in the extracellular region of LAG-3, 58% of the evaluated clones bound to domain 1, and 26% thereof bound to domain 2, so that monoclonal antibodies against portions close to the N terminus were preferentially obtained. Among them, most of the clones that strongly bound to human activated T cells (PHA blasts) in flow cytometry, including clone 6D7, bound to domain 1 of LAG-3, and all of them showed strong inhibitory activity in the LAG-3/MHC class II binding test described in Example 2)-3. These results are fully consistent with the conventional finding (Non Patent Literature 4) that domains 1 and 2 of the N terminus out of the four extracellular immunoglobulin-like domains of LAG-3 are important for binding of LAG-3 to MHC class II molecules and indicate that, in order to obtain an antibody that does not inhibit the binding of LAG-3 to MHC class II molecules, that is, the T cell suppression function of LAG-3, it is necessary to develop a monoclonal antibody by devising such an immunization method as in Example 1)-1.

Example 3. Determination of Nucleotide Sequence of cDNA Encoding Variable Regions of Rat Anti-Human LAG-3 Antibodies (rLA204, rLA212, rLA225, rLA869, and rLA1264)

3)-1 Determination of Nucleotide Sequence of cDNA Encoding Variable Region of rLA204
3)-1-1 Preparation of Total RNA from Hybridoma Producing rLA204

In order to amplify cDNAs comprising the variable regions of rLA204, total RNA was prepared from the hybridoma producing rLA204 using TRIzol Reagent (Ambion/Thermo Fisher Scientific Inc.).
3)-1-2 Synthesis of cDNA (5'-RACE-Ready cDNA)

The cDNA (5'-RACE-Ready cDNA) was synthesized using about 1 µg of the total RNA prepared in Example 3)-1-1 and SMARTer RACE cDNA Amplification Kit (Clontech Laboratories, Inc).
3)-1-3 5'-RACE PCR Amplification and Sequencing of cDNA Encoding Heavy Chain Variable Region of rLA204

The primers used for PCR amplification of the variable region-encoding cDNA of the heavy chain gene of rLA204 were oligonucleotides having the sequences of UPM (Universal Primer A Mix; attached to SMARTer RACE cDNA Amplification Kit) and 5'-CTCCAGAGTTCCAGGT-CACGGTGACTGGC-3' (RG2AR3: SEQ ID NO: 71). The UPM used was attached to SMARTer RACE cDNA Amplification Kit (Clontech Laboratories, Inc.), while RG2AR3 was designed from the sequences of rat heavy chain constant regions in the database.

cDNA comprising the heavy chain variable region of rLA204 was amplified by 5'-RACE PCR using this primer set and the cDNA (5'-RACE-Ready cDNA) synthesized in Example 3)-1-2 as a template. This PCR was carried out on the Touchdown PCR program according to the manual of SMARTer RACE cDNA Amplification Kit (Clontech Laboratories, Inc.) using polymerase KOD-Plus- (Toyobo Co., Ltd.).

The heavy chain variable region-comprising cDNA amplified by 5'-RACE PCR was purified using a MinElute PCR Purification Kit (Qiagen N.V.) and then cloned using a Zero Blunt TOPO PCR Cloning Kit (Invitrogen Corp.). The cloned heavy chain variable region-comprising cDNA was analyzed by sequencing.

The sequencing primers used were an oligonucleotide having the sequence 5'-CTCCAGAGTTCCAGGT-CACGGTGACTGGC-3' (RG2AR3; SEQ ID No: 71) designed from the sequences of rat heavy chain constant regions in the database, and NUP (Nested Universal Primer A: attached to SMART RACE cDNA Amplification Kit).

The determined nucleotide sequence of the cDNA encoding the heavy chain variable region of rLA204 is shown in SEQ ID NO: 1, and the amino acid sequence thereof is shown in SEQ ID NO: 2.
3)-1-4 5'-RACE PCR Amplification and Sequencing of cDNA Encoding Light Chain Variable Region of rLA204

The primers used for PCR amplification of the variable region-encoding cDNA of the light chain gene of rLA204 were UPM (Universal Primer A Mix; attached to SMARTer RACE cDNA Amplification Kit) and an oligonucleotide having the sequence of 5'-TCAGTAACACTGTCCAGGACACCATCTC-3' (RKR5: SEQ ID NO: 72). The UPM used was attached to SMARTer RACE cDNA Amplification Kit (Clontech Laboratories, Inc.), while RKR5 was designed from the sequences of rat light chain constant regions in the database.

cDNA comprising the light chain variable region of rLA204 was amplified by 5'-RACE PCR using this primer set and the cDNA (5'-RACE-Ready cDNA) synthesized in Example 3)-1-2 as a template. This PCR was carried out on the Touchdown PCR program according to the manual of SMARTer RACE cDNA Amplification Kit (Clontech Laboratories, Inc.) using polymerase KOD-Plus- (Toyobo Co., Ltd.).

The light chain variable region-comprising cDNA amplified by 5'-RACE PCR was purified using a MinElute PCR Purification Kit (Qiagen N.V.) and then cloned using a Zero Blunt TOPO PCR Cloning Kit (Invitrogen Corp.). The cloned light chain variable region-encoding cDNA was analyzed by sequencing.

The sequencing primers used were an oligonucleotide having the sequence 5'-TCAGTAACACTGTCCAGGACACCATCTC-3' (RKR5; SEQ ID No: 72) designed from the sequences of rat light chain constant regions in the database, and NUP (Nested Universal Primer A: attached to SMART RACE cDNA Amplification Kit).

The determined nucleotide sequence of the cDNA encoding the light chain variable region of rLA204 is shown in SEQ ID NO: 3, and the amino acid sequence thereof is shown in SEQ ID NO: 4.
3)-2 Determination of Nucleotide Sequence of cDNA Encoding Variable Region of rLA212

The sequence was determined in the same manner as in Example 3)-1.

The determined nucleotide sequence of the cDNA encoding the heavy chain variable region of rLA212 is shown in SEQ ID NO: 5, and the amino acid sequence thereof is shown in SEQ ID NO: 6. The nucleotide sequence of the cDNA encoding the light chain variable region thereof is shown in SEQ ID NO: 7, and the amino acid sequence thereof is shown in SEQ ID NO: 8.
3)-3 Determination of Nucleotide Sequence of cDNA Encoding Variable Region of rLA225

The sequence was determined in the same manner as in Example 3)-1.

The determined nucleotide sequence of cDNA encoding the heavy chain variable region of rLA225 is shown in SEQ ID No: 9, and the amino acid sequence thereof is shown in SEQ ID No: 10. The nucleotide sequence of cDNA encoding the light chain variable region thereof is shown in SEQ ID No: 11, and the amino acid sequence thereof is shown in SEQ ID No: 12.
3)-4 Determination of Nucleotide Sequence of cDNA Encoding Variable Region of rLA869

The sequence was determined in the same manner as in Example 3)-1.

The determined nucleotide sequence of cDNA encoding the heavy chain variable region of rLA869 is shown in SEQ ID No: 13, and the amino acid sequence thereof is shown in SEQ ID No: 14. The nucleotide sequence of cDNA encoding the light chain variable region thereof is shown in SEQ ID No: 15, and the amino acid sequence thereof is shown in SEQ ID No: 16.
3)-5 Determination of Nucleotide Sequence of cDNA Encoding Variable Region of rLA1264

The sequence was determined in the same manner as in Example 3)-1.

The determined nucleotide sequence of cDNA encoding the heavy chain variable region of rLA1264 is shown in SEQ ID No: 17, and the amino acid sequence thereof is shown in SEQ ID No: 18. The nucleotide sequence of cDNA encoding the light chain variable region thereof is shown in SEQ ID No: 19, and the amino acid sequence thereof is shown in SEQ ID No: 20.

Example 4. Development of Human Chimeric Anti-Human LAG-3 Antibody (cLA212)

4)-1 Construction of Chimeric and Humanized Antibody Light Chain Expression Vector pCMA-LK A plasmid pcDNA3.3-TOPO/LacZ (Invitrogen Corp.) was digested with restriction enzymes XbaI and PmeI. The obtained fragment of approximately 5.4 kb was ligated with a DNA fragment comprising a DNA sequence shown in SEQ ID No: 21 and encoding a human light chain secretory signal and a human K chain constant region using In-Fusion Advantage PCR cloning kit (Clontech Laboratories, Inc.) to prepare pcDNA3.3/LK.

PCR was performed with pcDNA3.3/LK as a template using a primer set shown below. The obtained fragment of approximately 3.8 kb was phosphorylated and then self-ligated to construct a chimeric and humanized antibody light chain expression vector pCMA-LK having a signal sequence, a cloning site, and a human light chain constant region, downstream of the CMV promoter.

```
Primer set
                        (3.3-F1: SEQ ID NO: 73)
5'-TATACCGTCGACCTCTAGCTAGAGCTTGGC-3'

(3.3-R1: SEQ ID NO: 74)
5'-GCTATGGCAGGGCCTGCCGCCCCGACGTTG-3'
```

4)-2 Construction of Chimeric and Humanized Antibody IgG1 Type Heavy Chain Expression Vector pCMA-G1

The obtained DNA fragment from which the light chain secretory signal and the human K chain constant region were removed by digesting pCMA-LK with XbaI and PmeI was bound to a DNA fragment comprising the DNA sequence shown in SEQ ID No: 22 and encoding the amino acids of a human heavy chain signal sequence and a human IgG1 constant region using In-Fusion Advantage PCR cloning kit (Clontech Laboratories, Inc.) to construct a chimeric and humanized antibody IgG1 type heavy chain expression vector pCMA-G1 having a signal sequence, a cloning site, and a human IgG1 heavy chain constant region, downstream of the CMV promoter.

4)-3 Construction of cLA212 Heavy Chain Expression Vector

A DNA fragment comprising a heavy chain variable region-encoding cDNA was amplified with KOD-Plus- (Toyobo Co., Ltd.) and a primer set shown below, using the cDNA obtained in Example 3)-2 and comprising the heavy chain variable region of rLA212 as a template, and the amplified DNA fragment was inserted to the restriction enzyme BlpI-cleaved site of the chimeric and humanized IgG1 type heavy chain expression vector pCMA-G1 using an In-Fusion HD cloning kit (Clontech Laboratories, Inc.) to construct a cLA212 heavy chain expression vector. The obtained expression vector was designated as "pCMA-G1/cLA212". The nucleotide sequence of the cLA212 heavy chain is shown in SEQ ID No: 23, and the amino acid sequence thereof is shown in SEQ ID No: 24.

```
Primer set for cLA212 heavy chain
                        (212H-F; SEQ ID No: 75)
5'-CCAGATGGGTGCTGAGCGAGGTGCAGCTGGTGGAGTCTGGGGGAGG-
3'

(212H-R; SEQ ID No: 76)
5'-CTTGGTGGAGGCTGAGCTGACTGTGACCATGACTCCTTGGCCCCAG-
3'
```

4)-4 Construction of cLA212 Light Chain Expression Vector

A DNA fragment comprising a light chain variable region-encoding cDNA was amplified with KOD-Plus- (Toyobo Co., Ltd.) and a primer set shown below, using the cDNA obtained in Example 3)-2 and comprising the light chain variable region of rLA212 as a template, and the amplified DNA fragment was inserted to the restriction enzyme BsiWI-cleaved site of the chimeric and humanized light chain expression general vector pCMA-LK using an In-Fusion HD PCR cloning kit (Clontech Laboratories, Inc.) to construct a cLA212 light chain expression vector. The obtained expression vector was designated as "pCMA-LK/cLA212". The nucleotide sequence of the cLA212 light chain is shown in SEQ ID No: 25, and the amino acid sequence thereof is shown in SEQ ID No: 26.

```
Primer set for cLA212 light chain.
                        (212L-F; SEQ ID No: 77)
5'-ATCTCCGGCGCGTACGGCAACATTGTGATGACCCAGTCTCCCAAATC
C-3'

(212L-R; SEQ ID No: 78)
5'-GGAGGGGGCGGCCACAGCCCGTTTCAGTTCCAGCTCGGTCCCAGC-3'
```

4)-5 Production of cLA212

FreeStyle 293F cells (Invitrogen Corp.) were subcultured and cultured according to the manual. $1.2 \times 10^9$ FreeStyle 293F cells (Invitrogen Corp.) in the logarithmic growth phase were inoculated to a 3-L Fernbach Erlenmeyer Flask (Corning Inc.), adjusted to $2.0 \times 10^6$ cells/ml by dilution with FreeStyle 293 expression medium (Invitrogen Corp.), and then shake-cultured at 90 rpm at 37° C. for 1 hour in an 8% $CO_2$ incubator. 1.8 mg of polyethyleneimine (Polysciences #24765) was dissolved in 20 ml of Opti-Pro SFM medium (Invitrogen Corp.). Next, each H chain expression vector (0.24 mg) and each L chain expression vector (0.36 mg) prepared using NucleoBond Xtra (Takara Bio Inc.) were added to 20 ml of Opti-Pro SFM medium (Invitrogen Corp.). 20 ml of the expression vector/Opti-Pro SFM mixed solution was added to 20 ml of the polyethyleneimine/Opti-Pro SFM mixed solution, and the mixture was gently stirred, left for 5 minutes, and then added to the FreeStyle 293F cells. The cells were shake-cultured at 90 rpm at 37° C. for 4 hours in an 8% $CO_2$ incubator. Then, 600 ml of EX-CELL VPRO medium (SAFC Biosciences), 18 ml of GlutaMAX I (GIBCO/Thermo Fisher Scientific Inc.), and 30 ml of Yeastolate Ultrafiltrate (GIBCO/Thermo Fisher Scientific Inc.) were added thereto. The cells were shake-cultured at 90 rpm at 37° C. for 7 days in an 8% $CO_2$ incubator, and the obtained culture supernatant was filtered through a Disposable Capsule Filter (Advantec #CCS-045-E1H).

The rLA212 human chimeric antibody obtained by the combination of pCMA-G1/cLA212 and pCMA-LK/cLA212 was designated as "cLA212".

4)-6 Purification of cLA212

The antibody was purified from the culture supernatant obtained in Example 4)-5 by rProtein A affinity chromatography (at 4 to 6° C.). The buffer replacement step after the rProtein A affinity chromatographic purification was carried out at 4 to 6° C. First, the culture supernatant was applied to a column filled with MabSelectSuRe (manufactured by GE Healthcare) equilibrated with PBS. After entry of the whole culture solution into the column, the column was washed with PBS in an amount of at least twice the column volume. Next, antibody-containing fractions were collected by elution with a 2 M arginine hydrochloride solution (pH 4.0). The fractions were buffer-replaced with HBSor (25 mM histidine and 5% sorbitol, pH 6.0) by dialysis (Thermo Fisher Scientific Inc., Slide-A-Lyzer Dialysis Cassette). Finally, the fractions were concentrated and adjusted to an IgG concentration of 25 mg/ml or higher using a Centrifugal UF Filter Device VIVASPIN 20 (molecular weight cutoff: UF10K, Sartorius AG, at 4° C.), and used as a purified sample. Finally, filtration with a Minisart-Plus filter (Sartorius AG) was performed to give a purified sample.

4)-7 Antigen Binding Activity of Human Chimeric Anti-LAG-3 Antibody (cLA212)

Figure 6:
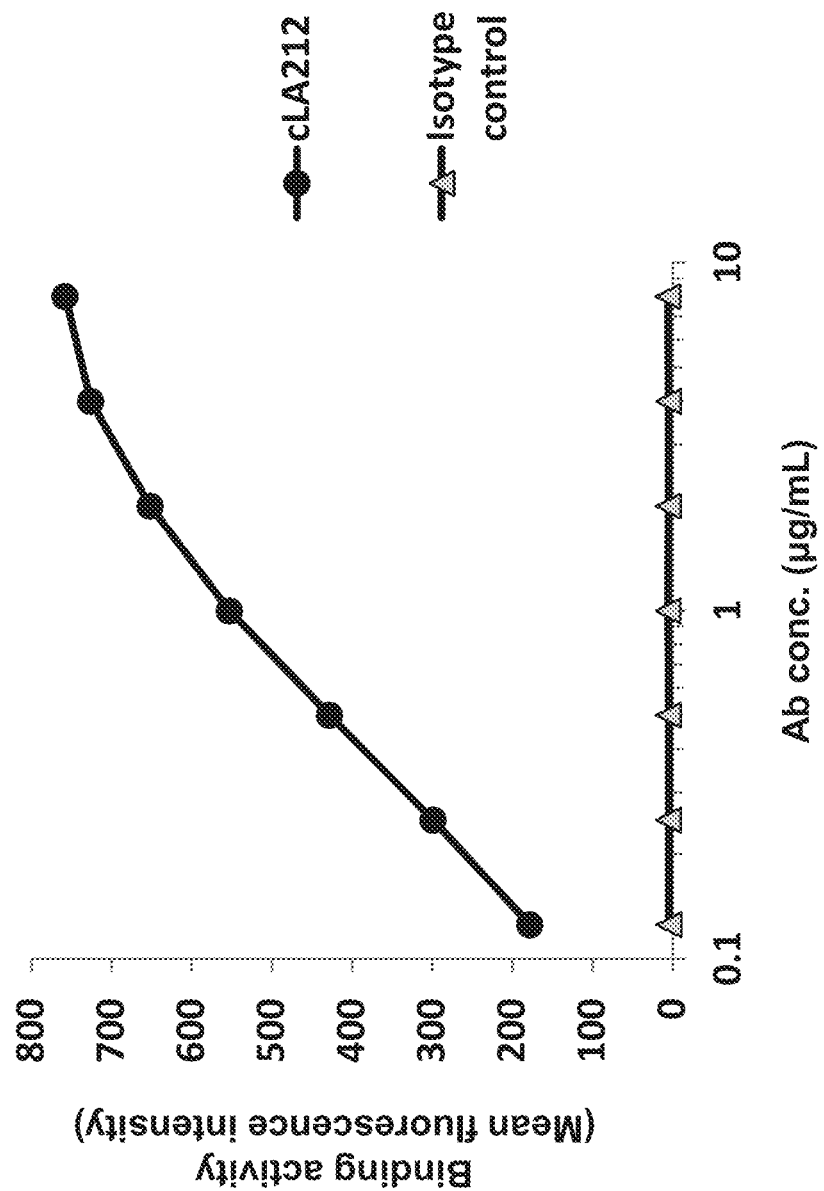
FIG. 6 is a diagram showing the results of testing the binding activity of human chimeric anti-LAG-3 antibody cLA212 to 293T-lacZ cells expressing human LAG-3 by flow cytometry. The vertical axis represents the mean fluorescence intensity measured by flow cytometry.

The expression plasmid pcDNA3.1-hLAG-3 of human LAG-3 was introduced into the 293T-lacZ cells (described in Example 1)-5-1), using Lipofectamine 2000 (manufactured by Invitrogen Corp.), and the cells were cultured for 1 day and thereafter used for flow cytometry. The flow cytometry was performed according to the method described in Example 1)-4, except that an Anti-Human IgG PE conjugate (manufactured by Jackson ImmunoResearch Laboratories, Inc.) diluted 200-fold with a FACS buffer was used as the secondary antibody. As shown in FIG. 6, it was revealed that the human chimeric anti-LAG-3 antibody cLA212 bound to the 293T-lacZ cells expressing human LAG-3 in a concentration-dependent manner and thus also maintained binding activity after chimerization.

Example 5. Design of Humanized Version (hLA212) of Rat Anti-Human LAG-3 Antibody (rLA212)

5-1 Design of Humanized Rat Anti-Human LAG-3 Antibody rLA212

5)-1-1 Molecular Modeling of rLA212 Variable Regions

The molecular modeling of the rLA212 variable regions was carried out by a method known as homology modeling (Methods in Enzymology, 203, 121-153, (1991)). The variable regions of rLA212 determined in Example 3)-2 were compared with the primary sequences (three-dimensional structures derived from X-ray crystal structures are available) of human immunoglobulin variable regions registered in Protein Data Bank (Nuc. Acid Res. 35, D301-D303 (2007)). As a result, 2GHW and 2ARJ were selected as having the highest sequence homology to the heavy and light chain variable regions of rLA212. The three-dimensional structures of the framework regions were developed by obtaining "framework models" by combining the coordinates of 2GHW and 2ARJ corresponding to the heavy chain and the light chain of rLA212. Subsequently, the typical conformations of CDRs were incorporated into the framework models. Finally, an energy calculation for excluding disadvantageous interatomic contact was conducted in order to obtain possible molecular models of the rLA212 variable regions in terms of energy. These procedures were performed using commercially available protein three-dimensional structural analysis program Discovery Studio (manufactured by Accelrys, Inc).

5)-1-2 Design of Amino Acid Sequences of Humanized Anti-Human LAG-3 Antibody hLA212

The humanized anti-human LAG-3 antibody hLA212 was constructed by a method generally known as CDR grafting (Proc. Natl. Acad. Sci. USA 86, 10029-10033 (1989)). An acceptor antibody was selected on the basis of the identity of amino acids in the framework regions.

The sequences of the framework regions of rLA212 were compared with the framework regions of the consensus sequences of human sub-groups and Germline sequences defined in KABAT et al. (Sequences of Proteins of Immunological Interest, 5th Ed. Public Health Service National Institutes of Health, Bethesda, MD (1991)). As a result, the consensus sequence of the human gamma chain sub-group 3 for the heavy chain and the consensus sequence of the human kappa chain sub-group 1 for the light chain were selected respectively as acceptors because of having high sequence identity in the framework regions. The amino acid residues in the framework regions for the acceptors were aligned with the amino acid residues for rLA212 to identify the positions where different amino acids were used. The positions of these residues were analyzed using the three-dimensional model of rLA212 constructed in Example 5)-1-1. Then, the donor residues to be grafted onto the acceptors were selected according to the criteria provided by Queen et al. (Proc. Natl. Acad. Sci. USA 86, 10029-10033 (1989)). Some donor residues thus selected were transferred to the acceptor antibodies to construct the humanized hLA212 sequences as described in the Examples below.

5)-2 Humanization of rLA212 Heavy Chain

5)-2-1 Humanized hLA212_H2 Type Heavy Chain

A humanized hLA212 heavy chain designed by the replacement of arginine at amino acid position 16 with glycine, lysine at amino acid position 19 with arginine, threonine at amino acid position 42 with glycine, arginine at amino acid position 43 with lysine, alanine at amino acid position 49 with glycine, aspartic acid at amino acid position 84 with asparagine, serine at amino acid position 88 with alanine, threonine at amino acid position 93 with valine, valine at amino acid position 115 with threonine, and methionine at amino acid position 116 with leucine, in the heavy chain variable region of the chimeric cLA212 shown in SEQ ID No: 24 was designated as "humanized hLA212_H2 type heavy chain" (which may be referred to also as "hLA212_H2").

The amino acid sequence of the humanized hLA212_H2 type heavy chain is described in SEQ ID No: 28 of the Sequence Listing In the amino acid sequence of SEQ ID No: 28, the sequence consisting of amino acid residues 1 to 19, the sequence consisting of amino acid residues 20 to 140, and the sequence consisting of amino acid residues 141 to 470 respectively correspond to the signal sequence, the heavy chain variable region, and the heavy chain constant region. The nucleotide sequence encoding the amino acid sequence of SEQ ID No: 28 is described in SEQ ID No: 27 of the Sequence Listing. In the nucleotide sequence of SEQ ID No: 27, the sequence consisting of nucleotides 1 to 57, the sequence consisting of nucleotides 58 to 420, and the sequence consisting of nucleotides 421 to 1410 respectively encode the signal sequence, the heavy chain variable region sequence, and the heavy chain constant region sequence. The nucleotide sequence of SEQ ID No: 27 and the amino acid sequence of SEQ ID No: 28 are also respectively described in FIGS. 42 and 43.

5)-2-2 Humanized hLA212_H3 Type Heavy Chain

A humanized hLA212 heavy chain designed by the replacement of arginine at amino acid position 16 with glycine, lysine at amino acid position 19 with arginine, threonine at amino acid position 42 with glycine, arginine at amino acid position 43 with lysine, serine at amino acid position 88 with alanine, threonine at amino acid position 93 with valine, valine at amino acid position 115 with threonine, and methionine at amino acid position 116 with leucine, in the heavy chain variable region of the chimeric cLA212 shown in SEQ ID No: 24 was designated as "humanized hLA212_H3 type heavy chain" (which may be referred to also as "hLA212_H3").

The amino acid sequence of the humanized hLA212_H3 type heavy chain is described in SEQ ID No: 30 of the Sequence Listing. In the amino acid sequence of SEQ ID No: 30, the sequence consisting of amino acid residues 1 to 19, the sequence consisting of amino acid residues 20 to 140, and the sequence consisting of amino acid residues 141 to 470 respectively correspond to the signal sequence, the heavy chain variable region, and the heavy chain constant region. The nucleotide sequence encoding the amino acid sequence of SEQ ID No: 30 is described in SEQ ID No: 29 of the Sequence Listing. In the nucleotide sequence of SEQ ID No: 29, the sequence consisting of nucleotides 1 to 57, the sequence consisting of nucleotides 58 to 420, and the sequence consisting of nucleotides 421 to 1410 respectively encode the signal sequence, the heavy chain variable region sequence, and the heavy chain constant region sequence. The nucleotide sequence of SEQ ID No: 29 and the amino acid sequence of SEQ ID No: 30 are also respectively described in FIGS. 44 and 45.

5)-3 Humanization of rLA212 Light Chain

5)-3-1 Humanized hLA212_L1 Type Light Chain

A humanized hLA212 light chain designed by the replacement of asparagine at amino acid position 1 with aspartic acid, valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, lysine at amino acid position 38 with glutamine, serine at amino acid position 43 with alanine, aspartic acid at amino acid position 60 with serine, threonine at amino acid position 63 with serine, glycine at amino acid position 65 with serine, tyrosine at amino acid position 67 with serine, asparagine at amino acid position 76 with serine, valine at amino acid position 78 with leucine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L1 type light chain" (which may be referred to also as "hLA212_L1").

The amino acid sequence of the humanized hLA212_L1 type light chain is described in SEQ ID No: 32 of the Sequence Listing In the amino acid sequence of SEQ ID No: 32, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 32 is described in SEQ ID No: 31 of the Sequence Listing. In the nucleotide sequence of SEQ ID No: 31, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 31 and the amino acid sequence of SEQ ID No: 32 are also respectively described in FIGS. 46 and 47.

5)-3-2 Humanized hLA212_L2 Type Light Chain

A humanized hLA212 light chain designed by the replacement of asparagine at amino acid position 1 with aspartic acid, valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, lysine at amino acid position 38 with glutamine, aspartic acid at amino acid position 60 with serine, threonine at amino acid position 63 with serine, glycine at amino acid position 65 with serine, asparagine at amino acid position 76 with serine, valine at amino acid position 78 with leucine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L2 type light chain" (which may be referred to also as "hLA212_L2").

The amino acid sequence of the humanized hLA212_L2 type light chain is described in SEQ ID No: 34 of the Sequence Listing In the amino acid sequence of SEQ ID No: 34, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 34 is described in SEQ ID No: 33 of the Sequence Listing. In the nucleotide sequence of SEQ ID No: 33, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 33 and the amino acid sequence of SEQ ID No: 34 are also respectively described in FIGS. 48 and 49.

5)-3-3 Humanized hLA212_L3 Type Light Chain

A humanized hLA212 light chain designed by the replacement of valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, threonine at amino acid position 63 with serine, asparagine at amino acid position 76 with serine, valine at amino acid position 78 with leucine, alanine at amino acid position 80 with proline, alanine at amino acid position 83 with phenylalanine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L3 type light chain" (which may also be referred to as "hLA212_L3").

The amino acid sequence of the humanized hLA212_L3 type light chain is described in SEQ ID No: 36 of the Sequence Listing. In the amino acid sequence of SEQ ID No: 36, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 36 is described in SEQ ID No: 35 of the Sequence Listing. In the nucleotide sequence of SEQ ID No: 35, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 35 and the amino acid sequence of SEQ ID No: 36 are respectively described also in FIGS. 50 and 51.

5)-3-4 Humanized hLA212_L4 Type Light Chain

A humanized hLA212 light chain designed by the replacement of asparagine at amino acid position 1 with aspartic acid, valine at amino acid position 3 with glutamine, lysine at amino acid position 9 with serine, asparagine at amino acid position 22 with threonine, aspartic acid at amino acid position 60 with serine, threonine at amino acid position 63 with serine, glycine at amino acid position 65 with serine, tyrosine at amino acid position 67 with serine, asparagine at amino acid position 76 with serine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, and alanine at amino acid position 109 with threonine, in the light chain variable region of the chimeric cLA212 shown in SEQ ID No: 26 was designated as "humanized hLA212_L4 type light chain" (which may also be referred to as "hLA212_L4").

The amino acid sequence of the humanized hLA212_L4 type light chain is described in SEQ ID No: 38 of the Sequence Listing. In the amino acid sequence of SEQ ID No: 38, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 38 is described in SEQ ID No: 37 of the Sequence Listing. In the nucleotide sequence of SEQ ID No: 37, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 37 and the amino acid sequence of SEQ ID No: 38 are respectively described also in FIGS. 52 and 53.

5)-3-5 Humanized hLA212_L5 Type Light Chain

A humanized hLA212 light chain designed by the replacement of valine at amino acid position 3 with glutamine, lysine at amino acid position 9 with serine, asparagine at amino acid position 22 with threonine, threonine at amino acid position 63 with serine, asparagine at amino acid position 76 with serine, alanine at amino acid position 80 with proline, alanine at amino acid position 100 with glutamine, glutamic acid at amino acid position 103 with lysine, and alanine at amino acid position 109 with threonine, in the light chain variable region of the chimeric cLA212 shown in SEQ ID No: 26 was designated as "humanized hLA212_L5 type light chain" (which may also be referred to as "hLA212_L5").

The amino acid sequence of the humanized hLA212_L5 type light chain is described in SEQ ID No: 40 of the Sequence Listing. In the amino acid sequence of SEQ ID No: 40, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 40 is described in SEQ ID No: 39 of the Sequence Listing. In the nucleotide sequence of SEQ ID No: 39, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 39 and the amino acid sequence of SEQ ID No: 40 are respectively described also in FIGS. 54 and 55.

5)-4 Design of Humanized hLA212 by Combination of Heavy Chain and Light Chain

An antibody consisting of the humanized hLA212_H2 type heavy chain and the humanized hLA212_L1 type light chain was designed and designated as "humanized hLA212_H2/L1" (which may also be referred to as "hLA212_H2/L1"). An antibody consisting of the humanized hLA212_H2 type heavy chain and the humanized hLA212_L2 type light chain was designed and designated as "humanized hLA212_H2/L2" (which may also be referred to as "hLA212_H2/L2"). An antibody consisting of the humanized hLA212_H2 type heavy chain and the humanized hLA212_L3 type light chain was designed and designated as "humanized hLA212_H2/L3" (which may also be referred to as "hLA212_H2/L3"). An antibody consisting of the humanized hLA212_H2 type heavy chain and the humanized hLA212_L4 type light chain was designed and designated as "humanized hLA212_H2/L4" (which may also be referred to as "hLA212_H2/L4"). An antibody consisting of the humanized hLA212_H2 type heavy chain and the humanized hLA212_L5 type light chain was designed and designated as "humanized hLA212_H2/L5" (which may also be referred to as "hLA212_H2/L5"). An antibody consisting of the humanized hLA212_H3 type heavy chain and the humanized hLA212_L1 type light chain was designed and designated as "humanized hLA212_H3/L1" (which may also be referred to as "hLA212_H3/L1"). An antibody consisting of the humanized hLA212_H3 type heavy chain and the humanized hLA212_L2 type light chain was designed and designated as "humanized hLA212_H3/L2" (which may also be referred to as "hLA212_H3/L2"). An antibody consisting of the humanized hLA212_H3 type heavy chain and the humanized hLA212_L3 type light chain was designed and designated as "humanized hLA212_H3/L3" (which may also be referred to as "hLA212_H3/L3"). An antibody consisting of the humanized hLA212_H3 type heavy chain and the humanized hLA212_L4 type light chain was designed and designated as "humanized hLA212_H3/L4" (which may also be referred to as "hLA212_H3/L4"). An antibody consisting of the humanized hLA212_H3 type heavy chain and the humanized hLA212_L5 type light chain was designed and designated as "humanized hLA212_H3/L5" (which may also be referred to as "hLA212_H3/L5").

The antibodies designed as above can be fabricated according to Example 6 and evaluated according to Example 7 and Example 8.

Example 6. Expression and Purification of Humanized Antibody (hLA212) of Human Chimeric Anti-LAG-3 Antibody cLA212

6)-1 Construction of hLA212 Heavy Chain Expression Vector

6)-1-1 Construction of hLA212_H2 Type Heavy Chain Expression Vector

DNA fragments comprising the DNA sequences encoding the variable regions of hLA212_H2 shown in nucleotide positions 36 to 437 of the nucleotide sequence of hLA212_H2 of SEQ ID No: 27 were synthesized (Strings DNA Fragments, Geneart AG). The synthesized DNA fragments were inserted into a site of the chimeric and humanized antibody IgG1 type heavy chain expression vector pCMA-G1 cleaved by restriction enzyme BlpI, using an In-Fusion HD PCR cloning kit (Clontech Laboratories, Inc.) to construct an hLA212_H2 expression vector. The obtained expression vector was designated as "pCMA/hLA212_H2".

6)-1-2 Construction of hLA212_H3 Type Heavy Chain Expression Vector

DNA fragments comprising the DNA sequences encoding the variable regions of hLA212_H2 shown in nucleotide positions 36 to 437 of the nucleotide sequence of hLA212_H3 of SEQ ID No: 29 were synthesized (Strings DNA Fragments, Geneart AG). In the same manner as in Example 6)-1-1, an hLA212_H3 expression vector was constructed. The obtained expression vector was designated as "pCMA/hLA212_H3".

6)-2 Construction of hLA212 Light Chain Expression Vectors

6)-2-1 Construction of hLA212_L1 Type Light Chain Expression Vector

DNA fragments comprising the DNA sequences encoding the variable regions of hLA212_L1 shown in nucleotide positions 37 to 402 of the nucleotide sequence of hLA212_L1 of SEQ ID No: 31 were synthesized (Strings DNA Fragments, Geneart AG). The synthesized DNA fragments were inserted into a site of the chimeric and humanized antibody light chain expression vector pCMA-LK cleaved by restriction enzyme BsiWI, using an In-Fusion HD PCR cloning kit (Clontech Laboratories, Inc.) to construct an hLA212_L1 expression vector. The obtained expression vector was designated as "pCMA/hLA212_L1".

6)-2-2 Construction of hLA212_L2 Type Light Chain Expression Vector

DNA fragments comprising the DNA sequences encoding the variable regions of hLA212_L2 shown in nucleotide positions 37 to 402 of the nucleotide sequence of hLA212_L2 of SEQ ID No: 33 were synthesized (Strings DNA Fragments, Geneart AG). In the same manner as in Example 6)-2-1, an hLA212_L2 expression vector was constructed. The obtained expression vector was designated as "pCMA/hLA212_L2".

6)-2-3 Construction of hLA212_L3 Type Light Chain Expression Vector

DNA fragments comprising the DNA sequences encoding the variable regions of hLA212_L3 shown in nucleotide positions 37 to 402 of the nucleotide sequence of hLA212_L3 of SEQ ID No: 35 were synthesized (Strings DNA Fragments, Geneart AG). In the same manner as in Example 6)-2-1, an hLA212_L3 expression vector was constructed. The obtained expression vector was designated as "pCMA/hLA212_L3".

6)-2-4 Construction of hLA212_L4 Type Light Chain Expression Vector

DNA fragments comprising the DNA sequences encoding the variable regions of hLA212_L4 shown in nucleotide positions 37 to 402 in the nucleotide sequence of hLA212_L4 of SEQ ID No: 37 were synthesized (Strings DNA Fragments, Geneart AG). In the same manner as in Example 6)-2-1, an hLA212_L4 expression vector was constructed. The obtained expression vector was designated as "pCMA/hLA212_L4".

6)-2-5 Construction of hLA212_L5 Type Light Chain Expression Vector

DNA fragments comprising the DNA sequences encoding the variable regions of hLA212_L5 shown in nucleotide positions 37 to 402 in the nucleotide sequence of hLA212_L5 of SEQ ID No: 39 were synthesized (Strings DNA Fragments, Geneart AG). In the same manner as in Example 6)-2-1, an hLA212_L5 expression vector was constructed. The obtained expression vector was designated as "pCMA/hLA212_L5".

6)-3 Preparation of hLA212 Antibodies

6)-3-1 Production of hLA212 Antibodies

The production was carried out in the same manner as in Example 4)-5. That is, hLA212_H2/L1 was obtained by the combination of pCMA/hLA212_H2 and pCMA/hLA212_L1; hLA212_H2/L2 was obtained by the combination of pCMA/hLA212_H2 and pCMA/hLA212_L2; hLA212_H2/L3 was obtained by the combination of pCMA/hLA212_H2 and pCMA/hLA212_L3; hLA212_H2/L4 was obtained by the combination of pCMA/hLA212_H2 and pCMA/hLA212_L4; hLA212_H2/L5 was obtained by the combination of pCMA/hLA212_H2 and pCMA/hLA212_L5; hLA212_H3/L1 was obtained by the combination of pCMA/hLA212_H3 and pCMA/hLA212_L1; hLA212_H3/L2 was obtained by the combination of pCMA/hLA212_H3 and pCMA/hLA212_L2; hLA212_H3/L3 was obtained by the combination of pCMA/hLA212_H3 and pCMA/hLA212_L3; hLA212_H3/L4 was obtained by the combination of pCMA/hLA212_H3 and pCMA/hLA212_L4; and hLA212_H3/L5 was obtained by the combination of pCMA/hLA212_H3 and pCMA/hLA212_L5.

6)-3-2 Purification of hLA212 Antibody

The culture supernatant obtained in 6)-3-1 was applied to purification in the same manner as in Example 4)-6.

Example 7. In Vitro Evaluation of Humanized Anti-Human LAG-3 Antibody (hLA212)

7)-1 Antigen Binding Activity Assay of Humanized Anti-Human LAG-3 Antibody (hLA212) Using Biacore FreeStyle 293F cells (Invitrogen Corp.) were applied to express C-terminally His-tagged protein LAG-3_D3D4-His of the 3rd and 4th (region of positions 263-450) domains from the N terminus out of the four extracellular immunoglobulin-like domains of human LAG-3. The obtained culture supernatant was subjected to buffer replacement (20 mM HEPES, 300 mM NaCl, and pH 7.5), to purify the human LAG-3_D3D4-His protein using a HisTrap HP column (GE Healthcare) and a Superdex75 column (GE Healthcare). The final buffer was PBS.

The antibody was assayed for its dissociation constant for the antigen (LAG-3_D3D4-His) using Biacore T200 (GE Healthcare) by the capture method, which involves capturing the antibody as a ligand with an immobilized anti-human IgG(Fc) antibody (Human Antibody Capture kit, GE Healthcare) and assaying with the antigen as an analyte. The anti-human IgG(Fc) antibody was covalently bound to a CM5 sensor chip (GE Healthcare) by amine coupling, targeting approximately 1000 RU. Similarly, this antibody was immobilized onto a reference cell. The running buffer used was HBS-EP+ (10 mM HEPES (pH 7.4), 0.15 M NaCl, 3 mM EDTA, and 0.05% Surfactant P20). After each antibody was added for about 1 minute onto the anti-human IgG(Fc) antibody-immobilized chip, serial dilutions (0.06 to 20 nM) of the antigen were added thereto at a flow rate of 90 μl/minute for 300 seconds, and subsequently the dissociation phase was monitored for 3600 seconds. A 3M magnesium chloride solution was added thereto as a regenerating solution at a flow rate of 10 μl/minute for 30 seconds. The data was analyzed using a 1:1 binding model in analytical software (Biacore T200 Evaluation Software, version 1.0) to calculate an association rate constant ka, a dissociation rate constant kd, and a dissociation constant (KD; KD=kd/ka). FIG. 7 shows the dissociation constant.

Figure 8:
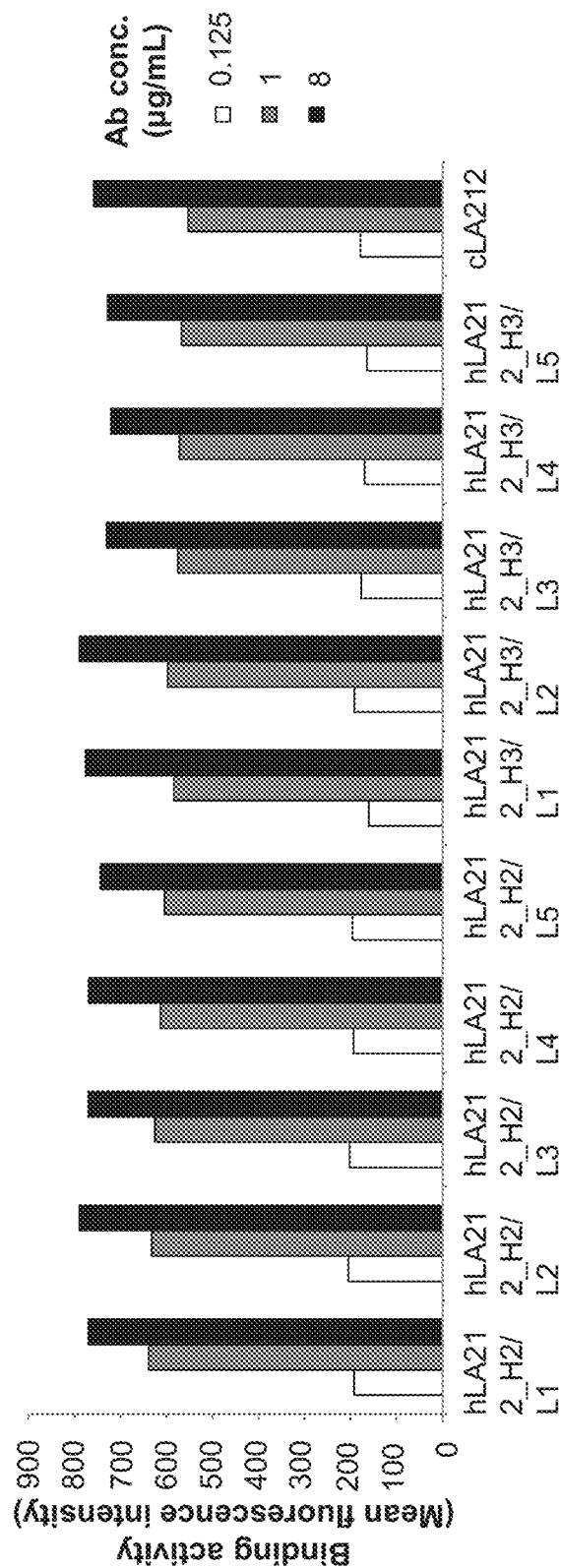
FIG. 8 is a diagram showing the results of testing the binding activity of 10 types of humanized anti-LAG-3 antibodies and human chimeric anti-LAG-3 antibody cLA212 to 293T-lacZ cells expressing human LAG-3 by flow cytometry. The vertical axis represents the mean fluorescence intensity measured by flow cytometry.

7)-2 Investigation on Binding Activity of Humanized Anti-Human LAG-3 Antibody (hLA212) to Cells Expressing Human LAG-3 by Flow Cytometry The human LAG-3-expression plasmid pcDNA3.1/hLAG-3 was introduced into the 293T-lacZ cells (described in Example 1)-5-1), using Lipofectamine 2000 (manufactured by Invitrogen Corp.), and the cells were cultured for 1 day and thereafter used for flow cytometry. The flow cytometry was performed according to the method described in Example 1)-4, but an Anti-Human IgG PE conjugate (manufactured by Jackson ImmunoResearch Laboratories, Inc.) diluted 200-fold with a FACS buffer was used as the secondary antibody. As shown in FIG. 8, it was revealed that all 10 clones of the humanized anti-human LAG-3 antibodies (hLA212_H2/L1, hLA212_H2/L2, hLA212_H2/L3, hLA212_H2/L4, hLA212_H2/L5, hLA212_H3/L1, hLA212_H3/L2, hLA212_H3/L3, hLA212_H3/L4, and hLA212_H3/L5) exhibited concentration-dependent binding activity to the 293T-lacZ cells expressing human LAG-3, comparable to the human chimeric anti-LAG-3 antibody cLA212, and so maintained the binding activity even after humanization.

7)-3 ADCC Activity of Humanized Anti-Human LAG-3 Antibody (hLA212)

Figure 9:
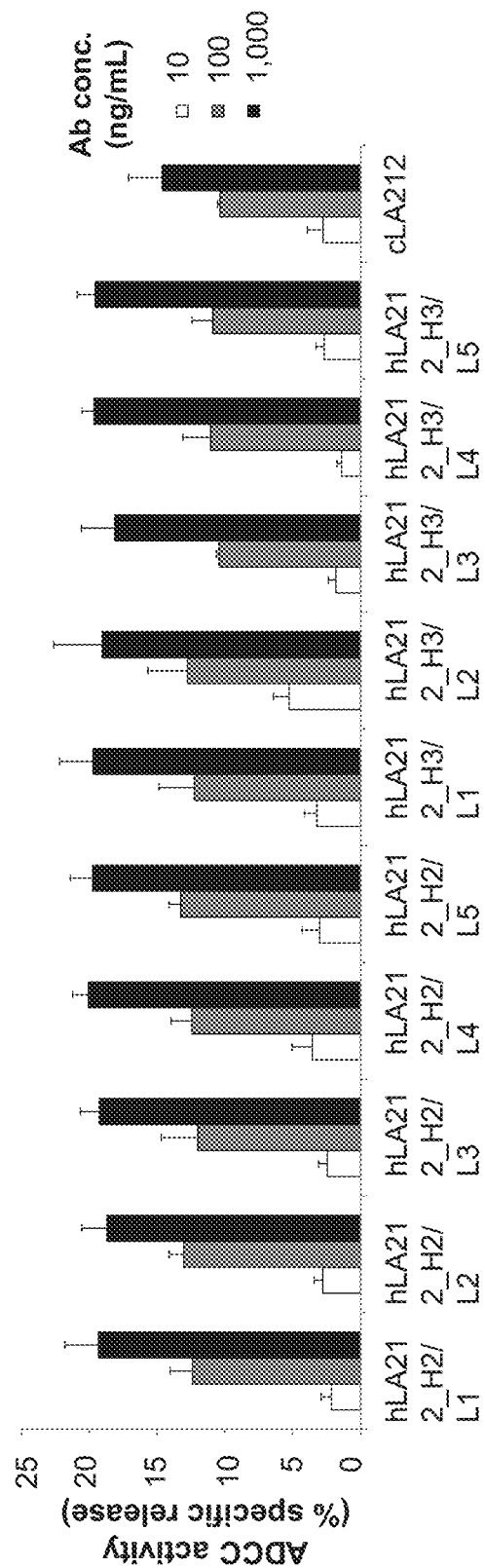
FIG. 9 is a diagram showing the ADCC activity of 10 types of humanized anti-LAG-3 antibodies and human chimeric anti-LAG-3 antibody cLA212. 293T-lacZ cells expressing human LAG-3 were used as target cells, and human PBMCs were used as effector cells.

The ADCC activity of the humanized anti-human LAG-3 antibodies (hLA212) was investigated by the method described in Example 2)-2. As shown in FIG. 9, the results revealed that all 10 clones of the humanized anti-human LAG-3 antibodies (hLA212_H2/L1, hLA212_H2/L2, hLA212_H2/L3, hLA212_H2/L4, hLA212_H2/L5, hLA212_H3/L1, hLA212_H3/L2, hLA212_H3/L3, hLA212_H3/L4, and hLA212_H3/L5) exhibited concentration-dependent ADCC activity against the 293T-lacZ cells expressing human LAG-3, almost comparable to the human chimeric anti-LAG-3 antibody cLA212 and so maintained the ADCC activity even after humanization.

7)-4 Investigation on Influence of Humanized Anti-Human LAG-3 Antibody hLA212_H3/L2 on T Cell Suppression Function of LAG-3

Figure 10:
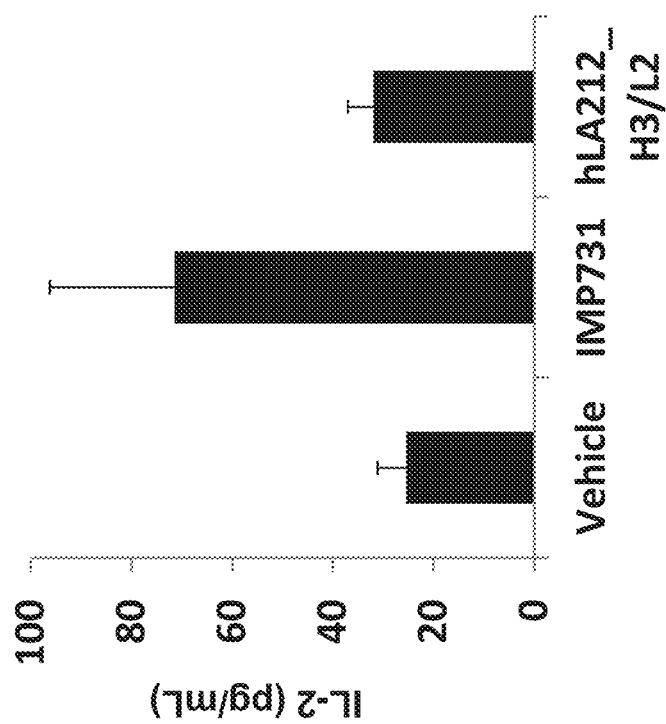
FIG. 10 is a diagram investigating the influence of humanized anti-LAG-3 antibody hLA212_H3/L2 and human chimeric anti-LAG-3 antibody IMP731 on the T cell suppression function of LAG-3. IL-2 production in culture supernatants was measured when human PBMCs were stimulated with SEB for 4 days in the presence of each antibody. Each antibody was evaluated at 10 μg/mL.

It is known that LAG-3 binds to MHC class II molecules, thereby transmitting some inhibitory signals to T cells to regulate the T cell function negatively (Non Patent Literature 1). For binding of LAG-3 to MHC class II molecules, the N-terminal domains 1 and 2 of the four extracellular immunoglobulin-like domains of LAG-3 are considered to be important (Non Patent Literature 4). It was revealed in Example 2 that all 5 clones of the rat anti-human LAG-3 antibodies (rLA204, rLA212, rLA225, rLA869, and rLA1264) obtained by the method of Example 1 recognized domain 3 and exhibited no inhibitory activity in the LAG-3/MHC class II binding test and the 293T-hLAG-3/Raji cell adhesion test, whereas the human chimeric anti-human LAG-3 antibody IMP731 that is a conventional antibody in the Citation List recognized domain 1 and exhibited a powerful inhibitory activity in the LAG-3/MHC class II binding test and the 293T-hLAG-3/Raji cell adhesion test. From these results, it was assumed that the clones obtained by the method of Example 1 and the humanized anti-human LAG-3 antibodies derived therefrom have no influence on the T cell suppression function inherent to LAG-3, whereas the IMP731 inhibits it. In order to confirm this experimentally, the influence of the humanized anti-human LAG-3 antibody hLA212_H3/L2 on the T cell suppression function of LAG-3 was investigated according to the previous report (Non Patent Literature 9). PBMCs separated from the human peripheral blood by Ficoll centrifugation were disseminated in a 96-well microplate in an amount of $2 \times 10^5$ cells/well, and the antibody was added thereto, followed by pre-incubation at 37° C. for 30 minutes. The IL-2 concentration in the culture supernatant when SEB (Staphylococcal Enterotoxin B, manufactured by Sigma-Aldrich) was added thereto to a final concentration of 1 ng/mL, and the cells were cultured for 4 days was quantitated by a Human IL-2 Immunoassay kit (manufactured by PerkinElmer Inc). As a result, the developed humanized anti-human LAG-3 antibody hLA212_H3/L2 had almost no influence on IL-2 production, whereas IMP731 increased IL-2 production, as shown in FIG. 10. That is, as initially predicted, it was revealed that the developed humanized anti-human LAG-3 antibody hLA212_H3/L2 had no influence on the T cell suppression function of LAG-3, whereas IMP731 inhibited this, thereby having a risk of activating the immune system adversely.

Example 8. Preparation of Humanized Antibody in which its Sugar Chain Modification is Adjusted A humanized antibody comprising a heavy chain comprising amino acid positions 20 to 470 of the amino acid sequence represented by SEQ ID No: 30 (FIG. 45) and a light chain comprising amino acid positions 21 to 234 of the amino acid sequence represented by SEQ ID No: 34 (FIG. 49) was defucosylated according to a known method, to adjust the sugar chain modification binding to the antibody protein, and the obtained antibody was designated as hLA212_H4/L2. This modified form was subjected to mass spectrometry. As a result, the peak(s) derived from a fucose-containing H chain were equal to or lower than the detection limit. In the present invention, an antibody whose sugar chain modification is adjusted, such as hLA212_H4/L2, is also referred to as an "antibody" or a "modified form of the antibody".

Example 9. In Vitro Evaluation of Humanized Anti-Human LAG-3 Antibody hLA212_H4/L2

9)-1 Binding Activity of Humanized Anti-Human LAG-3 Antibody hLA212_H4/L2 to Cells Expressing LAG-3

Figure 11:
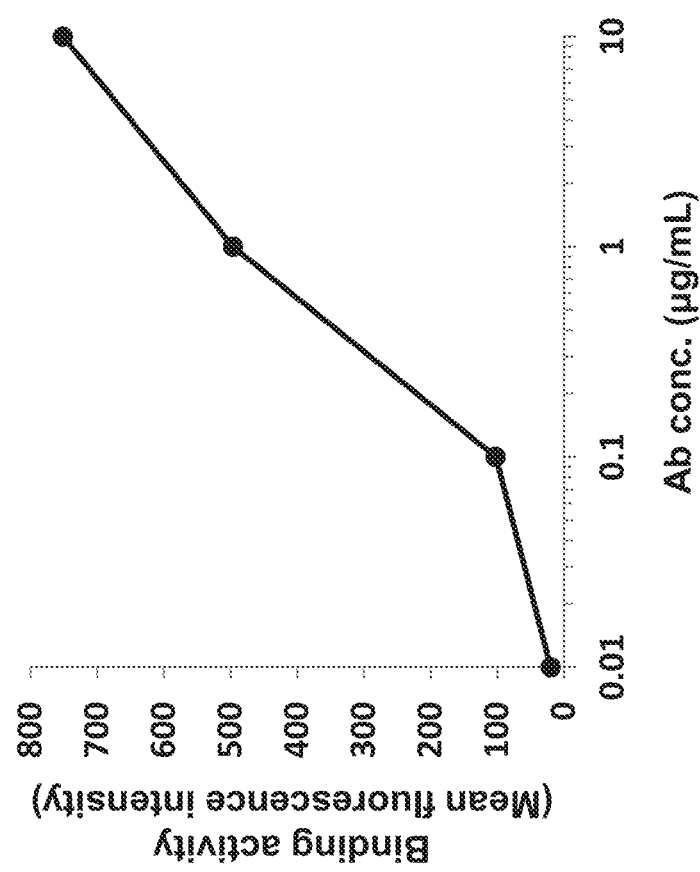
FIG. 11 is a diagram showing the results of testing the binding activity of humanized anti-LAG-3 antibody hLA212_H4/L2 to 293T-lacZ cells expressing human LAG-3 by flow cytometry. The vertical axis represents the mean fluorescence intensity measured by flow cytometry.

The binding of the humanized anti-human LAG-3 antibody hLA212_H4/L2 to human LAG-3-expressing 293T-lacZ cells was investigated by flow cytometry according to the method described in Example 7)-2. As a result, concentration-dependent binding of hLA212_H4/L2 was observed, as shown in FIG. 11.

9)-2 In Vitro ADCC Activity of Humanized Anti-Human LAG-3 Antibody hLA212_H4/L2

Figure 12:
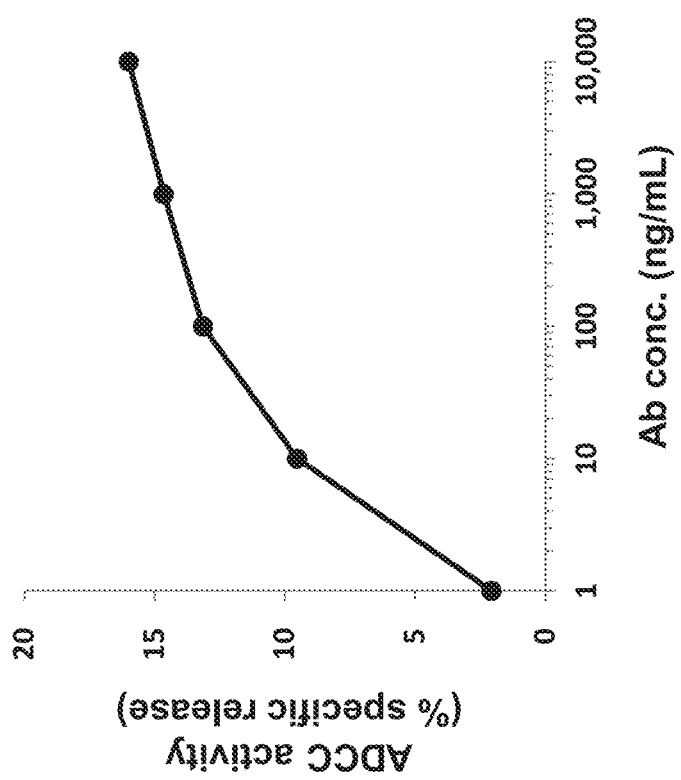
FIG. 12 is a diagram showing the ADCC activity of the humanized anti-LAG-3 antibody hLA212_H4/L2. 293T-lacZ cells expressing human LAG-3 were used as target cells, and human PBMCs were used as effector cells.

The in vitro ADCC activity of the humanized anti-human LAG-3 antibody hLA212_H4/L2 was evaluated by the method described in Example 7)-2. As a result, hLA212_H4/L2 exhibited a concentration-dependent ADCC activity against the 293T-lacZ cells expressing human LAG-3, as shown in FIG. 12. In contrast, it exhibited no ADCC activity on 293T-lacZ cells not expressing human LAG-3.

Example 10. Development of Human LAG-3/Human FcγRIIIA Double Transgenic Mice

It has been revealed that the humanized anti-human LAG-3 antibody hLA212_H4/L2 binds to human LAG-3, as shown in Example 9, but does not cross-react with LAG-3 of rodents. Therefore, for enabling the in vivo evaluation of hLA212_H4/L2, BAC (Bacterial Artificial Chromosome) transgenic mice allowed to physiologically express human LAG-3 using the expression regulation mechanism of mouse LAG-3 were developed. Further, human FcγIIIA is necessary for ADCC activity to be enhanced by adjusting the sugar chain modification as in hLA212_H4/L2 (Junttila, T. T., et al., Cancer Res., Vol. 70 (No. 11): pp. 4481-9 (2010)), and thus BAC comprising the human FcγRIIIA gene was additionally introduced according to the previous report (Non Patent Literature 10).

10)-1 Construction of Recombinant BAC Expression Vector Using Red/ET Reaction

A recombinant BAC clone of human LAG-3 Rebec was constructed using Red/ET Recombination Technology (Zhang Y et al, A new logic for DNA engineering using recombination in *E. Coli.*, Nature 20 (1998) 123-128), which is an active homologous recombination reaction in *Escherichia coli.*

BAC genome clones, RP11-101F21, and RP23-3001 each comprising a human LAG-3 or a mouse LAG-3 gene locus were obtained. As shown in the list below, the sequence of intron 5 of the human LAG-3 gene, the sequences at both ends of the genomic DNA sequence from the translation start codon to the stop codon of the human LAG-3 gene, and the 3' end and the 5' end of the genomic DNA sequence from the translation start codon to the stop codon of the LAG-3 gene of the mouse BAC clone were used as key sequences for the active homologous recombination reaction in *Escherichia coli.*

LAG-3-H1: Sequence near the start codon of human LAG-3 gene
(SEQ ID No: 79)
[5']ATGTGGGAGGCTCAGTTCCTGGGCTTGCTGTTTC[3']

LAG-3-H2: Sequence near the stop codon of human LAG-3 gene
(SEQ ID No: 80)
[5']GCCCGAGCCCGAGCCCGAGCCGGAGCAGCTCTGA[3']

LAG-3-H3: Rps1-kan insertion site, the 5' side
(SEQ ID No: 81)
[5']GAGTATGTGTTGACTGGTTGATAACTATCG[3']

LAG-3-H4: Rps1-kan insertion site, the 3' side
(SEQ ID No: 82)
[5']GCCATGACAGATTAGCCATGTCTGCAGCAC[3']

LAG-3-H5: 5'UTR of mouse LAG-3 gene
(SEQ ID No: 83)
[5']CAGGACCTTTTTCTAACCTCCCTTGGAGGGCTGGGGAGGCCCGGGCCATAGAGGAG[3']

LAG-3-H6: 3'UTR of mouse LAG-3 gene
(SEQ ID No: 84)
[5']CCTGGAGCCGAGGCAGCCAGCAGGTCTCAGCAGCTCCGCCCGCCCGCCCGCCCGCC[3']

First, in order to insert a positive/negative selection marker cassette (Rps1-kan) into intron 5 of the LAG-3 gene of the human BAC clone, DNA fragment(s) connecting the LAG-3-H3 sequence, the Rps1-kan, and the LAG-3-H4 sequence in tandem were constructed by PCR using LA-Taq (Takara Bio Inc.) (LAG-3 Rps1-Kan break-in fragment). The LAG-3 gene locus-containing human BAC clone and the LAG-3 Rps1-Kan break-in fragment were introduced into *Escherichia coli* strains having Red/ET reaction ability to induce Red/ET reaction in the host *Escherichia coli*, and colonies with chloramphenicol resistance and kanamycin resistance were picked up, thereby screening the recombinant BAC clone in which the LAG-3 Rps1-kan break-in fragment was inserted into intron 5 of the LAG-3 gene locus (human LAG-3 Intermediate). Then, in order to sub-clone the genomic DNA sequence of the human LAG-3 gene with the Rps1-kan cassette inserted therein into a plasmid vector from the human LAG-3 Intermediate, a DNA cassette connecting H2-H6-SacBpBluescript-H5-H1 in tandem was constructed (LAG-3 pre-transfer plasmid). In the same manner as above, a linearized LAG-3 pre-transfer plasmid was introduced into *Escherichia coli* strains having Red/ET reaction ability together with the human LAG-3 Intermediate to induce Red/ET reaction in the host *Escherichia coli*, and ampicillin and kanamycin resistant colonies were picked up, thereby screening a plasmid having the genomic DNA sequence of the human LAG-3 gene with the Rps1kan cassette inserted therein (human LAG-3 transfer plasmid).

Next, the genomic DNA sequence of the human LAG-3 gene having the H5 sequence and the H6 sequence derived from a mouse genome sequence at both ends with the Rps1-kan cassette inserted therein was excised from the human LAG-3 transfer plasmid vector by a restriction enzyme reaction (human LAG-3 transfer fragment). In the same manner as above, the human LAG-3 transfer fragment(s) were introduced into *Escherichia coli* strains having Red/ET reaction ability, together with the mouse LAG-3 BAC clone, to induce Red/ET reaction in the host *Escherichia coli*, and chloramphenicol and kanamycin resistant colonies were picked up, thereby screening the mouse LAG-3/human LAG-3 gene recombinant BAC clone in which the genomic DNA sequence from the translation start codon to the stop codon of the mouse LAG-3 gene was accurately replaced with the genomic DNA sequence from the translation start codon to the stop codon of the human LAG-3 transfer fragments (mouse LAG-3/human LAG-3 RecBAC Intermediate).

Finally, the intron 5 sequence of the human LAG-3 gene locus was amplified by PCR and used as a DNA sequence for removing the Rps1-Kan inserted into the intron 5 of the human LAG-3 gene by negative selection (human LAG-3 repair fragments). In the same manner as above, the human LAG-3 repair fragment(s) was(were) introduced into *Escherichia coli* strains having Red/ET reaction ability together with the mouse LAG-3/human LAG-3 RecBAC Intermediate to induce Red/ET reaction in the host *Escherichia coli*, and chloramphenicol and streptomycin resistant colonies were picked up, thereby constructing a mouse LAG-3/human LAG-3 gene recombinant BAC clone in which the genomic DNA sequence from the translation start codon to the stop codon of the mouse LAG-3 gene was accurately replaced with the genomic DNA sequence of the human LAG-3 gene from the translation start codon to the stop codon (human LAG-3 RecBAC). The genomic DNA sequences with H1 to H6 connected by Red/ET reaction were checked by sequence analysis.

10)-2 Purification of High-Purity BAC DNA Fragments

DH10B cells transformed by the recombinant BAC clone that is a construct for expressing the human LAG-3 RecBAC gene were cloned on an LB agar medium containing chloramphenicol, and a single colony was picked up and shake-cultured in a liquid medium all night and all day.

The human LAG-3 RecBAC recombinant BAC clone was purified using a plasmid extraction kit (MACHEREY-NAGEL GmbH & Co. KG, Nucleobond BAC100 kit) according to the method of Abe, et al., with partial modification (Exp Anim. 2004 53 (4): 311-20. Establishment of an efficient BAC transgenesis protocol and its application to functional characterization of the mouse Brachyury locus. Abe K, Hazama M, Katoh H, Yamamura K, Suzuki M), followed by addition of PI-SceI, thereby allowing reaction at 37° C. for 16 hours for digestion.

The linearized human LAG-3 RecBAC recombinant BAC clone was applied to a 1% SeaKem GTG agarose gel (Takara Bio Inc.), and electrophoresis was performed in conditions of 6 v/cm, 0.1 to 40 sec, 15 hr, and 14° C. using a pulsed field electrophoresis apparatus (CHEF DR-II, Bio-Rad Laboratories, Inc). By visualizing a part of the sample as a guide marker using a UV transilluminator, the linearized human LAG-3 RecBAC recombinant BAC clone separated in the agarose gel was excised with a razor without UV irradiation. The obtained long chain DNA fragment was extracted from the agarose gel by the electroelution method and was dialyzed with a TE buffer prepared for microinjection at 4° C. for 2 hours. The purified DNA fragment was applied to pulsed field electrophoresis to confirm that the long chain DNA fragment was highly purified without segmentation and determine the DNA concentration thereof using a NanoDrop spectrophotometer (AGC TECHNO GLASS CO., LTD). A solution of the DNA fragment was diluted to 0.5 ng/µl to prepare a solution of an expression construct for transgenic mouse creation.

10-3) C57BL/6J Mouse Embryonic Microinjection

PMSG and hCG were administered to female C57BL/6J mice to induce superovulation, followed by mating with male mice of the same strain, and then fertilized eggs were collected.

Using a micromanipulator, the purified human LAG-3 RecBAC/human FcγR BAC expression constructs were directly injected into the male nuclei of pronuclear stage embryos of C57BL/6J mice. The DNA injected embryos were transplanted into the fallopian tubes of pseudopregnancy-induced recipient female mice.

10-4) Southern Screening of Founders

Progenies obtained by spontaneous delivery from the C57BL/6J mouse fertilized eggs with the human LAG-3 RecBAC/human FcγR BAC expression constructs injected therein were nursed to weaning. Human LAG-3 RecBAC/human FcγR BAC transgenic mice founder candidate individuals, were weaned at 3-weeks' old and ear tagged for identifying the individuals. Thereafter, their tail tissues were biopsied and stored at −80° C. until analysis.

The tail tissues of the candidate individuals of the human LAG-3 RecBAC/human FcγR BAC transgenic mice that had been stored at −80° C. were melted at room temperature, and a lysis buffer containing 1% SDS (Wako Pure Chemical Industries, Ltd.), 1 mg/ml actinase E (KAKEN PHARMACEUTICAL CO., LTD.) and 0.15 mg/ml proteinase K (Merck KGaA) was added thereto, followed by shaking at 55° C. for 16 hours to solubilize the tissues. Proteins binding to the genomic DNA and solubilized from the tissues were removed by phenol extraction and phenol/chloroform extraction. The RNA mixed in with the genomic DNA was degraded with RNase A (Sigma-Aldrich), and thereafter a polymer genomic DNA was precipitated by isopropanol precipitation. The precipitated genomic DNA was washed with 70% ethanol, air-dried, and thereafter redissolved in 50 µl of TE.

The DNA concentration of the genomic DNA solution prepared from each specimen was determined by absorption spectroscopy, and the volume of the genomic DNA solution equivalent to 5 µg of DNA was calculated from the value of the DNA concentration of each specimen.

To the genomic DNA prepared from each specimen, the positive control DNA (the genomic DNA of the control mice to which the expression construct used for microinjection was added), and the negative control DNA (the genomic DNA of the control mice), was added a restriction enzyme, followed by reaction at 37° C. for 16 hours. The fragments of the genomic DNA produced were precipitated by isopropanol precipitation, washed with 70% ethanol, air-dried, and thereafter redissolved in TE. The genomic DNA fragments were applied to a 1.2% agarose gel for electrophoresis, and the genomic DNA fragments separated in the agarose gel were visualized using a UV transilluminator and photographed with scale.

The agarose gel was immersed in 0.25N hydrochloric acid and gently shaken for 10 minutes. Thereafter, it was further immersed in 0.4N sodium hydroxide and gently shaken for 10 minutes. The genomic DNA fragments separated in the agarose gel were transferred to a nylon membrane (Hybond-XL; GE Healthcare) at room temperature for 16 hours by the capillary method using 0.4N sodium hydroxide. The nylon membrane with the genomic DNA fragments transferred therein was immersed in 2×SSC, gently shaken for 10 minutes, thereafter air-dried, and stored at room temperature until use for hybridization.

Using a DNA labeling kit (Megaprime DNA Labelling System; GE Healthcare), DNA fragments were [32P]-labeled by the random prime method. Using Sephadex spin columns (ProbeQuant G-50 Micro Columns; GE Healthcare), the [32P]-labeled fragments were purified to give [32P]-labeled probes.

The nylon membrane with the genomic DNA fragments transferred therein was put into a hybridization buffer, followed by preincubation at 65° C. for 1 hour. Thereafter, the [32P]-labeled probe denatured by heating at 95° C. for 5 minutes and immediate cooling with ice for 5 minutes was added thereto, followed by incubation at 65° C. for 4 hours. The nylon membrane was taken out after the completion of the incubation and washed with 0.1% SDS and 0.5×SSC at 65° C. for about 15 minutes. The radioactivity derived from the probe bound to the membrane was monitored with a survey meter, and the washing was repeated until the radioactivity became approximately constant.

The washed membrane was covered with Saran Wrap, laminated with an X-ray film (BioMax MS; Eastman Kodak Company) in a darkroom, and put into an autoradiography cassette. After exposure at 4° C. for 1 week, the X-ray film was developed. Specific signals derived from the human LAG-3 RecBAC/human FcγR BAC expression constructs were detected by autoradiography, and individuals giving the signals specific to hybridization with the [32P]-labeled probes were identified as the founder individuals of human LAG-3 RecBAC/human FcγR BAC transgenic mice.

10-5) Creation and Proliferation of F1 Mice

Progeny animals of the founder individuals were obtained and genotyped to obtain established Tg mouse lines. The Tg mouse founders identified by Southern analysis and wild-type C57BL/6J mice were in vitro fertilized or naturally mated to create F1 individuals. The established lines, where transfer of the transgenes to the F1 individuals was confirmed by genotyping, were proliferated by in vitro fertilization or natural mating with wild type C57BL/6J mice, and mice with both the human LAG-3 and the human FcγRIIIA heterozygously introduced therein, which was revealed by genotyping, were used for the experiments.

Figure 13:
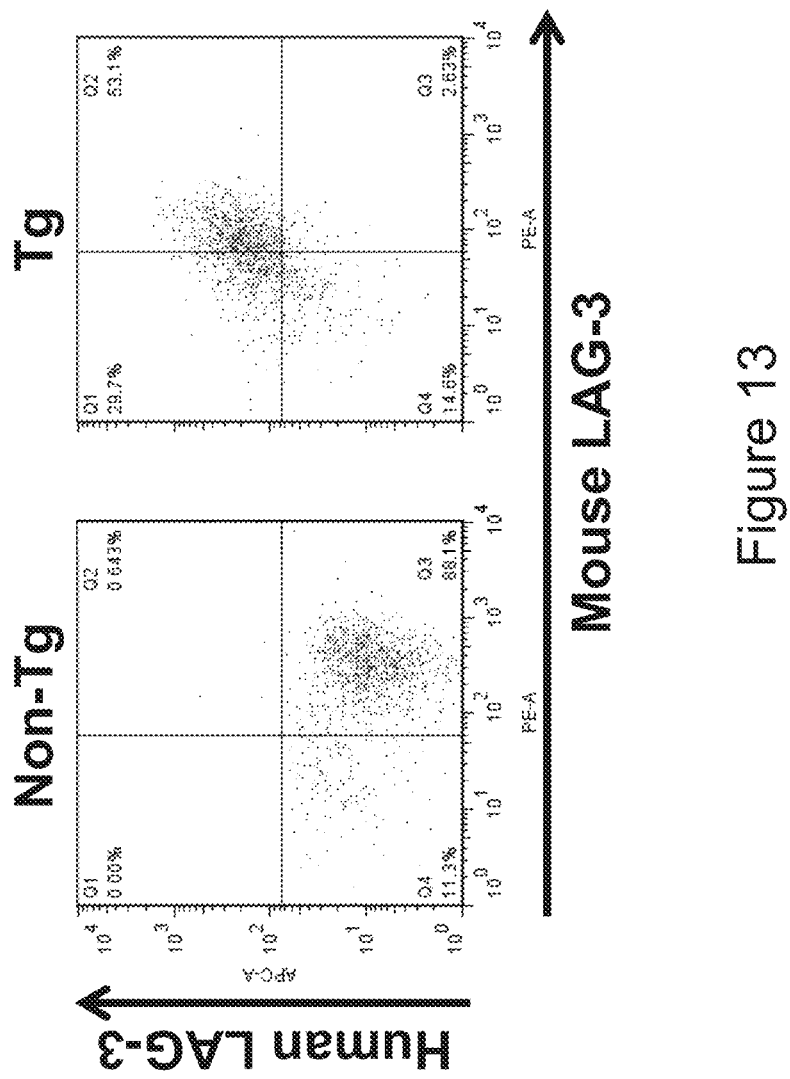
FIG. 13 is a diagram showing that the expression of human LAG-3 in human LAG-3/human FcγRIIIA double transgenic mice is consistent with the expression of mouse LAG-3. Human and mouse LAG-3 expression on activated T cells obtained by stimulating white blood cells obtained from the peripheral blood of human LAG-3/human FcγRIIIA double transgenic mice (Tg) and control wild type mice (Non-Tg) with Con A were investigated by flow cytometry (multiple staining). The results when CD3 positive T cells were gated for analysis are shown. The quadrants of the graph were set using samples free from staining antibodies to human and mouse LAG-3.

10-6) Confirmation of Phenotypes of Human LAG-3/Human FcγRIIIA Double Transgenic Mice The expression of the genes introduced into the obtained human LAG-3/human FcγRIIIA double transgenic mice was investigated by flow cytometry. The peripheral blood was collected from the tail vein of each mouse into a heparinized hematocrit capillary, and the red blood cells were hemolyzed by PharmLyse (manufactured by Becton, Dickinson and Company) to obtain white blood cells. The white blood cells were partially used for expression analysis of the human FcγRIIIA by flow cytometry, and the remainder was stimulated for 3 days with a medium containing 2 μg/mL Concanavalin A (Con A: Sigma-Aldrich) for inducing the expression of LAG-3 to obtain activated T cells. To the latter cells, were added a PE labeled anti-mouse LAG-3 antibody (manufactured by Becton, Dickinson and Company), an ATT0647 labeled anti-human LAG-3 antibody (manufactured by Enzo Life Sciences, Inc.), a FITC labeled anti-mouse CD3 antibody (manufactured by Becton, Dickinson and Company), and a LIVE/DEAD Fixable Dead Cell Stain Kit-near-IR fluorescent reactive dye (manufactured by Invitrogen Corp.) for suspension, followed by standing at 4° C. for 30 minutes. For use for identifying the positions of the negative populations, a control free from the PE labeled anti-mouse LAG-3 antibody and the ATT0647 labeled anti-human LAG-3 antibody was also prepared and treated in the same manner. After washing with a FACS buffer, the cells were resuspended in PBS containing 1% paraformaldehyde, followed by detection using a flow cytometer (Cantoll: manufactured by Becton, Dickinson and Company). The data was analyzed using FlowJo (manufactured by Tree Star Inc). After removal of LIVE/DEAD Fixable Dead Cell Stain Kit-near-IR fluorescent reactive dye-positive dead cells by gating, living cells were analyzed. As a result, only the expression of mouse LAG-3 was found, and the expression of human LAG-3 was not found on Con A activated T cells derived from the control wild-type mice, whereas the expression of both mouse LAG-3 and human LAG-3 were found on Con A activated T cells derived from the human LAG-3/human FcγRIIIA double transgenic mice, and dots in the dot plot representing the individual cells were distributed almost diagonally, as shown in FIG. 13. Almost no expressions of both mouse LAG-3 and human LAG-3 were found on resting T cells that were not activated. These results revealed that, in the developed human LAG-3/human FcγRIIIA double transgenic mice, human LAG-3 was expressed according to the endogenous expression pattern of mouse LAG-3, as initially planned, by using the BAC transgenic approach. Further, for the human FcγRIIIA, results comparable to the previous report (Non Patent Literature 10) were confirmed, in which the expression was observed on about 47% of peripheral blood NK cells (CD3$^-$ DX5$^+$) of the developed human LAG-3/human FcγRIIIA double transgenic mice.

Example 11. In Vivo Evaluation of Humanized Anti-Human LAG-3 Antibody hLA212_H4/L2

11-1) LAG-3 Positive Cell Depletion Activity of Humanized Anti-Human LAG-3 Antibody hLA212_H4/L2

Figure 14:
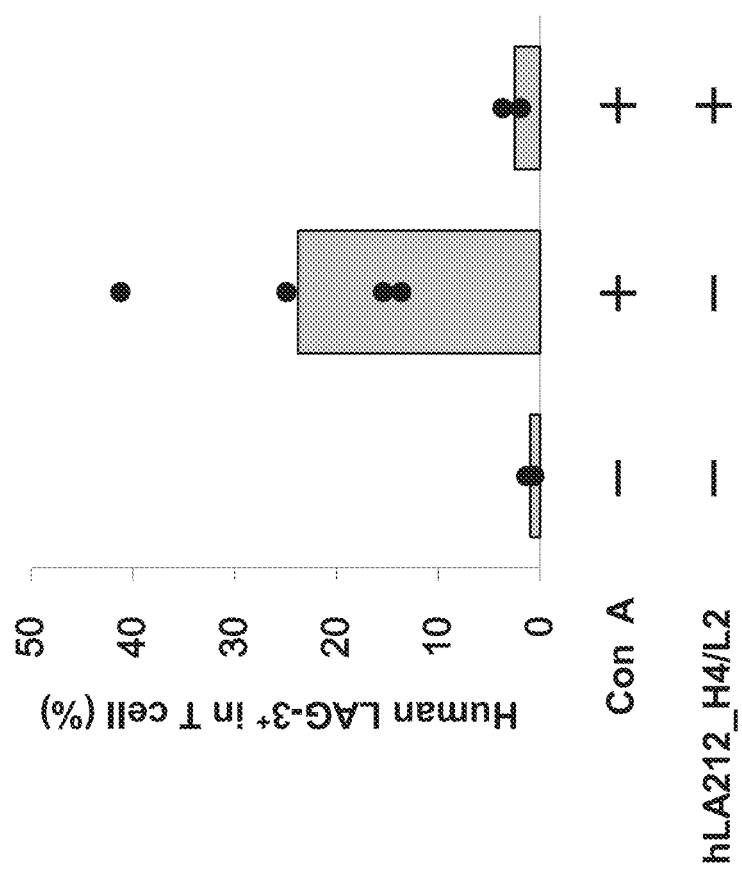
FIG. 14 is a diagram showing the depletion activity of the humanized anti-LAG-3 antibody hLA212_H4/L2 against LAG-3-expressing cells in vivo. The vertical axis represents human LAG-3 positivity in T cells of the peripheral blood of human LAG-3/human FcγRIIIA double transgenic mice two days after the administration of the antibody and Con A. The antibody was intraperitoneally administered at a dose of 30 mg/kg immediately before the administration of Con A.

Using the human LAG-3/human FcγRIIIA double transgenic mice of Example 10, it was investigated whether the humanized anti-human LAG-3 antibody hLA212_H4/L2 obtained has the activity of depleting LAG-3 positive cells in vivo. Immediately after the humanized anti-human LAG-3 antibody hLA212_H4/L2 (30 mg/kg) or a solvent was intraperitoneally administered to the human LAG-3/human FcγRIIIA double transgenic mice, Con A (manufactured by Sigma-Aldrich) having polyclonal T cell activating action was intravenously administered at a dose of 15 mg/kg. Red blood cells were hemolyzed from the blood collected 2 days thereafter with PharmLyse (manufactured by Becton, Dickinson and Company) to obtain white blood cells, and the white blood cells were used for the flow cytometry. The white blood cells were allowed to react with FcBlock (manufactured by Becton, Dickinson and Company), and thereafter a PE labeled anti-mouse LAG-3 antibody (manufactured by Becton, Dickinson and Company), an ATT0647 labeled anti-human LAG-3 antibody (manufactured by Enzo Life Sciences, Inc.), a FITC labeled anti-mouse CD3 antibody (manufactured by Becton, Dickinson and Company), and a LIVE/DEAD Fixable Dead Cell Stain Kit-near-IR fluorescent reactive dye (manufactured by Invitrogen Corp.) were added thereto for suspension, followed by standing at 4° C. for 30 minutes. For use for identifying the positions of the negative populations, a control free from the PE labeled anti-mouse LAG-3 antibody and the ATT0647 labeled anti-human LAG-3 antibody was also prepared and treated in the same manner. After washing with a FACS buffer, the cells were resuspended in PBS containing 1% paraformaldehyde, followed by detection using a flow cytometer (Cantoll: manufactured by Becton, Dickinson and Company). The data was analyzed using FlowJo (manufactured by Tree Star Inc). After removal of LIVE/DEAD Fixable Dead Cell Stain Kit-near-IR fluorescent reactive dye-positive dead cells by gating, living cells were analyzed. As a result of calculating the human LAG-3 positivity in CD3 positive T cells, as shown in FIG. 14, almost no human LAG-3 positive cells were found in the peripheral blood T cells of untreated human LAG-3/human FcγRIIIA double transgenic mice, whereas an average of 24% of the peripheral blood T cells in the antibody non-administration group became positive for human LAG-3 by the administration of the Con A having polyclonal T cell activating action. In contrast, the human LAG-3 positivity in the peripheral blood T cells of the Con A-administered mice to which hLA212_H4/L2 was administered remarkably decreased. A similar tendency was observed in splenic T cells and in the peripheral blood T cells obtained one day after the administration of the Con A, and similar results were also obtained for the positivity for mouse LAG-3 and CD69 which is another activation marker. These results revealed that the obtained humanized anti-human LAG-3 antibody hLA212_H4/L2 had the activity of depleting LAG-3 positive cells in vivo.

11-2) Activity of Humanized Anti-Human LAG-3 Antibody hLA212_H4/L2 on T Cell-Dependent Autoimmune Disease Model In order to reveal whether the humanized anti-human LAG-3 antibody hLA212_H4/L2 having the activity of depleting LAG-3 positive cells in vivo is useful for treating autoimmune diseases, the efficacy against an EAE (experimental autoimmune encephalomyelitis) model (Non Patent Literature 11) that is a typical T cell-dependent autoimmune disease (multiple sclerosis) model was investigated.

Figure 15:
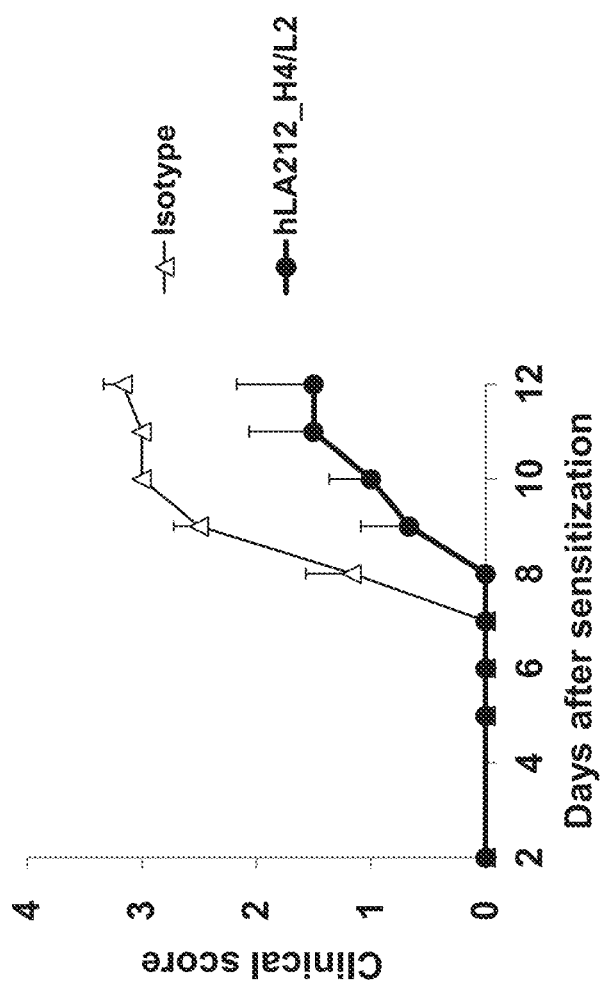
FIG. 15 is a diagram showing that the humanized anti-LAG-3 antibody hLA212_H4/L2 has an activity of suppressing an autoimmune disease model in vivo. The clinical scores of EAE in human LAG-3/human FcγRIIIA double transgenic mice in which EAE was induced and to which the humanized anti-LAG-3 antibody hLA212_H4/L2 or a control antibody was administered are shown over time. Each antibody was intravenously administered at a dose of 30 mg/kg on the day of sensitization and seven days thereafter.

A solution obtained by dissolving a peptide (amino acid 35-55, PEPTIDE INSTITUTE, INC.) derived from MOG (Myelin Oligodendrocyte Glycoprotein) that is one of the central nervous myelin component proteins in normal saline at a concentration of 4 mg/mL was mixed with a 8 mg/mL mixture of Killed *Mycobacterium Tuberculosis* H37Ra (manufactured by Becton, Dickinson and Company) and Freund's Incomplete Adjuvant (manufactured by Wako Pure Chemical Industries, Ltd.) in equal amounts to give an emulsion. This emulsion was subcutaneously injected on Day 0 into both flanks of the human LAG-3/human FcγRIIIA double transgenic mice in an amount of 50 μL each, and 0.2 μg of pertussis toxin diluted with normal saline was further intravenously administered thereto, to induce EAE. Thereafter, the clinical scores of EAE were observed daily as follows. That is, Score 0: Asymptomatic; Score 1: Limp tail; Score 2: Abnormal gait and loss of righting reflex; Score 3: Hind leg paralysis; Score 4: Partial paralysis of forelimbs; and Score 5: Death or euthanasia. The humanized anti-human LAG-3 antibody hLA212_H4/L2 and the control antibody were intravenously administered each at a dose of 30 mg/kg on Days 0 and 7. As a result, the average of the EAE clinical scores in the humanized anti-human LAG-3 antibody hLA212_H4/L2-administered group was suppressed to 50% or less during the observation period, as compared with that in the control antibody-administered group, as shown in FIG. 15. Further, in the hLA212_H4/L2 administered group, the weight loss with EAE progression was also suppressed. These results revealed that the humanized anti-human LAG-3 antibody hLA212_H4/L2 having an activity to deplete LAG-3 positive cells in vivo suppresses EAE that is a typical T cell-dependent autoimmune disease model, and can be a therapeutic medicine for human autoimmune diseases.

INDUSTRIAL APPLICABILITY

The antibody, the binding fragment thereof, and the like of the present invention are useful for treatment and/or prevention of diseases associated with LAG-3 positive cells such as autoimmune diseases.

Sequence Listing Free Text

SEQ ID No: 1: Nucleotide sequence encoding amino acid sequence of heavy chain variable region of rLA204 antibody (FIG. 16)
SEQ ID No: 2: Amino acid sequence of heavy chain variable region of rLA204 antibody (FIG. 17)
SEQ ID No: 3: Nucleotide sequence encoding amino acid sequence of light chain variable region of rLA204 antibody (FIG. 18)
SEQ ID No: 4: Amino acid sequence of light chain variable region of rLA204 antibody (FIG. 19)
SEQ ID No: 5: Nucleotide sequence encoding amino acid sequence of heavy chain variable region of rLA212 antibody (FIG. 20)
SEQ ID No: 6: Amino acid sequence of heavy chain variable region of rLA212 antibody (FIG. 21)
SEQ ID No: 7: Nucleotide sequence encoding amino acid sequence of light chain variable region of rLA212 antibody (FIG. 22)
SEQ ID No: 8: Amino acid sequence of light chain variable region of rLA212 antibody (FIG. 23)
SEQ ID No: 9: Nucleotide sequence encoding amino acid sequence of heavy chain variable region of rLA225 antibody (FIG. 24)
SEQ ID No: 10: Amino acid sequence of heavy chain variable region of rLA225 antibody (FIG. 25)
SEQ ID No: 11: Nucleotide sequence encoding amino acid sequence of light chain variable region of rLA225 antibody (FIG. 26)
SEQ ID No: 12: Amino acid sequence of light chain variable region of rLA225 antibody (FIG. 27)
SEQ ID No: 13: Nucleotide sequence encoding amino acid sequence of heavy chain variable region of rLA869 antibody (FIG. 28)
SEQ ID No: 14: Amino acid sequence of heavy chain variable region of rLA869 antibody (FIG. 29)
SEQ ID No: 15: Nucleotide sequence encoding amino acid sequence of light chain variable region of rLA869 antibody (FIG. 30)
SEQ ID No: 16: Amino acid sequence of light chain variable region of rLA869 antibody (FIG. 31)
SEQ ID No: 17: Nucleotide sequence of cDNA encoding amino acid sequence of heavy chain variable region of rLA1264 antibody (FIG. 32)
SEQ ID No: 18: Amino acid sequence of heavy chain variable region of rLA1264 antibody (FIG. 33)
SEQ ID No: 19: Nucleotide sequence encoding amino acid sequence of light chain variable region of rLA1264 antibody (FIG. 34)
SEQ ID No: 20: Amino acid sequence of light chain variable region of rLA1264 antibody (FIG. 35)
SEQ ID No: 21: Nucleotide sequence encoding amino acid sequences of human light chain secretion signal and human K chain constant region (FIG. 36)
SEQ ID No: 22: Nucleotide sequence encoding amino acid sequences of human heavy chain secretion signal and human IgG1 constant region (FIG. 37)
SEQ ID No: 23: Nucleotide sequence encoding amino acid sequence of heavy chain of cLA212 antibody (FIG. 38)
SEQ ID No: 24: Amino acid sequence of heavy chain of cLA212 antibody (FIG. 39)
SEQ ID No: 25: Nucleotide sequence encoding amino acid sequence of light chain of cLA212 antibody (FIG. 40)
SEQ ID No: 26: Amino acid sequence of light chain of cLA212 antibody (FIG. 41)
SEQ ID No: 27: Nucleotide sequence encoding amino acid sequence of heavy chain H2 of hLA212 antibody (FIG. 42)
SEQ ID No: 28: Amino acid sequence of heavy chain H2 of hLA212 antibody (FIG. 43)
SEQ ID No: 29: Nucleotide sequence encoding amino acid sequence of heavy chain H3 of hLA212 antibody (FIG. 44)
SEQ ID No: 30: Amino acid sequence of heavy chain H3 of hLA212 antibody (FIG. 45)
SEQ ID No: 31: Nucleotide sequence encoding amino acid sequence of light chain L1 of hLA212 antibody (FIG. 46)
SEQ ID No: 32: Amino acid sequence of light chain L1 of hLA212 antibody (FIG. 47)
SEQ ID No: 33: Nucleotide sequence encoding amino acid sequence of light chain L2 of hLA212 antibody (FIG. 48)
SEQ ID No: 34: Amino acid sequence of light chain L2 of hLA212 antibody (FIG. 49)
SEQ ID No: 35: Nucleotide sequence encoding amino acid sequence of light chain L3 of hLA212 antibody (FIG. 50)
SEQ ID No: 36: Amino acid sequence of light chain L3 of hLA212 antibody (FIG. 51)
SEQ ID No: 37: Nucleotide sequence encoding amino acid sequence of light chain L4 of hLA212 antibody (FIG. 52)

SEQ ID No: 38: Amino acid sequence of light chain L4 of hLA212 antibody (FIG. 53)
SEQ ID No: 39: Nucleotide sequence encoding amino acid sequence of light chain L5 of hLA212 antibody (FIG. 54)
SEQ ID No: 40: Amino acid sequence of light chain L5 of hLA212 antibody (FIG. 55)
SEQ ID No: 41: Amino acid sequence of heavy chain CDRH1 of rLA204 antibody (FIG. 56)
SEQ ID No: 42: Amino acid sequence of heavy chain CDRH2 of rLA204 antibody (FIG. 57)
SEQ ID No: 43: Amino acid sequence of heavy chain CDRH3 of rLA204 antibody (FIG. 58)
SEQ ID No: 44: Amino acid sequence of light chain CDRL1 of rLA204 antibody (FIG. 59)
SEQ ID No: 45: Amino acid sequence of light chain CDRL2 of rLA204 antibody (FIG. 60)
SEQ ID No: 46: Amino acid sequence of light chain CDRL3 of rLA204 antibody (FIG. 61)
SEQ ID No: 47: Amino acid sequence of heavy chain CDRH1 of rLA212 antibody (FIG. 62)
SEQ ID No: 48: Amino acid sequence of heavy chain CDRH2 of rLA212 antibody (FIG. 63)
SEQ ID No: 49: Amino acid sequence of heavy chain CDRH3 of rLA212 antibody (FIG. 64)
SEQ ID No: 50: Amino acid sequence of light chain CDRL1 of rLA212 antibody (FIG. 65)
SEQ ID No: 51: Amino acid sequence of light chain CDRL2 of rLA212 antibody (FIG. 66)
SEQ ID No: 52: Amino acid sequence of light chain CDRL3 of rLA212 antibody (FIG. 67)
SEQ ID No: 53: Amino acid sequence of heavy chain CDRH1 of rLA225 antibody (FIG. 68)
SEQ ID No: 54: Amino acid sequence of heavy chain CDRH2 of rLA225 antibody (FIG. 69)
SEQ ID No: 55: Amino acid sequence of heavy chain CDRH3 of rLA225 antibody (FIG. 70)
SEQ ID No: 56: Amino acid sequence of light chain CDRL1 of rLA225 antibody (FIG. 71)
SEQ ID No: 57: Amino acid sequence of light chain CDRL2 of rLA225 antibody (FIG. 72)
SEQ ID No: 58: Amino acid sequence of light chain CDRL3 of rLA225 antibody (FIG. 73)
SEQ ID No: 59: Amino acid sequence of heavy chain CDRH1 of rLA869 antibody (FIG. 74)
SEQ ID No: 60: Amino acid sequence of heavy chain CDRH2 of rLA869 antibody (FIG. 75)
SEQ ID No: 61: Amino acid sequence of heavy chain CDRH3 of rLA869 antibody (FIG. 76)
SEQ ID No: 62: Amino acid sequence of light chain CDRL1 of rLA869 antibody (FIG. 77)
SEQ ID No: 63: Amino acid sequence of light chain CDRL2 of rLA869 antibody (FIG. 78)
SEQ ID No: 64: Amino acid sequence of light chain CDRL3 of rLA869 antibody (FIG. 79)
SEQ ID No: 65: Amino acid sequence of heavy chain CDRH1 of rLA1264 antibody (FIG. 80)
SEQ ID No: 66: Amino acid sequence of heavy chain CDRH2 of rLA1264 antibody (FIG. 81)
SEQ ID No: 67: Amino acid sequence of heavy chain CDRH3 of rLA1264 antibody (FIG. 82)
SEQ ID No: 68: Amino acid sequence of light chain CDRL1 of rLA1264 antibody (FIG. 83)
SEQ ID No: 69: Amino acid sequence of light chain CDRL2 of rLA1264 antibody (FIG. 84)
SEQ ID No: 70: Amino acid sequence of light chain CDRL3 of rLA1264 antibody (FIG. 85)
SEQ ID No: 71: Primer RG2AR3 (FIG. 86)
SEQ ID No: 72: Primer RKR5 (FIG. 87)
SEQ ID No: 73: Primer 3.3-F1 (FIG. 88)
SEQ ID No: 74: Primer 3.3-R1 (FIG. 89)
SEQ ID No: 75: Primer 212H-F (FIG. 90)
SEQ ID No: 76: Primer 212H-R (FIG. 91)
SEQ ID No: 77: Primer 212L-F (FIG. 92)
SEQ ID No: 78: Primer 212L-R (FIG. 93)
SEQ ID No: 79: Oligonucleotide LAG-3-H1 (FIG. 94)
SEQ ID No: 80: Oligonucleotide LAG-3-H2 (FIG. 95)
SEQ ID No: 81: Oligonucleotide LAG-3-H3 (FIG. 96)
SEQ ID No: 82: Oligonucleotide LAG-3-H4 (FIG. 97)
SEQ ID No: 83: Oligonucleotide LAG-3-H5 (FIG. 98)
SEQ ID No: 84: Oligonucleotide LAG-3-H6 (FIG. 99)
SEQ ID No: 85: Nucleotide sequence encoding amino acid sequence of human LAG-3 (FIG. 100)
SEQ ID No: 86: Amino acid sequence of human LAG-3 (FIG. 101)

The invention claimed is:

1. A method for binding an antibody or a binding fragment thereof to human LAG-3 expressed on an activated human T cell without preventing binding of the human LAG-3 to human major histocompatibility complex class II molecules, comprising contacting the activated human T cell with the antibody or the binding fragment thereof, wherein the antibody or the binding fragment thereof binds to domain 3 of human LAG-3, wherein the antibody or binding fragment thereof comprises:
   (a) a heavy chain comprising a CDRH1 having the amino acid sequence represented by SEQ ID No: 41, a CDRH2 having the amino acid sequence represented by SEQ ID No: 42, and a CDRH3 having the amino acid sequence represented by SEQ ID No: 43, and a light chain comprising a CDRL1 having the amino acid sequence represented by SEQ ID No: 44, a CDRL2 having the amino acid sequence represented by SEQ ID No: 45, and a CDRL3 having the amino acid sequence represented by SEQ ID No: 46;
   (b) a heavy chain comprising CDRH1 having the amino acid sequence represented by SEQ ID No: 47, a CDRH2 having the amino acid sequence represented by SEQ ID No: 48, and a CDRH3 having the amino acid sequence represented by SEQ ID No: 49, and a light chain comprising a CDRL1 having the amino acid sequence represented by SEQ ID No: 50, a CDRL2 having the amino acid sequence represented by SEQ ID No: 51, and a CDRL3 having the amino acid sequence represented by SEQ ID No: 52;
   (c) a heavy chain comprising a CDRH1 having the amino acid sequence represented by SEQ ID No: 53, a CDRH2 having the amino acid sequence represented by SEQ ID No: 54, and a CDRH3 having the amino acid sequence represented by SEQ ID No: 55, and a light chain comprising a CDRL1 having the amino acid sequence represented by SEQ ID No: 56, a CDRL2 having the amino acid sequence represented by SEQ ID No: 57, and a CDRL3 having the amino acid sequence represented by SEQ ID No: 58;
   (d) a heavy chain comprising a CDRH1 having the amino acid sequence represented by SEQ ID No: 59, a CDRH2 having the amino acid sequence represented by SEQ ID No: 60, and a CDRH3 having the amino acid sequence represented by SEQ ID No: 61, and a light chain comprising a CDRL1 having the amino acid sequence represented by SEQ ID No: 62, a CDRL2 having the amino acid sequence represented by SEQ ID No: 63, and a CDRL3 having the amino acid sequence represented by SEQ ID No: 64; or
   (e) a heavy chain comprising a CDRH1 having the amino acid sequence represented by SEQ ID No: 65, a CDRH2 having the amino acid sequence represented by SEQ ID No: 66, and a CDRH3 having the amino acid sequence represented by SEQ ID No: 67, and a light chain comprising a CDRL1 having the amino acid sequence represented by SEQ ID No: 68, a CDRL2 having the amino acid sequence represented by SEQ ID No: 69, and a CDRL3 having the amino acid sequence represented by SEQ ID No: 70.

2. The method according to claim 1, wherein the antibody or binding fragment thereof comprises a deletion of one or two amino acids at the carboxyl terminus of one or two heavy chains.

3. The method according to claim 1, wherein the antibody or binding fragment thereof is in low fucose form.

4. The method according to claim 1, wherein the antibody or the binding fragment thereof comprises:
   a heavy chain amino acid sequence selected from the group consisting of SEQ ID Nos: 28 and 30, and an amino acid sequence in which one, two or three amino acids are deleted from the carboxyl terminus of SEQ ID No: 28 or 30; and
   a light chain amino acid sequence selected from the group consisting of SEQ ID Nos: 32, 34, 36, 38 and 40, and an amino acid sequence in which one, two or three amino acids are deleted from the carboxyl terminus of SEQ ID No: 32, 34, 36, 38 or 40.

5. The method according to claim 3, wherein the antibody is capable of reducing the number of LAG-3 positive cells in vivo.

6. The method according to claim 3, wherein the antibody is capable of suppressing experimental autoimmune encephalomyelitis in vivo.

7. The method according to claim 1, wherein the antibody or the binding fragment thereof binds to a site on the domain 3 of human LAG-3 recognized by an antibody with a heavy chain amino acid sequence comprising amino acid 20 to amino acid 470 of the amino acid sequence selected from the group consisting of SEQ ID Nos: 28 and 30 and a light chain amino acid sequence comprising amino acid 21 to amino acid 234 of the amino acid sequence selected from the group consisting of SEQ ID Nos: 32, 34, 36, 38, and 40, or a binding fragment thereof.

8. The method according to claim 1, wherein the antibody or the binding fragment thereof is an antibody that has one or both of the following properties:
   (i) the antibody has in vitro ADCC activity; and
   (ii) the presence of the antibody allows human LAG-3 to exert human T cell suppression function.

9. The method according to claim 1, wherein the antibody or the binding fragment thereof is a chimeric antibody or a humanized antibody.

10. The method according to claim 9, wherein the antibody or the binding fragment thereof is a humanized antibody.

11. The method according to claim 7, wherein the antibody or binding fragment thereof comprises a deletion of one or two amino acids at the carboxyl terminus of one or two heavy chains.

* * * * *

```
                        SEQUENCE LISTING

<160> NUMBER OF SEQ ID NOS: 86

<210> SEQ ID NO 1
<211> LENGTH: 366
<212> TYPE: DNA
<213> ORGANISM: Rattus norvegicus
<220> FEATURE:
<221> NAME/KEY: CDS
<222> LOCATION: (1)..(366)

<400> SEQUENCE: 1 gag gta gag ctg gtg gag tct ggg ggc ggc tta gtg cag cct gga agg      48
Glu Val Glu Leu Val Glu Ser Gly Gly Gly Leu Val Gln Pro Gly Arg
1               5                   10                  15 tcc atg aaa ctc tcc tgt gca gcc tca gga ttc act ttc aga acc tat      96
Ser Met Lys Leu Ser Cys Ala Ala Ser Gly Phe Thr Phe Arg Thr Tyr
            20                  25                  30 ggc atg gcc tgg gtc cgc cag gct cca acg aag ggt ctg gag tgg gtc     144
Gly Met Ala Trp Val Arg Gln Ala Pro Thr Lys Gly Leu Glu Trp Val
        35                  40                  45
```

```
gca tcc att agt act ggt ggt ggt agc act tac tat cgc gac tcc gtg      192
Ala Ser Ile Ser Thr Gly Gly Gly Ser Thr Tyr Tyr Arg Asp Ser Val
            50                  55                  60 aag ggc cga ttc act atc tcc aga gat aat gca aaa agc acc cta tac      240
Lys Gly Arg Phe Thr Ile Ser Arg Asp Asn Ala Lys Ser Thr Leu Tyr
 65                  70                  75                  80 ctg caa atg gac agt ctg agg tct gag gac acg gcc act tat tac tgt      288
Leu Gln Met Asp Ser Leu Arg Ser Glu Asp Thr Ala Thr Tyr Tyr Cys
                    85                  90                  95 aca aca gat cta att aac tac ccg ggt ata ggg ggg ttt gct ttc tgg      336
Thr Thr Asp Leu Ile Asn Tyr Pro Gly Ile Gly Gly Phe Ala Phe Trp
                100                 105                 110 ggc caa ggc act ctg gtc act gtc tct tca                              366
Gly Gln Gly Thr Leu Val Thr Val Ser Ser
            115                 120

<210> SEQ ID NO 2
<211> LENGTH: 122
<212> TYPE: PRT
<213> ORGANISM: Rattus norvegicus

<400> SEQUENCE: 2

Glu Val Glu Leu Val Glu Ser Gly Gly Gly Leu Val Gln Pro Gly Arg
 1               5                  10                  15

Ser Met Lys Leu Ser Cys Ala Ala Ser Gly Phe Thr Phe Arg Thr Tyr
                20                  25                  30

Gly Met Ala Trp Val Arg Gln Ala Pro Thr Lys Gly Leu Glu Trp Val
            35                  40                  45

Ala Ser Ile Ser Thr Gly Gly Gly Ser Thr Tyr Tyr Arg Asp Ser Val
        50                  55                  60

Lys Gly Arg Phe Thr Ile Ser Arg Asp Asn Ala Lys Ser Thr Leu Tyr
 65                 70                  75                  80

Leu Gln Met Asp Ser Leu Arg Ser Glu Asp Thr Ala Thr Tyr Tyr Cys
                85                  90                  95

Thr Thr Asp Leu Ile Asn Tyr Pro Gly Ile Gly Gly Phe Ala Phe Trp
            100                 105                 110

Gly Gln Gly Thr Leu Val Thr Val Ser Ser
        115                 120

<210> SEQ ID NO 3
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 3 aac att gtg atg acc cag tct ccc aaa tcc atg tcc ata tca gta gga       48
Asn Ile Val Met Thr Gln Ser Pro Lys Ser Met Ser Ile Ser Val Gly
 1               5                  10                  15 gac agg gtc acc atg aac tgc aag gcc agt cag aat gtg tat aat aat       96
Asp Arg Val Thr Met Asn Cys Lys Ala Ser Gln Asn Val Tyr Asn Asn
                20                  25                  30 ata gcc tgg tat caa cag aag cca ggg aaa tct cct aaa ctg ttg atc      144
Ile Ala Trp Tyr Gln Gln Lys Pro Gly Lys Ser Pro Lys Leu Leu Ile
            35                  40                  45 tac tat gca tct aac cgg tac act ggg gtc cct gat cgc ttc aca ggc      192
Tyr Tyr Ala Ser Asn Arg Tyr Thr Gly Val Pro Asp Arg Phe Thr Gly
        50                  55                  60
```

```
agt ggc tct ggg aca gat ttc act ctc acc atc cat agt gtg caa gct      240
Ser Gly Ser Gly Thr Asp Phe Thr Leu Thr Ile His Ser Val Gln Ala
 65                  70                  75                  80 gaa gat gca gcc ttt tat tac tgt cag cgt ctt tac aat tct cct ccg      288
Glu Asp Ala Ala Phe Tyr Tyr Cys Gln Arg Leu Tyr Asn Ser Pro Pro
                 85                  90                  95 acg ttc ggt gga ggc acc aag ctg gaa ttg aaa cgg gct                  327
Thr Phe Gly Gly Gly Thr Lys Leu Glu Leu Lys Arg Ala
            100                 105
```

<210> SEQ ID NO 4
<211> LENGTH: 109
<212> TYPE: PRT
<213> ORGANISM: Rattus norvegicus

<400> SEQUENCE: 4

```
Asn Ile Val Met Thr Gln Ser Pro Lys Ser Met Ser Ile Ser Val Gly
 1               5                  10                  15

Asp Arg Val Thr Met Asn Cys Lys Ala Ser Gln Asn Val Tyr Asn Asn
                20                  25                  30

Ile Ala Trp Tyr Gln Gln Lys Pro Gly Lys Ser Pro Lys Leu Leu Ile
            35                  40                  45

Tyr Tyr Ala Ser Asn Arg Tyr Thr Gly Val Pro Asp Arg Phe Thr Gly
 50                  55                  60

Ser Gly Ser Gly Thr Asp Phe Thr Leu Thr Ile His Ser Val Gln Ala
 65                  70                  75                  80

Glu Asp Ala Ala Phe Tyr Tyr Cys Gln Arg Leu Tyr Asn Ser Pro Pro
                 85                  90                  95

Thr Phe Gly Gly Gly Thr Lys Leu Glu Leu Lys Arg Ala
            100                 105
```

<210> SEQ ID NO 5
<211> LENGTH: 363
<212> TYPE: DNA
<213> ORGANISM: Rattus norvegicus
<220> FEATURE:
<221> NAME/KEY: CDS
<222> LOCATION: (1)..(363)

<400> SEQUENCE: 5

```
gag gtg cag ctg gtg gag tct ggg gga ggc tta gtg cag cct gga agg       48
Glu Val Gln Leu Val Glu Ser Gly Gly Gly Leu Val Gln Pro Gly Arg
 1               5                  10                  15 tcc ctg aaa ctc tcc tgt gca gcc tca gga ttc act tac cgt agc tat       96
Ser Leu Lys Leu Ser Cys Ala Ala Ser Gly Phe Thr Tyr Arg Ser Tyr
                20                  25                  30 gtc atg gcc tgg gtc cgc cag gct cca acg agg ggt ctg gag tgg gtc      144
Val Met Ala Trp Val Arg Gln Ala Pro Thr Arg Gly Leu Glu Trp Val
            35                  40                  45 gca tcc att agt act ggt ggt ggt aac act tac tat cga gac tcc gtg      192
Ala Ser Ile Ser Thr Gly Gly Gly Asn Thr Tyr Tyr Arg Asp Ser Val
 50                  55                  60 aag ggc cga ttc act atc tcc aga gat aat gca aag aac acc cta tac      240
Lys Gly Arg Phe Thr Ile Ser Arg Asp Asn Ala Lys Asn Thr Leu Tyr
 65                  70                  75                  80 cta caa atg gac agt ctg agg tct gag gac acg gcc act tat tac tgt      288
Leu Gln Met Asp Ser Leu Arg Ser Glu Asp Thr Ala Thr Tyr Tyr Cys
                 85                  90                  95
```

```
gca gaa gac atg agt aat tcg gga tac ggg ctc ttt gat tac tgg ggc      336
Ala Glu Asp Met Ser Asn Ser Gly Tyr Gly Leu Phe Asp Tyr Trp Gly
            100                 105                 110 caa gga gtc atg gtc aca gtc tcc tca                                  363
Gln Gly Val Met Val Thr Val Ser Ser
        115                 120

<210> SEQ ID NO 6
<211> LENGTH: 121
<212> TYPE: PRT
<213> ORGANISM: Rattus norvegicus

<400> SEQUENCE: 6

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Tyr Arg Ser Tyr
            20                  25                  30

Val Met Ala Trp Val Arg Gln Ala Pro Thr Arg Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Glu Asp Met Ser Asn Ser Gly Tyr Gly Leu Phe Asp Tyr Trp Gly
            100                 105                 110

Gln Gly Val Met Val Thr Val Ser Ser
        115                 120

<210> SEQ ID NO 7
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 7 aac att gtg atg acc cag tct ccc aaa tcc atg tcc ata tca gta gga      48
Asn Ile Val Met Thr Gln Ser Pro Lys Ser Met Ser Ile Ser Val Gly
1               5                   10                  15 gac agg gtc acc atg aac tgc aag gcc ggt cag aat gtg gat aat aat      96
Asp Arg Val Thr Met Asn Cys Lys Ala Gly Gln Asn Val Asp Asn Asn
            20                  25                  30 ata gcc tgg tat caa aag aaa cca ggg cag tct cct aaa ctg ttg atc      144
Ile Ala Trp Tyr Gln Lys Lys Pro Gly Gln Ser Pro Lys Leu Leu Ile
        35                  40                  45 tac tat gca tct aac cgg aac act ggg gtc cct gat cgc ttc aca ggc      192
Tyr Tyr Ala Ser Asn Arg Asn Thr Gly Val Pro Asp Arg Phe Thr Gly
    50                  55                  60 ggt gga tat ggg aca gat ttc act ctc acc atc aat agt gtg caa gct      240
Gly Gly Tyr Gly Thr Asp Phe Thr Leu Thr Ile Asn Ser Val Gln Ala
65                  70                  75                  80 gaa gat gca gcc ttt tat tac tgt cag cgt att tcc aat tct ccg tac      288
Glu Asp Ala Ala Phe Tyr Tyr Cys Gln Arg Ile Ser Asn Ser Pro Tyr
                85                  90                  95 acg ttt ggc gct ggg acc gag ctg gaa ctg aaa cgg gct                  327
Thr Phe Gly Ala Gly Thr Glu Leu Glu Leu Lys Arg Ala
            100                 105
```

<210> SEQ ID NO 8
<211> LENGTH: 109
<212> TYPE: PRT
<213> ORGANISM: Rattus norvegicus

<400> SEQUENCE: 8

```
Asn Ile Val Met Thr Gln Ser Pro Lys Ser Met Ser Ile Ser Val Gly
1               5                   10                  15

Asp Arg Val Thr Met Asn Cys Lys Ala Gly Gln Asn Val Asp Asn Asn
            20                  25                  30

Ile Ala Trp Tyr Gln Lys Lys Pro Gly Gln Ser Pro Lys Leu Leu Ile
        35                  40                  45

Tyr Tyr Ala Ser Asn Arg Asn Thr Gly Val Pro Asp Arg Phe Thr Gly
50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Ser Asn Ser Pro Tyr
                85                  90                  95

Thr Phe Gly Ala Gly Thr Glu Leu Glu Leu Lys Arg Ala
            100                 105
```

<210> SEQ ID NO 9
<211> LENGTH: 363
<212> TYPE: DNA
<213> ORGANISM: Rattus norvegicus
<220> FEATURE:
<221> NAME/KEY: CDS
<222> LOCATION: (1)..(363)

<400> SEQUENCE: 9

```
gag gtg cag ctg gtg gag tct ggg gga ggc tta gtg cag cct gga agg      48
Glu Val Gln Leu Val Glu Ser Gly Gly Gly Leu Val Gln Pro Gly Arg
1               5                   10                  15 tcc atg aaa ctc tcc tgt gta gcc tca gga ttc act ttc agt aac tat      96
Ser Met Lys Leu Ser Cys Val Ala Ser Gly Phe Thr Phe Ser Asn Tyr
            20                  25                  30 tac atg gcc tgg gtc cgc cag gct cca acg aag ggt ctg gag tgg gtc     144
Tyr Met Ala Trp Val Arg Gln Ala Pro Thr Lys Gly Leu Glu Trp Val
        35                  40                  45 gca tcc att agt act ggt ggt ggt aac act tac tat cga gac tcc gtg     192
Ala Ser Ile Ser Thr Gly Gly Gly Asn Thr Tyr Tyr Arg Asp Ser Val
50                  55                  60 aag ggc cga ttc act atc tcc aga gat aat gca aaa agc acc cta tac     240
Lys Gly Arg Phe Thr Ile Ser Arg Asp Asn Ala Lys Ser Thr Leu Tyr
65                  70                  75                  80 ctg caa atg gac agt ctg agg tct gag gac acg gcc act tat tac tgt     288
Leu Gln Met Asp Ser Leu Arg Ser Glu Asp Thr Ala Thr Tyr Tyr Cys
                85                  90                  95 gca aga ccc cca tat ggc tat aac tac ggt tgg ttt act tac tgg ggc     336
Ala Arg Pro Pro Tyr Gly Tyr Asn Tyr Gly Trp Phe Thr Tyr Trp Gly
            100                 105                 110 caa ggc act ctg gtc act gtc tct tca                                 363
Gln Gly Thr Leu Val Thr Val Ser Ser
        115                 120
```

<210> SEQ ID NO 10
<211> LENGTH: 121
<212> TYPE: PRT
<213> ORGANISM: Rattus norvegicus

<400> SEQUENCE: 10

```
Glu Val Gln Leu Val Glu Ser Gly Gly Leu Val Gln Pro Gly Arg
1               5                   10                  15
Ser Met Lys Leu Ser Cys Val Ala Ser Gly Phe Thr Phe Ser Asn Tyr
            20                  25                  30
Tyr Met Ala Trp Val Arg Gln Ala Pro Thr Lys Gly Leu Glu Trp Val
        35                  40                  45
Ala Ser Ile Ser Thr Gly Gly Asn Thr Tyr Tyr Arg Asp Ser Val
    50                  55                  60
Lys Gly Arg Phe Thr Ile Ser Arg Asp Asn Ala Lys Ser Thr Leu Tyr
65                  70                  75                  80
Leu Gln Met Asp Ser Leu Arg Ser Glu Asp Thr Ala Thr Tyr Tyr Cys
                85                  90                  95
Ala Arg Pro Pro Tyr Gly Tyr Asn Tyr Gly Trp Phe Tyr Trp Gly
            100                 105                 110
Gln Gly Thr Leu Val Thr Val Ser Ser
        115                 120
```

<210> SEQ ID NO 11
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 11

```
gac atc cag atg aca cag tct cca gct tcc ctg tct gca tct ctg gga      48
Asp Ile Gln Met Thr Gln Ser Pro Ala Ser Leu Ser Ala Ser Leu Gly
1               5                   10                  15 gaa act gtc acc atc gaa tgt cga gca agt gag gac att cac aat ggt      96
Glu Thr Val Thr Ile Glu Cys Arg Ala Ser Glu Asp Ile His Asn Gly
            20                  25                  30 tta gta tgg tat cag cag aag cca ggg aaa tct cct cag ctc ctg atc     144
Leu Val Trp Tyr Gln Gln Lys Pro Gly Lys Ser Pro Gln Leu Leu Ile
        35                  40                  45 tat aat gca aat agt atg cat act ggg gtc cca tca cgg ttc agt ggc     192
Tyr Asn Ala Asn Ser Met His Thr Gly Val Pro Ser Arg Phe Ser Gly
    50                  55                  60 agt gga tct ggt aca cag tat tct ctc aag ata aac agc ctg cag tct     240
Ser Gly Ser Gly Thr Gln Tyr Ser Leu Lys Ile Asn Ser Leu Gln Ser
65                  70                  75                  80 gaa gat gtc gca agt tat ttc tgt caa cag tat tac aat tat cct cgg     288
Glu Asp Val Ala Ser Tyr Phe Cys Gln Gln Tyr Tyr Asn Tyr Pro Arg
                85                  90                  95 acg ttc ggt gga ggc acc aag ctg gaa ttg aaa cgg gct                  327
Thr Phe Gly Gly Gly Thr Lys Leu Glu Leu Lys Arg Ala
            100                 105
```

<210> SEQ ID NO 12
<211> LENGTH: 109
<212> TYPE: PRT
<213> ORGANISM: Rattus norvegicus

<400> SEQUENCE: 12

```
Asp Ile Gln Met Thr Gln Ser Pro Ala Ser Leu Ser Ala Ser Leu Gly
1               5                   10                  15
Glu Thr Val Thr Ile Glu Cys Arg Ala Ser Glu Asp Ile His Asn Gly
            20                  25                  30
```

```
Leu Val Trp Tyr Gln Gln Lys Pro Gly Lys Ser Pro Gln Leu Leu Ile
             35                  40                  45

Tyr Asn Ala Asn Ser Met His Thr Gly Val Pro Ser Arg Phe Ser Gly
 50                      55                  60

Ser Gly Ser Gly Thr Gln Tyr Ser Leu Lys Ile Asn Ser Leu Gln Ser
 65                  70                  75                  80

Glu Asp Val Ala Ser Tyr Phe Cys Gln Gln Tyr Tyr Asn Tyr Pro Arg
                 85                  90                  95

Thr Phe Gly Gly Gly Thr Lys Leu Glu Leu Lys Arg Ala
                100                 105
```

```
<210> SEQ ID NO 13
<211> LENGTH: 369
<212> TYPE: DNA
<213> ORGANISM: Rattus norvegicus
<220> FEATURE:
<221> NAME/KEY: CDS
<222> LOCATION: (1)..(369)

<400> SEQUENCE: 13 gag gtg cag ctg gtg gag tct ggg gga ggc tta gtg cag cct gga agg      48
Glu Val Gln Leu Val Glu Ser Gly Gly Gly Leu Val Gln Pro Gly Arg
 1               5                  10                  15 tcc ctg aaa ctc tcc tgt gca gcc tca gga ttc act tat cgt acc tat      96
Ser Leu Lys Leu Ser Cys Ala Ala Ser Gly Phe Thr Tyr Arg Thr Tyr
             20                  25                  30 gtc atg gcc tgg gtc cgc cag ggt cca acg cag ggt ctg gag tgg gtc     144
Val Met Ala Trp Val Arg Gln Gly Pro Thr Gln Gly Leu Glu Trp Val
         35                  40                  45 gca tcc att agt act ggt ggt gtt agc act tat tat cga gac tcc gtg     192
Ala Ser Ile Ser Thr Gly Gly Val Ser Thr Tyr Tyr Arg Asp Ser Val
     50                  55                  60 aag ggc cga ttc act atc tcc aga gat aat gca aaa aac acc cta tac     240
Lys Gly Arg Phe Thr Ile Ser Arg Asp Asn Ala Lys Asn Thr Leu Tyr
 65                  70                  75                  80 ttg caa atg gac agt ctg agg tct gag gac acg gcc act tat tac tgt     288
Leu Gln Met Asp Ser Leu Arg Ser Glu Asp Thr Ala Thr Tyr Tyr Cys
                 85                  90                  95 gca aaa gac atg ttg aat ggt tat aac tct cag ggg ctt ttt gat tac     336
Ala Lys Asp Met Leu Asn Gly Tyr Asn Ser Gln Gly Leu Phe Asp Tyr
            100                 105                 110 tgg ggc caa gga gtc atg gtc aca gtc tcc tca                         369
Trp Gly Gln Gly Val Met Val Thr Val Ser Ser
        115                 120
```

```
<210> SEQ ID NO 14
<211> LENGTH: 123
<212> TYPE: PRT
<213> ORGANISM: Rattus norvegicus

<400> SEQUENCE: 14

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Tyr Arg Thr Tyr
             20                  25                  30

Val Met Ala Trp Val Arg Gln Gly Pro Thr Gln Gly Leu Glu Trp Val
         35                  40                  45

Ala Ser Ile Ser Thr Gly Gly Val Ser Thr Tyr Tyr Arg Asp Ser Val
     50                  55                  60
```

```
Lys Gly Arg Phe Thr Ile Ser Arg Asp Asn Ala Lys Asn Thr Leu Tyr
 65                  70                  75                  80

Leu Gln Met Asp Ser Leu Arg Ser Glu Asp Thr Ala Thr Tyr Tyr Cys
             85                  90                  95

Ala Lys Asp Met Leu Asn Gly Tyr Asn Ser Gln Gly Leu Phe Asp Tyr
            100                 105                 110

Trp Gly Gln Gly Val Met Val Thr Val Ser Ser
            115                 120

<210> SEQ ID NO 15
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 15 aac att gtg atg acc cag tct ccc aaa tcc atg tcc ata tca gtg gga      48
Asn Ile Val Met Thr Gln Ser Pro Lys Ser Met Ser Ile Ser Val Gly
 1               5                  10                  15 gac agg gtc acc atg aac tgc agg gcc agt cag aat gtg gat aat act      96
Asp Arg Val Thr Met Asn Cys Arg Ala Ser Gln Asn Val Asp Asn Thr
             20                  25                  30 ata gcc tgg tat caa cag aaa cca ggg cag tct cct aaa ctg ttg atc     144
Ile Ala Trp Tyr Gln Gln Lys Pro Gly Gln Ser Pro Lys Leu Leu Ile
         35                  40                  45 tac ttt gca tct gac cgg tac act ggg gtc cct gat cgc ttc aca ggc     192
Tyr Phe Ala Ser Asp Arg Tyr Thr Gly Val Pro Asp Arg Phe Thr Gly
     50                  55                  60 ggt gga tat ggg aca gat ttc act ctc acc atc aat agt gtg caa gct     240
Gly Gly Tyr Gly Thr Asp Phe Thr Leu Thr Ile Asn Ser Val Gln Ala
 65                  70                  75                  80 gaa gat gca gcc ttt tat tac tgt cag cgt att tac aat tct cca ctc     288
Glu Asp Ala Ala Phe Tyr Tyr Cys Gln Arg Ile Tyr Asn Ser Pro Leu
             85                  90                  95 acg ttc ggt tct ggg acc aag ctg gag atc aga cgg gct                 327
Thr Phe Gly Ser Gly Thr Lys Leu Glu Ile Arg Arg Ala
        100                 105

<210> SEQ ID NO 16
<211> LENGTH: 109
<212> TYPE: PRT
<213> ORGANISM: Rattus norvegicus

<400> SEQUENCE: 16

Asn Ile Val Met Thr Gln Ser Pro Lys Ser Met Ser Ile Ser Val Gly
 1               5                  10                  15

Asp Arg Val Thr Met Asn Cys Arg Ala Ser Gln Asn Val Asp Asn Thr
             20                  25                  30

Ile Ala Trp Tyr Gln Gln Lys Pro Gly Gln Ser Pro Lys Leu Leu Ile
         35                  40                  45

Tyr Phe Ala Ser Asp Arg Tyr Thr Gly Val Pro Asp Arg Phe Thr Gly
     50                  55                  60

Gly Gly Tyr Gly Thr Asp Phe Thr Leu Thr Ile Asn Ser Val Gln Ala
 65                  70                  75                  80

Glu Asp Ala Ala Phe Tyr Tyr Cys Gln Arg Ile Tyr Asn Ser Pro Leu
             85                  90                  95
```

```
Thr Phe Gly Ser Gly Thr Lys Leu Glu Ile Arg Arg Ala
                100                 105

<210> SEQ ID NO 17
<211> LENGTH: 357
<212> TYPE: DNA
<213> ORGANISM: Rattus norvegicus
<220> FEATURE:
<221> NAME/KEY: CDS
<222> LOCATION: (1)..(357)

<400> SEQUENCE: 17 gag gtg cag ctg gtg gaa tct ggg gga ggc tta gtg cag cct gga agg    48
Glu Val Gln Leu Val Glu Ser Gly Gly Gly Leu Val Gln Pro Gly Arg
1               5                   10                  15 tcc ctg aaa ctc tcc tgt gca gcc tca gga ttc act ttc agt tcc tat    96
Ser Leu Lys Leu Ser Cys Ala Ala Ser Gly Phe Thr Phe Ser Ser Tyr
            20                  25                  30 tac atg gcc tgg gtc cgc cag gct cca acg aag ggt ctg gag tgg gtc   144
Tyr Met Ala Trp Val Arg Gln Ala Pro Thr Lys Gly Leu Glu Trp Val
        35                  40                  45 gca tac atc agt aat ggt ggt tat agc act tac tat cga gac tcc gtg   192
Ala Tyr Ile Ser Asn Gly Gly Tyr Ser Thr Tyr Tyr Arg Asp Ser Val
    50                  55                  60 aag ggc cga ttc act atc tcc aga gaa aat gca aaa agc acc ctt tac   240
Lys Gly Arg Phe Thr Ile Ser Arg Glu Asn Ala Lys Ser Thr Leu Tyr
65                  70                  75                  80 ctg caa atg gac agt ctg agg tct gag gac acg gcc act tat tac tgt   288
Leu Gln Met Asp Ser Leu Arg Ser Glu Asp Thr Ala Thr Tyr Tyr Cys
                85                  90                  95 aca atc aca gat cat tcg ggg tac agg ttt act tac tgg ggc caa ggc   336
Thr Ile Thr Asp His Ser Gly Tyr Arg Phe Thr Tyr Trp Gly Gln Gly
            100                 105                 110 act ctg gtc act gtc tct tca                                        357
Thr Leu Val Thr Val Ser Ser
        115

<210> SEQ ID NO 18
<211> LENGTH: 119
<212> TYPE: PRT
<213> ORGANISM: Rattus norvegicus

<400> SEQUENCE: 18

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ser Tyr
            20                  25                  30

Tyr Met Ala Trp Val Arg Gln Ala Pro Thr Lys Gly Leu Glu Trp Val
        35                  40                  45

Ala Tyr Ile Ser Asn Gly Gly Tyr Ser Thr Tyr Tyr Arg Asp Ser Val
    50                  55                  60

Lys Gly Arg Phe Thr Ile Ser Arg Glu Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Ile Thr Asp His Ser Gly Tyr Arg Phe Thr Tyr Trp Gly Gln Gly
            100                 105                 110

Thr Leu Val Thr Val Ser Ser
        115
```

<210> SEQ ID NO 19
<211> LENGTH: 324
<212> TYPE: DNA
<213> ORGANISM: Rattus norvegicus
<220> FEATURE:
<221> NAME/KEY: CDS
<222> LOCATION: (1)..(324)

<400> SEQUENCE: 19

| gac | atc | cag | atg | acc | cag | tct | cct | tca | ctc | ctg | tca | gca | tct | gtg | gga | 48 |
|---|---|---|---|---|---|---|---|---|---|---|---|---|---|---|---|---|
| Asp | Ile | Gln | Met | Thr | Gln | Ser | Pro | Ser | Leu | Leu | Ser | Ala | Ser | Val | Gly | |
| 1 | | | | 5 | | | | | 10 | | | | | 15 | | |

| gac | aga | gtc | act | ctc | agc | tgc | aaa | gca | agt | cag | agt | att | tac | aac | agc | 96 |
|---|---|---|---|---|---|---|---|---|---|---|---|---|---|---|---|---|
| Asp | Arg | Val | Thr | Leu | Ser | Cys | Lys | Ala | Ser | Gln | Ser | Ile | Tyr | Asn | Ser | |
| | | | 20 | | | | | 25 | | | | | 30 | | | |

| tta | gcc | tgg | tat | cag | caa | aaa | ctt | gga | gaa | gct | ccc | aaa | ctc | ctc | ata | 144 |
|---|---|---|---|---|---|---|---|---|---|---|---|---|---|---|---|---|
| Leu | Ala | Trp | Tyr | Gln | Gln | Lys | Leu | Gly | Glu | Ala | Pro | Lys | Leu | Leu | Ile | |
| | | | 35 | | | | | 40 | | | | | 45 | | | |

| tat | gat | gca | aac | agt | ttg | caa | acg | ggc | atc | cca | tca | agg | ttc | agt | ggc | 192 |
|---|---|---|---|---|---|---|---|---|---|---|---|---|---|---|---|---|
| Tyr | Asp | Ala | Asn | Ser | Leu | Gln | Thr | Gly | Ile | Pro | Ser | Arg | Phe | Ser | Gly | |
| 50 | | | | | 55 | | | | | 60 | | | | | | |

| agt | gga | tct | ggt | aca | gat | ttc | aca | ctc | acc | atc | agc | agc | ctg | cag | cct | 240 |
|---|---|---|---|---|---|---|---|---|---|---|---|---|---|---|---|---|
| Ser | Gly | Ser | Gly | Thr | Asp | Phe | Thr | Leu | Thr | Ile | Ser | Ser | Leu | Gln | Pro | |
| 65 | | | | 70 | | | | | 75 | | | | | 80 | | |

| gaa | gat | gtt | gcc | aca | tat | ttc | tgc | cag | aag | tat | tat | agc | ggg | aac | acg | 288 |
|---|---|---|---|---|---|---|---|---|---|---|---|---|---|---|---|---|
| Glu | Asp | Val | Ala | Thr | Tyr | Phe | Cys | Gln | Lys | Tyr | Tyr | Ser | Gly | Asn | Thr | |
| | | | | 85 | | | | | 90 | | | | | 95 | | |

| ttt | gga | gct | ggg | acc | aag | ctg | gaa | ctg | aaa | cgg | gct | | | | | 324 |
|---|---|---|---|---|---|---|---|---|---|---|---|---|---|---|---|---|
| Phe | Gly | Ala | Gly | Thr | Lys | Leu | Glu | Leu | Lys | Arg | Ala | | | | | |
| | | | 100 | | | | | 105 | | | | | | | | |

<210> SEQ ID NO 20
<211> LENGTH: 108
<212> TYPE: PRT
<213> ORGANISM: Rattus norvegicus

<400> SEQUENCE: 20

Asp Ile Gln Met Thr Gln Ser Pro Ser Leu Leu Ser Ala Ser Val Gly
1               5                   10                  15

Asp Arg Val Thr Leu Ser Cys Lys Ala Ser Gln Ser Ile Tyr Asn Ser
            20                  25                  30

Leu Ala Trp Tyr Gln Gln Lys Leu Gly Glu Ala Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Lys Tyr Tyr Ser Gly Asn Thr
                85                  90                  95

Phe Gly Ala Gly Thr Lys Leu Glu Leu Lys Arg Ala
            100                 105

<210> SEQ ID NO 21
<211> LENGTH: 449
<212> TYPE: DNA
<213> ORGANISM: Homo sapiens

<400> SEQUENCE: 21
gcctccggac tctagagcca ccatggtgct gcagacccag gtgttcatct ccctgctgct      60
gtggatctcc ggcgcgtacg gcgatatcgt gatgattaaa cgtacggtgg ccgccccctc     120

```
cgtgttcatc ttcccccct ccgacgagca gctgaagtcc ggcaccgcct ccgtggtgtg     180
cctgctgaat aacttctacc ccagagaggc caaggtgcag tggaaggtgg acaacgccct     240
gcagtccggg aactcccagg agagcgtgac cgagcaggac agcaaggaca gcacctacag     300
cctgagcagc accctgaccc tgagcaaagc cgactacgag aagcacaagg tgtacgcctg     360
cgaggtgacc caccagggcc tgagctcccc cgtcaccaag agcttcaaca ggggggagtg     420 ttagggccc gtttaaacgg gggaggcta                                        449

<210> SEQ ID NO 22
<211> LENGTH: 1132
<212> TYPE: DNA
<213> ORGANISM: Homo sapiens

<400> SEQUENCE: 22
gcctccggac tctagagcca ccatgaaaca cctgtggttc ttcctcctgc tggtggcagc     60
tcccagatgg gtgctgagcc aggtgcaatt gtgcaggcgg ttagctcagc ctccaccaag    120
ggcccaagcg tcttcccct ggcaccctcc tccaagagca cctctggcgg cacagccgcc    180
ctgggctgcc tggtcaagga ctacttcccc gaacccgtga ccgtgagctg gaactcaggc    240
gccctgacca gcggcgtgca caccttcccc gctgtcctgc agtcctcagg actctactcc    300
ctcagcagcg tggtgaccgt gccctccagc agcttgggca cccagaccta catctgcaac    360
gtgaatcaca agcccagcaa caccaaggtg gacaagagag ttgagcccaa atcttgtgac    420
aaaactcaca catgcccacc ctgcccagca cctgaactcc tggggggacc ctcagtcttc    480 ctcttcccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccc cgggaggagc agtacaacag cacgtaccgg    660
gtggtcagcg tcctcaccgt cctgcaccag gactggctga atggcaagga gtacaagtgc    720
aaggtctcca acaaagccct cccagccccc atcgagaaaa ccatctccaa agccaaaggc    780
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg gccagcccga gaacaactac aagaccaccc ctcccgtgct ggactccgac    960
ggctccttct cctctacag caagctcacc gtggacaaga gcaggtggca gcagggcaac   1020
gtcttctcat gctccgtgat gcatgaggct ctgcacaacc actacaccca gaagagcctc   1080
tccctgtctc ccggcaaatg agatatcggg cccgtttaaa cggggggaggc ta           1132

<210> SEQ ID NO 23
<211> LENGTH: 1410
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (1)..(1410)

<400> SEQUENCE: 23 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtg ctg agc gag gtg cag ctg gtg gag tct ggg gga ggc tta gtg cag     96
Val Leu Ser Glu Val Gln Leu Val Glu Ser Gly Gly Gly Leu Val Gln
            20                  25                  30
```

-continued

| | | | | | | | | | | | | | | | |
|---|---|---|---|---|---|---|---|---|---|---|---|---|---|---|---|
| cct | gga | agg | tcc | ctg | aaa | ctc | tcc | tgt | gca | gcc | tca | gga | ttc | act | tac | 144 |
| Pro | Gly | Arg | Ser | Leu | Lys | Leu | Ser | Cys | Ala | Ala | Ser | Gly | Phe | Thr | Tyr |
| | | 35 | | | | 40 | | | | 45 | | | | | | cgt agc tat gtc atg gcc tgg gtc cgc cag gct cca acg agg ggt ctg  192
Arg Ser Tyr Val Met Ala Trp Val Arg Gln Ala Pro Thr Arg Gly Leu
        50              55              60 gag tgg gtc gca tcc att agt act ggt ggt ggt aac act tac tat cga  240
Glu Trp Val Ala Ser Ile Ser Thr Gly Gly Gly Asn Thr Tyr Tyr Arg
65              70              75              80 gac tcc gtg aag ggc cga ttc act atc tcc aga gat aat gca aag aac  288
Asp Ser Val Lys Gly Arg Phe Thr Ile Ser Arg Asp Asn Ala Lys Asn
            85              90              95 acc cta tac cta caa atg gac agt ctg agg tct gag gac acg gcc act  336
Thr Leu Tyr Leu Gln Met Asp Ser Leu Arg Ser Glu Asp Thr Ala Thr
        100             105             110 tat tac tgt gca gaa gac atg agt aat tcg gga tac ggg ctc ttt gat  384
Tyr Tyr Cys Ala Glu Asp Met Ser Asn Ser Gly Tyr Gly Leu Phe Asp
        115             120             125 tac tgg ggc caa gga gtc atg gtc aca gtc agc tca gcc tcc acc aag  432
Tyr Trp Gly Gln Gly Val Met Val Thr Val Ser Ser Ala Ser Thr Lys
130             135             140 ggc cca agc gtc ttc ccc ctg gca ccc tcc tcc aag agc acc tct ggc  480
Gly Pro Ser Val Phe Pro Leu Ala Pro Ser Ser Lys Ser Thr Ser Gly
145             150             155             160 ggc aca gcc gcc ctg ggc tgc ctg gtc aag gac tac ttc ccc gaa ccc  528
Gly Thr Ala Ala Leu Gly Cys Leu Val Lys Asp Tyr Phe Pro Glu Pro
            165             170             175 gtg acc gtg agc tgg aac tca ggc gcc ctg acc agc ggc gtg cac acc  576
Val Thr Val Ser Trp Asn Ser Gly Ala Leu Thr Ser Gly Val His Thr
        180             185             190 ttc ccc gct gtc ctg cag tcc tca gga ctc tac tcc ctc agc agc gtg  624
Phe Pro Ala Val Leu Gln Ser Ser Gly Leu Tyr Ser Leu Ser Ser Val
        195             200             205 gtg acc gtg ccc tcc agc agc ttg ggc acc cag acc tac atc tgc aac  672
Val Thr Val Pro Ser Ser Ser Leu Gly Thr Gln Thr Tyr Ile Cys Asn
210             215             220 gtg aat cac aag ccc agc aac acc aag gtg gac aag aga gtt gag ccc  720
Val Asn His Lys Pro Ser Asn Thr Lys Val Asp Lys Arg Val Glu Pro
225             230             235             240 aaa tct tgt gac aaa act cac aca tgc cca ccc tgc cca gca cct gaa  768
Lys Ser Cys Asp Lys Thr His Thr Cys Pro Pro Cys Pro Ala Pro Glu
            245             250             255 ctc ctg ggg gga ccc tca gtc ttc ctc ttc ccc cca aaa ccc aag gac  816
Leu Leu Gly Gly Pro Ser Val Phe Leu Phe Pro Pro Lys Pro Lys Asp
        260             265             270 acc ctc atg atc tcc cgg acc cct gag gtc aca tgc gtg gtg gtg gac  864
Thr Leu Met Ile Ser Arg Thr Pro Glu Val Thr Cys Val Val Val Asp
        275             280             285 gtg agc cac gaa gac cct gag gtc aag ttc aac tgg tac gtg gac ggc  912
Val Ser His Glu Asp Pro Glu Val Lys Phe Asn Trp Tyr Val Asp Gly
290             295             300 gtg gag gtg cat aat gcc aag aca aag ccc cgg gag gag cag tac aac  960
Val Glu Val His Asn Ala Lys Thr Lys Pro Arg Glu Glu Gln Tyr Asn
305             310             315             320 agc acg tac cgg gtg gtc agc gtc ctc acc gtc ctg cac cag gac tgg  1008
Ser Thr Tyr Arg Val Val Ser Val Leu Thr Val Leu His Gln Asp Trp
            325             330             335

```
ctg aat ggc aag gag tac aag tgc aag gtc tcc aac aaa gcc ctc cca      1056
Leu Asn Gly Lys Glu Tyr Lys Cys Lys Val Ser Asn Lys Ala Leu Pro
        340                 345                 350 gcc ccc atc gag aaa acc atc tcc aaa gcc aaa ggc cag ccc cgg gaa      1104
Ala Pro Ile Glu Lys Thr Ile Ser Lys Ala Lys Gly Gln Pro Arg Glu
            355                 360                 365 cca cag gtg tac acc ctg ccc cca tcc cgg gag gag atg acc aag aac      1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc      1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc      1344
Leu Thr Val Asp Lys Ser Arg Trp Gln Gln Gly Asn Val Phe Ser Cys
                435                 440                 445 tcc gtg atg cat gag gct ctg cac aac cac tac acc cag aag agc ctc      1392
Ser Val Met His Glu Ala Leu His Asn His Tyr Thr Gln Lys Ser Leu
450                 455                 460 tcc ctg tct ccc ggc aaa                                              1410
Ser Leu Ser Pro Gly Lys
465                 470

<210> SEQ ID NO 24
<211> LENGTH: 470
<212> TYPE: PRT
<213> ORGANISM: Artificial Sequence
<220> FEATURE:
<223> OTHER INFORMATION: Synthetic Construct

<400> SEQUENCE: 24

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Tyr
        35                  40                  45

Arg Ser Tyr Val Met Ala Trp Val Arg Gln Ala Pro Thr Arg Gly Leu
    50                  55                  60

Glu Trp Val Ala Ser Ile Ser Thr Gly Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asp Ser Leu Arg Ser Glu Asp Thr Ala Thr
            100                 105                 110

Tyr Tyr Cys Ala Glu Asp Met Ser Asn Ser Gly Tyr Gly Leu Phe Asp
        115                 120                 125

Tyr Trp Gly Gln Gly Val Met Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175
```

-continued

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 25
<211> LENGTH: 702
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (1)..(702)

<400> SEQUENCE: 25 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gcg tac ggc aac att gtg atg acc cag tct ccc aaa tcc atg tcc    96
Gly Ala Tyr Gly Asn Ile Val Met Thr Gln Ser Pro Lys Ser Met Ser
            20                  25                  30

| | |
|---|---|
| ata tca gta gga gac agg gtc acc atg aac tgc aag gcc ggt cag aat<br>Ile Ser Val Gly Asp Arg Val Thr Met Asn Cys Lys Ala Gly Gln Asn<br>35                     40                     45 | 144 |
| gtg gat aat aat ata gcc tgg tat caa aag aaa cca ggg cag tct cct<br>Val Asp Asn Asn Ile Ala Trp Tyr Gln Lys Lys Pro Gly Gln Ser Pro<br>50                     55                     60 | 192 |
| aaa ctg ttg atc tac tat gca tct aac cgg aac act ggg gtc cct gat<br>Lys Leu Leu Ile Tyr Tyr Ala Ser Asn Arg Asn Thr Gly Val Pro Asp<br>65                     70                     75                     80 | 240 |
| cgc ttc aca ggc ggt gga tat ggg aca gat ttc act ctc acc atc aat<br>Arg Phe Thr Gly Gly Gly Tyr Gly Thr Asp Phe Thr Leu Thr Ile Asn<br>85                     90                     95 | 288 |
| agt gtg caa gct gaa gat gca gcc ttt tat tac tgt cag cgt att tcc<br>Ser Val Gln Ala Glu Asp Ala Ala Phe Tyr Tyr Cys Gln Arg Ile Ser<br>100                   105                 110 | 336 |
| aat tct ccg tac acg ttt ggc gct ggg acc gag ctg gaa ctg aaa cgg<br>Asn Ser Pro Tyr Thr Phe Gly Ala Gly Thr Glu Leu Glu Leu Lys Arg<br>115                   120                 125 | 384 |
| gct gtg gcc gcc ccc tcc gtg ttc atc ttc ccc ccc tcc gac gag cag<br>Ala Val Ala Ala Pro Ser Val Phe Ile Phe Pro Pro Ser Asp Glu Gln<br>130                   135                 140 | 432 |
| ctg aag tcc ggc acc gcc tcc gtg gtg tgc ctg ctg aat aac ttc tac<br>Leu Lys Ser Gly Thr Ala Ser Val Val Cys Leu Leu Asn Asn Phe Tyr<br>145                   150                 155                 160 | 480 |
| ccc aga gag gcc aag gtg cag tgg aag gtg gac aac gcc ctg cag tcc<br>Pro Arg Glu Ala Lys Val Gln Trp Lys Val Asp Asn Ala Leu Gln Ser<br>165                   170                 175 | 528 |
| ggg aac tcc cag gag agc gtg acc gag cag gac agc aag gac agc acc<br>Gly Asn Ser Gln Glu Ser Val Thr Glu Gln Asp Ser Lys Asp Ser Thr<br>180                   185                 190 | 576 |
| tac agc ctg agc agc acc ctg acc ctg agc aaa gcc gac tac gag aag<br>Tyr Ser Leu Ser Ser Thr Leu Thr Leu Ser Lys Ala Asp Tyr Glu Lys<br>195                   200                 205 | 624 |
| cac aag gtg tac gcc tgc gag gtg acc cac cag ggc ctg agc tcc ccc<br>His Lys Val Tyr Ala Cys Glu Val Thr His Gln Gly Leu Ser Ser Pro<br>210                   215                 220 | 672 |
| gtc acc aag agc ttc aac agg ggg gag tgt<br>Val Thr Lys Ser Phe Asn Arg Gly Glu Cys<br>225                   230 | 702 |

<210> SEQ ID NO 26
<211> LENGTH: 234
<212> TYPE: PRT
<213> ORGANISM: Artificial Sequence
<220> FEATURE:
<223> OTHER INFORMATION: Synthetic Construct

<400> SEQUENCE: 26

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Lys Ser Met Ser
            20                  25                  30

Ile Ser Val Gly Asp Arg Val Thr Met Asn Cys Lys Ala Gly Gln Asn
        35                  40                  45

Val Asp Asn Asn Ile Ala Trp Tyr Gln Lys Lys Pro Gly Gln Ser Pro
    50                  55                  60

Lys Leu Leu Ile Tyr Tyr Ala Ser Asn Arg Asn Thr Gly Val Pro Asp
65                  70                  75                  80

Arg Phe Thr Gly Gly Gly Tyr Gly Thr Asp Phe Thr Leu Thr Ile Asn
                85                  90                  95

```
Ser Val Gln Ala Glu Asp Ala Ala Phe Tyr Tyr Cys Gln Arg Ile Ser
            100                 105                 110

Asn Ser Pro Tyr Thr Phe Gly Ala Gly Thr Glu Leu Glu Leu Lys Arg
            115                 120                 125

Ala Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 27
<211> LENGTH: 1410
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(1410)

<400> SEQUENCE: 27 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtg cag ctg gtg gaa tct ggc ggc gga ctg gtg cag      96
Val Leu Ser Glu Val Gln Leu Val Glu Ser Gly Gly Gly Leu Val Gln
            20                  25                  30 cct ggc gga tct ctg aga ctg agc tgt gcc gcc agc ggc ttc acc tac     144
Pro Gly Gly Ser Leu Arg Leu Ser Cys Ala Ala Ser Gly Phe Thr Tyr
        35                  40                  45 cgg tct tac gtg atg gcc tgg gtg cgc cag gcc cct gga aaa gga ctg     192
Arg Ser Tyr Val Met Ala Trp Val Arg Gln Ala Pro Gly Lys Gly Leu
    50                  55                  60 gaa tgg gtg gga tcc atc agc acc ggc gga ggc aac acc tac tac cgg     240
Glu Trp Val Gly Ser Ile Ser Thr Gly Gly Gly Asn Thr Tyr Tyr Arg
65                  70                  75                  80 gat agc gtg aag ggc cgg ttc acc atc agc cgg gac aac gcc aag aac     288
Asp Ser Val Lys Gly Arg Phe Thr Ile Ser Arg Asp Asn Ala Lys Asn
                85                  90                  95 acc ctg tac ctg cag atg aac agc ctg cgg gcc gag gac acc gcc gtg     336
Thr Leu Tyr Leu Gln Met Asn Ser Leu Arg Ala Glu Asp Thr Ala Val
            100                 105                 110 tac tat tgc gcc gag gat atg agc aac agc ggc tac ggc ctg ttc gac     384
Tyr Tyr Cys Ala Glu Asp Met Ser Asn Ser Gly Tyr Gly Leu Phe Asp
        115                 120                 125 tac tgg ggc cag gga acc ctc gtg acc gtc agc tca gcc tcc acc aag     432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc     480
Gly Pro Ser Val Phe Pro Leu Ala Pro Ser Ser Lys Ser Thr Ser Gly
```

```
145                 150                 155                 160 ggc aca gcc gcc ctg ggc tgc ctg gtc aag gac tac ttc ccc gaa ccc         528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc         576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg         624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac         672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc         720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa         768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac         816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac         864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc         912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac         960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg        1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca        1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa        1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac        1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc        1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc        1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag        1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc        1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc        1392
Ser Val Met His Glu Ala Leu His Asn His Tyr Thr Gln Lys Ser Leu
    450                 455                 460
```

```
tcc ctg tct ccc ggc aaa                                           1410
Ser Leu Ser Pro Gly Lys
465             470

<210> SEQ ID NO 28
<211> LENGTH: 470
<212> TYPE: PRT
<213> ORGANISM: Artificial Sequence
<220> FEATURE:
<223> OTHER INFORMATION: Synthetic Construct

<400> SEQUENCE: 28
```

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Tyr
            35                  40                  45

Arg Ser Tyr Val Met Ala Trp Val Arg Gln Ala Pro Gly Lys Gly Leu
    50                  55                  60

Glu Trp Val Gly Ser Ile Ser Thr Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Glu Asp Met Ser Asn Ser Gly Tyr Gly Leu Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

```
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Glu Glu Met Thr Lys Asn
370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
            405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
            450                 455                 460
Ser Leu Ser Pro Gly Lys
465                 470

<210> SEQ ID NO 29
<211> LENGTH: 1410
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(1410)

<400> SEQUENCE: 29 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtg cag ctg gtg gaa tct ggc ggc gga ctg gtg cag      96
Val Leu Ser Glu Val Gln Leu Val Glu Ser Gly Gly Gly Leu Val Gln
            20                  25                  30 cct ggc gga tct ctg aga ctg agc tgt gcc gcc agc ggc ttc acc tac     144
Pro Gly Gly Ser Leu Arg Leu Ser Cys Ala Ala Ser Gly Phe Thr Tyr
        35                  40                  45 cgg tct tac gtg atg gcc tgg gtg cgc cag gcc cct gga aaa gga ctg     192
Arg Ser Tyr Val Met Ala Trp Val Arg Gln Ala Pro Gly Lys Gly Leu
    50                  55                  60 gaa tgg gtg gcc agc atc agc acc ggc gga ggc aac acc tac tac cgg     240
Glu Trp Val Ala Ser Ile Ser Thr Gly Gly Gly Asn Thr Tyr Tyr Arg
65                  70                  75                  80 gat agc gtg aag ggc cgg ttc acc atc agc cgg gac aac gcc aag aac     288
Asp Ser Val Lys Gly Arg Phe Thr Ile Ser Arg Asp Asn Ala Lys Asn
                85                  90                  95 acc ctg tac ctg cag atg gac agc ctg cgg gcc gag gat acc gcc gtg     336
Thr Leu Tyr Leu Gln Met Asp Ser Leu Arg Ala Glu Asp Thr Ala Val
            100                 105                 110 tac tac tgt gcc gag gac atg agc aac agc ggc tac ggc ctg ttc gac     384
Tyr Tyr Cys Ala Glu Asp Met Ser Asn Ser Gly Tyr Gly Leu Phe Asp
        115                 120                 125 tac tgg ggc cag gga acc ctc gtg acc gtc agc tca gcc tcc acc aag     432
Tyr Trp Gly Gln Gly Thr Leu Val Thr Val Ser Ser Ala Ser Thr Lys
    130                 135                 140
```

```
ggc cca agc gtc ttc ccc ctg gca ccc tcc tcc aag agc acc tct ggc      480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc      528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc      576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg      624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc      720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa      768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
        435                 440                 445
```

```
tcc gtg atg cat gag gct ctg cac aac cac tac acc cag aag agc ctc          1392
Ser Val Met His Glu Ala Leu His Asn His Tyr Thr Gln Lys Ser Leu
    450                 455                 460 tcc ctg tct ccc ggc aaa                                                  1410
Ser Leu Ser Pro Gly Lys
465                 470
```

<210> SEQ ID NO 30
<211> LENGTH: 470
<212> TYPE: PRT
<213> ORGANISM: Artificial Sequence
<220> FEATURE:
<223> OTHER INFORMATION: Synthetic Construct

<400> SEQUENCE: 30

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Tyr
        35                  40                  45

Arg Ser Tyr Val Met Ala Trp Val Arg Gln Ala Pro Gly Lys Gly Leu
    50                  55                  60

Glu Trp Val Ala Ser Ile Ser Thr Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asp Ser Leu Arg Ala Glu Asp Thr Ala Val
            100                 105                 110

Tyr Tyr Cys Ala Glu Asp Met Ser Asn Ser Gly Tyr Gly Leu Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320
```

-continued

```
Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465             470

<210> SEQ ID NO 31
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 31 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc cct agc agc ctg agc      96
Gly Ala Tyr Gly Asp Ile Gln Met Thr Gln Ser Pro Ser Ser Leu Ser
            20                  25                  30 gcc agc gtg ggc gac aga gtg acc atc acc tgt aaa gcc ggc cag aac     144
Ala Ser Val Gly Asp Arg Val Thr Ile Thr Cys Lys Ala Gly Gln Asn
        35                  40                  45 gtg gac aac aat atc gcc tgg tat cag cag aag ccc ggc cag gcc cct     192
Val Asp Asn Asn Ile Ala Trp Tyr Gln Gln Lys Pro Gly Gln Ala Pro
    50                  55                  60 aag ctg ctg atc tac tac gcc agc aac cgg aac acc ggc gtg ccc agc     240
Lys Leu Leu Ile Tyr Tyr Ala Ser Asn Arg Asn Thr Gly Val Pro Ser
65                  70                  75                  80 aga ttt tct ggc agc ggc tcc ggc acc gac ttc acc ctg aca atc agc     288
Arg Phe Ser Gly Ser Gly Ser Gly Thr Asp Phe Thr Leu Thr Ile Ser
                85                  90                  95 agc ctg cag ccc gag gac ttc gcc acc tac tac tgc cag aga atc agc     336
Ser Leu Gln Pro Glu Asp Phe Ala Thr Tyr Tyr Cys Gln Arg Ile Ser
            100                 105                 110 aac agc ccc tac acc ttc ggc cag ggc acc aag gtg gaa atc aag cgt     384
Asn Ser Pro Tyr Thr Phe Gly Gln Gly Thr Lys Val Glu Ile Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140
```

```
ctg aag tcc ggc acc gcc tcc gtg gtg tgc ctg ctg aat aac ttc tac    480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc    528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc    576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag    624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc    672
His Lys Val Tyr Ala Cys Glu Val Thr His Gln Gly Leu Ser Ser Pro
    210                 215                 220 gtc acc aag agc ttc aac agg ggg gag tgt                            702
Val Thr Lys Ser Phe Asn Arg Gly Glu Cys
225                 230
```

<210> SEQ ID NO 32
<211> LENGTH: 234
<212> TYPE: PRT
<213> ORGANISM: Artificial Sequence
<220> FEATURE:
<223> OTHER INFORMATION: Synthetic Construct

<400> SEQUENCE: 32

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Gly Gln Asn
        35                  40                  45

Val Asp Asn Asn Ile Ala Trp Tyr Gln Gln Lys Pro Gly Gln Ala Pro
    50                  55                  60

Lys Leu Leu Ile Tyr Tyr Ala Ser Asn Arg Asn Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Arg Ile Ser
            100                 105                 110

Asn Ser Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 33
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 33

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc cct agc agc ctg agc      96
Gly Ala Tyr Gly Asp Ile Gln Met Thr Gln Ser Pro Ser Ser Leu Ser
            20                  25                  30 gcc agc gtg ggc gac aga gtg acc atc acc tgt aaa gcc ggc cag aac     144
Ala Ser Val Gly Asp Arg Val Thr Ile Thr Cys Lys Ala Gly Gln Asn
        35                  40                  45 gtg gac aac aat atc gcc tgg tat cag cag aag ccc ggc cag agc ccc     192
Val Asp Asn Asn Ile Ala Trp Tyr Gln Gln Lys Pro Gly Gln Ser Pro
    50                  55                  60 aag ctg ctg atc tac tac gcc agc aac cgg aac acc ggc gtg ccc agc     240
Lys Leu Leu Ile Tyr Tyr Ala Ser Asn Arg Asn Thr Gly Val Pro Ser
65                  70                  75                  80 aga ttt tcc ggc agc ggc tac ggc acc gac ttc acc ctg aca atc agc     288
Arg Phe Ser Gly Ser Gly Tyr Gly Thr Asp Phe Thr Leu Thr Ile Ser
                85                  90                  95 agc ctg cag ccc gag gac ttc gcc acc tac tac tgc cag aga atc agc     336
Ser Leu Gln Pro Glu Asp Phe Ala Thr Tyr Tyr Cys Gln Arg Ile Ser
            100                 105                 110 aac agc ccc tac acc ttc ggc cag ggc acc aag gtg gaa atc aag cgt     384
Asn Ser Pro Tyr Thr Phe Gly Gln Gly Thr Lys Val Glu Ile Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc     576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag     624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc     672
His Lys Val Tyr Ala Cys Glu Val Thr His Gln Gly Leu Ser Ser Pro
    210                 215                 220 gtc acc aag agc ttc aac agg ggg gag tgt                             702
Val Thr Lys Ser Phe Asn Arg Gly Glu Cys
225                 230
```

<210> SEQ ID NO 34
<211> LENGTH: 234
<212> TYPE: PRT
<213> ORGANISM: Artificial Sequence
<220> FEATURE:

<223> OTHER INFORMATION: Synthetic Construct

<400> SEQUENCE: 34

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Gly Gln Asn
        35                  40                  45

Val Asp Asn Asn Ile Ala Trp Tyr Gln Gln Lys Pro Gly Gln Ser Pro
50                  55                  60

Lys Leu Leu Ile Tyr Tyr Ala Ser Asn Arg Asn Thr Gly Val Pro Ser
65                  70                  75                  80

Arg Phe Ser Gly Ser Gly Tyr Gly Thr Asp Phe Thr Leu Thr Ile Ser
                85                  90                  95

Ser Leu Gln Pro Glu Asp Phe Ala Thr Tyr Tyr Cys Gln Arg Ile Ser
            100                 105                 110

Asn Ser Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 35
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 35 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc aac atc cag atg acc cag agc ccc agc agc ctg tct      96
Gly Ala Tyr Gly Asn Ile Gln Met Thr Gln Ser Pro Ser Ser Leu Ser
            20                  25                  30 gcc agc gtg ggc gac aga gtg acc atc aca tgc aag gcc ggc cag aac     144
Ala Ser Val Gly Asp Arg Val Thr Ile Thr Cys Lys Ala Gly Gln Asn
        35                  40                  45 gtg gac aac aat atc gcc tgg tat cag aag aag ccc ggc cag tcc ccc     192
Val Asp Asn Asn Ile Ala Trp Tyr Gln Lys Lys Pro Gly Gln Ser Pro
50                  55                  60

-continued

```
aag ctg ctg atc tac tac gcc agc aac cgg aac acc ggc gtg ccc gac      240
Lys Leu Leu Ile Tyr Tyr Ala Ser Asn Arg Asn Thr Gly Val Pro Asp
 65                  70                  75                  80 aga ttt tcc ggc gga ggc tac ggc acc gac ttc acc ctg acc atc agc      288
Arg Phe Ser Gly Gly Gly Tyr Gly Thr Asp Phe Thr Leu Thr Ile Ser
                     85                  90                  95 tcc ctg cag ccc gag gac ttc gcc ttc tac tac tgt cag cgg atc agc      336
Ser Leu Gln Pro Glu Asp Phe Ala Phe Tyr Tyr Cys Gln Arg Ile Ser
                 100                 105                 110 aac agc ccc tac acc ttc ggc cag ggc acc aag gtg gaa atc aag cgt      384
Asn Ser Pro Tyr Thr Phe Gly Gln Gly Thr Lys Val Glu Ile Lys Arg
             115                 120                 125 acg gtg gcc gcc ccc tcc gtg ttc atc ttc ccc ccc tcc gac gag cag      432
Thr Val Ala Ala Pro Ser Val Phe Ile Phe Pro Pro Ser Asp Glu Gln
130                 135                 140 ctg aag tcc ggc acc gcc tcc gtg gtg tgc ctg ctg aat aac ttc tac      480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc      528
Pro Arg Glu Ala Lys Val Gln Trp Lys Val Asp Asn Ala Leu Gln Ser
                 165                 170                 175 ggg aac tcc cag gag agc gtg acc gag cag gac agc aag gac agc acc      576
Gly Asn Ser Gln Glu Ser Val Thr Glu Gln Asp Ser Lys Asp Ser Thr
             180                 185                 190 tac agc ctg agc agc acc ctg acc ctg agc aaa gcc gac tac gag aag      624
Tyr Ser Leu Ser Ser Thr Leu Thr Leu Ser Lys Ala Asp Tyr Glu Lys
         195                 200                 205 cac aag gtg tac gcc tgc gag gtg acc cac cag ggc ctg agc tcc ccc      672
His Lys Val Tyr Ala Cys Glu Val Thr His Gln Gly Leu Ser Ser Pro
210                 215                 220 gtc acc aag agc ttc aac agg ggg gag tgt                              702
Val Thr Lys Ser Phe Asn Arg Gly Glu Cys
225                 230
```

<210> SEQ ID NO 36
<211> LENGTH: 234
<212> TYPE: PRT
<213> ORGANISM: Artificial Sequence
<220> FEATURE:
<223> OTHER INFORMATION: Synthetic Construct

<400> SEQUENCE: 36

```
Met Val Leu Gln Thr Gln Val Phe Ile Ser Leu Leu Leu Trp Ile Ser
 1               5                  10                  15

Gly Ala Tyr Gly Asn Ile Gln Met Thr Gln Ser Pro Ser Ser Leu Ser
                 20                  25                  30

Ala Ser Val Gly Asp Arg Val Thr Ile Thr Cys Lys Ala Gly Gln Asn
             35                  40                  45

Val Asp Asn Asn Ile Ala Trp Tyr Gln Lys Lys Pro Gly Gln Ser Pro
         50                  55                  60

Lys Leu Leu Ile Tyr Tyr Ala Ser Asn Arg Asn Thr Gly Val Pro Asp
 65                  70                  75                  80

Arg Phe Ser Gly Gly Gly Tyr Gly Thr Asp Phe Thr Leu Thr Ile Ser
                 85                  90                  95

Ser Leu Gln Pro Glu Asp Phe Ala Phe Tyr Tyr Cys Gln Arg Ile Ser
             100                 105                 110

Asn Ser Pro Tyr Thr Phe Gly Gln Gly Thr Lys Val Glu Ile Lys Arg
         115                 120                 125
```

```
Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 37
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 37 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc ccc agc agc atg agc      96
Gly Ala Tyr Gly Asp Ile Gln Met Thr Gln Ser Pro Ser Ser Met Ser
            20                  25                  30 atc agc gtg ggc gac aga gtg acc atg acc tgc aag gcc ggc cag aac     144
Ile Ser Val Gly Asp Arg Val Thr Met Thr Cys Lys Ala Gly Gln Asn
        35                  40                  45 gtg gac aac aat atc gcc tgg tat cag aag aag ccc ggc cag tcc ccc     192
Val Asp Asn Asn Ile Ala Trp Tyr Gln Lys Lys Pro Gly Gln Ser Pro
    50                  55                  60 aag ctg ctg atc tac tac gcc agc aac cgg aac acc ggc gtg ccc agc     240
Lys Leu Leu Ile Tyr Tyr Ala Ser Asn Arg Asn Thr Gly Val Pro Ser
65                  70                  75                  80 aga ttt tct ggc agc ggc tcc ggc acc gac ttc acc ctg aca atc agc     288
Arg Phe Ser Gly Ser Gly Ser Gly Thr Asp Phe Thr Leu Thr Ile Ser
                85                  90                  95 agc gtg cag ccc gag gac ttc gcc acc tac tac tgc cag aga atc agc     336
Ser Val Gln Pro Glu Asp Phe Ala Thr Tyr Tyr Cys Gln Arg Ile Ser
            100                 105                 110 aac agc ccc tac acc ttc ggc cag ggc acc aag ctg gaa ctg aag cgt     384
Asn Ser Pro Tyr Thr Phe Gly Gln Gly Thr Lys Leu Glu Leu Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175
```

```
ggg aac tcc cag gag agc gtg acc gag cag gac agc aag gac agc acc    576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag    624
Tyr Ser Leu Ser Ser Thr Leu Thr Leu Ser Lys Ala Asp Tyr Glu Lys
            195                 200                 205 cac aag gtg tac gcc tgc gag gtg acc cac cag ggc ctg agc tcc ccc    672
His Lys Val Tyr Ala Cys Glu Val Thr His Gln Gly Leu Ser Ser Pro
            210                 215                 220 gtc acc aag agc ttc aac agg ggg gag tgt                            702
Val Thr Lys Ser Phe Asn Arg Gly Glu Cys
225                 230

<210> SEQ ID NO 38
<211> LENGTH: 234
<212> TYPE: PRT
<213> ORGANISM: Artificial Sequence
<220> FEATURE:
<223> OTHER INFORMATION: Synthetic Construct

<400> SEQUENCE: 38

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Met Ser
            20                  25                  30

Ile Ser Val Gly Asp Arg Val Thr Met Thr Cys Lys Ala Gly Gln Asn
            35                  40                  45

Val Asp Asn Asn Ile Ala Trp Tyr Gln Lys Pro Gly Gln Ser Pro
50                  55                  60

Lys Leu Leu Ile Tyr Tyr Ala Ser Asn Arg Asn Thr Gly Val Pro Ser
65                  70                  75                  80

Arg Phe Ser Gly Ser Gly Ser Gly Thr Asp Phe Thr Leu Thr Ile Ser
                85                  90                  95

Ser Val Gln Pro Glu Asp Phe Ala Thr Tyr Tyr Cys Gln Arg Ile Ser
            100                 105                 110

Asn Ser Pro Tyr Thr Phe Gly Gln Gly Thr Lys Leu Glu Leu Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 39
<211> LENGTH: 702
<212> TYPE: DNA
<213> ORGANISM: Artificial Sequence
<220> FEATURE:
<223> OTHER INFORMATION: humanized
```

```
<220> FEATURE:
<221> NAME/KEY: CDS
<222> LOCATION: (1)..(702)

<400> SEQUENCE: 39 atg gtg ctg cag acc cag gtg ttc atc tcc ctg ctg tgg atc tcc       48
Met Val Leu Gln Thr Gln Val Phe Ile Ser Leu Leu Trp Ile Ser
1               5                   10                  15 ggc gcg tac ggc aac atc cag atg acc cag agc ccc agc agc atg agc   96
Gly Ala Tyr Gly Asn Ile Gln Met Thr Gln Ser Pro Ser Ser Met Ser
                20                  25                  30 atc agc gtg ggc gac aga gtg acc atg acc tgc aag gcc ggc cag aac   144
Ile Ser Val Gly Asp Arg Val Thr Met Thr Cys Lys Ala Gly Gln Asn
            35                  40                  45 gtg gac aac aat atc gcc tgg tat cag aag aag ccc ggc cag tcc ccc   192
Val Asp Asn Asn Ile Ala Trp Tyr Gln Lys Lys Pro Gly Gln Ser Pro
        50                  55                  60 aag ctg ctg atc tac tac gcc agc aac cgg aac acc ggc gtg ccc gac   240
Lys Leu Leu Ile Tyr Tyr Ala Ser Asn Arg Asn Thr Gly Val Pro Asp
65                  70                  75                  80 aga ttt tcc ggc gga ggc tac ggc acc gac ttc acc ctg aca atc agc   288
Arg Phe Ser Gly Gly Gly Tyr Gly Thr Asp Phe Thr Leu Thr Ile Ser
                85                  90                  95 agc gtg cag ccc gag gac gcc gcc ttc tac tac tgt cag cgg atc agc   336
Ser Val Gln Pro Glu Asp Ala Ala Phe Tyr Tyr Cys Gln Arg Ile Ser
                100                 105                 110 aac agc ccc tac acc ttc ggc cag ggc acc aag ctg gaa ctg aag cgt   384
Asn Ser Pro Tyr Thr Phe Gly Gln Gly Thr Lys Leu Glu Leu Lys Arg
            115                 120                 125 acg gtg gcc gcc ccc tcc gtg ttc atc ttc ccc ccc tcc gac gag cag   432
Thr Val Ala Ala Pro Ser Val Phe Ile Phe Pro Pro Ser Asp Glu Gln
        130                 135                 140 ctg aag tcc ggc acc gcc tcc gtg gtg tgc ctg ctg aat aac ttc tac   480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc   528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc   576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag   624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc   672
His Lys Val Tyr Ala Cys Glu Val Thr His Gln Gly Leu Ser Ser Pro
    210                 215                 220 gtc acc aag agc ttc aac agg ggg gag tgt                           702
Val Thr Lys Ser Phe Asn Arg Gly Glu Cys
225                 230

<210> SEQ ID NO 40
<211> LENGTH: 234
<212> TYPE: PRT
<213> ORGANISM: Artificial Sequence
<220> FEATURE:
<223> OTHER INFORMATION: Synthetic Construct

<400> SEQUENCE: 40

Met Val Leu Gln Thr Gln Val Phe Ile Ser Leu Leu Trp Ile Ser
1               5                   10                  15
```

Gly Ala Tyr Gly Asn Ile Gln Met Thr Gln Ser Pro Ser Ser Met Ser
            20                  25                  30

Ile Ser Val Gly Asp Arg Val Thr Met Thr Cys Lys Ala Gly Gln Asn
        35                  40                  45

Val Asp Asn Asn Ile Ala Trp Tyr Gln Lys Lys Pro Gly Gln Ser Pro
50                  55                  60

Lys Leu Leu Ile Tyr Tyr Ala Ser Asn Arg Asn Thr Gly Val Pro Asp
65                  70                  75                  80

Arg Phe Ser Gly Gly Tyr Gly Thr Asp Phe Thr Leu Thr Ile Ser
                85                  90                  95

Ser Val Gln Pro Glu Asp Ala Ala Phe Tyr Tyr Cys Gln Arg Ile Ser
            100                 105                 110

Asn Ser Pro Tyr Thr Phe Gly Gln Gly Thr Lys Leu Glu Leu Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 41
<211> LENGTH: 10
<212> TYPE: PRT
<213> ORGANISM: Rattus norvegicus

<400> SEQUENCE: 41

Gly Phe Thr Phe Arg Thr Tyr Gly Met Ala
1               5                   10

<210> SEQ ID NO 42
<211> LENGTH: 17
<212> TYPE: PRT
<213> ORGANISM: Rattus norvegicus

<400> SEQUENCE: 42

Ser Ile Ser Thr Gly Gly Gly Ser Thr Tyr Tyr Arg Asp Ser Val Lys
1               5                   10                  15

Gly

<210> SEQ ID NO 43
<211> LENGTH: 13
<212> TYPE: PRT
<213> ORGANISM: Rattus norvegicus

<400> SEQUENCE: 43

Asp Leu Ile Asn Tyr Pro Gly Ile Gly Gly Phe Ala Phe
1               5                   10

<210> SEQ ID NO 44

```
<211> LENGTH: 11
<212> TYPE: PRT
<213> ORGANISM: Rattus norvegicus

<400> SEQUENCE: 44

Lys Ala Ser Gln Asn Val Tyr Asn Asn Ile Ala
1               5                   10

<210> SEQ ID NO 45
<211> LENGTH: 7
<212> TYPE: PRT
<213> ORGANISM: Rattus norvegicus

<400> SEQUENCE: 45

Tyr Ala Ser Asn Arg Tyr Thr
1               5

<210> SEQ ID NO 46
<211> LENGTH: 9
<212> TYPE: PRT
<213> ORGANISM: Rattus norvegicus

<400> SEQUENCE: 46

Gln Arg Leu Tyr Asn Ser Pro Pro Thr
1               5

<210> SEQ ID NO 47
<211> LENGTH: 10
<212> TYPE: PRT
<213> ORGANISM: Rattus norvegicus

<400> SEQUENCE: 47

Gly Phe Thr Tyr Arg Ser Tyr Val Met Ala
1               5                   10

<210> SEQ ID NO 48
<211> LENGTH: 17
<212> TYPE: PRT
<213> ORGANISM: Rattus norvegicus

<400> SEQUENCE: 48

Ser Ile Ser Thr Gly Gly Gly Asn Thr Tyr Tyr Arg Asp Ser Val Lys
1               5                   10                  15

Gly

<210> SEQ ID NO 49
<211> LENGTH: 12
<212> TYPE: PRT
<213> ORGANISM: Rattus norvegicus

<400> SEQUENCE: 49

Asp Met Ser Asn Ser Gly Tyr Gly Leu Phe Asp Tyr
1               5                   10

<210> SEQ ID NO 50
<211> LENGTH: 11
<212> TYPE: PRT
<213> ORGANISM: Rattus norvegicus

<400> SEQUENCE: 50

Lys Ala Gly Gln Asn Val Asp Asn Asn Ile Ala
1               5                   10

<210> SEQ ID NO 51
```

```
<211> LENGTH: 7
<212> TYPE: PRT
<213> ORGANISM: Rattus norvegicus

<400> SEQUENCE: 51

Tyr Ala Ser Asn Arg Asn Thr
1               5

<210> SEQ ID NO 52
<211> LENGTH: 9
<212> TYPE: PRT
<213> ORGANISM: Rattus norvegicus

<400> SEQUENCE: 52

Gln Arg Ile Ser Asn Ser Pro Tyr Thr
1               5

<210> SEQ ID NO 53
<211> LENGTH: 10
<212> TYPE: PRT
<213> ORGANISM: Rattus norvegicus

<400> SEQUENCE: 53

Gly Phe Thr Phe Ser Asn Tyr Tyr Met Ala
1               5                   10

<210> SEQ ID NO 54
<211> LENGTH: 17
<212> TYPE: PRT
<213> ORGANISM: Rattus norvegicus

<400> SEQUENCE: 54

Ser Ile Ser Thr Gly Gly Gly Asn Thr Tyr Tyr Arg Asp Ser Val Lys
1               5                   10                  15

Gly

<210> SEQ ID NO 55
<211> LENGTH: 12
<212> TYPE: PRT
<213> ORGANISM: Rattus norvegicus

<400> SEQUENCE: 55

Pro Pro Tyr Gly Tyr Asn Tyr Gly Trp Phe Thr Tyr
1               5                   10

<210> SEQ ID NO 56
<211> LENGTH: 11
<212> TYPE: PRT
<213> ORGANISM: Rattus norvegicus

<400> SEQUENCE: 56

Arg Ala Ser Glu Asp Ile His Asn Gly Leu Val
1               5                   10

<210> SEQ ID NO 57
<211> LENGTH: 7
<212> TYPE: PRT
<213> ORGANISM: Rattus norvegicus

<400> SEQUENCE: 57

Asn Ala Asn Ser Met His Thr
1               5

<210> SEQ ID NO 58
```

```
<211> LENGTH: 9
<212> TYPE: PRT
<213> ORGANISM: Rattus norvegicus

<400> SEQUENCE: 58

Gln Gln Tyr Tyr Asn Tyr Pro Arg Thr
1               5

<210> SEQ ID NO 59
<211> LENGTH: 10
<212> TYPE: PRT
<213> ORGANISM: Rattus norvegicus

<400> SEQUENCE: 59

Gly Phe Thr Tyr Arg Thr Tyr Val Met Ala
1               5                   10

<210> SEQ ID NO 60
<211> LENGTH: 17
<212> TYPE: PRT
<213> ORGANISM: Rattus norvegicus

<400> SEQUENCE: 60

Ser Ile Ser Thr Gly Gly Val Ser Thr Tyr Tyr Arg Asp Ser Val Lys
1               5                   10                  15

Gly

<210> SEQ ID NO 61
<211> LENGTH: 14
<212> TYPE: PRT
<213> ORGANISM: Rattus norvegicus

<400> SEQUENCE: 61

Asp Met Leu Asn Gly Tyr Asn Ser Gln Gly Leu Phe Asp Tyr
1               5                   10

<210> SEQ ID NO 62
<211> LENGTH: 11
<212> TYPE: PRT
<213> ORGANISM: Rattus norvegicus

<400> SEQUENCE: 62

Arg Ala Ser Gln Asn Val Asp Asn Thr Ile Ala
1               5                   10

<210> SEQ ID NO 63
<211> LENGTH: 7
<212> TYPE: PRT
<213> ORGANISM: Rattus norvegicus

<400> SEQUENCE: 63

Phe Ala Ser Asp Arg Tyr Thr
1               5

<210> SEQ ID NO 64
<211> LENGTH: 9
<212> TYPE: PRT
<213> ORGANISM: Rattus norvegicus

<400> SEQUENCE: 64

Gln Arg Ile Tyr Asn Ser Pro Leu Thr
1               5

<210> SEQ ID NO 65
```

```
<211> LENGTH: 10
<212> TYPE: PRT
<213> ORGANISM: Rattus norvegicus

<400> SEQUENCE: 65

Gly Phe Thr Phe Ser Ser Tyr Tyr Met Ala
1               5                   10

<210> SEQ ID NO 66
<211> LENGTH: 17
<212> TYPE: PRT
<213> ORGANISM: Rattus norvegicus

<400> SEQUENCE: 66

Tyr Ile Ser Asn Gly Gly Tyr Ser Thr Tyr Tyr Arg Asp Ser Val Lys
1               5                   10                  15

Gly

<210> SEQ ID NO 67
<211> LENGTH: 10
<212> TYPE: PRT
<213> ORGANISM: Rattus norvegicus

<400> SEQUENCE: 67

Thr Asp His Ser Gly Tyr Arg Phe Thr Tyr
1               5                   10

<210> SEQ ID NO 68
<211> LENGTH: 11
<212> TYPE: PRT
<213> ORGANISM: Rattus norvegicus

<400> SEQUENCE: 68

Lys Ala Ser Gln Ser Ile Tyr Asn Ser Leu Ala
1               5                   10

<210> SEQ ID NO 69
<211> LENGTH: 7
<212> TYPE: PRT
<213> ORGANISM: Rattus norvegicus

<400> SEQUENCE: 69

Asp Ala Asn Ser Leu Gln Thr
1               5

<210> SEQ ID NO 70
<211> LENGTH: 8
<212> TYPE: PRT
<213> ORGANISM: Rattus norvegicus

<400> SEQUENCE: 70

Gln Lys Tyr Tyr Ser Gly Asn Thr
1               5

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
ctccagagtt ccaggtcacg gtgactggc                                   29
```

<210> SEQ ID NO 72
<211> LENGTH: 28
<212> TYPE: DNA
<213> ORGANISM: Artificial Sequence
<220> FEATURE:
<223> OTHER INFORMATION: primer

<400> SEQUENCE: 72
tcagtaacac tgtccaggac accatctc         28

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
tataccgtcg acctctagct agagcttggc       30

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
gctatggcag ggcctgccgc cccgacgttg       30

<210> SEQ ID NO 75
<211> LENGTH: 46
<212> TYPE: DNA
<213> ORGANISM: Artificial Sequence
<220> FEATURE:
<223> OTHER INFORMATION: primer

<400> SEQUENCE: 75
ccagatgggt gctgagcgag gtgcagctgg tggagtctgg gggagg       46

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76
cttggtggag gctgagctga ctgtgaccat gactccttgg ccccag       46

<210> SEQ ID NO 77
<211> LENGTH: 48
<212> TYPE: DNA
<213> ORGANISM: Artificial Sequence
<220> FEATURE:
<223> OTHER INFORMATION: primer

<400> SEQUENCE: 77
atctccggcg cgtacggcaa cattgtgatg acccagtctc ccaaatcc     48

<210> SEQ ID NO 78
<211> LENGTH: 45
<212> TYPE: DNA
<213> ORGANISM: Artificial Sequence
<220> FEATURE:
<223> OTHER INFORMATION: primer

<400> SEQUENCE: 78 ggaggggggcg gccacagccc gtttcagttc cagctcggtc ccagc                45

<210> SEQ ID NO 79
<211> LENGTH: 34
<212> TYPE: DNA
<213> ORGANISM: Homo sapiens

<400> SEQUENCE: 79
atgtgggagg ctcagttcct gggcttgctg tttc                34

<210> SEQ ID NO 80
<211> LENGTH: 34
<212> TYPE: DNA
<213> ORGANISM: Homo sapiens

<400> SEQUENCE: 80
gcccgagccc gagcccgagc cggagcagct ctga                34

<210> SEQ ID NO 81
<211> LENGTH: 30
<212> TYPE: DNA
<213> ORGANISM: Artificial Sequence
<220> FEATURE:
<223> OTHER INFORMATION: oligonucleotide

<400> SEQUENCE: 81
gagtatgtgt tgactggttg ataactatcg                30

<210> SEQ ID NO 82
<211> LENGTH: 30
<212> TYPE: DNA
<213> ORGANISM: Artificial Sequence
<220> FEATURE:
<223> OTHER INFORMATION: oligonucleotide

<400> SEQUENCE: 82
gccatgacag attagccatg tctgcagcac                30

<210> SEQ ID NO 83
<211> LENGTH: 56
<212> TYPE: DNA
<213> ORGANISM: Mus musculus

<400> SEQUENCE: 83
caggaccttt ttctaacctc ccttggaggg ctggggaggc ccgggccata gaggag        56

<210> SEQ ID NO 84
<211> LENGTH: 56
<212> TYPE: DNA
<213> ORGANISM: Mus musculus

<400> SEQUENCE: 84
cctggagccg aggcagccag caggtctcag cagctccgcc cgcccgcccg cccgcc        56

<210> SEQ ID NO 85
<211> LENGTH: 1575
<212> TYPE: DNA
<213> ORGANISM: Homo sapiens
<220> FEATURE:
<221> NAME/KEY: CDS
<222> LOCATION: (1)..(1575)

<400> SEQUENCE: 85

| | | | | | | | | | | | | | | | | |
|---|---|---|---|---|---|---|---|---|---|---|---|---|---|---|---|---|
| atg | tgg | gag | gct | cag | ttc | ctg | ggc | ttg | ctg | ttt | ctg | cag | ccg | ctt | tgg | 48 |
| Met | Trp | Glu | Ala | Gln | Phe | Leu | Gly | Leu | Leu | Phe | Leu | Gln | Pro | Leu | Trp | |
| 1 | | | | 5 | | | | | 10 | | | | | 15 | | |

| gtg | gct | cca | gtg | aag | cct | ctc | cag | cca | ggg | gct | gag | gtc | ccg | gtg | gtg | 96 |
|---|---|---|---|---|---|---|---|---|---|---|---|---|---|---|---|---|
| Val | Ala | Pro | Val | Lys | Pro | Leu | Gln | Pro | Gly | Ala | Glu | Val | Pro | Val | Val | |
| | | | 20 | | | | | 25 | | | | | 30 | | | |

| tgg | gcc | cag | gag | ggg | gct | cct | gcc | cag | ctc | ccc | tgc | agc | ccc | aca | atc | 144 |
|---|---|---|---|---|---|---|---|---|---|---|---|---|---|---|---|---|
| Trp | Ala | Gln | Glu | Gly | Ala | Pro | Ala | Gln | Leu | Pro | Cys | Ser | Pro | Thr | Ile | |
| | 35 | | | | | 40 | | | | | 45 | | | | | |

| ccc | ctc | cag | gat | ctc | agc | ctt | ctg | cga | aga | gca | ggg | gtc | act | tgg | cag | 192 |
|---|---|---|---|---|---|---|---|---|---|---|---|---|---|---|---|---|
| Pro | Leu | Gln | Asp | Leu | Ser | Leu | Leu | Arg | Arg | Ala | Gly | Val | Thr | Trp | Gln | |
| 50 | | | | | 55 | | | | | 60 | | | | | | |

| cat | cag | cca | gac | agt | ggc | ccg | ccc | gct | gcc | gcc | ccc | ggc | cat | ccc | ctg | 240 |
|---|---|---|---|---|---|---|---|---|---|---|---|---|---|---|---|---|
| His | Gln | Pro | Asp | Ser | Gly | Pro | Pro | Ala | Ala | Ala | Pro | Gly | His | Pro | Leu | |
| 65 | | | | 70 | | | | | 75 | | | | | 80 | | |

| gcc | ccc | ggc | cct | cac | ccg | gcg | gcg | ccc | tcc | tcc | tgg | ggg | ccc | agg | ccc | 288 |
|---|---|---|---|---|---|---|---|---|---|---|---|---|---|---|---|---|
| Ala | Pro | Gly | Pro | His | Pro | Ala | Ala | Pro | Ser | Ser | Trp | Gly | Pro | Arg | Pro | |
| | | | | 85 | | | | | 90 | | | | | 95 | | |

| cgc | cgc | tac | acg | gtg | ctg | agc | gtg | ggt | ccc | gga | ggc | ctg | cgc | agc | ggg | 336 |
|---|---|---|---|---|---|---|---|---|---|---|---|---|---|---|---|---|
| Arg | Arg | Tyr | Thr | Val | Leu | Ser | Val | Gly | Pro | Gly | Gly | Leu | Arg | Ser | Gly | |
| | | | 100 | | | | | 105 | | | | | 110 | | | |

| agg | ctg | ccc | ctg | cag | ccc | cgc | gtc | cag | ctg | gat | gag | cgc | ggc | cgg | cag | 384 |
|---|---|---|---|---|---|---|---|---|---|---|---|---|---|---|---|---|
| Arg | Leu | Pro | Leu | Gln | Pro | Arg | Val | Gln | Leu | Asp | Glu | Arg | Gly | Arg | Gln | |
| | | 115 | | | | | 120 | | | | | 125 | | | | |

| cgc | ggg | gac | ttc | tcg | cta | tgg | ctg | cgc | cca | gcc | cgg | cgc | gcg | gac | gcc | 432 |
|---|---|---|---|---|---|---|---|---|---|---|---|---|---|---|---|---|
| Arg | Gly | Asp | Phe | Ser | Leu | Trp | Leu | Arg | Pro | Ala | Arg | Arg | Ala | Asp | Ala | |
| | 130 | | | | | 135 | | | | | 140 | | | | | |

| ggc | gag | tac | cgc | gcc | gcg | gtg | cac | ctc | agg | gac | cgc | gcc | ctc | tcc | tgc | 480 |
|---|---|---|---|---|---|---|---|---|---|---|---|---|---|---|---|---|
| Gly | Glu | Tyr | Arg | Ala | Ala | Val | His | Leu | Arg | Asp | Arg | Ala | Leu | Ser | Cys | |
| 145 | | | | | 150 | | | | | 155 | | | | | 160 | |

| cgc | ctc | cgt | ctg | cgc | ctg | ggc | cag | gcc | tcg | atg | act | gcc | agc | ccc | cca | 528 |
|---|---|---|---|---|---|---|---|---|---|---|---|---|---|---|---|---|
| Arg | Leu | Arg | Leu | Arg | Leu | Gly | Gln | Ala | Ser | Met | Thr | Ala | Ser | Pro | Pro | |
| | | | | 165 | | | | | 170 | | | | | 175 | | |

| gga | tct | ctc | aga | gcc | tcc | gac | tgg | gtc | att | ttg | aac | tgc | tcc | ttc | agc | 576 |
|---|---|---|---|---|---|---|---|---|---|---|---|---|---|---|---|---|
| Gly | Ser | Leu | Arg | Ala | Ser | Asp | Trp | Val | Ile | Leu | Asn | Cys | Ser | Phe | Ser | |
| | | | 180 | | | | | 185 | | | | | 190 | | | |

| cgc | cct | gac | cgc | cca | gcc | tct | gtg | cat | tgg | ttc | cgg | aac | cgg | ggc | cag | 624 |
|---|---|---|---|---|---|---|---|---|---|---|---|---|---|---|---|---|
| Arg | Pro | Asp | Arg | Pro | Ala | Ser | Val | His | Trp | Phe | Arg | Asn | Arg | Gly | Gln | |
| | | 195 | | | | | 200 | | | | | 205 | | | | |

| ggc | cga | gtc | cct | gtc | cgg | gag | tcc | ccc | cat | cac | cac | tta | gcg | gaa | agc | 672 |
|---|---|---|---|---|---|---|---|---|---|---|---|---|---|---|---|---|
| Gly | Arg | Val | Pro | Val | Arg | Glu | Ser | Pro | His | His | His | Leu | Ala | Glu | Ser | |
| | 210 | | | | | 215 | | | | | 220 | | | | | |

| ttc | ctc | ttc | ctg | ccc | caa | gtc | agc | ccc | atg | gac | tct | ggg | ccc | tgg | ggc | 720 |
|---|---|---|---|---|---|---|---|---|---|---|---|---|---|---|---|---|
| Phe | Leu | Phe | Leu | Pro | Gln | Val | Ser | Pro | Met | Asp | Ser | Gly | Pro | Trp | Gly | |
| 225 | | | | | 230 | | | | | 235 | | | | | 240 | |

| tgc | atc | ctc | acc | tac | aga | gat | ggc | ttc | aac | gtc | tcc | atc | atg | tat | aac | 768 |
|---|---|---|---|---|---|---|---|---|---|---|---|---|---|---|---|---|
| Cys | Ile | Leu | Thr | Tyr | Arg | Asp | Gly | Phe | Asn | Val | Ser | Ile | Met | Tyr | Asn | |
| | | | | 245 | | | | | 250 | | | | | 255 | | |

| ctc | act | gtt | ctg | ggt | ctg | gag | ccc | cca | act | ccc | ttg | aca | gtg | tac | gct | 816 |
|---|---|---|---|---|---|---|---|---|---|---|---|---|---|---|---|---|
| Leu | Thr | Val | Leu | Gly | Leu | Glu | Pro | Pro | Thr | Pro | Leu | Thr | Val | Tyr | Ala | |
| | | | 260 | | | | | 265 | | | | | 270 | | | |

| gga | gca | ggt | tcc | agg | gtg | ggg | ctg | ccc | tgc | cgc | ctg | cct | gct | ggt | gtg | 864 |
|---|---|---|---|---|---|---|---|---|---|---|---|---|---|---|---|---|
| Gly | Ala | Gly | Ser | Arg | Val | Gly | Leu | Pro | Cys | Arg | Leu | Pro | Ala | Gly | Val | |
| | | 275 | | | | | 280 | | | | | 285 | | | | |

| ggg | acc | cgg | tct | ttc | ctc | act | gcc | aag | tgg | act | cct | cct | ggg | gga | ggc | 912 |
|---|---|---|---|---|---|---|---|---|---|---|---|---|---|---|---|---|
| Gly | Thr | Arg | Ser | Phe | Leu | Thr | Ala | Lys | Trp | Thr | Pro | Pro | Gly | Gly | Gly | |
| | 290 | | | | | 295 | | | | | 300 | | | | | |

```
cct gac ctc ctg gtg act gga gac aat ggc gac ttt acc ctt cga cta    960
Pro Asp Leu Leu Val Thr Gly Asp Asn Gly Asp Phe Thr Leu Arg Leu
305                 310                 315                 320 gag gat gtg agc cag gcc cag gct ggg acc tac acc tgc cat atc cat   1008
Glu Asp Val Ser Gln Ala Gln Ala Gly Thr Tyr Thr Cys His Ile His
                325                 330                 335 ctg cag gaa cag cag ctc aat gcc act gtc aca ttg gca atc atc aca   1056
Leu Gln Glu Gln Gln Leu Asn Ala Thr Val Thr Leu Ala Ile Ile Thr
            340                 345                 350 gtg act ccc aaa tcc ttt ggg tca cct gga tcc ctg ggg aag ctg ctt   1104
Val Thr Pro Lys Ser Phe Gly Ser Pro Gly Ser Leu Gly Lys Leu Leu
        355                 360                 365 tgt gag gtg act cca gta tct gga caa gaa cgc ttt gtg tgg agc tct   1152
Cys Glu Val Thr Pro Val Ser Gly Gln Glu Arg Phe Val Trp Ser Ser
    370                 375                 380 ctg gac acc cca tcc cag agg agt ttc tca gga cct tgg ctg gag gca   1200
Leu Asp Thr Pro Ser Gln Arg Ser Phe Ser Gly Pro Trp Leu Glu Ala
385                 390                 395                 400 cag gag gcc cag ctc ctt tcc cag cct tgg caa tgc cag ctg tac cag   1248
Gln Glu Ala Gln Leu Leu Ser Gln Pro Trp Gln Cys Gln Leu Tyr Gln
                405                 410                 415 ggg gag agg ctt ctt gga gca gca gtg tac ttc aca gag ctg tct agc   1296
Gly Glu Arg Leu Leu Gly Ala Ala Val Tyr Phe Thr Glu Leu Ser Ser
            420                 425                 430 cca ggt gcc caa cgc tct ggg aga gcc cca ggt gcc ctc cca gca ggc   1344
Pro Gly Ala Gln Arg Ser Gly Arg Ala Pro Gly Ala Leu Pro Ala Gly
        435                 440                 445 cac ctc ctg ctg ttt ctc atc ctt ggt gtc ctt tct ctg ctt ctt ttg   1392
His Leu Leu Leu Phe Leu Ile Leu Gly Val Leu Ser Leu Leu Leu Leu
    450                 455                 460 gtg act gga gcc ttt ggc ttt cac ctt tgg aga aga cag tgg cga cca   1440
Val Thr Gly Ala Phe Gly Phe His Leu Trp Arg Arg Gln Trp Arg Pro
465                 470                 475                 480 aga cga ttt tct gcc tta gag caa ggg att cac cct ccg cag gct cag   1488
Arg Arg Phe Ser Ala Leu Glu Gln Gly Ile His Pro Pro Gln Ala Gln
                485                 490                 495 agc aag ata gag gag ctg gag caa gaa ccg gag ccg gag ccg gag ccg   1536
Ser Lys Ile Glu Glu Leu Glu Gln Glu Pro Glu Pro Glu Pro Glu Pro
            500                 505                 510 gaa ccg gag ccc gag ccc gag ccc gag ccg gag cag ctc               1575
Glu Pro Glu Pro Glu Pro Glu Pro Glu Pro Glu Gln Leu
        515                 520                 525

<210> SEQ ID NO 86
<211> LENGTH: 525
<212> TYPE: PRT
<213> ORGANISM: Homo sapiens

<400> SEQUENCE: 86

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80
```

```
Ala Pro Gly Pro His Pro Ala Ala Pro Ser Trp Gly Pro Arg Pro
                85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495
```

-continued

```
Ser Lys Ile Glu Glu Leu Glu Gln Glu Pro Glu Pro Glu Pro
            500                 505                 510

Glu Pro Glu Pro Glu Pro Glu Pro Glu Pro Glu Gln Leu
        515                 520                 525
```